United States Patent
Mann et al.

(10) Patent No.: US 12,391,734 B2
(45) Date of Patent: *Aug. 19, 2025

(54) PD-1 HOMING ENDONUCLEASE VARIANTS, COMPOSITIONS, AND METHODS OF USE

(71) Applicant: REGENERON PHARMACEUTICALS, INC., Tarrytown, NY (US)

(72) Inventors: Jasdeep Mann, Seattle, WA (US); Joel Gay, Seattle, WA (US); Jordan Jarjour, Seattle, WA (US); Joy Zhang, Seattle, WA (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/584,363

(22) Filed: Feb. 22, 2024

(65) Prior Publication Data
US 2024/0301018 A1 Sep. 12, 2024

Related U.S. Application Data

(63) Continuation of application No. 17/738,484, filed on May 6, 2022, now Pat. No. 11,912,746, which is a continuation of application No. 16/330,039, filed as application No. PCT/US2017/050774 on Sep. 8, 2017, now Pat. No. 11,365,226.

(60) Provisional application No. 62/414,279, filed on Oct. 28, 2016, provisional application No. 62/385,079, filed on Sep. 8, 2016.

(51) Int. Cl.
| | | |
|---|---|---|
| C07K 14/47 | (2006.01) | |
| A61K 40/11 | (2025.01) | |
| A61K 40/31 | (2025.01) | |
| A61K 40/36 | (2025.01) | |
| A61K 40/42 | (2025.01) | |
| C12N 15/86 | (2006.01) | |

(52) U.S. Cl.
CPC .......... *C07K 14/4702* (2013.01); *A61K 40/11* (2025.01); *A61K 40/31* (2025.01); *A61K 40/36* (2025.01); *A61K 40/4211* (2025.01); *A61K 40/4215* (2025.01); *C12N 15/86* (2013.01); *C07K 2319/80* (2013.01)

(58) Field of Classification Search
None
See application file for complete search history.

(56) References Cited

U.S. PATENT DOCUMENTS

| | | |
|---|---|---|
| 4,751,180 A | 6/1988 | Cousens et al. |
| 4,873,192 A | 10/1989 | Kunkel |
| 4,935,233 A | 6/1990 | Bell et al. |
| 5,804,413 A | 9/1998 | DeLuca |
| 5,837,532 A | 11/1998 | Preston et al. |
| 5,846,782 A | 12/1998 | Wickham et al. |
| 5,994,136 A | 11/1999 | Naldini et al. |
| 6,013,516 A | 1/2000 | Verma et al. |
| 6,649,595 B2 | 11/2003 | Clackson et al. |
| 6,682,907 B1 | 1/2004 | Charneau et al. |
| 6,692,736 B2 | 2/2004 | Yu et al. |
| 8,614,092 B2 | 12/2013 | Zhang et al. |
| 8,735,553 B1 | 5/2014 | Li et al. |
| 8,784,799 B2 | 7/2014 | Samulski et al. |
| 8,809,058 B2 | 8/2014 | Ferrari et al. |
| 8,889,641 B2 | 11/2014 | Asokan et al. |
| 9,012,224 B2 | 4/2015 | Bowles et al. |
| 9,017,967 B2 | 4/2015 | Bonas et al. |
| 9,169,492 B2 | 10/2015 | Monahan et al. |
| 9,169,494 B2 | 10/2015 | Hewitt et al. |
| 9,506,120 B2 | 11/2016 | Doyon et al. |
| 11,345,754 B2 | 5/2022 | Hu et al. |
| 11,779,654 B2 | 10/2023 | Jarjour et al. |
| 2011/0256607 A1 | 10/2011 | Hausner |
| 2013/0337454 A1 | 12/2013 | Duchateau et al. |
| 2014/0148361 A1 | 5/2014 | Stoddard et al. |
| 2015/0266973 A1 | 9/2015 | Jarjour et al. |
| 2016/0102323 A1 | 4/2016 | Jarjour et al. |
| 2016/0130569 A1 | 5/2016 | Jarjour et al. |
| 2017/0298329 A1 | 10/2017 | Takeuchi et al. |
| 2021/0040165 A1 | 2/2021 | Mann et al. |

FOREIGN PATENT DOCUMENTS

| | | |
|---|---|---|
| CN | 101679959 A | 3/2010 |
| CN | 106749666 A | 5/2017 |
| CN | 106939049 A | 7/2017 |
| EA | 201492222 A1 | 5/2015 |
| EP | 2215223 B1 | 8/2010 |
| IN | 201617011596 | 11/2021 |

(Continued)

OTHER PUBLICATIONS

Chan et al, The Design and In Vivo Evaluation of Engineered I-OnuI-based Enzymes for HEG Gene Drive, 8(9) PLoS ONE 1-5 (Sep. 2013).

(Continued)

*Primary Examiner* — Marsha Tsay
(74) *Attorney, Agent, or Firm* — Panitch Schwarze Belisario & Nadel LLP; Stephany G. Small; Travis W. Bliss

(57) ABSTRACT

The present disclosure provides improved genome editing compositions and methods for editing a PD-1 gene. The disclosure further provides genome edited cells for the prevention, treatment, or amelioration of at least one symptom of, a cancer, an infectious disease, an autoimmune disease, an inflammatory disease, or an immunodeficiency.

27 Claims, 41 Drawing Sheets

Specification includes a Sequence Listing.

(56) References Cited

FOREIGN PATENT DOCUMENTS

| | | |
|---|---|---|
| JP | 2010539929 A | 12/2010 |
| JP | 2016520308 A | 7/2016 |
| WO | 9102788 A1 | 3/1991 |
| WO | 9604394 A1 | 2/1996 |
| WO | 9815637 A1 | 4/1998 |
| WO | 9906583 A1 | 2/1999 |
| WO | 2006010834 A1 | 2/2006 |
| WO | 2007049095 A1 | 5/2007 |
| WO | 2011156430 A2 | 12/2011 |
| WO | 2012068380 A2 | 5/2012 |
| WO | 2012118717 A2 | 9/2012 |
| WO | 2013126794 A1 | 8/2013 |
| WO | 201414744 A1 | 1/2014 |
| WO | 2014184741 A1 | 11/2014 |
| WO | 2014184744 A1 | 11/2014 |
| WO | 2014191525 A1 | 12/2014 |
| WO | 2014191527 A1 | 12/2014 |
| WO | 2015017214 A1 | 2/2015 |
| WO | 2017156484 A1 | 9/2017 |
| WO | 2017177137 A1 | 10/2017 |
| WO | 2018022619 A1 | 2/2018 |
| WO | 2018035141 A1 | 2/2018 |
| WO | 2018035423 A1 | 2/2018 |
| WO | 2018039333 A1 | 3/2018 |
| WO | 2018049226 A1 | 3/2018 |
| WO | 2018071565 A1 | 4/2018 |
| WO | 2018075541 A1 | 4/2018 |
| WO | 2018218194 A1 | 11/2018 |
| WO | 2020072059 A1 | 4/2020 |
| WO | 2020123375 | 6/2020 |

OTHER PUBLICATIONS

Sethuraman et al., Genes within Genes: Multiple LAGLIDADG Homing Endonucleases Target the Ribosomal Protein S3 Gene Encoded within an rnl Group I Intron of Ophiostoma and Related Taxa, 26(10) Mol Biol Evol. 2299-2315 (2009).

Zhang et al., Research progress in engineered nucleases for genome site-specific editing, 33(12) Basic & Clinical Medicine 1634-1637 (Dec. 2013) (English abstract).

Jarjour et al., "High-resolution profiling of homing endonuclease binding and catalytic specificity using yeast surface display," Nucleic Acids Research, vol. 37, No. 20, pp. 6871-6880 (2009).

Jones et al., "Isolation of Deletion and Substitution Mutants of Adenovirus Type 5," Cell, vol. 13, pp. 181-188 (1978).

Kay et al., "A Bacterial Effector Acts as a Plant Transcription Factor and Induces a Cell Size Regulator," Science, vol. 318, No. 5850, pp. 648-651 (Oct. 26, 2007).

Kay, "Structure-function relationships in the FK506-binding protein (FKBP) family of peptidylprolyl cis-trans isomerases," Biochem J., vol. 314, pp. 361-385 (1996).

Kim et al., "Hybrid restriction enzymes: zinc finger fusions to Fok I cleavage domain," Proceedings of the National Academy of Sciences, vol. 93, No. 3, pp. 1156-1160 (1996).

Kozak, M., "An analysis of 5'-noncoding sequences from 699 vertebrate messenger RNAs," Nucleic Acids Research, vol. 15, No. 20, pp. 8125-8148 (1987).

Kozak, M., "Point Mutations Define a Sequence Flanking the AUG Initiator Codon That Modulates Translation by Eukaryotic Ribosomes," Cell, vol. 44, No. 2, pp. 283-292 (1986).

Kunkel, et al "Rapid and efficient site-specific mutagenesis without phenotypic selection", Methods in Enzymol. (1987); 154: 367-382.

Kunkel, T. A., "Rapid and efficient site-specific mutagenesis without phenotypic selection," Proc. Natl. Acad. Sci. USA, vol. 82, No. 2, pp. 488-492 (1985).

Kutner et al., "Production, concentration and titration of pseudotyped HIV-1-based lentiviral vectors," Nature Protocols, vol. 4, No. 4, pp. 495-505 (2009).

Kutner et al., "Simplified production and concentration of HIV-1-based lentiviral vectors using HYPERFlask vessels and anion exchange membrane chromatography," BMC Biotechnology, vol. 9, No. 10, pp. 1-7 (2009).

Lai et al., "Long-Term Evaluation of AAV-Mediated sFlt-1 Gene Therapy for Ocular Neovascularization in Mice and Monkeys," Molecular Therapy, vol. 12, No. 4, pp. 659-668 (2005).

Le Gal La Salle et al., "An Adenovirus Vector for Gene Transfer into Neurons and Glia in the Brain," Science, vol. 259, pp. 988-990 (1993).

Levrero et al., "Defective and nondefective adenovirus vectors for expressing foreign genes in vitro and in vivo," Gene, vol. 101, pp. 195-202 (1991).

Liu et al., "Design of polydactyl zinc-finger proteins for unique addressing within complex genomes," Proceedings of the National Academy of Sciences USA, vol. 94, No. 11, pp. 5525-5530 (1997).

Liu et al., "HnRNP L binds a cis-acting RNA sequence element that enables intron-dependent gene expression," Genes & Development, vol. 9, pp. 1766-1780 (1995).

Liu et al., "Poly(cationic lipid)-mediated in vivo gene delivery to mouse liver," Gene Therapy, vol. 10, No. 2, pp. 180-187 (2003).

Maratea et al., "Deletion and fusion analysis of the phage phi X174 lysis gene E," Gene, vol. 40, No. 1, pp. 39-46 (1985).

McMurrough et al., "Control of catalytic efficiency by a coevolving network of catalytic and noncatalytic residues," PNAS, pp. E2376-E2383 (2014).

Murphy et al., "Genetic construction, expression, and melanoma-selective cytotoxicity of a diphtheria toxin-related alpha-melanocyte-stimulating hormone fusion protein," Proc. Natl. Acad. Sci. U S A., vol. 83, No. 21, pp. 8258-8262 (Nov. 1986).

Nakayama et al., "Structure of a Hyperthermophilic Archael Homing Endonuclease, I-Tsp061I: Contribution of Cross-domain Polar Networks to Thermostability," Journal of Molecular Biology, vol. 365, pp. 362-378 (2007).

Naldini et al., "Efficient transfer, integration, and sustained long-term expression of the transgene in adult rat brains injected with a lentiviral vector," Proc. Natl. Acad. Sci. USA, vol. 93, No. 21, pp. 11382-11388 (1996).

Naldini et al., "In vivo gene delivery and stable transduction of nondividing cells by a lentiviral vector," Science, vol. 272, No. 5259, pp. 263-267 (1996).

Naldini, L., "Lentiviruses as gene transfer agents for delivery to non-dividing cells," Current Opinion in Biotechnology, vol. 9, pp. 457-463 (1998).

Patel et al., "Impact of chimeric immune receptor extracellular protein domains on T cell function," Gene Therapy, vol. 6, pp. 412-419 (1999).

Platten et al., "Tryptophan Catabolismin Cancer: Beyond IDO and Tryptophan Depletion," Cancer Research, vol. 72, No. 21, pp. 5435-5440 (2012).

Pomerantz et al., "Analysis of homeodomain function by structure-based design of a transcription factor," Proc. Natl. Acad. Sci. USA, vol. 92, No. 21, pp. 9752-9756 (1995).

Pomerantz, et al., "Structure-based design of transcription factors." Science (1995); 267.5194: 93-96.

Pâques et al., "Meganucleases and DNA Double-Strand Break-Induced Recombination: Perspectives for Gene Therapy," Current Gene Therapy, vol. 7, pp. 49-66 (2007).

Ragot et al., "Efficient adenovirus-mediated transfer of a human minidystrophin gene to skeletal muscle of mdx mice," Nature, vol. 361, pp. 647-650 (1993).

Reich et al., "Efficient Trans-Splicing in the Retina Expands the Utility of Adeno-Associated Virus as a Vector for Gene Therapy," Human Gene Therapy, vol. 14, No. 1, pp. 37-44 (2003).

Rosenfeld et al., "Adenovirus-Mediated Transfer of a Recombinant alpha1-Antitrypsin Gene to the Lung Epithelium in Vivo," Science, vol. 252, pp. 431-434 (1991).

Rosenfeld et al., "In Vivo Transfer of the Human Cystic Fibrosis Transmembrane Conductance Regulator Gene to the Airway Epithelium," Cell, vol. 68, pp. 143-155 (1992).

Ryan et al., "Virus-encoded proteinases of the picornavirus supergroup," Journal of General Virology, vol. 78 (Pt 4), pp. 699-723 (1997).

Sather et al., "Efficient modification of CCR5 in primary human hematopoietic cells using a megaTAL nuclease and AAV donor template," Sci. Transl Med., vol. 7, No. 307, pp. 1-14 (2015).

(56) References Cited

OTHER PUBLICATIONS

Standaert et al., "Molecular cloning and overexpression of the human FK506-binding protein FKBP," Nature, vol. 346, pp. 671-674 (1990).
Sterman et al., "Adenovirus-Mediated Herpes Simplex Virus Thymidine Kinase/Ganciclovir Gene Therapy in Patients with Localized Malignancy: Results of a Phase I Clinical Trial in Malignant Mesothelioma," Human Gene Therapy, vol. 9, No. 7, pp. 1083-1092 (1998).
Stoddard, "Homing endonuclease structure and function," Quarterly Reviews of Biophysics 2005; 38(1): pp. 49-95.
Stoddard, "Homing Endonucleases: From Microbial Genetic Invaders to Reagents for Targeted DNA Modification," Structure, vol. 19, pp. 7-15 (2011).
Szymczak et al., "Correction of multi-gene deficiency in vivo using a single 'self-cleaving' 2A peptide-based retroviral vector," Nature Biotechnology, vol. 22, No. 5, pp. 589-594 (2004).
Takeuchi et al., "Engineering of customized meganucleases via in vitro compartmentalization and in cellulo optimization," Methods Mol. Biol., vol. 1239, pp. 105-132 (2015).
Takeuchi et al., "Tapping natural reservoirs of homing endonucleases for targeted gene modification," Proceedings of the National Academy of Sciences, vol. 108, No. 32, pp. 13077-13082 (2011).
Yan et al., "Trans-splicing vectors expand the utility of adeno-associated virus for gene therapy," PNAS, vol. 97, No. 12, pp. 6716-6721 (2000).
Zennou et al., "HIV-1 genome nuclear import is mediated by a central DNA flap," Cell, vol. 101, No. 2, pp. 173-185 (2000).
Zhong et al., "Chimeric Antigen Receptors Combining 4-1BB and CD28 Signaling Domains Augment PI3kinase/AKT/Bcl-XL Activation and CD8+ T Cell-mediated Tumor Eradication," Molecular Therapy, vol. 18, No. 2, pp. 413-420 (2010).
Zufferey et al., "Multiply attenuated lentiviral vector achieves efficient gene delivery in vivo," Nat. Biotechnol., vol. 15, No. 9, pp. 871-875 (1997).
Zufferey et al., "Woodchuck hepatitis virus posttranscriptional regulatory element enhances expression of transgenes delivered by retroviral vectors," Journal of Virology, vol. 73, No. 4, pp. 2886-2892 (1999).
Ashworth et al., "Computational redesign of endonuclease DNA binding and cleavage specificity," Nature, vol. 441, No. 7093, pp. 656-659 (2006).
Balazs et al., "Liposomes for Use in Gene Delivery," Journal of Drug Delivery, vol. 2011, pp. 1-12 (2011).
Baxter et al., "Engineering domain fusion chimeras from I-Onul family LAGLIDADG homing endonucleases," Nucleic Acids Research, vol. 40, No. 16, pp. 7985-8000 (2012).
Belfort et al., "Homing Endonucleases: From Genetic Anomalies to Programmable Genomic Clippers," Methods in Molecular Biology, vol. 1123, pp. 1-26 (2014).
Bennardo et al., "Limiting the Persistence of a Chromosome Break Diminishes Its Mutagenic Potential," PLoS Genetics, vol. 5, Issue 10, e1000683, pp. 1-14 (Oct. 2009).
Bird et al., "Single-chain antigen-binding proteins," Science, vol. 242, No. 4877, pp. 423-427 (1988).
Boissel et al., "megaTALS: a rare-cleaving nuclease architecture for therapeutic genome engineering," Nucleic Acids Research, vol. 42, No. 4, pp. 2591-2601 (2014).
Brinkman et al., "Easy quantitative assessment of genome editing by sequence trace decomposition" Nucleic Acids Research, vol. 42, No. 22, e168, pp. 1-8 (2014).
Brown et al., "A mammalian protein targeted by G1-arresting rapamycin-receptor complex," Nature, vol. 369, No. 6483, pp. 756-758 (1994).
Brunner et al., "Cytotoxic T cells: Double-barreled shot guns," Nature Medicine, vol. 5, No. 1, p. 20 (1999).
Certo et al., "Coupling endonucleases with DNA end-processing enzymes to drive gene disruption," Nat Methods, vol. 9, No. 10, pp. 973-975 (2012).
Certo et al., "Tracking genome engineering outcome at individual DNA breakpoints," Nat Methods. Jul. 10, 2011;8 (8):671-6.

Challita et al., "Multiple Modifications in cis Elements of the Long Terminal Repeat of Retroviral Vectors Lead to Increased Expression and Decreased DNA Methylation in Embryonic Carcinoma Cells," Journal of Virology, vol. 69, No. 2, pp. 748-755 (1995).
Chaudhary et al. "A rapid method of cloning functional variable-region antibody genes in Escherichia coli as single-chain immunotoxins," Proceedings of the National Academy of Sciences USA, vol. 87, pp. 1066-1070 (and correction) (1990).
Chevalier et al., "Design, Activity, and Structure of a Highly Specific Artificial Endonuclease," Molecular Cell, vol. 10, pp. 895-905 (Oct. 2002).
Clever et al., "RNA Secondary Structure and Binding Sites for gag Gene Products in the 5' Packaging Signal of Human Immunodeficiency Virus Type 1," Journal of Virology, vol. 69, No. 4, pp. 2101-2109 (1995).
Cox et al., "Therapeutic genome editing: prospects and challenges", Nature Medicine, vol. 21, No. 2, pp. 121-131 (2015).
Cullen et al., "Regulatory Pathways Governing HIV-1 Replication", Cell, vol. 58, pp. 423-426 (1989).
Cullen, B.R., "Human Immunodeficiency Virus as a Prototypic Complex Retrovirus," Journal of Virology, vol. 65, No. 3, pp. 1053-1056 (1991).
DATABASE Geneseq [Online] Oct. 24, 2013 (Oct. 24, 2013), "1-0nul homing endonuclease, SEQ 15," XP002798406, retrieved from EBI accession No. GSP:BAS88181 Database accession No. BAS88181 *sequence*, 1 page.
Dayhoff et al., "A model of evolutionary change in proteins. In: Atlas of Protein Sequence and Structure," M.O. Dayhoff, ed., National Biomedical Research Foundation, Washington, DC., pp. 345-358 (1978).
de Felipe et al., "Targeting of Proteins Derived from Self-Processing Polyproteins Containing Multiple Signal Sequences," Traffic, vol. 5, No. 8, pp. 616-626 (2004).
Desjarlais et al., "Length-encoded multiplex binding site determination: application to zinc finger proteins," Proceedings of the National Academy of Sciences USA, vol. 91, pp. 11099-11103 (1994).
Desjarlais et al., "Use of a zinc-finger consensus sequence framework and specificity rules to design specific DNA binding proteins," Proceedings of the National Academy of Sciences USA, vol. 90, pp. 2256-2260 (1993).
Donnelly et al., "The 'cleavage' activities of foot-and-mouth disease virus 2A site-directed mutants and naturally occurring '2A-like' sequences," Journal of General Virology, vol. 82 (Pt 5), pp. 1027-1041 (2001).
Duan et al., "Expanding AAV Packaging Capacity with Trans-splicing or Overlapping Vectors: A Quantitative Comparison," Mol Ther. Oct. 2001;4(4):383-91.
Duke et al., "Sequence and Structural Elements That Contribute to Efficient Encephalomyocarditis Virus RNA Translation," Journal of Virology, vol. 66, No. 3, pp. 1602-1609 (1992).
Dull et al., "A Third-Generation Lentivirus Vector with a Conditional Packaging System," Journal of Virology, vol. 72, No. 11, pp. 8463-8471 (1998).
Epinat et al., "A novel engineered meganuclease induces homologous recombination in yeast and mammalian cells," Nucleic Acids Research, vol. 31, No. 11, pp. 2952-2962 (2003).
Extended European Search Report mailed on Jun. 15, 2020, for European Application No. 17849655.0, 9 pages.
GenBank Accession No. AAA58476.1, "FK506-binding protein 12 [*Homo sapiencs*]," Jun. 10, 2016, 2 pages.
GenBank Accession No. L34075.1, "Human FKBP-rapamycin associated protein (FRAP) mRNA, complete cds," Dec. 31, 1994, 4 paqes.
Ghosh et al., "A Hybrid Vector System Expands Adena-associated Viral Vector Packaging Capacity in a Transoene-independent Manner," Molecular Therapy, vol. 16, No. 1, pp. 124-130 (2008).
Ghosh et al., "Efficient Transgene Reconstitution with Hybrid Dual AAV Vectors Carrying the Minimized Bridging Sequences," Human Gene Therapy, vol. 22, No. 1, pp. 77-83 (2011).

(56) References Cited

OTHER PUBLICATIONS

Ghosh et al., "Viral serotype and the transgene sequence influence overlapping adeno-associated viral (AAV) vector-mediated gene transfer in skeletal muscle," J. Gene Med., vol. 8, No. 3, pp. 298-305 (2006).

Gomez-Foix et al., "Adenovirus-mediated Transfer of the Muscle Glycogen Phosphorylase Gene into Hepatocytes Confers Altered Regulation of Glycogen Metabolism," Journal of Biological Chemistry, vol. 267, No. 35, pp. 25129-25134 (1992).

Graham et al., "Adenovirus-Based Expression Vectors and Recombinant Vaccines," Vaccines: New Approaches to Immunological Problems, Chapter 16, pp. 363-390 (1992).

Graham et al., "Characteristics of a Human Cell Line Transformed by DNA from Human Adenovirus Type 5," J. gen. Virol., vol. 36, pp. 59-72 (1977).

Graham et al., "Manipulation of Adenovirus Vectors," Methods in Molecular Biology, vol. 7: Gene transfer and Expression Protocols, Chapter 11, pp. 109-128 (1991).

Grunhaus et al., "Adenoviruses as cloning vectors," Semin. Virol., vol. 3, pp. 237-252 (1992).

Hensgens et al., "Two Intron Sequences in Yeast Mitochondrial COX1 Gene: Homology among URF-Containing Introns and Strain-Dependent Variation in Flanking Exons," Cell, vol. 32, pp. 379-389 (Feb. 1983).

Herz et al., "Adenovirus-mediated transfer of low density lipoprotein receptor gene acutely accelerates cholesterol clearance in normal mice," PNAS USA, vol. 90, pp. 2812-2816 (1993).

Huang et al., "Role of the Hepatitis B Virus Posttranscriptional Regulatory Element in Export of Intronless Transcripts," Molecular and Cellular Biology, vol. 15, No. 7, pp. 3864-3869 (1995).

Huez et al., "Two Independent Internal Ribosome Entry Sites Are Involved in Translation Initiation of Vascular Endothelial Growth Factor mRNA," Molecular and Cellular Biology, vol. 18, No. 11, pp. 6178-6190 (Nov. 1998).

International Search Report and Written Opinion issued Mar. 4, 2020 in International Application No. PCT/US2019/065223.

International Search Report and Written Opinion issued Jul. 20, 2020 in International Application No. PCT/US2019/065211.

International Search Report and Written Opinion issued Nov. 16, 2017 in International Application No. PCT/US2017/050774.

Irion et al., "Identification and targeting of the ROSA26 locus in human embryonic stem cells," Nature Biotechnology, vol. 25, No. 12, pp. 1477-1482 (2007).

Jackson et al., "Internal initiation of translation in eukaryotes: the picornavirus paradigm and beyond," RNA, vol. 1, No. 10, pp. 985-1000 (1995).

Jackson et al., "The novel mechanism of initiation of picornavirus RNA translation," Trends Biochem. Sci., vol. 15, No. 12, pp. 477-483 (1990).

GenPept 6BD0_A, Chain A, Ribosomal protein 3/homing endonuclease-like protein fusion (available through NCBI; disclosed by Brown, C., Zhang, K., Laforet, M., McMurrough, T.A., Gloor, G.B., Edgell, D.R.and Junop, M. in 2017) 2 pages (Mar. 13, 2024).

Lambert et al., "Indirect DNA sequence recognition and its impact on nuclease cleavage activity," Structure 24(6): 862-873 (Jun. 7, 2016).

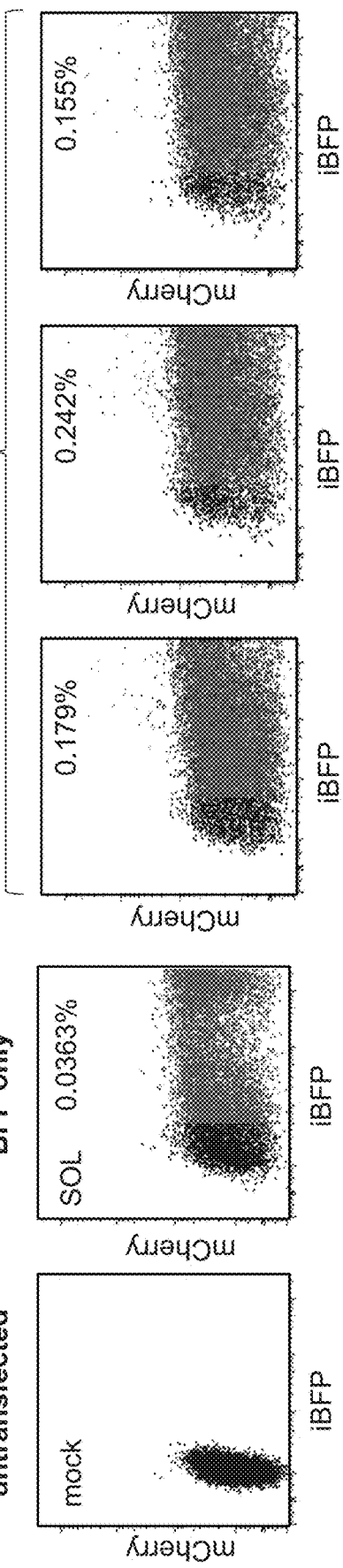
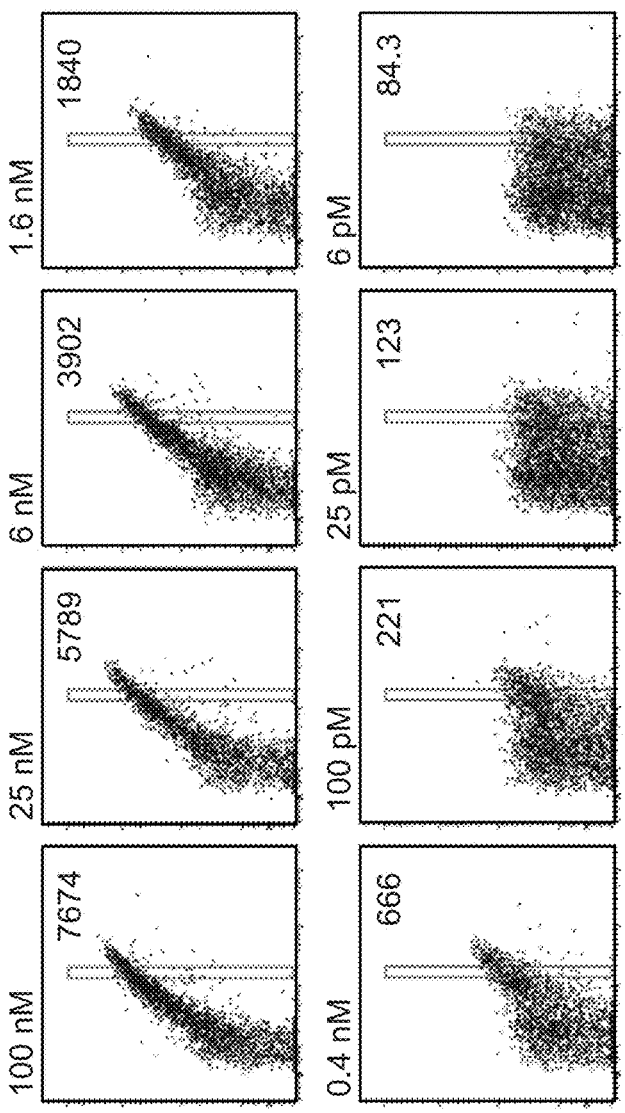
FIGURE 3A
FIGURE 3B

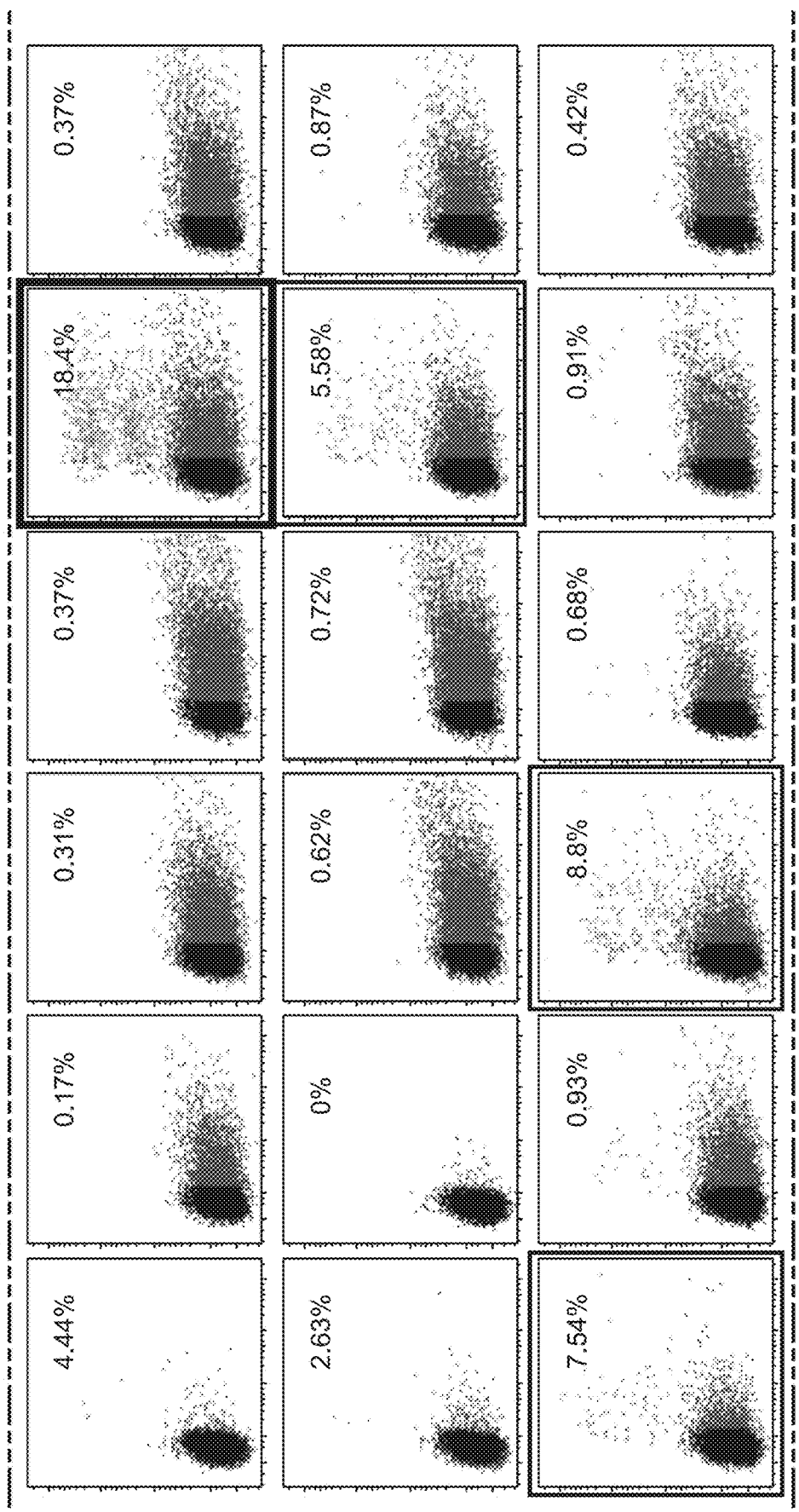

| | | | | |
|---|---|---|---|---|
| AAC | 1.24 | 1.01 | 1.02 | 1.04 |
| TAG | 1.24 | 1.01 | 1.03 | 1.00 |
| CCC | 1.03 | 1.01 | 1.04 | 1.05 |
| CAA | 1.16 | 1.01 | 1.01 | 1.03 |
| GCT | 1.22 | 1.01 | 1.02 | 1.03 |
| TGT | 1.21 | 1.01 | 1.03 | 1.01 |
| CAT | 1.12 | 1.01 | 1.04 | 1.04 |
| ACT | 1.16 | 1.00 | 1.02 | 1.01 |
| AAT | 1.23 | 1.00 | 1.03 | 1.02 |
| TGC | 1.18 | 1.00 | 0.97 | 1.00 |
| ACC | 1.17 | 1.00 | 1.01 | 1.04 |
| TGA | 1.21 | 0.99 | 1.02 | 0.99 |
| AAA | 1.22 | 0.99 | 1.02 | 1.03 |

1.0

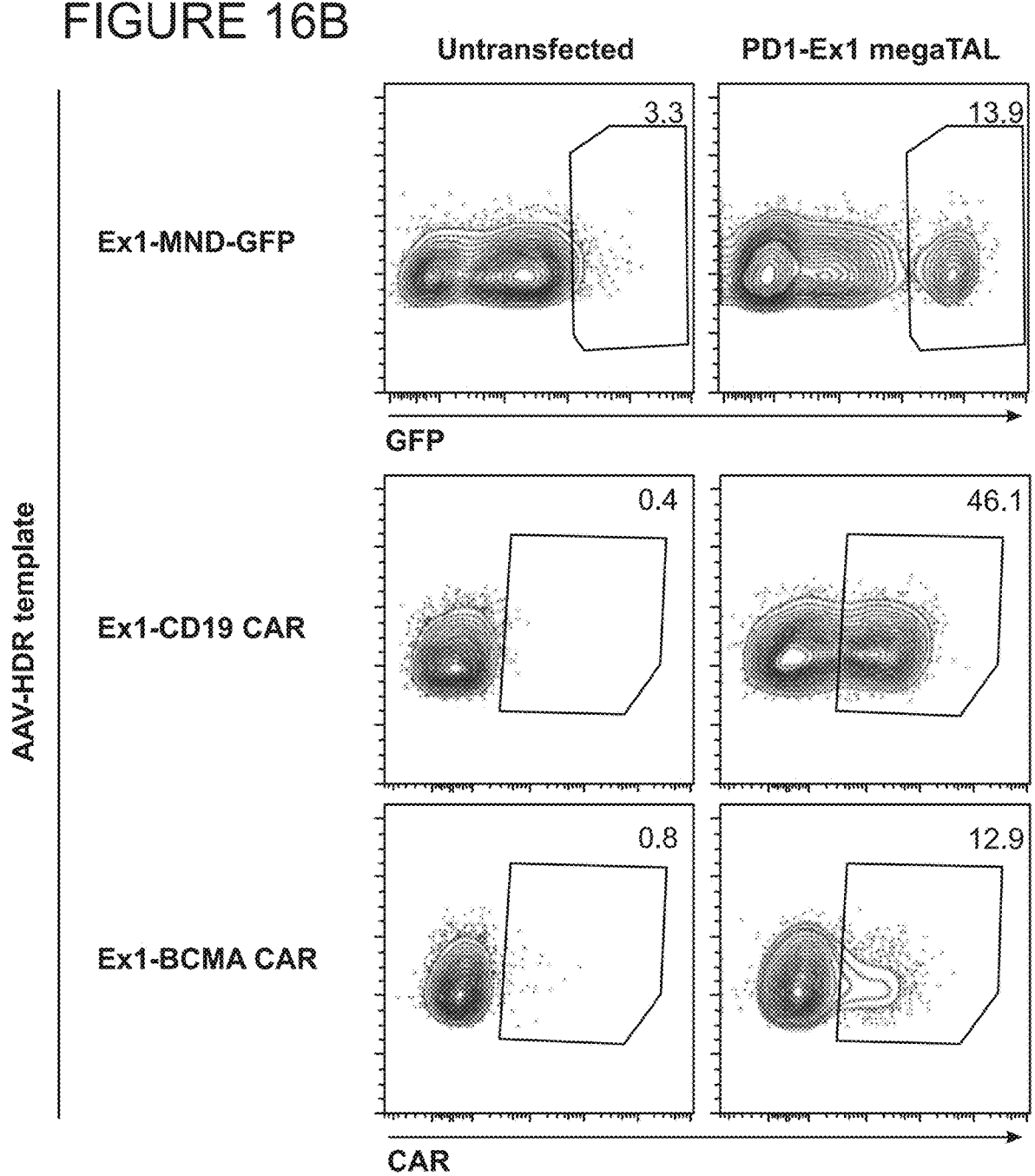

SEQUENCE LISTING

```
Sequence total quantity: 123
SEQ ID NO: 1            moltype = AA  length = 303
FEATURE                 Location/Qualifiers
source                  1..303
                        mol_type = protein
                        note = subsp. americana (mitochondrion)
                        organism = Ophiostoma novo-ulmi
SEQUENCE: 1
MAYMSRRESI NPWILTGFAD AEGSFLLRIR NNNKSSVGYS TELGFQITLH NKDKSILENI   60
QSTWKVGVIA NSGDNAVSLK VTRFEDLKVI IDHFEKYPLI TQKLGDYMLF KQAFCVMENK  120
EHLKINGIKE LVRIKAKLNW GLTDELKKAF PEIISKERSL INKNIPNFKW LAGFTSGEGC  180
FFVNLIKSKS KLGVQVQLVF SITQHIKDKN LMNSLITYLG CGYIKEKNKS EFSWLDFVVT  240
```

```
KFSDINDKII PVFQENTLIG VKLEDFEDWC KVAKLIEEKK HLTESGLDEI KKIKLNMNKG   300
RVF                                                                303

SEQ ID NO: 2            moltype = AA  length = 303
FEATURE                 Location/Qualifiers
source                  1..303
                        mol_type = protein
                        note = subsp. americana (mitochondrion)
                        organism = Ophiostoma novo-ulmi
SEQUENCE: 2
MAYMSRRESI NPWILTGFAD AEGSFLLRIR NNNKSSVGYS TELGFQITLH NKDKSILENI    60
QSTWKVGVIA NSGDNAVSLK VTRFEDLKVI IDHFEKYPLI TQKLGDYKLF KQAFSVMENK   120
EHLKENGIKE LVRIKAKLNW GLTDELKKAF PENISKERSL INKNIPNFKW LAGFTSGEGC   180
FFVNLIKSKS KLGVQVQLVF SITQHIKDKN LMNSLITYLG CGYIKEKNKS EFSWLDFVVT   240
KFSDINDKII PVFQENTLIG VKLEDFEDWC KVAKLIEEKK HLTESGLDEI KKIKLNMNKG   300
RVF                                                                303

SEQ ID NO: 3            moltype = AA  length = 303
FEATURE                 Location/Qualifiers
VARIANT                 1..3
                        note = Any amino acid or absent
source                  1..303
                        mol_type = protein
                        note = subsp. americana (mitochondrion)
                        organism = Ophiostoma novo-ulmi
SEQUENCE: 3
XXXMSRRESI NPWILTGFAD AEGSFLLRIR NNNKSSVGYS TELGFQITLH NKDKSILENI    60
QSTWKVGVIA NSGDNAVSLK VTRFEDLKVI IDHFEKYPLI TQKLGDYKLF KQAFSVMENK   120
EHLKENGIKE LVRIKAKLNW GLTDELKKAF PENISKERSL INKNIPNFKW LAGFTSGEGC   180
FFVNLIKSKS KLGVQVQLVF SITQHIKDKN LMNSLITYLG CGYIKEKNKS EFSWLDFVVT   240
KFSDINDKII PVFQENTLIG VKLEDFEDWC KVAKLIEEKK HLTESGLDEI KKIKLNMNKG   300
RVF                                                                303

SEQ ID NO: 4            moltype = AA  length = 303
FEATURE                 Location/Qualifiers
VARIANT                 1..4
                        note = Any amino acid or absent
VARIANT                 302..303
                        note = Any amino acid or absent
source                  1..303
                        mol_type = protein
                        note = subsp. americana (mitochondrion)
                        organism = Ophiostoma novo-ulmi
SEQUENCE: 4
XXXXSRRESI NPWILTGFAD AEGSFLLRIR NNNKSSVGYS TELGFQITLH NKDKSILENI    60
QSTWKVGVIA NSGDNAVSLK VTRFEDLKVI IDHFEKYPLI TQKLGDYKLF KQAFSVMENK   120
EHLKENGIKE LVRIKAKLNW GLTDELKKAF PENISKERSL INKNIPNFKW LAGFTSGEGC   180
FFVNLIKSKS KLGVQVQLVF SITQHIKDKN LMNSLITYLG CGYIKEKNKS EFSWLDFVVT   240
KFSDINDKII PVFQENTLIG VKLEDFEDWC KVAKLIEEKK HLTESGLDEI KKIKLNMNKG   300
RXX                                                                303

SEQ ID NO: 5            moltype = AA  length = 303
FEATURE                 Location/Qualifiers
VARIANT                 1..8
                        note = Any amino acid or absent
VARIANT                 302..303
                        note = Any amino acid or absent
source                  1..303
                        mol_type = protein
                        note = subsp. americana (mitochondrion)
                        organism = Ophiostoma novo-ulmi
SEQUENCE: 5
XXXXXXXXSI NPWILTGFAD AEGSFLLRIR NNNKSSVGYS TELGFQITLH NKDKSILENI    60
QSTWKVGVIA NSGDNAVSLK VTRFEDLKVI IDHFEKYPLI TQKLGDYKLF KQAFSVMENK   120
EHLKENGIKE LVRIKAKLNW GLTDELKKAF PENISKERSL INKNIPNFKW LAGFTSGEGC   180
FFVNLIKSKS KLGVQVQLVF SITQHIKDKN LMNSLITYLG CGYIKEKNKS EFSWLDFVVT   240
KFSDINDKII PVFQENTLIG VKLEDFEDWC KVAKLIEEKK HLTESGLDEI KKIKLNMNKG   300
RXX                                                                303

SEQ ID NO: 6            moltype = AA  length = 303
FEATURE                 Location/Qualifiers
REGION                  1..303
                        note = Synthesized I-OnuI variant PD-1.ITSM.ex5_RD1_CV3-08
VARIANT                 1..4
                        note = Any amino acid or absent
VARIANT                 302..303
                        note = Any amino acid or absent
source                  1..303
                        mol_type = protein
```

```
                            organism = synthetic construct
SEQUENCE: 6
XXXXSRRESI NPWILTGFAD AEGSFQLEIR NVNPNIPRYK TRLRFEIDLH NKDKSILENI    60
QSTWKVGKIY NQGDSYVKLR VTRFEDLKVI IDHFEKYPLI TQKLGDYKLF KQAFSVMENK   120
EHLKENGIKE LVRIKAKMNW GLNDELKKAF PENISKERPL INKNIPNLKW LAGFTSGEGH   180
FGVILAKRRP ASPVQVRLRF AIGQHIRDKN LMNSLITYLG CGRIREKNIS EKSWLEFEVT   240
KFSDINDKII PVFQENTLIG VKLEDFEDWC KVAKLIEEKK HLTESGLDEI KKIKLNMNKG   300
RXX                                                                303

SEQ ID NO: 7              moltype = AA  length = 303
FEATURE                   Location/Qualifiers
REGION                    1..303
                          note = Synthesized I-OnuI variant PD-1.ITSM.ex5_RD2_73
VARIANT                   1..4
                          note = Any amino acid or absent
VARIANT                   302..303
                          note = Any amino acid or absent
source                    1..303
                          mol_type = protein
                          organism = synthetic construct
SEQUENCE: 7
XXXXSRRESI NPWILTGFAD AEGSFQLEIR NVNPNIPRYR TRLRFEIDLH NKDKSILEDI    60
QSTWKVGKIY NRGDSYVKLR VTRFEDLKVI IDHFEKYPLI TQKLGDYKLF KQAFSVMENK   120
EHLKENGIKE LVRIKAKMNW GLNDELKKAF PENISKERPL INKNIPNLKW LAGFTSGEGH   180
FGVILAKRRP ASPVQVRLRF AIGQHIRDKN LMNSLITYLG CGRTREKNIS EKSWLEFEVT   240
KFSDINDKII PVFQENTLIG VKLEDFEDWC KVAKLIEEKK HLTESGLDEI KKIKLNMNKG   300
RXX                                                                303

SEQ ID NO: 8              moltype = AA  length = 303
FEATURE                   Location/Qualifiers
REGION                    1..303
                          note = Synthesized I-OnuI variant PD-1.ITSM.ex5_RD3_03
VARIANT                   1..4
                          note = Any amino acid or absent
VARIANT                   302..303
                          note = Any amino acid or absent
source                    1..303
                          mol_type = protein
                          organism = synthetic construct
SEQUENCE: 8
XXXXSRRESI NPWILTGFAD AEGSFQLEIR NVNPNIPRYR TRLRFEIDLH NKDKSILEDI    60
QSTWKVGKIY NQGDSYVKLR VTRFEDLKVI IDHFEKYPLI TQKLGDYKLF KQAFSVMENK   120
EHLKENGIKE LVRIKAKMNW GLNDELKKAF PENISKERPL INKNIPNLKW LAGFTSGEGH   180
FGVILAKRRP ASPVQVRLRF AIGQHIRDKN LMNSLITYLG CGRTREKNIS EKSWLEFEVT   240
KFSDINDKII PVFQENTLIG VKLEDFEDWC KVAKLIEEKK HLTESGLDEI KKIKLNMNKG   300
RXX                                                                303

SEQ ID NO: 9              moltype = AA  length = 303
FEATURE                   Location/Qualifiers
REGION                    1..303
                          note = Synthesized I-OnuI variant PD-1.ITSM.ex5_RD4_CV23
VARIANT                   1..4
                          note = Any amino acid or absent
VARIANT                   302..303
                          note = Any amino acid or absent
source                    1..303
                          mol_type = protein
                          organism = synthetic construct
SEQUENCE: 9
XXXXSRRESI NPWILTGFAD AEGSFQLEIR NVNPNIPRYR TRLRFEIDLH NKDKSILEDI    60
QSTWKVGKIY NQGDSYVKLR VTRFEDLKVI IDHFEKYPLI TQKLGDYKLF KQAFSVMENK   120
EHLKENGIKE LVRIKAKMNW GLNDELKKAF PENISKERPL INKNIPNLKW LAGFTSGDGH   180
FGVILAKRRP ASPVQVRLRF AIGQHIRDKN LMNSLITYLG CGRIREKNKS EKSWLEFEVT   240
KFSDINDKII PVFQENTLIG VKLEDFEDWC KVAKLIEEKK HLTESGLDEI KKIKLNMNKG   300
RXX                                                                303

SEQ ID NO: 10             moltype = AA  length = 303
FEATURE                   Location/Qualifiers
REGION                    1..303
                          note = Synthesized I-OnuI variant PD-1.ITSM.ex5_RD5_CV23MK
VARIANT                   1..4
                          note = Any amino acid or absent
VARIANT                   302..303
                          note = Any amino acid or absent
source                    1..303
                          mol_type = protein
                          organism = synthetic construct
SEQUENCE: 10
XXXXSRRESI NPWILTGFAD AEGSFQLEIR NVNPNIPRYR TRLRFEIDLH NKDKSILEDI    60
```

```
QSTWKVGKIY NQGDSYVKLR VTRFEDLKVI IDHFEKYPLI TQKLGDYKLF KQAFSVMENK    120
EHLKENGIKE LVRIKAKMNW GLNDELKKAF PENISKERPL INKNIPNLKW LAGFTSGDGH    180
FGVILAKRRP ASPVQVRLRF MIGQHIKDKN LMNSLITYLG CGRIREKNKS EKSWLEFEVT    240
KFSDINDKII PVFQENTLIG VKLEDFEDWC KVAKLIEEKK HLTESGLDEI KKIKLNMNKG    300
RXX                                                                  303

SEQ ID NO: 11               moltype = AA  length = 303
FEATURE                     Location/Qualifiers
REGION                      1..303
                            note = Synthesized I-OnuI variant PD-1.ile3.exon1_RD1_B1
VARIANT                     1..4
                            note = Any amino acid or absent
VARIANT                     302..303
                            note = Any amino acid or absent
source                      1..303
                            mol_type = protein
                            organism = synthetic construct
SEQUENCE: 11
XXXXSRRESI NPWILTGFAD AEGSFGLSIL NRNRGTARYH TRLSFAIVLH NKDKSILENI     60
QSTWKVGIIT NDGDRYVRLR VTRFEDLKVI IDHFEKYPLV TQKLGDYKLF KQAFSVMENK    120
EHLKENGIKE LVRIKAKMNW GLNDELKKAF PENISKERPL INKNIPNFKW LAGFTSGDGS    180
FFVRLRKSNV NARVRVQLVF EISQHIRDKN LMNSLITYLG CGHIYEGNKS ERSWLQFRVE    240
KFSDINDKII PVFQENTLIG VKLEDFEDWC KVAKLIEEKK HLTESGLDEI KKIKLNMNKG    300
RXX                                                                  303

SEQ ID NO: 12               moltype = AA  length = 303
FEATURE                     Location/Qualifiers
REGION                      1..303
                            note = Synthesized I-OnuI variant PD-1.ile3.exon1_RD2_B1H8
VARIANT                     1..4
                            note = Any amino acid or absent
VARIANT                     302..303
                            note = Any amino acid or absent
source                      1..303
                            mol_type = protein
                            organism = synthetic construct
SEQUENCE: 12
XXXXSRRESI NPWILTGFAD AEGSFGLSIL NRNRGTARYH TRLSFTIVLH NKDKSILENI     60
QSTWKVGIIT NDGDRYVRLC VTRFEDLKVI IDHFEKYPLV TQKLGDYKLF KQAFSVMENK    120
EHLKENGIKE LARIKAKMNW GLNDELKKAF PENIGKERPL INKNIPNFKW LAGFTSGDGS    180
FFVRLRKSNV NARVRVQLVF EISQHIRDKN LMNSLITYLG CGHIYEGNKS ERSWLQFRVE    240
KFSDINDKII PVFQENTLIG VKLEDFEDWC KVAKLIEEKK HLTESGLDEI KKIKLNMNKG    300
RXX                                                                  303

SEQ ID NO: 13               moltype = AA  length = 303
FEATURE                     Location/Qualifiers
REGION                      1..303
                            note = Synthesized I-OnuI variant PD-1.IgV.exon2_RD1_G5
VARIANT                     1..4
                            note = Any amino acid or absent
VARIANT                     302..303
                            note = Any amino acid or absent
source                      1..303
                            mol_type = protein
                            organism = synthetic construct
SEQUENCE: 13
XXXXSRRESI NPWILTGFAD AEGSFQLYIS NVNNNRSRYR ARLRFAIELH NKDKSILENI     60
QSTWKVGVIN NIGDTSVRLS VGRFEDLKVI IDHFEKYPLI TQKLGDYKLF KQAFSVMENK    120
EHLKENGIKE LVRIKAKMNW GLNDELKKAF PENISKERPL INKNIPNLKW LAGFTSGDGN    180
FYVHLKKSGR TTRVYVQLRF SIAQHIRDKN LMNSLITYLG CGYINEWNAS ERSALEFRVT    240
KFSDINDKII PVFQENTLIG VKLEDFEDWC KVAKLIEEKK HLTESGLDEI KKIKLNMNKG    300
RXX                                                                  303

SEQ ID NO: 14               moltype = AA  length = 303
FEATURE                     Location/Qualifiers
REGION                      1..303
                            note = Synthesized I-OnuI variant PD-1.IgV.exon2_RD1_PS3
VARIANT                     1..4
                            note = Any amino acid or absent
VARIANT                     302..303
                            note = Any amino acid or absent
source                      1..303
                            mol_type = protein
                            organism = synthetic construct
SEQUENCE: 14
XXXXSRRESI NPWILTGFAD AEGCFLLHIR NLNRTSTKYR TRLSFEIELH NKDKSILENI     60
QSTWKVGIIN NIGNRRVRLS VRRFEDLKVI IDHFEKYPLI TQKLGDYKLF KQAFSLMENK    120
EHLKENGIKE LVRIKAKMNW GLNDELKKAF PENISKERPL INKNIPNLKW LAGFTSGDGN    180
FYVHLKKSGR TTRVYVQLRF SISQHIRDKN LMNSLITYLG CGYITESNPS ERSDLEFRVT    240
```

```
KFSDINDKII PVFQENTLIG VKLEDFEDWC KVAKLIEEKK HLTESGLDEI KKIKLNMNKG   300
RXX                                                                303

SEQ ID NO: 15            moltype = AA  length = 870
FEATURE                  Location/Qualifiers
REGION                   1..870
                         note = Synthesized megaTAL PD-1.ITSM.ex5_RD1_CV3-08
source                   1..870
                         mol_type = protein
                         organism = synthetic construct
SEQUENCE: 15
MGSAPPKKKR KVVDLRTLGY SQQQQEKIKP KVRSTVAQHH EALVGHGFTH AHIVALSQHP   60
AALGTVAVTY QHIITALPEA THEDIVGVGK QWSGARALEA LLTDAGELRG PPLQLDTGQL  120
VKIAKRGGVT AMEAVHASRN ALTGAPLNLT PDQVVAIASN GGGKQALETV QRLLPVLCQD  180
HGLTPDQVVA IASHDGGKQA LETVQRLLPV LCQDHGLTPD QVVAIASNGG KQALETVQRL  240
LPVLCQDHGL TPDQVVAIAS NNGGKQALET VQRLLPVLCQ DHGLTPDQVV AIASHDGGKQ  300
ALETVQRLLP VLCQDHGLTP DQVVAIASNG GGKQALETVQ RLLPVLCQDH GLTPDQVVAI  360
ASNIGGKQAL ETVQRLLPVL CQDHGLTPDQ VVAIASNNGG KQALETVQRL LPVLCQDHGL  420
TPDQVVAIAS NNGGKQALET VQRLLPVLCQ DHGLTPDQVV AIASNIGGKQ ALETVQRLLP  480
VLCQDHGLTP DQVVAIASNI GGKQALESIV AQLSRPDPAL AALTNDHLVA LACLGGRPAM  540
DAVKKGLPHA PELIRRVNRR IGERTSHRVA ISRSRRESIN PWILTGFADA EGSFQLEIRN  600
VNPNIPRYKT RLRFEIDLHN KDKSILENIQ STWKVGKIYN QGDSYVKLRV TRFEDLKVII  660
DHFEKYPLIT QKLGDYKLFK QAFSVMENKE HLKENGIKEL VRIKAKMNWG LNDELKKAFP  720
ENISKERPLI NKNIPNLKWL AGFTSGEGHF GVILAKRRPA SPVQVRLRFA IGQHIRDKNL  780
MNSLITYLGC GRIREKNISE KSWLEFEVTK FSDINDKIIP VFQENTLIGV KLEDFEDWCK  840
VAKLIEEKKH LTESGLDEIK KIKLNMNKGR                                   870

SEQ ID NO: 16            moltype = AA  length = 870
FEATURE                  Location/Qualifiers
REGION                   1..870
                         note = Synthesized megaTAL PD-1.ITSM.ex5_RD2_73
source                   1..870
                         mol_type = protein
                         organism = synthetic construct
SEQUENCE: 16
MGSAPPKKKR KVVDLRTLGY SQQQQEKIKP KVRSTVAQHH EALVGHGFTH AHIVALSQHP   60
AALGTVAVTY QHIITALPEA THEDIVGVGK QWSGARALEA LLTDAGELRG PPLQLDTGQL  120
VKIAKRGGVT AMEAVHASRN ALTGAPLNLT PDQVVAIASN GGGKQALETV QRLLPVLCQD  180
HGLTPDQVVA IASHDGGKQA LETVQRLLPV LCQDHGLTPD QVVAIASNGG KQALETVQRL  240
LPVLCQDHGL TPDQVVAIAS NNGGKQALET VQRLLPVLCQ DHGLTPDQVV AIASHDGGKQ  300
ALETVQRLLP VLCQDHGLTP DQVVAIASNG GGKQALETVQ RLLPVLCQDH GLTPDQVVAI  360
ASNIGGKQAL ETVQRLLPVL CQDHGLTPDQ VVAIASNNGG KQALETVQRL LPVLCQDHGL  420
TPDQVVAIAS NNGGKQALET VQRLLPVLCQ DHGLTPDQVV AIASNIGGKQ ALETVQRLLP  480
VLCQDHGLTP DQVVAIASNI GGKQALESIV AQLSRPDPAL AALTNDHLVA LACLGGRPAM  540
DAVKKGLPHA PELIRRVNRR IGERTSHRVA ISRSRRESIN PWILTGFADA EGSFQLEIRN  600
VNPNIPRYRT RLRFEIDLHN KDKSILEDIQ STWKVGKIYN RGDSYVKLRV TRFEDLKVII  660
DHFEKYPLIT QKLGDYKLFK QAFSVMENKE HLKENGIKEL VRIKAKMNWG LNDELKKAFP  720
ENISKERPLI NKNIPNLKWL AGFTSGEGHF GVILAKRRPA SPVQVRLRFA IGQHIRDKNL  780
MNSLITYLGC GRTREKNISE KSWLEFEVTK FSDINDKIIP VFQENTLIGV KLEDFEDWCK  840
VAKLIEEKKH LTESGLDEIK KIKLNMNKGR                                   870

SEQ ID NO: 17            moltype = AA  length = 870
FEATURE                  Location/Qualifiers
REGION                   1..870
                         note = Synthesized megaTAL PD-1.ITSM.ex5_RD3_03
source                   1..870
                         mol_type = protein
                         organism = synthetic construct
SEQUENCE: 17
MGSAPPKKKR KVVDLRTLGY SQQQQEKIKP KVRSTVAQHH EALVGHGFTH AHIVALSQHP   60
AALGTVAVTY QHIITALPEA THEDIVGVGK QWSGARALEA LLTDAGELRG PPLQLDTGQL  120
VKIAKRGGVT AMEAVHASRN ALTGAPLNLT PDQVVAIASN GGGKQALETV QRLLPVLCQD  180
HGLTPDQVVA IASHDGGKQA LETVQRLLPV LCQDHGLTPD QVVAIASNGG KQALETVQRL  240
LPVLCQDHGL TPDQVVAIAS NNGGKQALET VQRLLPVLCQ DHGLTPDQVV AIASHDGGKQ  300
ALETVQRLLP VLCQDHGLTP DQVVAIASNG GGKQALETVQ RLLPVLCQDH GLTPDQVVAI  360
ASNIGGKQAL ETVQRLLPVL CQDHGLTPDQ VVAIASNNGG KQALETVQRL LPVLCQDHGL  420
TPDQVVAIAS NNGGKQALET VQRLLPVLCQ DHGLTPDQVV AIASNIGGKQ ALETVQRLLP  480
VLCQDHGLTP DQVVAIASNI GGKQALESIV AQLSRPDPAL AALTNDHLVA LACLGGRPAM  540
DAVKKGLPHA PELIRRVNRR IGERTSHRVA ISRSRRESIN PWILTGFADA EGSFQLEIRN  600
VNPNIPRYRT RLRFEIDLHN KDKSILEDIQ STWKVGKIYN QGDSYVKLRV TRFEDLKVII  660
DHFEKYPLIT QKLGDYKLFK QAFSVMENKE HLKENGIKEL VRIKAKMNWG LNDELKKAFP  720
ENISKERPLI NKNIPNLKWL AGFTSGDGHF GVILAKRRPA SPVQVRLRFA IGQHIRDKNL  780
MNSLITYLGC GRTREKNISE KSWLEFEVTK FSDINDKIIP VFQENTLIGV KLEDFEDWCK  840
VAKLIEEKKH LTESGLDEIK KIKLNMNKGR                                   870

SEQ ID NO: 18            moltype = AA  length = 870
FEATURE                  Location/Qualifiers
REGION                   1..870
                         note = Synthesized megaTAL PD-1.ITSM.ex5_RD4_CV23
```

```
                              source          1..870
                                              mol_type = protein
                                              organism = synthetic construct
                              SEQUENCE: 18
MGSAPPKKKR KVVDLRTLGY SQQQQEKIKP KVRSTVAQHH EALVGHGFTH AHIVALSQHP    60
AALGTVAVTY QHIITALPEA THEDIVGVGK QWSGARALEA LLTDAGELRG PPLQLDTGQL   120
VKIAKRGGVT AMEAVHASRN ALTGAPLNLT PDQVVAIASN GGGKQALETV QRLLPVLCQD   180
HGLTPDQVVA IASHDGGKQA LETVQRLLPV LCQDHGLTPD QVVAIASNGG KQALETVQRL   240
LPVLCQDHGL TPDQVVAIAS NNGGKQALET VQRLLPVLCQ DHGLTPDQVV AIASHDGGKQ   300
ALETVQRLLP VLCQDHGLTP DQVVAIASNG GGKQALETVQ RLLPVLCQDH GLTPDQVVAI   360
ASNIGGKQAL ETVQRLLPVL CQDHGLTPDQ VVAIASNNGG KQALETVQRL LPVLCQDHGL   420
TPDQVVAIAS NNGGKQALET VQRLLPVLCQ DHGLTPDQVV AIASNIGGKQ ALETVQRLLP   480
VLCQDHGLTP DQVVAIASNI GGKQALESIV AQLSRPDPAL AALTNDHLVA LACLGGRPAM   540
DAVKKGLPHA PELIRRVNRR IGERTSHRVA ISRSRRESIN PWILTGFADA EGSFQLEIRN   600
VNPNIPRYRT RLRFEIDLHN KDKSILEDIQ STWKVGKIYN QGDSYVKLRV TRFEDLKVII   660
DHFEKYPLIT QKLGDYKLFK QAFSVMENKE HLKENGIKEL VRIKAKMNWG LNDELKKAFP   720
ENISKERPLI NKNIPNLKWL AGFTSGDGHF GVILAKRRPA SPVQVRLRFA IGQHIRDKNL   780
MNSLITYLGC GRIREKNKSE KSWLEFEVTK FSDINDKIIP VFQENTLIGV KLEDFEDWCK   840
VAKLIEEKKH LTESGLDEIK KIKLNMNKGR                                    870

SEQ ID NO: 19          moltype = AA  length = 870
FEATURE                Location/Qualifiers
REGION                 1..870
                       note = Synthesized megaTAL PD-1.ITSM.ex5_RD5_CV23MK
source                 1..870
                       mol_type = protein
                       organism = synthetic construct
SEQUENCE: 19
MGSAPPKKKR KVVDLRTLGY SQQQQEKIKP KVRSTVAQHH EALVGHGFTH AHIVALSQHP    60
AALGTVAVTY QHIITALPEA THEDIVGVGK QWSGARALEA LLTDAGELRG PPLQLDTGQL   120
VKIAKRGGVT AMEAVHASRN ALTGAPLNLT PDQVVAIASN GGGKQALETV QRLLPVLCQD   180
HGLTPDQVVA IASHDGGKQA LETVQRLLPV LCQDHGLTPD QVVAIASNGG KQALETVQRL   240
LPVLCQDHGL TPDQVVAIAS NNGGKQALET VQRLLPVLCQ DHGLTPDQVV AIASHDGGKQ   300
ALETVQRLLP VLCQDHGLTP DQVVAIASNG GGKQALETVQ RLLPVLCQDH GLTPDQVVAI   360
ASNIGGKQAL ETVQRLLPVL CQDHGLTPDQ VVAIASNNGG KQALETVQRL LPVLCQDHGL   420
TPDQVVAIAS NNGGKQALET VQRLLPVLCQ DHGLTPDQVV AIASNIGGKQ ALETVQRLLP   480
VLCQDHGLTP DQVVAIASNI GGKQALESIV AQLSRPDPAL AALTNDHLVA LACLGGRPAM   540
DAVKKGLPHA PELIRRVNRR IGERTSHRVA ISRSRRESIN PWILTGFADA EGSFQLEIRN   600
VNPNIPRYRT RLRFEIDLHN KDKSILEDIQ STWKVGKIYN QGDSYVKLRV TRFEDLKVII   660
DHFEKYPLIT QKLGDYKLFK QAFSVMENKE HLKENGIKEL VRIKAKMNWG LNDELKKAFP   720
ENISKERPLI NKNIPNLKWL AGFTSGDGHF GVILAKRRPA SPVQVRLRFM IGQHIKDKNL   780
MNSLITYLGC GRIREKNKSE KSWLEFEVTK FSDINDKIIP VFQENTLIGV KLEDFEDWCK   840
VAKLIEEKKH LTESGLDEIK KIKLNMNKGR                                    870

SEQ ID NO: 20          moltype = AA  length = 841
FEATURE                Location/Qualifiers
REGION                 1..841
                       note = Synthesized megaTAL PD-1.ile3.exon1_RD1 B1
source                 1..841
                       mol_type = protein
                       organism = synthetic construct
SEQUENCE: 20
MGSAPPKKKR KVVDLRTLGY SQQQQEKIKP KVRSTVAQHH EALVGHGFTH AHIVALSQHP    60
AALGTVAVTY QHIITALPEA THEDIVGVGK QWSGARALEA LLTDAGELRG PPLQLDTGQL   120
VKIAKRGGVT AMEAVHASRN ALTGAPLNLT PDQVVAIASN NGGKQALETV QRLLPVLCQD   180
HGLTPDQVVA IASNNGGKQA LETVQRLLPV LCQDHGLTPD QVVAIASNGG GKQALETVQR   240
LLPVLCQDHG LTPDQVVAIA SNNGGKQALE TVQRLLPVLC QDHGLTPDQV VAIASNNGGK   300
QALETVQRLL PVLCQDHGLT PDQVVAIASN NGGKQALETV QRLLPVLCQD HGLTPDQVVA   360
IASNNGGKQA LETVQRLLPV LCQDHGLTPD QVVAIASHDG GKQALETVQR LLPVLCQDHG   420
LTPDQVVAIA SNGGGKQALE TVQRLLPVLC QDHGLTPDQV VAIASNNGGK QALESIVAQL   480
SRPDPALAAL TNDHLVALAC LGGRPAMDAV KKGLPHAPEL IRRVNRRIGE RTSHRVAISR   540
VGGSSRRESI NPWILTGFAD AEGSFGLSIL NRNRGTARYH TRLSFAIVLH NKDKSILENI   600
QSTWKVGIIT NDGDRYVRLR VTRFEDLKVI IDHFEKYPLF TQKLGDYKLF KQAFSVMENK   660
EHLKENGIKE LVRIKAKMNW GLNDELKKAF PENISKERPL INKNIPNFKW LAGFTSGDGS   720
FFVRLRKSNV NARVRVQLVF EISQHIRDKN LMNSLITYLG CGHIYEGNKS ERSWLQFRVE   780
KFSDINDKII PVFQENTLIG VKLEDFEDWC KVAKLIEEKK HLTESGLDEI KKIKLNMNKG   840
R                                                                   841

SEQ ID NO: 21          moltype = AA  length = 841
FEATURE                Location/Qualifiers
REGION                 1..841
                       note = Synthesized megaTAL PD-1.ile3.exon1_RD2_B1H8
source                 1..841
                       mol_type = protein
                       organism = synthetic construct
SEQUENCE: 21
MGSAPPKKKR KVVDLRTLGY SQQQQEKIKP KVRSTVAQHH EALVGHGFTH AHIVALSQHP    60
AALGTVAVTY QHIITALPEA THEDIVGVGK QWSGARALEA LLTDAGELRG PPLQLDTGQL   120
VKIAKRGGVT AMEAVHASRN ALTGAPLNLT PDQVVAIASN NGGKQALETV QRLLPVLCQD   180
```

```
HGLTPDQVVA IASNNGGKQA LETVQRLLPV LCQDHGLTPD QVVAIASNGG KQALETVQR    240
LLPVLCQDHG LTPDQVVAIA SNNGGKQALE TVQRLLPVLC QDHGLTPDQV VAIASNNGGK   300
QALETVQRLL PVLCQDHGLT PDQVVAIASN NGGKQALETV QRLLPVLCQD HGLTPDQVVA   360
IASNNGGKQA LETVQRLLPV LCQDHGLTPD QVVAIASHDG GKQALETVQR LLPVLCQDHG   420
LTPDQVVAIA SNGGGKQALE TVQRLLPVLC QDHGLTPDQV VAIASNNGGK QALESIVAQL   480
SRPDPALAAL TNDHLVALAC LGGRPAMDAV KKGLPHAPEL IRRVNRRIGE RTSHRVAISR   540
VGGSSRRESI NPWILTGFAD AEGSFGLSIL NRNRGTARYH TRLSFTIVLH NKDKSILENI   600
QSTWKVGIIT NDGDRYVRLC VTRFEDLKVI IDHFEKYPLV TQKLGDYKLF KQAFSVMENK   660
EHLKENGIKE LARIKAKMNW GLNDELKKAF PENIGKERPL INKNIPNFKW LAGFTSGDGS   720
FFVRLRKSNV NARVRVQLVF EISQHIRDKN LMNSLITYLG CGHIYEGNKS ERSWLQFRVE   780
KFSDINDKII PVFQENTLIG VKLEDFEDWC KVAKLIEEKK HLTESGLDEI KKIKLNMNKG   840
R                                                                 841

SEQ ID NO: 22           moltype = AA  length = 909
FEATURE                 Location/Qualifiers
REGION                  1..909
                        note = Synthesized megaTAL PD-1.IgV.exon2_RD1_G5
source                  1..909
                        mol_type = protein
                        organism = synthetic construct
SEQUENCE: 22
MGSAPPKKKR KVVDLRTLGY SQQQQEKIKP KVRSTVAQHH EALVGHGFTH AHIVALSQHP    60
AALGTVAVTY QHIITALPEA THEDIVGVGK QWSGARALEA LLTDAGELRG PPLQLDTGQL   120
VKIAKRGGVT AMEAVHASRN ALTGAPLNLT PDQVVAIASN NGGKQALETV QRLLPVLCQD   180
HGLTPDQVVA IASNGGGKQA LETVQRLLPV LCQDHGLTPD QVVAIASHDG GKQALETVQR   240
LLPVLCQDHG LTPDQVVAIA SNIGGKQALE TVQRLLPVLC QDHGLTPDQV VAIASHDGGK   300
QALETVQRLL PVLCQDHGLT PDQVVAIASN IGGKQALETV QRLLPVLCQD HGLTPDQVVA   360
IASHDGGKQA LETVQRLLPV LCQDHGLTPD QVVAIASNIG GKQALETVQR LLPVLCQDHG   420
LTPDQVVAIA SNIGGKQALE TVQRLLPVLC QDHGLTPDQV VAIASHDGGK QALETVQRLL   480
PVLCQDHGLT PDQVVAIASN GGGKQALETV QRLLPVLCQD HGLTPDQVVA IASNNGGKQA   540
LESIVAQLSR PDPALAALTN DHLVALACLG GRPAMDAVKK GLPHAPELIR RVNRRIGERT   600
SHRVAISRVG GSSRRESINP WILTGFADAE GSFQLYISNV NNNRSRYRAR LRFAIELHNK   660
DKSILENIQS TWKVGIINNI GDTSVRLSVG RFEDLKVIID HFEKYPLITQ KLGDYKLFKQ   720
AFSVMENKEH LKENGIKELV RIKAKMNWGL NDELKKAFPE NISKERPLIN KNIPNLKWLA   780
GFTSGDGNFY VHLKKSGRTT RVYVQLRFSI AQHIRDKNLM NSLITYLGCG YINEWNASER   840
SALEFRVTKF SDINDKIIPV FQENTLIGVK LEDFEDWCKV AKLIEEKKHL TESGLDEIKK   900
IKLNMNKGR                                                          909

SEQ ID NO: 23           moltype = AA  length = 909
FEATURE                 Location/Qualifiers
REGION                  1..909
                        note = Synthesized megaTAL PD-1.IgV.exon2_RD1_PS3
source                  1..909
                        mol_type = protein
                        organism = synthetic construct
SEQUENCE: 23
MGSAPPKKKR KVVDLRTLGY SQQQQEKIKP KVRSTVAQHH EALVGHGFTH AHIVALSQHP    60
AALGTVAVTY QHIITALPEA THEDIVGVGK QWSGARALEA LLTDAGELRG PPLQLDTGQL   120
VKIAKRGGVT AMEAVHASRN ALTGAPLNLT PDQVVAIASN NGGKQALETV QRLLPVLCQD   180
HGLTPDQVVA IASNGGGKQA LETVQRLLPV LCQDHGLTPD QVVAIASHDG GKQALETVQR   240
LLPVLCQDHG LTPDQVVAIA SNIGGKQALE TVQRLLPVLC QDHGLTPDQV VAIASHDGGK   300
QALETVQRLL PVLCQDHGLT PDQVVAIASN IGGKQALETV QRLLPVLCQD HGLTPDQVVA   360
IASHDGGKQA LETVQRLLPV LCQDHGLTPD QVVAIASNIG GKQALETVQR LLPVLCQDHG   420
LTPDQVVAIA SNIGGKQALE TVQRLLPVLC QDHGLTPDQV VAIASHDGGK QALETVQRLL   480
PVLCQDHGLT PDQVVAIASN GGGKQALETV QRLLPVLCQD HGLTPDQVVA IASNNGGKQA   540
LESIVAQLSR PDPALAALTN DHLVALACLG GRPAMDAVKK GLPHAPELIR RVNRRIGERT   600
SHRVAISRVG GSSRRESINP WILTGFADAE GCFLLHIRNL NRTSTKYRTR LSFEIELHNK   660
DKSILENIQS TWKVGIINNI GNRRVRLSVR RFEDLKVIID HFEKYPLITQ KLGDYKLFKQ   720
AFSVMENKEH LKENGIKELV RIKAKMNWGL NDELKKAFPE NISKERPLIN KNIPNLKWLA   780
GFTSGDGNFY VHLKKSGRTT RVYVQLRFSI SQHIRDKNLM NSLITYLGCG YITESNPSER   840
SDLEFRVTKF SDINDKIIPV FQENTLIGVK LEDFEDWCKV AKLIEEKKHL TESGLDEIKK   900
IKLNMNKGR                                                          909

SEQ ID NO: 24           moltype = AA  length = 236
FEATURE                 Location/Qualifiers
source                  1..236
                        mol_type = protein
                        organism = Mus musculus
SEQUENCE: 24
MSEPPRAETF VFLDLEATGL PNMDPEIAEI SLFAVHRSSL ENPERDDSGS LVLPRVLDKL    60
TLCMCPERPF TAKASEITGL SSESLMHCGK AGFNGAVVRT LQGFLSRQEG PICLVAHNGF   120
DYDFPLLCTG LQRLGAHLPQ DTVCLDTLPA LRGLDRAHSH GTRAQGRKSY SLASLFHRYF   180
QAEPSAAHSA EGDVHTLLLI FLHRAPELLA WADEQARSWA HIEPMYVPPD GPSLEA       236

SEQ ID NO: 25           moltype = DNA  length = 22
FEATURE                 Location/Qualifiers
source                  1..22
                        mol_type = genomic DNA
                        organism = Homo sapiens
```

-continued

```
SEQUENCE: 25
aatggtggca tactccgtct gc                                                  22

SEQ ID NO: 26           moltype = DNA   length = 11
FEATURE                 Location/Qualifiers
source                  1..11
                        mol_type = genomic DNA
                        organism = Homo sapiens
SEQUENCE: 26
tccgctagga a                                                              11

SEQ ID NO: 27           moltype = DNA   length = 37
FEATURE                 Location/Qualifiers
source                  1..37
                        mol_type = genomic DNA
                        organism = Homo sapiens
SEQUENCE: 27
tccgctagga aagacaatgg tggcatactc cgtctgc                                  37

SEQ ID NO: 28           moltype = DNA   length = 22
FEATURE                 Location/Qualifiers
source                  1..22
                        mol_type = genomic DNA
                        organism = Homo sapiens
SEQUENCE: 28
aatggtggca tacaaccttt ta                                                  22

SEQ ID NO: 29           moltype = DNA   length = 22
FEATURE                 Location/Qualifiers
source                  1..22
                        mol_type = genomic DNA
                        organism = Homo sapiens
SEQUENCE: 29
tttccactta tactccgtct gc                                                  22

SEQ ID NO: 30           moltype = DNA   length = 22
FEATURE                 Location/Qualifiers
source                  1..22
                        mol_type = genomic DNA
                        organism = Homo sapiens
SEQUENCE: 30
ggcatgcaga tcccacaggc gc                                                  22

SEQ ID NO: 31           moltype = DNA   length = 14
FEATURE                 Location/Qualifiers
source                  1..14
                        mol_type = genomic DNA
                        organism = Homo sapiens
SEQUENCE: 31
ggtggggctg ctcc                                                           14

SEQ ID NO: 32           moltype = DNA   length = 37
FEATURE                 Location/Qualifiers
source                  1..37
                        mol_type = genomic DNA
                        organism = Homo sapiens
SEQUENCE: 32
ggtggggctg ctccaggcat gcagatccca caggcgc                                  37

SEQ ID NO: 33           moltype = DNA   length = 22
FEATURE                 Location/Qualifiers
source                  1..22
                        mol_type = genomic DNA
                        organism = Homo sapiens
SEQUENCE: 33
ggcatgcaga tccaacccttt ta                                                 22

SEQ ID NO: 34           moltype = DNA   length = 22
FEATURE                 Location/Qualifiers
source                  1..22
                        mol_type = genomic DNA
                        organism = Homo sapiens
SEQUENCE: 34
tttccactta tcccacaggc gc                                                  22

SEQ ID NO: 35           moltype = DNA   length = 22
FEATURE                 Location/Qualifiers
source                  1..22
                        mol_type = genomic DNA
```

```
                        organism = Homo sapiens
SEQUENCE: 35
acgggcgtga cttccacatg ag                                              22

SEQ ID NO: 36           moltype = DNA  length = 12
FEATURE                 Location/Qualifiers
source                  1..12
                        mol_type = genomic DNA
                        organism = Homo sapiens
SEQUENCE: 36
gtcacacaac tg                                                         12

SEQ ID NO: 37           moltype = DNA  length = 38
FEATURE                 Location/Qualifiers
source                  1..38
                        mol_type = genomic DNA
                        organism = Homo sapiens
SEQUENCE: 37
gtcacacaac tgcccaacgg gcgtgacttc cacatgag                             38

SEQ ID NO: 38           moltype = DNA  length = 22
FEATURE                 Location/Qualifiers
source                  1..22
                        mol_type = genomic DNA
                        organism = Homo sapiens
SEQUENCE: 38
acgggcgtga cttaaccttt ta                                              22

SEQ ID NO: 39           moltype = DNA  length = 22
FEATURE                 Location/Qualifiers
source                  1..22
                        mol_type = genomic DNA
                        organism = Homo sapiens
SEQUENCE: 39
tttccactta cttccacatg ag                                              22

SEQ ID NO: 40           moltype = RNA  length = 2650
FEATURE                 Location/Qualifiers
misc_feature            1..2650
                        note = Synthesized PD-1 Exon5 RD5_CV23MK megaTAL mRNA
source                  1..2650
                        mol_type = other RNA
                        organism = synthetic construct
SEQUENCE: 40
atgggatccg cccccccaa  gaagaagcgc aaggtggtgg acctgagaac cctgggtac    60
agccagcagc aacaggagaa gatcaaaccg aaggtgcgca gcacggtggc ccagcaccat   120
gaagccctcg tgggtcatgg attcacgcac gcccacatcg tggccctgtc gcagcatccg   180
gccgccctgg gcaccgtggc ggtgacctac cagcacatca tcaccgccct gcccgaagcc   240
acccacgagg acatcgtggg agtgggcaag cagtggtccg agcacgcgc  cctggaggcc   300
ctgctgaccg acgccgggga actgcgcggc ccgcctctgc agctggatac cggccaactg   360
gtcaagatcg ccaagagagg cggagtgacc gcgatgaagg ccgtccacgc ctcccggaac   420
gctctgaccg gtgcccgct  caatctgact ccggaccagg tggtggctat cgccagcaac   480
ggaggaggaa aacaggccct cgaaacagtg cagaggctgc tgcctgtcct ttgtcaagat   540
cacgggctga ctcccgacca ggtcgtggcc attgccagcc acgacggcgg caagcaggct   600
ttggagactg tgcagcggct cctgccagtg ctgtgcaag  atcacgtct  gaccccagat   660
caggtcgtcg ccattgcttc aacggaggc  aaacaagcgc tggaaacggt ccaacgcctg   720
ctgccggtgc tttgtcagga tcacggcctg accctgatc  aggtggtggc catcgcgtcc   780
aataacgggg gaagcaggc  actcgagact gtccagaggc cctgcctgt  gctctgccag   840
gaccacgggc tcacacccga tcaggtcgtc gctatcgcgt cgcacgacgg tggaaagcag   900
gccctggaaa ccgtgcagcg cctgttgccg gtgctgtgtc aggaccatgg ccttactccg   960
gatcaggtcg tcgcgatcgc atctaatggt ggaggaaagc aggccctgga cacagtccag  1020
cgcctgctcc cggtgttgtg ccaagaccat ggtcttaccc ctgaccaggt ggtcgctatt  1080
gcctcgaaca tcggcggaaa gcaagccctg gaaaccgtgc agcgacttct gccggtcctg  1140
tgccaggatc atgaaatgac cccagaccag gtggtggcaa ttgccagcaa caacggcggg  1200
aagcaagcgt tggaaccgt  ccagagactg cttcctgtgc tgtgccaaga ccacggtttg  1260
accccgacc  aagtcgtcgc catcgcttcc aacaacggag ggaagcaggc actcgaaact  1320
gtgcaacggt tgctgcccgt gctctgtcag gatcacggac tcacccctga tcaggtggtg  1380
gccatcgcaa gcaacatcgg tggcaaacag gctctgcaaa ctgtccaaag actgctgccc  1440
gtgctttgcc aggaccacgg actgactcct gaccaagtgg tggcaattgc ctccaactc  1500
ggaggcaagc aagcgctcga atccatcgtg gcgcagctca gccggccaga ccccgccctg  1560
gccgccctga ctaacgatca cctggtggcc ctggcgtgcc tcggcggtcg ccccgctatg  1620
gacgcggtga gaaggggct  gccccacgcc cccgagctca ttcggcgggt gaaccgccgg  1680
atcggagaaa gaacctccca tcgggtggcc atctcgagat cacggcggga atccattaac  1740
ccctgatcc  tgactggctt tgccgacgcc gagggatcc  tccactgga  aatccggaac  1800
gtgaacccaa acatccccg  gtatcgcacc agactgcggt tcgagatcga ccttcacaac  1860
aaggacaagt ccattctgga ggacatccag tcaacctgga aagtgggaaa gatctacaac  1920
caggggggac tatacgtgaa gctgcgggtg accgcttcg  aagatctcaa agtgatcatc  1980
gaccatttcg agagtaccc  cctgatcact cagaagcttg agactacaa  actgttcaag  2040
caggcattct ccgtgatgga gaacaaggag cacctgaagg agaacgggat taaggagctg  2100
```

```
gtgcgaatta aggcgaaaat gaactgggga ttgaacgatg agctgaagaa ggcgttccg    2160
gaaaacattt ccaaggagcg cccgctcatc aacaagaaca tccctaatct gaagtggctc  2220
gcggggttta cctctggcga cggccatttc ggagtgattc tcgcaaagcg caggcccgcc  2280
agccctgtgc aagtgcggct gcggttcatg atcggccagc acattaagga caagaacctg  2340
atgaactcgc tcatcaccta ccttggatgc ggccgcatgc gcgaaaagaa caagagcgag  2400
aagtcctggc tggaatttga agtgaccaag ttcagcgaca tcaacgacaa gatcattccg  2460
gtgttccagg aaaacaccct gattggcgtg aagctggagg acttcgagga ttggtgcaag  2520
gtggccaagc tcatcgaaga aaagaagcac ctgactgaat ccggcttgga cgagatcaag  2580
aagattaagc tgaatatgaa caaggaagg  tgatagcgcg ctagccgtac ggaaaaaaaa  2640
aaaaaaaaa                                                         2650

SEQ ID NO: 41         moltype = RNA  length = 2526
FEATURE               Location/Qualifiers
misc_feature          1..2526
                      note = Synthesized PD-1 Exon1 RD2_B1H8 megaTAL mRNA
source                1..2526
                      mol_type = other RNA
                      organism = synthetic construct
SEQUENCE: 41
atgggaagcg ccccgccgaa gaagaagcgc aaggtggtgg atctgagaac cctgggatac  60
agccagcagc agcaggagaa gatcaagccg aaggtccggt ctaccgtggc ccagcaccat  120
gaggcccttg tgggccacgg cttcacacat gcacacatcg tcgccctgtc gcagcatccc  180
gccgccctgg ggaccgtggc cgtgacctat caacacatca ttaccgccct gccggaggcc  240
acccacgagg acatcgtggg tgtggggaag cagtggagcg gagccagggc actcgaagcc  300
ctcctcactg acgctggaga actgcgcgga ccgcctctcc agctggacac cggacagctg  360
gtgaaaatcg ccaagcgggg aggagtgacc gccatggaag tcgcacgc ctcgaggaac   420
gcgctgactg gcgcccctct gaacctgacc cctgatcagg tcgtggctat cgcctcaaac  480
aacgggggta agcaggcgct ggagacagtg caacgacttc tgccagtgct ttgtcaggac  540
catggtctga cccccgacca ggtcgtcgcc attgcatcca acaatggtgg caagcaggca  600
ctggagactg tccagaggct gctcccggtg ctgtgccaga accacgggct caccccgccc  660
caagtggtcg ccatcgcctc caacggagga ggaaaacaag ctctggagac tgtgcaacgc  720
ctgctgcctg tgttgtgcca agaccacgga ctgacgcccg atcaggtggt ggcgatcgca  780
tcgaacaacg gaggaaagca agcgctgaaa accgtcagc gcctcctgcc cgtcctctgc  840
caggatcacg gcctgactcc ggaccaggtg gtcgcgatcg ccagcaataa cggggggaag  900
caagccctcg agactgtgca gcggttgctg cccgtgctct gccaagatca tggccttacc  960
ccagaccaag tcgtggccat tgcttccaac aacggtggca acaggcgct  cgaaaccgtc  1020
cagcggctgt tgcccgtgct tgccaggat cacggactca cccctgatca ggtggtggca  1080
attgcgtcca caaacggtgg aaagcaggcc ctggaaacgg tgcagcggct gcttccggtc  1140
ctgtgtcagg atcatgggct gactcccgac caggtcgtgc ccattgcatc ccacgatggg  1200
ggtaaacagg ccctcgaaac agtgcagaga ctcctgccag tcctgtgcca agaccacgga  1260
cttaccccgg atcaggtggt ggccatagcc tcgaacggcg gcgggaaaca ggctctggaa  1320
actgtgcaaa gactcctccc ggtgttgtgt caagaccatg gactgacccc agatcaggtg  1380
gtggctattg cctctaacaa cggcggcaag caagcactcg agcccagttg  1440
tcacgccccg accccgcact ggctgccctg acgaatgacc atctggtggc gctggcctgc  1500
ctgggaggga ggccagcgat ggatgcgtg aagaagggac tgcccccatgc tccggagctg  1560
attcggagag tgaataggcg catcggagag agaacttcac atcgggtggc catttctaga  1620
gtgggcggca gctcccggcg cgagtccatt aaccctgga tcctgaccgg ctttgccgac  1680
gccgaagggt ccttcggcct ctcgatcctg aaccggaacc ggggtaccgc tcggtaccac  1740
accagactgt ccttcaccat cgtgctgcac aacaaggaca agagcatcct gaaaacatt   1800
cagtcaacgt ggaaggtggg aattattact aacgacggcg acagatacgt gcgcctgtgc  1860
gtgaccggt ttgaggacct gaaggtcatt atcgaccact tcgagaagta ccccccagttg 1920
actcagaagc tgggagacta caagctgttc aagcaggcgt tctcggtgat ggaaaacaag  1980
gagcacctga aggagaacgg catcaaggag ctcgccgga tcaaggccaa gatgaactgg  2040
ggcctgaatg atgaactcaa gaaggcgttc cctgaaaaca tcggtaaaga acggcccctg  2100
atcaacaaga acatcccgaa cttcaagtgg cttgccgat tcacctccgg cgacggatcc  2160
ttcttcgtcc ggctgcgcaa gtccaacgtg aacgcgagag tgcgggtgca attggtcttt  2220
gaaatctcac agcacatcag ggacaagaat ttgatgaact ccctcatcac ctacctgggt  2280
tgcggacaca tctacgaagg caataagtcg gagcggagct ggctgcagtt cgcgtggaa   2340
aagttctccg acattaacga caagatcatc ccagtgttcc aggaaaacac tctgattggc  2400
gtgaagcttg aggatttcga ggactggtgc aaggtggcca agctgattga agagaagaag  2460
cacctgaccg agtccggcct ggacgaaatc aagaaaatca agctgaacat gaacaaggga  2520
cggtga                                                            2526

SEQ ID NO: 42         moltype = RNA  length = 2730
FEATURE               Location/Qualifiers
misc_feature          1..2730
                      note = Synthesized PD-1 Exon2 RD1_G5 megaTAL mRNA
source                1..2730
                      mol_type = other RNA
                      organism = synthetic construct
SEQUENCE: 42
atgggaagcg cccctccgaa gaagaagcgc aaggtcgtgg acctcagaac cctgggttac  60
tcccagcagc agcaggagaa aattaagccg aaggtgcgct ccaccgtggc tcaacaccac  120
gaggcccttg tgggccatgg attcactcac gcccatatcg tggccctgtc ccagcaccg   180
gccgccctgg gcaccgtggc ggtgacctac cagcacatca tcaccgcgct gcctgaagcc  240
acccacgagg acatcgtcgg tgtgggtaag cagtggtccg gagccagagc cctgaggct   300
ctgctgaccg acgccggaga actcagaggc cgcctctgc agctggacac cggacagctg  360
gtgaagatag ccaagagagg cggcgtgacc gccatggaag tcgcacgcc gtcatgc     420
gcactgaccg ggggcccccct gaacctgact ccagaccaag tggtggctat cgccagcaac  480
```

```
aatggaggaa agcaagcctt ggaaaccgtg cagcggctgc tcccggtcct ttgccaagac    540
cacggcctga cacccgatca ggtggtggca atcgcatcga atggcggcgg gaagcaggcc    600
ctcgagactg tgcagaggct cctgcctgtg ctgtgccagg accatgggct gaccccagac    660
caggtggtcg caatcgcctc gcacgacgga ggcaagcaag ccctgaaaac tgtccagcgc    720
ctgctccctg tcctgtgtca agatcatggg ctcactcctg atcaggtcgt cgccatcgcc    780
tcgaacattg gtggcaagca ggcgctcgaa accgtccagc ggttgctgcc agtgctttgc    840
caggaccatg gtctgacccc cgatcaagtg gtcgcgattg cctcacacga tggcggtaag    900
caggctttgg aaaccgtgca acggctgttg cctgtcctct gccaggacca cggcttgact    960
cccgaccagg tggtggccat agcctcaaac atcggaggga aacaagccct cgaaaccgtc   1020
cagaggctgc tgccggtgtt gtgccaggat cacggattga ccccagacca ggtggtcgcc   1080
attgcttccc acgatggggg aaagcaggcc ctggagactg tgcagcgcct ccttcccgtc   1140
ctgtgtcagg atcatggact taccccccgac caagtcgtgg cgattgcttc caatatcgga   1200
ggcaaacagg cccttgaaac agtgcagcgc ctgttgccgg tgctctgcca agatcacgga   1260
ctgaccccctg accaggtggt ggcgatcgcg tcaaatatcg gcggcaagca ggcactggag   1320
acagtccaga gactcctgcc ggtcctctgc caggaccacg gtcttactcc tgaccaagtg   1380
gtggctatcg catcccatga tggtgggaaa caggctcttg aaactgtgca acgcctgctg   1440
cccgtgctgt gccaagacca cggactgact ccggaccagg tcgtgccat cgcttcaaac   1500
ggaggggaa aacaggcact tgaaacggtg cagagactgc tgcctgtcct ttgtcaggac   1560
cacgggttga ccccgacca ggtcgtggct attgcctcga caacggggg gaagcaagcc   1620
ctcgagtcca ttgtgcccca gctcgagccg cctgatcccg cactggccgc gctgaccaac   1680
gatcacctg tggccctcgc ctgtctggc ggacggccgg ccatgacgc cgtgaagaag   1740
ggactgccgc acgcgccga gctgatccgc cgcgtgaaca ggcggattgg agaacgcacc   1800
tcccaccggg tggccatctc gagagtggga ggatcctcta gacggagtc cattaacccg   1860
tggatcctga ctggattcgc cgacgccgag gggtccttcc agctgtacat ctccaacgtg   1920
aacaacaacc gcagcagata cagggcccgg ctgcggttcg cgatcgaact gcacaataag   1980
gacaagacca tcctcgagaa cattcagtcc acttggaagg tgggcgtgat taacaacatc   2040
ggcgatacca gcgtgcggct ctccgtgggg cggttcgaag atctcaaggt gatcatcgac   2100
cacttcgaga agtaccgct gatcacccag aagctgggag actacaagct gttcaagcaa   2160
gctttcagcg tgatgaaaa caaggaacat ctgaaagaga acggtatcaa ggaactggtg   2220
cggattaagg ccaagatgaa ctggggtctg aacgatgaac tgaagaaggc gttcccggag   2280
aatatcagca aggagcgccc cctgattaac aaaaacatcc caaacctcaa gtggctcgcc   2340
ggctttactt ccggagatgg taacttctac gtgcacctga agaagtccgg aagaaccacc   2400
cgggtctacg tgcagctgag gttctccatc gcccagcaca tccgggacaa gaacttgatg   2460
aactccctga tcacctacct cggttgcgga tacatcaacg aatggaagc cagcgagaga   2520
tcggcccctgg agttcagggt gactaagttc tccgacatca acgacaagat tatccccgtg   2580
tttcaggaaa ataccctcat cggcgtgaag ctggaggact ttgaggactg gtgcaaggtg   2640
gccaagctga tcgaggaaaa gaaacatctg accgagagcg gcctggacga aatcaagaag   2700
attaagctga acatgaacaa gggacgatga                                    2730

SEQ ID NO: 43         moltype = RNA  length = 711
FEATURE               Location/Qualifiers
source                1..711
                      mol_type = mRNA
                      organism = Mus musculus
SEQUENCE: 43
atgtctgagc cacctcgggc tgagacctttt gtattcctgg acctagaagc cactgggctc     60
ccaaacatgg accctgagat tgcagagata tccctttttg ctgttcaccg ctcttccctg    120
gagaacccag aacgggatga ttctggttcc ttggtgctgc cccgtgttct ggacaagctc    180
acactgtgca tgtgcccgga gcgccccttt actgccaagg ccagtgagat tactggtttg    240
agcagcgaaa gcctgatgca ctgcgggaag gctggtttca atggcgctgt ggtaaggaca    300
ctgcaggggct tcctaagccg ccaggagggc cccatctgcc ttgtggccca caatggcttc    360
gattatgact tcccactgct gtgcacgggg ctacaacgtc tgggtgccca tctgccccaa    420
gacactgtct gcctggacac actgcctgca ttgcgggggcc tggaccgtgc tcacagccac    480
ggcaccaggg ctcaaggccg caaaagctac agcctggcca gtctcttcca ccgctacttc    540
caggctgaac ccagtgctgc ccattcagca gaaggtactg gcacacccct gcttctgatc    600
ttcctgcatc gtgctcctga gctgctcgca tgggcagatg agcaggcccg cagctgggct    660
catattgagc ccatgtacgt gccacctgat ggtccaagcc tcgaagcctg a             711

SEQ ID NO: 44         moltype = DNA  length = 7601
FEATURE               Location/Qualifiers
misc_feature          1..7601
                      note = Synthesized rAAV PD-1 Exon5_MND-BFP construct
source                1..7601
                      mol_type = other DNA
                      organism = synthetic construct
SEQUENCE: 44
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac gtagaattca    180
gtccagggct ctgtcctgca cctgggaat ggtgaccggc atctctgtcc tctagctctg    240
gaagcacccc agccctcta gtctgccctc acccctgacc ctgaccctcc acctgaccc     300
cgtcctaacc cctgaccttt gtgccttcc agagagaagg gcagaagtgc ccacagccca    360
ccccagcccc tcacccaggc cagccggcca gttccaaacc ctggtggttg gtgtcgtggg    420
cggcctgctg ggcagcctgg tgctgctagt ctgggtccgc cgtcatct gctcccgggc    480
cgcacgaggt aacgtcatcc cagccctcg gcctgccctg cctaaccct ctgggcggc    540
ctcactcccg cctccccttc ctccaccctt ccctcacccc accccacctc ccccatctc    600
cccgccaggc taagtccctg atgaaggccc ctggactaag accccccacc taggagcacg    660
gctcagggtc ggcctggtga ccccaagtgt gtttctctgc agggacaata ggagccaggc    720
gcaccggcca gcccctggtg agtctcactc ttttcctgca tgatccactg tgccttcctt    780
```

```
cctgggtggg cagaggtgga aggacaggct gggaccacac ggcctgcagg actcacattc    840
tattatagcc aggaccccac ctccccagcc cccaggcagc aacctcaatc cctaaagcca    900
tgatctgggg ccccagccca cctgcggtct cggggggtgc ccggcccatg tgtgtgcctg    960
cctgcggtct ccaggggtgc ctggcccacg cgtgtgcccg cctgcggtct ctggggtgc    1020
ccggcccaca tatgtgcctg cctgcggtct ccaggtgtgc cagcccatg cgtgtgccca    1080
cctgcgaggg cgtggggtgg gcttggtcat ttcttatctt acattggaga caggagagct    1140
tgaaaagtca cattttggaa tcctaaatct gcaagaatgc cagggacatt tcagaggggg    1200
acattgagcc agagaggagg ggtggtgtcc ccagatcaca cagagggcag tggtgggaca    1260
gctcagggta agcagctcat agtgggggc ccaggttcgg tgccggtact gcagccaggc    1320
tgtggagccg cgggcctcct tcctgcggtg ggccgtcggg ctgactccct ctccctttct    1380
cctcaaagaa ggaggacccc tcagccgtgc ctgtgttctc tgtggactat ggggagctgg    1440
atttccagtg gcgagagaag accccggagc ccccgtgcc ctgtgtccct gagcagacgg    1500
agtaatgcat gaacagagaa acaggagaat atgggccaaa caggatatct gtggtaagca    1560
gttcctgccc cggctcaggg ccaagaacag ttggaacagc agaatatggg ccaaacagga    1620
tatctgtggt aagcagttcc tgccccggct cagggccaag aacagatggt ccccagatgc    1680
ggtcccgccc tcagcagttt ctagagaacc atcagatgtt tccagggtgc cccaaggacc    1740
tgaaatgacc ctgtgcctta tttgaactaa ccaatcagtt cgcttctcgc ttctgttcgc    1800
gcgcttctgc tccccgagct ctatataagc agagctcgtt tagtgaaccg tcagatcgcc    1860
tggagacgcc atccacgctg ttttgacttc catagaagga tctcgaggcc accatggcta    1920
gcgagctgat taaggagaac atgcacatga agctgtacat ggagggcacc gtggacaacc    1980
atcacttcaa gtgcacatcc gagggcgaag gcaagccta cgagggcacc cagaccatga    2040
gaatcaaggt ggtcgagggc ggccctctcc ccttcgcctt cgacatcctg gctactagct    2100
tcctctacgg cagcaagacc ttcatcaacc acacccaggg catccccgac ttcttcaagc    2160
agtccttccc tgagggcttc acatgggaga gagtcaccac atacgaggac ggggggcgtgc   2220
tgaccgctac ccaggacacc agcctccagg acggctgcct catctacaac gtcaagatca    2280
gagggtgaa cttcacatcc aaacgccctg tgatgcagaa gaaaacactc ggctgggagg    2340
ccttcaccga gacgctgtac cccgctgacg gcggcctgga aggcagaaac gacatgaccc    2400
tgaagctcgt gggcgggagc catctgatcg caaacatcaa gaccacatat agatccaaga    2460
aacccgctaa gaacctcaag atgcctgcg tctactatgt ggactacaga ctggaaagaa    2520
tcaaggagc caacaacgag acctacgtcg agcagcacga ggtggcagtg gccagatact    2580
gcgacctccc tagcaaactg gggcacaagc taaattgaaa gctttgcttt atttgtgaaa    2640
tttgtgatgc tattgcttta tttgtaacca ttataagctg caataaacaa gtttaacaac    2700
aacaattgca ttcatttat gtttcaggtt caggggagg tgtgggaggt tttttaaagt    2760
cgacccacca ttgtctttcc tagcggaatg ggcacctcat cccccgcccg caggggctca    2820
gctgacggcc ctcggagtgc ccagcactg aggcctgagg atggacactg ctcttggccc    2880
ctctgaccgg cttccttggc caccagtgtt ctgcagaccc tccaccatga gcccgggtca    2940
gcgcatttcc tcaggagaag caggcagggt gcaggccatt gcaggccgtc caggggctga    3000
gctgcctggg ggcgaccggg gctccagcct gcacctgcac caggcacagc cccaccacag    3060
gactcatgtc tcaatgccca cagtgagccc aggcagcagg tgtcaccgtc ccctacaggg    3120
agggccagat gcagtcactg cttcaggtcc tgccagcaca gagctgcctg cgtccagctc    3180
cctgaatctc tgctgctgct gctgctgctg ctgctgctgc ctgcggcccg gggctcaagg    3240
cgccgtggcc ctgcctgacg ccccggagcc tcctgcctga acttggggc tggttggaga    3300
tggccttgga gcagccaagg tgcccctggc agtggcatcc cgaaacgcc tggacgcagg    3360
gcccaagact gggcacagga gtgggaggta catgggctg gggactcccc aggagttatc    3420
tgctccctgc aggcctagag aagtttcagg gaagtcaga agagctcctg gctgtggtgg    3480
gcagggcagg aaacccctcc acctttacac atgcccaggc agcacctcag gcccttggtg    3540
gggcagggaa gctgaggcag taagcaggca ggcagagctg aggcctttc aggcccagcc    3600
agcactctgg cctcctgccg ccgcattcca ccccagcccc tcacaccact cgggagaggg    3660
acatcctacg gtcccaaggt caggagggca gggctgggt tgactcaggc ccctcccagc    3720
tgtgccacc tgggtgttgg gagggcagaa gtgcaggcac ctagggcccc ccatgtgccc    3780
accctgggag ctctccttgg aacccattcc tgaaattatt taaaggggtt ggccggacta    3840
gttacgtaga taagtagcat ggcgggttaa tcattaacta caaggaaccc ctagtgatgg    3900
agttggccac tccctctctg cgcgctcgct cgctcactga ggccgggcga ccaaaggtcg    3960
cccgacgccc gggctttgcc cgggcggcct cagtgagcga gcgagcgcgc cagctggcgt    4020
aatagcgaag aggcccgcac cgatcgccct cccaacagt tgcgcagcct gaatggcgaa    4080
tggcgattcc gttgcaatgg ctggcggtaa tattgttctg gatattacca gcaaggccga    4140
tagtttgagt tcttctactc aggcaagtga tgttattact aatcaaagaa gtattgcgac    4200
aacggttaat ttgcgtgatg gacagactct tttactcggt ggcctcactg attataaaaa    4260
cacttctcag gattctggcg taccgttcct gtctaaaatc cctttaatcg gcctcctgtt    4320
tagctcccgc tctgattcta acgaggaaag cacgttatac gtgctcgtca aagcaaccat    4380
agtacgcgcc ctgtagcggc gcattaagcg cggcgggtgt ggtggttacg cgcagcgtga    4440
ccgctacact tgccagcgcc ctagcgcccg ctcctttcgc tttcttccct tcctttctcg    4500
ccacgttcgc cggctttccc cgtcaagctc taaatcgggg gctccctta gggttccgat    4560
ttagtgcttt acggcacctc gaccccaaaa aacttgatta gggtgatggt tcacgtagtg    4620
ggccatcgcc ctgatagacg gtttttcgcc ctttgacgtt ggagtccacg ttctttaata    4680
gtggactctt gttccaaact ggaacaacac tcaaccctat ctcggtctat tcttttgatt    4740
tataaggat tttgccgatt tcggcctatt ggttaaaaaa tgagctgatt taacaaaaat    4800
ttaacgcgaa ttttaacaaa atattaacgt ttacaattta aatatttgct tatacaatct    4860
tcctgttttt ggggcttttc tgattatcaa ccggggtaca tatgattgac atgctagttt    4920
tacgattacc gttcatcgat tctcttgttt gctccagact tcaggcaat gacctgatag    4980
cctttgtaga gacctctcaa aaatagctac cctctccggc atgaatttat cagctagaac    5040
ggttgaatat catattgatg gtgatttgac tgtctccggc ctttctcacc cgtttgaatc    5100
tttacctaca cattactcag gcattgcatt taaaatatat gagggttcta aaaattttta    5160
tccttgcgtt gaaataaagg cttctccccg caaaagtatta caggtttttta    5220
tacaaccgat ttagctttat gctctgaggc tttattgctt aattttgcta attctttgcc    5280
ttgcctgtat gatttattgg atgttggaat cgcctgatgc ggtattttct ccttacgcat    5340
ctgtgcggta tttcacaccg catatggtgc actctcagta caatctgctc tgatgccgca    5400
tagttaagcc agccccgaca cccgccaaca cccgctgacg cgccctgacg gcttgtctg    5460
ctcccggcat ccgcttacag acaagctgtg accgtctccg ggagctgcat gtgtcagagg    5520
```

```
ttttcaccgt catcaccgaa acgcgcgaga cgaaagggcc tcgtgatacg cctatttta   5580
taggttaatg tcatgataat aatggtttct tagacgtcag gtggcacttt tcggggaaat   5640
gtgcgcggaa ccccctatttg tttattttc taaatacatt caaatatgta tccgctcatg   5700
agacaataac cctgataaat gcttcaataa tattgaaaaa ggaagagtat gagtattcaa   5760
catttccgtg tcgcccttat tccctttttt gcggcatttt gccttcctgt ttttgctcac   5820
ccagaaacgc tggtgaaagt aaaagatgct gaagatcagt tgggtgcacg agtgggttac   5880
atcgaactgg atctcaacag cggtaagatc cttgagagtt ttcgccccga gaacgttttt   5940
ccaatgatga gcacttttaa agttctgcta tgtggcgcgg tattatcccg tattgacgcc   6000
gggcaagagc aactcggtcg ccgcatacac tattctcaga atgacttggt tgagtactca   6060
ccagtcacag aaaagcatct tacggatggc atgacagtaa gagaattatg cagtgctgcc   6120
ataaccatga gtgataacac tgcggccaac ttacttctga caacgatcgg aggaccgaag   6180
gagctaaccg cttttttgca caacatgggg gatcatgtaa ctcgccttga tcgttgggaa   6240
ccggagctga atgaagccat accaaacgac gagcgtgaca ccacgatgcc tgtagcaatg   6300
gcaacaacgt tgcgcaaact attaactggc gaactactta ctctagcttc ccggcaacaa   6360
ttaatagact ggatggaggc ggataaagtt gcaggaccac ttctgcgctc ggcccttccg   6420
gctggctggt ttattgctga taaatctgga gccggtgagc gtgggtctcg cggtatcatt   6480
gcagcactgg ggccagatgg taagccctcc cgtatcgtag ttatctacac gacggggagt   6540
caggcaacta tggatgaacg aaatagacag atcgctgaga taggtgcctc actgattaag   6600
cattggtaac tgtcagacca agtttactca tatatacttt agattgattt aaaacttcat   6660
ttttaattta aaaggatcta ggtgaagatc ctttttgata atctcatgac caaaatccct   6720
taacgtgagt tttcgttcca ctgagcgtca gaccccgtag aaaagatcaa aggatcttct   6780
tgagatcctt ttttttctgcg cgtaatctgc tgcttgcaaa caaaaaaacc accgctacca   6840
gcggtggttt gtttgccgga tcaagagcta ccaactcttt ttccgaaggt aactggcttc   6900
agcagagcgc agataccaaa tactgtcctt ctagtgtagc cgtagttagg ccaccacttc   6960
aagaactctg tagcaccgcc tacatacctc gctctgctaa tcctgttacc agtggctgct   7020
gccagtggcg ataagtcgtg tcttaccggg ttggactcaa gacgatagtt accggataag   7080
gcgcagcggt cgggctgaac ggggggttcg tgcacacagc ccagcttgga gcgaacgacc   7140
tacaccgaac tgagatacct acagcgtgag ctatgagaaa gcgccacgct tcccgaaggg   7200
agaaaggcgg acaggtatcc ggtaagcggc agggtcggaa caggagagcg cacgagggag   7260
cttccagggg gaaacgcctg gtatctttat agtcctgtcg ggtttcgcca cctctgactt   7320
gagcgtcgat ttttgtgatg ctcgtcaggg gggcggagcc tatggaaaaa cgccagcaac   7380
gcggcctttt tacggttcct ggccttttgc tggccttttg ctcacatgtt ctttcctgcg   7440
ttatcccctg attctgtgga taaccgtatt accgcctttg agtgagctga taccgctcgc   7500
cgcagccgaa cgaccgagcg cagcgagtca gtgagcgagg aagcggaaga gcgcccaata   7560
cgcaaaccgc ctctccccgc gcgttggccg attcattaat g                     7601

SEQ ID NO: 45          moltype = DNA   length = 1325
FEATURE                Location/Qualifiers
source                 1..1325
                       mol_type = genomic DNA
                       organism = Homo sapiens
SEQUENCE: 45
agtccagggc tctgtcctgc acctggggaa tggtgaccgg catctctgtc ctctagctct   60
ggaagcaccc cagcccctct agtctgccct caccccctgac cctgaccctc caccctgacc   120
ccgtcctaac ccctgacctt tgtgcccttc cagagagaag ggcagaagtg cccacagccc   180
accccagccc ctcacccagg ccagccggcc agttccaaac cctggtggtt ggtgtcgtgg   240
gcggcctgct gggcagcctg gtgctgctag tctgggtcct gcgtgtcatc tgctcccggg   300
ccgcacgagg taacgtcatc ccagcccctc ggcctgccct gccctaaccc tgctggcggc   360
cctcactccc gcctcccctt cctccaccct tccctcaccc cacccacct ccccccatct   420
ccccgccagg ctaagtccct gatgaaggcc cctggactaa gacccccac ctaggagcac   480
ggctcagggt cggcctggtg accccaagtg tgtttcctg cagggacaat aggagccagg   540
cgcaccggcc agccctggt gagtctcact cttttcctgc atgatccact gtgccttcct   600
tcctgggtgg gcagaggtgg aaggacaggc tgggaccaca cggcctgcag gactcacatt   660
ctattatagc caggacccca cctccccagc ccccaggcag caacctcaat ccctaaagcc   720
atgatctggg gcccagccc acctgcggtc tccgggggtg cccggcccat gtgtgtgcct   780
gcctgcggtc tccaggggtg cctgcccac gcgtgtgccc gcctgcggtc tctgggggtg   840
cccggcccac atatgtgcct gcctgcggtc tccaggtgtg cccggcccat gcgtgtgccc   900
acctgcgagg gcgtggggtg ggcttggtca tttcttatct tacattggag acaggagagc   960
ttgaaaagtc acattttgga atcctaaatc tgcaagaatc agggacat ttcagagggg   1020
gacattgagc cagagaggag gggtggtgtc cccagatcac acagagggca gtggtgggac   1080
agctcagggt aagcagctca tagtgggggg cccaggttcg gtgccggtac tgcagccagg   1140
ctgtggagcc gcgggcctcc ttcctgcggt gggccgtggg gctgactccc tctcccttc   1200
tcctcaaaga aggaggaccc ctcagccgtg cctgtgttct ctgtggacta tggggagctg   1260
gatttccagt ggcgagagaa gacccggag ccccccgtgc cctgtgtccc tgagcagacg   1320
gagta                                                              1325

SEQ ID NO: 46          moltype = DNA   length = 1072
FEATURE                Location/Qualifiers
source                 1..1072
                       mol_type = genomic DNA
                       organism = Homo sapiens
SEQUENCE: 46
ccaccattgt ctttcctagc ggaatgggca cctcatcccc cgcccgcagg ggctcagctg   60
acggccctcg gagtgcccag ccactgaggc ctgaggatgg acactgctct tggcccctct   120
gaccggcttc cttggccacc agtgttctgc agacccttca ccatgagccc gggtcagcgc   180
atttcctcag gagaagcagg cagggtgcag gccattgcag gccgtccagg ggctgagctg   240
cctgggggcg accggggctc cagcctgcac ctgcaccagg cacagcccca ccacaggact   300
catgtctcaa tgcccacagt gagcccaggc agcaggtgtc accgtcccct acagggaggg   360
ccagatgcag tcactgcttc aggtcctgcc agcacagagc tgcctgcgtc cagctccctg   420
```

```
aatctctgct gctgctgctg ctgctgctgc tgctgcctgc ggcccggggc tgaaggcgcc    480
gtggccctgc ctgacgcccc ggagcctcct gcctgaactt gggggctggt tggagatggc    540
cttggagcag ccaaggtgcc cctggcagtg gcatcccgaa acgccctgga cgcagggccc    600
aagactgggc acaggagtgg gaggtacatg gggctgggga ctccccagga gttatctgct    660
ccctgcaggc ctagagaagt ttcagggaag gtcagaagac ctcctggctg tggtgggcag    720
ggcaggaaac ccctccacct ttacacatgc ccaggcagca cctcaggccc tttgtggggc    780
agggaagctg aggcagtaag cgggcaggca gagctggagg cctttcaggc ccagccagca    840
ctctggcctc ctgccgccgc attccacccc agccctcac accactcggg agagggacat     900
cctacggtcc caaggtcagg agggcagggc tggggttgac tcaggcccct cccagctgtg    960
gccacctggg tgttgggagg gcagaagtgc aggcacctag ggcccccat gtgcccaccc     1020
tgggagctct ccttggaacc cattcctgaa attatttaaa ggggttggcc gg            1072

SEQ ID NO: 47            moltype = DNA   length = 7601
FEATURE                  Location/Qualifiers
misc_feature             1..7601
                         note = Synthesized rAAV PD-1 Exon5_MND-BFP 3'-Homology Arm
                         SNP construct
source                   1..7601
                         mol_type = other DNA
                         organism = synthetic construct
SEQUENCE: 47
cagctgcgcg ctcgctcgct cactgaggcc gcccgggcaa agcccggcg tcgggcgacc      60
tttggtcgcc cggcctcagt gagcgagcga gcgcgcagag agggagtggc caactccatc   120
actagggggtt ccttgtagtt aatgattaac ccgccatgct acttatctac gtagaattca   180
gtccagggct ctgtcctgca cctggggaat ggtgaccggc atctctgtcc tctagctctg   240
gaagcacccc agcccctcta gtctgccctc acccctgacc ctgaccctca accctgaccc   300
cgtcctaacc cctgaccttt gtgcccttcc agagagaagg gcagaagtgc ccacagccca   360
ccccagcccc tcacccaggc cagccggcca gttccaaacc ctggtggttg gtgtcgtggg   420
cggcctgctg ggcagcctgg tgctgctagt ctgggtcctg gccgtcatct gctcccgggc   480
cgcacgaggt aacgtcatcc cagcccctcg gcctgccctg ccctaaccct gctgcgggcc   540
ctcactcccg cctcccctt c tccacccttt ccctcaccc accccacctc ccccatctc    600
cccgccaggc taagtccctg atgaaggcc ctggactaag acccccacc taggagcacg     660
gctcagggtc ggcctggtga ccccaagtgt gtttctctgc agggacaata ggagccaggc   720
gcaccggcca gcccctggtg agtctcactc ttttcctgca tgatccactg tgccttcctt   780
cctggggtgg cagaggtgga aggacaggct gggaccacac ggcctgcagg actcacattc   840
tattatagcc aggaccccac ctccccagcc cccaggcagc aacctcaatc cctaaagcca   900
tgatctgggg ccccagccca cctgcggtct ccggggtgc ccggccatg tgtgtgcctg     960
cctgcggtct ccagggtgc ctggcccacg cgtgtgcccg cctgcggtct ctgggggtgc   1020
ccggcccaca tatgtgcctg cctgcggtct ccaggtgtgc cagtgcccatg cgtgtgccca   1080
cctgcgaggg cgtggggtgg gcttggtcat ttcttatctt acattggaga caggagagct   1140
tgaaaagtca cattttggaa tcctaaatct gcaagaatgc cagggacatt tcagaggggg   1200
acattgagcc agagaggagg ggtggtgtcc ccagatcaca cagagggcag tggtgggaca   1260
gctcagggta agcagctcat agtgggggc ccaggttcgg tgccggtact gcagccaggc    1320
tgtggagccg cgggcctcct tcctgcggtg ggccgtgggg ctgactccct ctcccttttct  1380
cctcaaagaa ggaggacccc tcagccgtgc ctgtgttctc tgtggactat ggggagctgg   1440
atttccagtg gcgagagaag accccggagc ccccgtgcc ctgtgtccct gagcagacgg    1500
agtaatgcat gaacagagaa acaggagaat atggggcagc caggatatct gtggtaagca   1560
gttcctgccc cggctcaggg ccaagaacag ttggaacagc agaatatggg ccaaacagga   1620
tatctgtggt aagcagttcc tgccccggct caggcaag aacagatggt ccccagatgc     1680
ggtcccgccc tcagcagttt ctagagaacc atcagatgtt tccagggtgc cccaaggacc   1740
tgaaatgacc ctgtgcctta tttgaactaa ccaatcagtt cgcttctcgc ttctgttcgc   1800
gcgcttctgc tccccgagct ctatataagc agagctcgtt tagtgaaccg tcagatcgc     1860
tggagacgcc atccacgctg ttttgacttc catagaagga tctcgaggcc accatggcta   1920
gcgagctgat taaggagaac atgcacatga agctgtacat ggagggcacc gtggacaacc   1980
atcacttcaa gtgcacatcc gagggcgaag gcaagccta caggggacc cagaccatga     2040
gaatcaaggt ggtcgaggc ggccctctcc ccttcgcctt cgacatcctg gctactagct     2100
tcctctacgg cagcaagacc ttcatcaacc acacccaggg catccccgac ttcttcaagc   2160
agtccttccc tgagggcttc acatgggaga gagtcaccac atacgaggac gggggcgtgc   2220
tgaccgctac ccaggacacc agcctccagg acggctgcct catctacaac gtcaagatca   2280
gaggggtgaa cttcacatcc aacgccctg tgatgcagaa gaaaacactc ggctgggagg    2340
ccttcaccga gacgctgtac cccgctgacg gcgcctgga aggcagaaac gacatggccc    2400
tgaagctcgt gggcgggagc catctgatcg caaacatcaa gaccacatat agatccaaga   2460
aaacccgcta agaacctcaag atgcctgcg tctactatgt ggactacaga ctggaaagaa    2520
tcaaggagga caacaacgag acctacgtcg agcagcacga ggtggcagtg gccagatact   2580
gcgacctccc tagcaaactg gggcacaagc taaattgaaa gctttgcttt atttgtgaaa   2640
tttgtgatgc tattgcttta tttgtaacca ttataagctg caataacaa gtttaacaac    2700
aacaattgca ttcatttat gtttcaggtt caggggggagg tgtgggaggt ttttttaaagt   2760
cgacccacca ttgtctttcc tagcggaatg ggcacctcat cccccgcccg caggggtca   2820
gccgacgggc ctcggagtgc ccagccactg aggcctgagg atggacactg ctcttggctc   2880
ctctgaccgg cttccttggc caccagtgtt ctgcagaccc tccaccatga gcccgggtca   2940
gcgcatttcc tcaggagaag caggcagggt gcaggccatt gcaggccgtc caggggctga   3000
gctgcctggg ggcgacccgg gctccagcct gcacctgcac caggcacagc cccaccacag   3060
gactcatgtc tcaatgccca cagtgagccc aggcagcagg tgtcaccgtc ccctacaggg   3120
agggccagat gcagtcactg cttcaggtcc tgccagcaga gccctccctc                3180
cctgaatctc tgctgctgct gctgctgctg ctgctgctgc ctgcggcccg ggctgaaggg   3240
cgccgtggcc ctgcctgacg cccccggagc ctcctgcctga acttggggc tggttggaga    3300
tggccttgga gcagccaagg tgcccctggc agtggcatcc cgaaacgccc tggacgcagg   3360
gcccaagact gggcacagga gtgggaggta catgggggctg ggactcccc aggagttatc    3420
tgctccctgc aggcctagag aagtttcagg gaaggtcaga gagctcctg gctgtggtgg     3480
```

```
gcagggcagg aaacccctcc acctttacac atgcccaggc agcacctcag gcccttgtg   3540
gggcagggaa gctgaggcag taagcgggca ggcagagctg gaggcctttc aggcccagcc   3600
agcactctgg cctcctgccg ccgcattcca ccccagcccc tcacaccact cgggagaggg   3660
acatcctacg gtcccaaggt caggagggca gggctggggt tgactcaggc ccctcccagc   3720
tgtggccacc tgggtgttgg gagggcagaa gtgcaggcac ctaggggccc ccatgtgcc    3780
accctgggag ctctccttgg aacccattcc tgaaattatt taaaggggtt ggccggacta   3840
gttacgtaga taagtagcat ggcggggttaa tcattaacta caaggaaccc ctagtgatgg   3900
agttggccac tccctctctg cgcgctcgct cgctcactga ggccgggcga ccaaaggtcg   3960
cccgacgccc gggctttgcc cgggcggcct cagtgagcga gcgagcgcgc cagctggcgt   4020
aatagcgaag aggcccgcac cgatcgccct cccaacagt tgcgcagcct gaatggcgaa    4080
tggcgattcc gttgcaatgg ctggcggtaa tattgttctg gatattacca gcaaggccga   4140
tagtttgagt tcttctactc aggcaagtga tgttattact aatcaaagaa gtattgcgac   4200
aacgttaat ttgcgtgatg acagactct tttactcggg ggcctcactg attataaaaa    4260
cacttctcag gattctggcg taccgttcct gtctaaaatc cctttaatcg gcctcctgtt   4320
tagctcccgc tctgattcta acgaggaaag cacgttatac gtgctcgtca aagcaaccat   4380
agtacgcgcc ctgtagcggc gcattaagcg cggcgggtgt ggtggttacg cgcagcgtga   4440
ccgctacact tgccagcgcc ctagcgcccg ctcctttcgc tttcttccct tcctttctcg   4500
ccacgttcgc cggctttccc cgtcaagctc taaatcgggg gctcccttta gggttccgat   4560
ttagtgcttt acggcacctc gaccccaaaa aacttgatta gggtgatggt tcacgtagtg   4620
ggccatcgcc ctgatagacg gtttttcgcc ctttgacgtt ggagtccacg ttctttaata   4680
gtggactctt gttccaaact ggaacaacac tcaaccctat ctcggtctat tcttttgatt   4740
tataagggat tttgccgatt tcggcctatt ggttaaaaaa tgagctgatt taacaaaaat   4800
ttaacgcgaa ttttaacaaa atattaacgt ttacaattta aatatttgct tatacaatct   4860
tcctgttttt ggggcttttc tgattatcaa ccggggtaca tatgattgac atgctagttt   4920
tacgattacc gttcatcgat tctcttgttt gctccagact ctcaggcaat gacctgatag   4980
cctttgtaga gacctctcaa aaatagctac ccctctccgg atgaatttat cagctagaac   5040
ggttgaatat catattgatg gtgatttgac tgtctccggc cttttctcacc cgtttgaatc   5100
tttacctaca cattactcag gcattgcatt taaaatatat gagggttcta aaaattttta   5160
tccttgcgtt gaaataaagg cttctcccgc aaaagtatta caggggtcata atgttttttgg   5220
tacaaccgat ttagctttat gctctgaggc tttattgctt aattttgcta attctttgcc   5280
ttgcctgtat gatttattgg atgttggaat cgcctgatgc ggtattttct ccttacgcat   5340
ctgtgcggta tttcacaccg catatggtgc actctcagta caatctgctc tgatgccgca   5400
tagttaagcc agccccgaca cccgccaaca cccgctgacg cgccctgacg ggcttgtctg   5460
ctcccggcat ccgcttacag acaagctgtg accgtctccg ggagctgcat gtgtcagagg   5520
ttttcaccgt catcaccgaa acgcgcgaga cgaaagggcc tcgtgatacg cctatttta   5580
taggttaatg tcatgataat aatggtttct tagacgtcag gtggcacttt tcggggaaat   5640
gtgcgcggaa cccctatttg tttattttc taaatacatt caaatatgta tccgctcatg   5700
agacaataac cctgataaat gcttcaataa tattgaaaaa ggaagagtat gagtattcaa   5760
catttccgtg tcgcccttat tccctttttt gcggcatttt gccttcctgt ttttgctcac   5820
ccagaaacgc tggtgaaagt aaaagatgct gaagatcagt tgggtgcacg agtgggttac   5880
atcgaactgg atctcaacag cggtaagatc cttgagagtt ttcgccccga agaacgtttt   5940
ccaatgatga gcacttttaa agttctgcta tgtggcgcgg tattatcccg tattgacgcc   6000
gggcaagagc aactcggtcg ccgcatacac tattctcaga atgacttggt tgagtactca   6060
ccagtcacag aaaagcatct tacgatggc atgacagtaa gagaattatg cagtgctgcc   6120
ataaccatga gtgataacac tgcggccaac ttacttctga caacgatcgg aggaccgaag   6180
gagctaaccg cttttttgca caacatgggg gatcatgtaa ctcgccttga tcgttgggaa   6240
ccggagctga atgaagccat accaaacgac gagcgtgaca ccacgatgcc tgtagcaatg   6300
gcaacaacgt tgcgcaaact attaactggc gaactactta ctctagcttc ccggcaacaa   6360
ttaatagact ggatggaggc ggataaagtt gcaggaccac ttctgcgctc ggcccttccg   6420
gctggctggt ttattgctga taaatctgga gccggtgagc gtgggtctcg cggtatcatt   6480
gcagcactgg ggccagatgg taagccctcc cgtatcgtag ttatctacac gacgggggag   6540
caggcaacta tggatgaacg aaatagacag atcgctgaga taggtgcctc actgattaag   6600
cattggtaac tgtcagacca agtttactca tatatacttt agattgattt aaaacttcat   6660
ttttaattta aaaggatcta ggtgaagatc ctttttgata atctcatgac caaaatccct   6720
taacgtgagt tttcgttcca ctgagcgtca gaccccgtag aaaagatcaa aggatcttct   6780
tgagatcctt tttttctgcg cgtaatctgc tgcttgcaaa caaaaaaacc accgctacca   6840
gcggtggttt gtttgccgga tcaagagcta ccaactcttt ttccgaaggt aactggcttc   6900
agcagagcgc agataccaaa tactgtcctt ctagtgtagc cgtagttagg ccaccacttc   6960
aagaactctg tagcaccgcc tacatacctc gctctgctaa tcctgttacc agtggctgct   7020
gccagtggcg ataagtcgtg tcttaccggg ttggactcaa gacgatagtt accggataag   7080
gcgcagcggt cgggctgaac ggggggttcg tgcacacagc ccagcttgga gcgaacgacc   7140
tacaccgaac tgagatacct acagcgtgag ctatgagaaa gcgccacgct tcccgaaggg   7200
agaaaggcgg acaggtatcc ggtaagcggc agggtcggaa caggagagcg cacgagggag   7260
cttccagggg gaaacgcctg gtatctttat agtcctgtcg ggtttcgcca cctctgactt   7320
gagcgtcgat ttttgtgatg ctcgtcaggg gggcggagcc tatggaaaaa cgccagcaac   7380
gcggcctttt tacggttcct ggccttttgc tggccttttg ctcacatgtt ctttcctgcg   7440
ttatcccctg attctgtgga taaccgtatt accgcctttg agtgagctga taccgctcgc   7500
cgcagccgaa cgaccgagcg cagcgagtca gtgagcgagg aagcggaaga gcgcccaata   7560
cgcaaaccgc ctctccccgc gcgttggccg attcattaat g                       7601

SEQ ID NO: 48         moltype = DNA   length = 7601
FEATURE               Location/Qualifiers
misc_feature          1..7601
                      note = Synthesized rAAV PD-1 Exon5_MND-BFP 5'-Homology Arm
                       SNP construct
source                1..7601
                      mol_type = other DNA
                      organism = synthetic construct
SEQUENCE: 48
```

```
cagctgcgcg ctcgctcgct cactgaggcc gcccgggcaa agcccgggcg tcgggcgacc    60
tttggtcgcc cggcctcagt gagcgagcga gcgcgcagag agggagtggc caactccatc   120
actagggtt ccttgtagtt aatgattaac ccgccatgct acttatctac gtagaattca   180
gtccagggct ctgtcctgca cctggggaat ggtgaccggc atctctgtcc tctagctctg   240
gaagcacccc agcccctcta gtctgccctc acccctgacc ctgaccctcc accctgaccc   300
cgtcctaacc cctgaccttt gtgcccttcc agagagaagg gcagaagtgc ccacagccca   360
ccccagcccc tcacccaggc cagccggcca gttccaaacc ctggtggttg gtgtcgtggg   420
cggcctgctg ggcagcctgg tgctgctagt ctgggtcctg gccgtcatct gctcccgggc   480
cgcacgaggt aacgtcatcc cagcccctcg gcctgccctg ccctaaccct gctggcggcc   540
ctcactcccg cctcccctcc ctccaccctt ccctccaccc accccacctc cccccatctc   600
cccgccaggc taagtcctg atgaaggccc ctggactaag accccccacc taggagcacg   660
gctcagggtc ggcctggtga ccccaagtgt gtttctctgc agggacaata ggagccaggc   720
gcaccggcca gccccctggtg agtctcactc ttttcctgca tgatccactg tgccttcctt   780
cctgggtggg cagaggtgga aggacaggct gggaccacac ggcctgcagg actcacattc   840
tattatagcc aggaccccac ctccccagcc cccaggcagc aacctcaatc cctaaagcca   900
tgatctgggg ccccagccca cctgcggtct ccggggggtgc ccggcccatg tgtgtgcctg   960
cctgcggtct ccagggggtgc ctggcccacg cgtgtgcccg cctgcggtct ctgggggtgc  1020
ccggcccaca tatgtgcctg ccgcggtct ccaggtgtgc ccggcccatg cgtgtgccca  1080
cctgcgaggg cgtggggtgg gcttggtcat ttcttatctt acattggaga caggagagct  1140
tgaaaagtca cattttggaa tcctaaatct gcaagaatgc cagggacatt tcagagggg   1200
acattgagcc agagaggagg ggtggtgtcc ccagatcaca cagagggcag tggtgggaca  1260
gctcagggta agcagctcgt agtggggggta ccaggttcgg tgccggtact gcagccaggc  1320
tgtggagccg cgggcctcct tcctgcggtg ggcgtgggg ctgactccct ctccctttct  1380
cctcaaagaa ggaggacccc tcagccgtgc ctgtgttctc tgtggactat ggggagctgg  1440
atttccagtg gcgagagaag accccggagc ccccgtgcc ctgtgtccct gagcagacgg  1500
agtaatgcat gaacagagaa acaggagaat atgggccacc caggatatct gtggtaagca  1560
gttcctgccc cggctcaggg ccaagaacag ttggaacagc agaatatggg ccaaacagga  1620
tatctgtggt aagcagttcc tgccccggct cagggccaag aacagatggt ccccagatgc  1680
ggtcccgccc tcagcagttt ctagagaacc atcagatgtt tccagggtgc cccaaggacc  1740
tgaaatgacc ctgtgcctta tttgaactaa ccaatcagtt cgcttctcgc ttctgttcgc  1800
gcgcttctgc tccccgagct ctatataagc agagctcgtt tagtgaaccg tcagatcgcc  1860
tggagacgcc atccacgctg ttttgacttc catagaagga tctcgaggcc accatggcta  1920
gcgagctgat taaggagaac atgcacatga agctgtacat ggagggcacc gtggacaacc  1980
atcacttcaa gtgcacatcc gaggggcaag gcaagccctt cgagggcacc cagaccatga  2040
gaatcaaggt ggtcgagggc ggccctctcc ccttcgcctt cgacatcctg gctactagct  2100
tcctctacgg cagcaagacc ttcatcaacc acacccaggg catccccgac ttcttcaagc  2160
agtccttccc tgagggcttc acatgggaga gagtcaccac atacgaggac gggggcgtgc  2220
tgaccgctac ccaggacacc agcctccagg acggctgcct catctacaac gtcaagatca  2280
gaggggtgaa cttcacatcc aacgccctg tgatgcagaa gaaaacactc ggctgggagg  2340
ccttcaccga gacgctgtac cccgctgacg gcggcctgga aggcagaaac gacatgccc  2400
tgaagctcgt gggcgggagc catctgatcg caaacatcaa gaccacatat agatccaaga  2460
aacccgctaa gaacctcaag atgcctggcg tctactatgt ggactacaga ctggaaagaa  2520
tcaaggaggc caacaacgag acctacgtcg agcagcacga ggtggcagtg gccagatact  2580
gcgacctccc tagcaaactg gggcacaagc taaattgaaa gctttgcttt atttgtgaaa  2640
tttgtgatgc tattgctta tttgtaacca ttataagctg caataaacaa gtttaacaac  2700
aacaattgca ttcattttat gtttcaggtt caggggagg tgtgggaggt ttttaaagt   2760
cgaccacca ttgtctttcc tagcggaatg ggcacctcat cccccgcccg caggggctca  2820
gctgacggcc ctcggagtgc ccagccactg aggcctgagg atggacactg ctcttggccc  2880
ctctgaccgg cttccttggc caccagtgtt ctgcagaccc tccaccatga gcccgggtca  2940
gcgcatttcc tcaggagaag caggcagggt gcaggccatt gcaggccgtc cagggggctga  3000
gctgcctggg ggcgaccggg gctccagcct gcacctgcac caggcacagc ccaccacag   3060
gactcatgtc tcaatgccca cagtgagccc aggcagcagg tgtcaccgtc ccctacaggg  3120
agggccagat gcagtcactg cttcaggtcc tgccagcaca gagctgcctg cgtccagctc  3180
cctgaatctc tgctgctgct gctgctgctg ctgctgctgc ctgcgcccg gggctgaagg  3240
cgccgtggcc ctgcctgacg ccccggagcc tcctgcctga acttggggc tggttggaga  3300
tggccttgga gcagcaaagg tgccctggc agtggcatcc cgaaacgccc tggacgcagg  3360
gcccaagact gggcacagga gtgggaggta catgggctg gggactcccc aggagttatc   3420
tgctccctgc aggcctagag aagtttcagg gaaggtcaga agagcctg gctgtggtgg  3480
gcagggcagg aaaccctcc accttttacac atgccaggc agcacctcag gcccctttgtg  3540
gggcagggaa gctgaggcag taagcgggca ggcagagctg gaggccttc aggcccagcc  3600
agcactctgg cctcctgccg ccgcattcca ccccagcccc tcacaccact cgggagaggg  3660
acatcctacg gtcccaaggt caggagggca gggctgggt tgactcaggc ccctcccagc  3720
tgtggccacc tgggtgttgg gagggcagaa gtgcaggcac ctagggcccc ccatgtgccc  3780
accctgggag ctctccttgg aacccattcc tgaaattatt taaaggggtt ggccggacta  3840
gttacgtaga taagtagcat ggcgggttaa tcattaacta caaggaaccc ctagtgatgg  3900
agttggccac tccctctctg cgcgctcgct cgctcactga ggccgggcga ccaaaggtcg  3960
cccgacgccc gggctttgcc cggcggcct cagtgagcga gcgagcgcgc cagctggcgt  4020
aatagcgaag aggcccgcac cgatcgccct cccaacagt tgccagcct gaatggcgaa  4080
tggcgattcc gttgcaatgg ctggcggtaa tattgttctg gatattacca gcaaggccga  4140
tagtttgagt tcttctactc aggcaagtga tgttattact aatcaaagaa gtattgcgac  4200
aacggttaat ttgcgtgatg gacagactct tttactcggt ggcctcactg attataaaaa  4260
cacttctcag gattctggcg taccgttcct gtctaaaatc cctttaatcg gcctcctgtt  4320
tagctcccgc tctgattcta acgaggaaag cacgttatac gtgctcgtca aagcaaccat  4380
agtacgcgc ctgtagcgc gcattaagcg cggcgggtgt ggtggttacg cgcagcgtga  4440
ccgctacact tgccagcgcc ctagcgcccg ctcctttcgc tttcttccct ccttctcg    4500
ccacgttcgc cggctttccc cgtcaagctc taaatcgggg ctccctttta gggttccgat  4560
ttagtgcttt acggcacctc gaccccaaaa aacttgatta gggtgatggt tcacgtagtg  4620
ggccatcgcc ctgatagacg gttttcgcc ctttgacgtt ggagtccacg ttctttaata  4680
gtggactctt gttccaaact ggaacaacac tcaacccat ctcggtctat tcttttgatt  4740
```

-continued

```
tataagggat tttgccgatt tcggcctatt ggttaaaaaa tgagctgatt taacaaaaat   4800
ttaacgcgaa tttaacaaa atattaacgt ttacaattta aatatttgct tatacaatct   4860
tcctgttttt ggggcttttc tgattatcaa ccggggtaca tatgattgac atgctagttt   4920
tacgattacc gttcatcgat tctcttgttt gctccagact ctcaggcaat gacctgatag   4980
cctttgtaga gacctctcaa aaatagctac cctctccggc atgaatttat cagctagaac   5040
ggttgaatat catattgatg gtgatttgac tgtctccggc cttctctacc cgtttgaatc   5100
tttacctaca cattactcag gcattgcatt taaaatatat gagggttcta aaaatttta   5160
tccttgcgtt gaaataaagg cttctcccgc aaaagtatta cagggtcata atgtttttgg   5220
tacaaccgat ttagctttat gctctgaggc tttattgctt aattttgcta attctttgcc   5280
ttgcctgtat gatttattgg atgttggaat cgcctgatgc ggtattttct ccttacgcat   5340
ctgtgcggta tttcacaccg catatggtgc actctcagta caatctgctc tgatgccgca   5400
tagttaagcc agcccgaca cccgccaaca cccgctgacg cgccctgacg ggcttgtctg   5460
ctcccggcat ccgcttacag acaagctgtg accgtctccg ggagctgcat gtgtcagagg   5520
ttttcaccgt catcaccgaa acgcgcgaga cgaaaggcc tcgtgatacg cctatttta   5580
taggttaatg tcatgataat aatgggttct tagacgtcag gtggcacttt tcggggaaat   5640
gtgcgcggaa cccctatttg tttatttttc taaatacatt caaatatgta tccgctcatg   5700
agacaataac cctgataaat gcttcaataa tattgaaaaa ggaagagtat gagtattcaa   5760
catttccgtg tcgcccttat tcccttttt gcggcatttt gccttcctgt ttttgctcac   5820
ccagaaacgc tggtgaaagt aaaagatgct gaagatcagt tgggtgcacg agtgggttac   5880
atcgaactgg atctcaacag cggtaagatc cttgagagtt tcgccccga agaacgtttt   5940
ccaatgatga gcacttttaa agttctgcta tgtggcgcgg tattatccg tattgacgcc   6000
gggcaagagc aactcggtcg ccgcatacac tattctcaga atgacttggt tgagtactca   6060
ccagtcacag aaaagcatct tacgatggc atgacagtaa gagaattatg cagtgctgcc   6120
ataaccatga gtgataacac tgcggccaac ttacttctga caacgatcgg aggaccgaag   6180
gagctaaccg cttttttgca caacatgggg gatcatgtaa ctcgccttga tcgttgggaa   6240
ccggagctga atgaagccat accaaacgac gagcgtgaca ccacgatgcc tgtagcaatg   6300
gcaacaacgt tgcgcaaact attaactggc gaactactta ctctagcttc ccggcaacaa   6360
ttaatagact ggatggaggc ggataaagtt gcaggaccac ttctgcgctc ggcccttccg   6420
gctggctggt ttattgctga taaatctgga gccggtgagc gtgggtctcg cggtatcatt   6480
gcagcactgg ggccagatgg taagccctcc cgtatcgtag ttatctacac gacggggagt   6540
caggcaacta tggatgaacg aaatagacag atcgctgaga taggtgcctc actgattaag   6600
cattggtaac tgtcagacca agtttactca tatatacttt agattgattt aaaacttcat   6660
ttttaattta aaaggatcta ggtgaagatc cttttgata atctcatgac caaaatccct   6720
taacgtgagt tttcgttcca ctgagcgtca ccccgtag aaaagatcaa aggatcttct   6780
tgagatcctt ttttctgcg cgtaatctgc tgcttgcaaa caaaaaaacc accgctacca   6840
gcggtggttt gtttgccgga tcaagagcta ccaactcttt ttccgaaggt aactggcttc   6900
agcagagcgc agataccaaa tactgtcctt ctagtgtagc cgtagttagg ccaccacttc   6960
aagaactctg tagcaccgcc tacatacctc gctctgctaa tcctgttacc agtggctgct   7020
gccagtggcg ataagtcgtg tcttaccggg ttggactcaa gacgatagtt accggataag   7080
gcgcagcggt cgggctgaac ggggggttcg tgcacacagc ccagcttgga gcgaacgacc   7140
tacaccgaac tgagatacct acagcgtgag ctatgagaaa gcgccacgct tcccgaaggg   7200
agaaaggcgg acaggtatcc ggtaagcggc agggtcggaa caggagagcg cacgagggag   7260
cttccagggg gaaacgcctg gtatctttat agtcctgtcg ggtttcgcca cctctgactt   7320
gagcgtcgat ttttgtgatg ctcgtcaggg gggcggagcc tatggaaaaa cgccagcaac   7380
gcggcctttt tacggttcct ggccttttgc tggccttttg ctcacatgtt ctttcctgcg   7440
ttatcccctg attctgtgga taaccgtatt accgcctttg agtgagctga taccgctcgc   7500
cgcagccgaa cgaccgagcg cagcgagtca gtgagcgagg aagcggaaga gcgcccaata   7560
cgcaaaccgc ctctccccgc gcgttggccg attcattaat g                       7601
```

```
SEQ ID NO: 49          moltype = DNA   length = 1325
FEATURE                Location/Qualifiers
source                 1..1325
                       mol_type = genomic DNA
                       organism = Homo sapiens
SEQUENCE: 49
agtccagggc tctgtcctgc acctggggaa tggtgaccgg catctctgtc ctctagctct     60
ggaagcaccc cagcccctct agtctgccct caccctgac cctgaccctc caccctgacc    120
ccgtcctaac ccctgacctt tgtgcccttc cagagagaag gcagaagtg cccacagccc    180
accccagccc ctcacccagg ccagcccggcc agttccaaac ctcggtggtt ggtgtcgtgg   240
gcggcctgct gggcagcctg gtgctgctag tctgggtcct ggccgtcatc tgctcccggg   300
ccgcacgagg taacgtcatc ccagcccctc ggcctgccct gccctaaccc tgctggcggc   360
cctcactccc gcctccccct tctccaccct tccctcaccc caccccacct cccccatct    420
ccccgccagg ctaagtccct gatgaaggcc cctggactaa gacccccac ctaggagcac    480
ggctcagggt cggcctggtg accccaagtg tgtttctgtc agggacaat aggagccagg    540
cgcaccggcc agccctggt gagtctcact cttttcctgc atgatccact gtgccttcct    600
tcctgggtgg gcagaggtgg aaggacaggc tgggaccaca cggcctgcag gactcacatt   660
ctattatagc caggacccca cctccccagc ccccaggcag caacctcaat ccctaaagcc   720
atgatctggg gcccagccc acctgcggtc tccggggtg cccggccggtc gtgtgtcct    780
gcctcggtc tccagggtg cctggccac gcgtgtcccc gcgtgtgcac tctgggggtg    840
cccggcccac atatgtgcct gcctgcggtc tccaggtgtg cccggccat gcgtgtgccc   900
acctgcgagg gcgtggggtg ggcttggtca tttcttatct tacattggag acaggagagc    960
ttgaaaagtc acattttgga atcctaaatc tgcaagaatg ccaggacat ttcagagggg   1020
gacattgagc cagagaggag gggtggtgtc cccagatcac acagagggca gtggtgggac   1080
agctcagggt aagcagctcg tagtgggggg cccaggttcg gtgccggtac tgcagccagg   1140
ctgtggagcc gcgggcctcc ttcctgcggt gggccgtggg gctgactccc tctccctttc   1200
tcctcaaaga aggaggaccc ctcagccgtg cctgtgttct ctgtggacta tggggagctg   1260
gatttccagt ggcgagagaa gaccccggag ccccccgtgc cctgtgtccc tgagcagacg   1320
gagta                                                               1325
```

| SEQ ID NO: 50 | moltype = DNA length = 1072 |
|---|---|
| FEATURE | Location/Qualifiers |
| source | 1..1072 |
| | mol_type = genomic DNA |
| | organism = Homo sapiens |

SEQUENCE: 50

```
ccaccattgt ctttcctagc ggaatgggca cctcatcccc cgcccgcagg ggctcagccg    60
acggccctcg gagtgcccag ccactgaggc ctgaggatgg acactgctct tggcccctct   120
gaccggcttc cttggccacc agtgttctgc agaccctcca ccatgagccc gggtcagcgc   180
atttcctcag gagaagcagg cagggtgcag gccattgcag gccgtccagg ggctgagctg   240
cctgggggcg accggggctc cagcctgcac ctgcaccagg cacagcccca ccacaggact   300
catgtctcaa tgcccacagt gagcccaggc agcaggtgtc accgtcccct acagggaggg   360
ccagatgcag tcactgcttc aggtcctgcc agcacagagc tgcctgcgtc cagctccctg   420
aatctctgct gctgctgctg ctgctgctgc tgctgccggg c tgaaggcgcc   480
gtggccctgc ctgacgcccc ggagcctcct gcctgaactt gggggctggt tggagatggc   540
cttggagcag ccaaggtgcc cctggcagtg catcccgaaa cgccctgga cgcagggccc   600
aagactgggc acaggagtgg gaggtacatg gggctgggga ctccccagga gttatctgct   660
ccctgcaggc ctagagaagt ttcagggaag gtcagaagag ctcctggctg tggtgggcag   720
ggcaggaaac ccctccacct ttacacatgc ccaggcagca cctcaggccc tttgtggggc   780
agggaagctg aggcagtaag cgggcaggca gagctggagg cctttcaggc ccagccagca   840
ctctggcctc ctgccgccgc attccacccc agccctcac accactcggg agaggacat    900
cctacggtcc caaggtcagg aagggcagggc tggggttgac tcaggccccct cccagctgtg   960
gccacctggg tgttgggagg gcagaagtgc aggcacctag ggcccccat gtgcccaccc  1020
tgggagctct ccttggaacc cattcctgaa attatttaaa ggggttggcc gg          1072
```

| SEQ ID NO: 51 | moltype = DNA length = 7880 |
|---|---|
| FEATURE | Location/Qualifiers |
| misc_feature | 1..7880 |
| | note = Synthesized rAAV PD-1 Exon5_MND-PD-1-CD28 Switch |
| | Receptor construct |
| source | 1..7880 |
| | mol_type = other DNA |
| | organism = synthetic construct |

SEQUENCE: 51

```
cagctgcgcg ctcgctcgct cactgaggcc gccgggcaa agcccgggcg tcggcgacc     60
tttggtcgcc cggcctcagt gagcgagcga gcgcgcagag agggagtggc caactccatc   120
actaggggtt ccttgtagtt aatgattaac ccgccatgct acttatctac gtagaattca   180
gtccaggcct ctgtcctgca cctggggaat ggtgaccggc atctctgtcc tctagctctg   240
gaagcaccgc agcccctcta gtctgccctc accctgaccc ctgaccctcc accctgaccc   300
cgtcctaacc cctgaccttt gtgcccttcc agagagaagg gcagaagtgc ccacagccca   360
ccccagcccc tcacccaggc cagccggcca gttccaaacc ctggtggttg gtgtcgtggg   420
cggcctgctg ggcagcctgg tgctgctagt ctgggtcctg gccgtcatct gctcccgggc   480
cgcacgaggt aacgtcatcc cagcccctcg gcctgccctg ccctaaccct gctggcgccc   540
ctcactcccg cctcccttc ctccacccct ccctcacccc accccacctc ccccatctc    600
cccgccaggc taagtccctg atgaaggccc tggactaag acccccacc taggagcacg   660
gctcagggtc ggcctggtga ccccaagtgt gtttctctgc agggacaata ggagccaggc   720
gcaccggcca gcccctggtg agtctcactc ttttcctgcc tgatccactg tgccttcctt   780
cctgggtggg cagaggtgga aggacaggct gggaccacac ggcctgcagg actcacattc   840
tattatagcc aggaccccac ctcccagcc ccaggcagc aacctcaatc cctaaagcca    900
tgatctgggg ccccagccca cctgcggtct ccggggtgc ccggcccatg tgtgtgcctg    960
cctgcgtct ccaggggtgc ctggccacg cgtgtgccg cctgcggtct ctgggggtg     1020
ccggcccaca tatgtgcctg cctgcgtct ccaggtgtgc ccggcccatg cgtgtgccca   1080
cctgcgaggg cgtggggtgg gcttggtcat ttcttatctt acattggaga caggagagct  1140
tgaaagtca catttggaa tcctaaatct gcaagaatgc cagggacatt tcagaggggg    1200
acattgagcc agagaggagg ggtggtgtcc ccagatcaca cagagggcag tggtgggaca  1260
gctcagggta agcagctcat agtgggggc ccaggttcgg tgccggtact gcagccaggc   1320
tgtgagccgc cgggcctcct tcctgcggtg ggccgtgggg ctgactccct ctcctttct    1380
cctcaaagaa ggaggacccc tcagccgtgc ctgtgttctc tgtggactat ggggagctgg  1440
atttccagtg gcgagagaag acccccggagc ccccgtgcc ctgtgtcct gagcagacgga  1500
agtaatgcat gaacagagaa acaggagaat atgggccaaa caggatatct gtgctaagca  1560
gttcctgccc cggctcaggg ccaagaacag ttggaacagc agaatatggg ccaaacagga  1620
tatctgtggt aagcagttcc tgcccgcct cagggcaag acagatggt cccagatgc      1680
ggtcccgccc tcagcagttt ctagagaacc atcagatgtt tccagggtgc cccaaggacc  1740
tgaaatgacc ctgtgcctta tttgaactaa ccaatcgatt cgcttctgc ttctgttcgc    1800
gcgcttctgc tccccgagct ctatataagc agagctcgtt tagtgaaccg tcagatcgcc  1860
tggagacgcc atccacgctg ttttgacttc catagaagga tctgaggcc accatgcaga   1920
tccccgcaag ccctggcca gtcgtctgg cggtgctaca actgggctgg cggccaggat   1980
ggttcttaga ctcccccgac aggccctgga accccccca cttctccccca gccctgctcg  2040
tgggtgaccga aggggacaac gccaccttca cctgcagctt ctccaacaca tcggagagct  2100
tcgtgctaaa ctggtaccgc atgagcccca gcaaccagac ggacaagctg gccgccttcc  2160
ccgaggaccg cagccagccc ggccaggact ccgcttccg tgtcacacaa ctgcccaacg   2220
ggcgtgactt ccacatgagc gtggtcaggg cccggcgcaa tgacagcggc acctacctct   2280
gtggggccat ctccctggcc ccaaggcgc agatcaaaga gagcctgcgg gcagagctca   2340
gggtgacaga gagaagggca gaagtgccca gcccaccc cagcccctca cccagccag    2400
ccggccagtt ccaaacctg gtggttggtg tcgtggcg cctgctgggc agcctggtgc    2460
tgctagtctg gtcctggcc gtcatcagga gtaagaggag caggctcctg cacagtgact   2520
acatgaacat gactccccgc cgccccggc ccacccgcaa gcattaccag ccctatgccc   2580
caccacgcga cttcgcagcc tatcgctccg gtgagggcag aggaagtctt ctaacatgcg   2640
gtgacgtgga ggagaatccg ggccctgtga gcaagggcga ggaggataac tccgccatca   2700
```

```
tcaaggagtt cctgcgcttc aaggtgcaca tggagggctc cgtgaacggc cacgagttcg    2760
agatcgaggg cgaggcgag ggccgcccct acgagggcac ccagaccgcc aagctgaagg    2820
tgaccaaggg tggcccctg cccttcgcct gggacatcct gtccctcag ttcatgtacg    2880
gctccaaggc ctacgtgaag caccccgccg acatccccga ctacttgaag ctgtccttcc    2940
ccgagggctt caagtgggag cgcgtgatga acttcgagga cggcggcgtg gtgaccgtga    3000
cccaggactc ctctctgcag gacgcgagt tcatctacaa ggtgaagctg cgcggcacca    3060
acttcccctc cgacggcccc gtaatgcaga agaagaccat gggctgggag gcctcctccg    3120
agcggatgta cccccgaggac ggcgccctga agggcgagat caagcagagg ctgaagctga    3180
aggacggcgg ccactacgac gctgaggtca agaccaccta caaggccaag aagcccgtgc    3240
agctgcccgg cgcctacaac gtcaacatca agttggacat cacctcccac aacgaggact    3300
acaccatcgt ggaacagtac gaacgcgccg agggccgcca ctccaccggc ggcatggacg    3360
agctgtacaa gtgatgaaag cttgctttta tttgtgaaat ttgtgatgct attgctttat    3420
ttgtaaccat tataagctgc aataaacaag tttaacaaca acaattgcat tcattttatg    3480
tttcaggttc aggggaggt gtgggaggtt ttttaaagtc gacgtggccc tgcctgacgc    3540
cccggagcct cctgcctgaa cttgggggct ggttggagat ggccttggag cagccaaggt    3600
gcccctggca gtggcatccc gaaacgccct ggacgcaggg cccaagactg ggcacaggag    3660
tgggaggtac atgggctgg ggactcccca ggagttatct gctccctgca ggcctagaga    3720
agtttcaggg aaggtcagaa gagctcctgg ctgtggtggg acgggcagga aaccccctcca    3780
cctttacaca tgcccaggca gcacctcagg ccctttgtgg ggcagggaag ctgaggcagt    3840
aagcgggcag gcagagctgg aggcctttca ggcccagcca gcactctggc ctcctgccgc    3900
cgcattccac cccagcccct cacaccactc gggagaggga catcctacgg tcccaaggtc    3960
aggaggggcg ggctggggtt gactcaggcc cctcccagct gtggccacct gggtgttggg    4020
agggcagaag tgcaggcacc tagggcccc catgtgccca ccctgggagc tctccttgga    4080
acccattcct gaaattattt aaggggttg gccggactag ttacgtagat aagtagcatg    4140
gcgggttaat cattaactac aaggaacccc tagtgatgga gttggccact ccctctctgc    4200
gcgctcgctc gctcactgag gccgggcgac caaaggtcgc ccgacgcccg ggctttgccc    4260
gggcggcctc agtgagcgag cgagcgcgcc agctggcgta atagcgaaga ggcccgcacc    4320
gatcgccctt cccaacagtt gcgcagcctg aatggcgaat ggcgattccg ttgcaatggc    4380
tggcggtaat attgttctgg atattaccag caaggccgat agtttgagtt cttctactca    4440
ggcaagtgat gttattacta atcaaagaag tattgcgaca acggttaatt tgcgtgatgg    4500
acagactctt ttactcggtg gcctcactga ttataaaaac acttctcagg attctggcgt    4560
accgttcctg tctaaaatcc ctttaatcgg cctcctgttt agctcccgct ctgattctaa    4620
cgaggaaagc acgttatacg tgctcgtcaa agcaaccata gtacgcgccc tgtagcggcg    4680
cattaagcgc ggcgggtgtg gtggttacgc gcagcgtgac cgctacactt gccagcgccc    4740
tagcgcccgc tccttctcgct ttcttccctt ccttctcgc cacgttcgcc ggctttcccc    4800
gtcaagctct aaatcggggg ctccctttag ggttccgatt tagtgcttta cggcacctcg    4860
accccaaaaa acttgattag ggtgatggtt cacgtagtgg gccatcgccc tgatagacgg    4920
tttttcgccc tttgacgttg gagtccacgt tctttaatag tggactcttg ttccaaactg    4980
gaacaacact caaccctatc tcggtctatt cttttgattt ataagggatt ttgccgattt    5040
cggcctattg gttaaaaaat gagctgattt aacaaaaatt taacgcgaat tttaacaaaa    5100
tattaacgtt tacaatttaa atatttgctt atacaatctt cctgtttttg ggcttttct    5160
gattatcaac cggggtacat atgattgaca tgctagtttt acgattaccg ttcatcgatt    5220
ctcttgtttg ctccagactc tcaggcaatg acctgataagc ctttgtagag acctctcaaa    5280
aatagctacc ctctccggca tgaatttatc agctagaacg gttgaatatc atattgatgg    5340
tgatttgact gtctccggcc tttctcaccc gtttgaatct ttacctacac attactcagg    5400
cattgcattt aaaatatatg agggttctaa aaattttat ccttgcgttg aaataaaggc    5460
ttctcccgca aaagtattac agggtcataa tgttttttggt acaaccgatt tagctttatg    5520
ctctgaggct ttattgctta attttgctaa ttctttgcct tgcctgtatg atttattgga    5580
tgttggaatc gcctgatgcg gtattttctc cttacgcatc tgtgcggtat ttcacaccgc    5640
atatggtgca ctctcagtac aatctgctct gatgccgcat agttaagcca gccccgacac    5700
ccgccaacac ccgctgacgc gccctgacgg gcttgtctgc tcccggcatc cgcttacaga    5760
caagctgtga ccgtctccgg gagctgcatg tgtcagaggt tttcaccgtc atcaccgaaa    5820
cgcgcgagac gaaagggcct cgtgatacgc ctatttttat aggttaatgt catgataata    5880
atggtttctt agacgtcagg tggcactttt cggggaaatg tgcgcggaac ccctatttgt    5940
ttatttttct aaatacattc aaatatgtat ccgctcatga gacaataacc ctgataaatg    6000
cttcaataat attgaaaaag gaagagtatg agtattcaac atttccgtgt cgcccttatt    6060
ccctttttg cggcattttg ccttcctgtt tttgctcacc cagaaacgct ggtgaaagta    6120
aaagatgctg aagatcagtt gggtgcacga gtgggttaca tcgaactgga tctcaacagc    6180
ggtaagatcc ttgagagttt tcgccccgaa gaacgttttc caatgatgag cactttaaa    6240
gttctgctat gtggcgcggt attatcccgt attgacgccg ggcaagagca actcggtcgc    6300
cgcatacact attctcagaa tgacttggtt gagtactcac cagtcacaga aaagcatctt    6360
acggatggca tgacagtaag agaattatgc agtgctgcca taaccatgag tgataacact    6420
gcggccaact tacttctgac aacgatcgga ggaccgaagg agctaaccgc ttttttgcac    6480
aacatggggg atcatgtaac tcgccttgat cgttgggaac cggagctgaa tgaagccata    6540
ccaaacgacg agcgtgacac cacgatgcct gtagcaatgg caacaacgtt gcgcaaacta    6600
ttaactggcg aactacttac tctagcttcc cggcaacaat taatagactg gatggaggcg    6660
gataaagttg caggaccact tctgcgctcg gcccttccgg ctggctggtt tattgctgat    6720
aaatctggag ccggtgagcg tgggtctcgc ggtatcattg cagcactggg gccagatggt    6780
aagccctccc gtatcgtagt tatctacacg acggggagtc aggcaactat ggatgaacga    6840
aatagacaga tcgctgagat aggtgcctca ctgattaagc attggtaact gtcagaccaa    6900
gtttactcat atatacttta gattgattta aaacttcatt tttaatttaa aaggatctag    6960
gtgaagatc ttttttgataa tctcatgacc aaaatccctt aacgtgagtt ttcgttccac    7020
tgagcgtcag accccgtaga aaagatcaaa ggatcttctt gagatccttt ttttctgcgc    7080
gtaatctgct gcttgcaaac aaaaaaacca ccgctaccag cggtggtttg tttgccggat    7140
caagagctac caactctttt tccgaaggta actggcttca gcagagcgca gataccaaat    7200
actgtccttc tagtgtagcc gtagttaggc caccacttca agaactctgt agcaccgcct    7260
acatacctcg ctctgctaat cctgttacca gtggctgctg ccagtggcga taagtcgtgt    7320
cttaccgggt tggactcaag acgatagtta ccggataagg cgcagcggtc gggctgaacg    7380
gggggttcgt gcacacagcc cagcttggag cgaacgacct acaccgaact gagatacccta    7440
```

```
cagcgtgagc tatgagaaag cgccacgctt cccgaaggga gaaaggcgga caggtatccg   7500
gtaagcggca gggtcggaac aggagagcgc acgagggagc ttccagggggg aaacgcctgg   7560
tatctttata gtcctgtcgg gtttcgccac ctctgacttg agcgtcgatt tttgtgatgc   7620
tcgtcagggg ggcggagcct atggaaaaac gccagcaacg cggcctttt  acggttcctg   7680
gccttttgct ggccttttgc tcacatgttc tttcctgcgt tatccctga  ttctgtggat   7740
aaccgtatta ccgcctttga gtgagctgat accgctcgcc gcagccgaac gaccgagcgc   7800
agcgagtcag tgagcgagga agcggaagag cgcccaatac gcaaaccgcc tctccccgcg   7860
cgttggccga ttcattaatg                                                7880
```

SEQ ID NO: 52            moltype = DNA   length = 7593
FEATURE                  Location/Qualifiers
misc_feature             1..7593
                         note = Synthesized rAAV PD-1 Exon5_MND-BFP_distal
                         5'-Homology Arm construct
source                   1..7593
                         mol_type = other DNA
                         organism = synthetic construct
SEQUENCE: 52
```
cagctgcgcg ctcgctcgct cactgaggcc gccggcaa  agcccgggcg tcggcgacc    60
tttggtcgcc cggcctcagt gagcgagcga gcgcgcagag agggagtggc caactccatc  120
actagggggt ccttgtagtt aatgattaac ccgccatgct acttatctac gtagaattcg  180
gccccactgc ccactgccca gggcagcaat gcccatacca cgtggtccca gctccgagct  240
tgtcctgaaa aggggggcaaa gactggaccc tgagcctgcc aagggggccac actcctccca  300
gggctgggggt ctccatgggc aggccccccac ccacccagac cagttacact cccctgtgcc  360
agagcagtgc agacaggacc aggccaggat gcccaagggt caggggctgg ggatgggtag  420
cccccaaaca gccctttctg aggggactggc ctcaacgggga aaggggggtga aggctcttag  480
taggaaatca gggagaccca agtcagagcc aggcgctgtg cagaagctgc agcctcacgt  540
agaaggaaga gcctctgcag tggaggccag tgcccatccc cgggtggcag aggcccagc  600
agagacttct caatgacatt ccagctgggg tggcccttcc agagcccttg ctgcccgagg  660
gatgtgagca ggtggccggg gaggctttgt ggggcaccaa agccccttcc tcacctctct  720
ccatctctca gactcccag acaggccctg gaaccccccc accttctccc cagccctgct  780
cgtggtgacc aagggggaca acgccacctt cacctgcagc ttctccaaca catcggagag  840
cttcgtgcta aactggtacc gcatgagccc cagcaaccag acggacaagc tggccgcctt  900
ccccgaggac cgcagccagc ccggcgagga ctgccgcttc cgtgtcacac aactgcccaa  960
cgggcgtgac ttccacatga gcgtggtcag ggcccggcgc aatgacagcg gcacctacct  1020
ctgtggggcc atctccctgg ccccaaggc  gcagatcaaa gagagcctgc gggcagagct  1080
cagggtgaca ggtgcggcct cggaggcccc gggccagggg tgagctgagc cggtcctggg  1140
gtgggttgcc cctcctgcac aggatcagga gctccaggtt cgtaggggcag gaccccca    1200
gctccagtcc agggctctgt cctgacctg gggaatggtg accggcatct ctgtcctcta   1260
gctctggaag cacccccagcc cctctagtct gccctcaccc ctgaccctga ccctccaccc  1320
tgaccccgtc ctaaccctg acctttgtgc ccttccagag agaaggggcag aagtgccacc  1380
agcccacccc agccctccac ccaggccagc cggccagttc caaaccctgg tggttggttgt  1440
cgtggggggc ctgctgggca gcctggtgct gctagtctgg gtcctggccg tcatctatgc  1500
atgaacagag aaacaggaga atatgggcca acaggatat  ctgtggtaag cagttcctgc  1560
cccggctcag ggcaagaac agttggaaca gcagaatatg ggccaaacag gatatctgtg  1620
gtaagcagtt cctgccccgg ctcagggcca agaacagatg tccccagat  gcggtcccgc  1680
cctcagcagt ttctagagaa ccatcagatg tttccaagga cctgaaatga  1740
ccctgtgcct tatttgaact aaccaatcag ttcgcttctc gcttctgttc gcgcgcttct  1800
gctccccgag ctctatataa gcagagctcg tttagtgaac cgtcagatcg cctggagacg  1860
ccatccacgc tgttttgact tccatagaag gatctcgagg ccaccatggc tagcgagctg  1920
attaaggaga acatgcacat gaagctgtac atggagggca ccgtgacaa  ccatcactcg  1980
aagtgcacat ccgagggcga aggcaagccc tacgagggca cccagaccat gagaatcaag  2040
gtggtcgagg gcggccctct cccccttcgcc ttcgacatcc tggctactag cttcctctac  2100
ggcagcaaga ccttcatcaa ccacacccag ggcatccccg acttcttcaa gcagtccttc  2160
cctgagggct tcacatggga gagagtcacc acatacgagg acgggggcgt gctgaccgct  2220
acccaggaca ccagcctcca ggacggctgc ctcatctaca acgtcaagat cagagggggtg  2280
aacttcacat ccaacggccc tgtgatgcag aagaaaacac tcggctggga ggcctttcacc  2340
gagacgctgt accccgctga cggcggcctg aaggcagaa  acgacatggc cctgaagctc  2400
gtgggcggga gccatctgat cgcaaacatc aagaccacat atagatccaa gaaacccgct  2460
aagaacctca agatgcctgg cgtctactat gtggactaca gactggaaag aatcaaggag  2520
gccaacaacg agacctacgt cgagcagcac gaggtggcag tggccagata ctgcgacctc  2580
cctagcaaac tggggcacaa gctaaattga aagctttgct ttatttgtga aatttgtgat  2640
gctattgctt tatttgtaac cattataagc tgcaataaac aagtttaaca acaacaattg  2700
cattcatttt atgttttcagg ttcaggggga ggtgtgggga gttttttaaa gtcgacccac  2760
cattgtcttt cctagcggaa tgggccactc atccccgcc  cgcagggggct cagctgacgg  2820
ccctcggagt gccagccac tgaggcctga ggatggacac tgctcttggc ccctctgacc  2880
ggcttccttg gccaccagtg ttctgcagac cctccaccat gagcccgggt cagcgcattt  2940
cctcaggaga agcaggcagg gtgcaggcca ttgcaggccg tccaggggct gagctgcctg  3000
gggcgaccg gggtccagc ctgcacctgc accaggcaca gcccaccac  aggactcatg  3060
tctcaatgcc cacagtgagc ccaggcagca ggtgtcaccg tccccctacag ggaggggccag  3120
atgcagtcac tgcttcaggt cctgccagca cagagctgcc tgcgtccagc ccctgaatc   3180
tctgctgctg ctgctgctgc tgctgctgct gcctgcggcc cgggggctgaa ggcgccgtgg  3240
ccctgcctga cgcccggag ccctcctgcct gaacttgggg gctggttgga gatggccttg  3300
gagcagccaa ggtccccctg ccagtggcat ccgcaaacgc cctccccaaga  3360
ctgggcacag gagtgggagg tacatggggc tggggactcc ccaggagtta tctgctccct  3420
gcaggcctag agaagtttca ggggaaggtca gaagagctcc tggctgtggt gggcagggca  3480
ggaaaccccct ccaccttttac acatgcccag gcagcacctc aggccctttg tggggcaggg  3540
aagctgaggc agtaagcggg caggcagagc tggaggcctt tcaggcccag ccagcactct  3600
ggcctcctgc cgcgcattc cacccagcc cctcacacca ctcggagag  ggacatccta   3660
```

```
cggtcccaag gtcaggaggg cagggctggg gttgactcag gccccctccca gctgtggcca    3720
cctgggtgtt gggagggcag aagtgcaggc acctagggcc ccccatgtgc ccaccctggg    3780
agctctcctt ggaacccatt cctgaaatta tttaaagggg ttggccggac tagttacgta    3840
gataagtagc atggcgggtt aatcattaac tacaaggaac ccctagtgat ggagttggcc    3900
actccctctc tgccgctcg ctcgctcact gaggccgggc gaccaaaggt cgcccgacgc    3960
ccgggctttg cccgggcggc ctcagtgagc gagcgagcgc gccagctggc gtaatagcga    4020
agaggcccgc accgatcgcc cttcccaaca gttgcgcagc ctgaatggcg aatggcgatt    4080
ccgttgcaat ggctggcggt aatattgttc tggatattac cagcaaggcc gatagtttga    4140
gttcttctac tcaggcaagt gatgttatta ctaatcaaag aagtattgcg acaacggtta    4200
atttgcgtga tggacagact cttttactcg gtgcctcac tgattataaa aacacttctc    4260
aggattctgg cgtaccgttc ctgtctaaaa tcccttaat cggcctcctg tttagctccc    4320
gctctgattc taacgaggaa agcacgttat acgtgctcgt caaagcaacc atagtacgcg    4380
ccctgtagcg gcgcattaag cgcggcgggt gtggtggtta cgcgcagcgt gaccgctaca    4440
cttgccagcg ccctagcgcc cgctcctttc gctttcttcc cttcctttct cgccacgttc    4500
gccggctttc cccgtcaagc tctaaatcgg gggctcccct tagggttccg atttagtgct    4560
ttacggcacc tcgaccccaa aaaacttgat tagggtgatg gttcacgtag tgggccatcg    4620
ccctgataga cggtttttcg ccctttgacg ttggagtcca cgttctttaa tagtggactc    4680
ttgttccaaa ctggaacaac actcaaccct atctcggtct attcttttga tttataaggg    4740
attttgccga tttcggccta ttggttaaaa aatgagctga tttaacaaaa atttaacgcg    4800
aattttaaca aaatattaac gtttacaatt taaatatttg cttatacaat cttcctgttt    4860
ttggggcttt tctgattatc aaccgggta catatgattg acatgctagt tttacgatta    4920
ccgttcatcg attctcttgt ttgctccaga ctctcaggca atgacctgat agcctttgta    4980
gagacctctc aaaaatagct acccctctccg gcatgaattt atcagctaga acggttgaat    5040
atcatattga tggtgatttg actgtctccg gcctttctca cccgtttgaa tctttaccta    5100
cacattactc aggcattgca tttaaaatat atgagggttc taaaaatttt tatccttgcg    5160
ttgaaataaa ggcttctccc gcaaaagtat tacagggtca taatgttttt ggtacaaccg    5220
atttagcttt atgctctgag gctttattgc ttaattttgc taattctttg ccttgcctgt    5280
atgatttatt ggatgttgga atcgcctgat gcggtatttt ctccttacgc atctgtgcgg    5340
tatttcacac cgcatatggt gcactctcag tacaatctgc tctgatgccg catagttaag    5400
ccagccccga cacccgccaa cacccgctga cgcgccctga cgggcttgtc tgctcccggc    5460
atccgcttac agacaagctg tgaccgtctc cgggagctgc atgtgtcaga ggttttcacc    5520
gtcatcaccg aaacgcgcga cgaaaaggg cctcgtgata cgcctatttt tataggttaa    5580
tgtcatgata taatggtttc ttagacgtc aggtggcact tttcggggaa atgtgcgcgg    5640
aacccctatt tgtttatttt tctaaataca ttcaaatata tatccgctca tgagacaata    5700
accctgataa atgcttcaat aatattgaaa aaggaagagt atgagtattc aacatttccg    5760
tgtcgccctt attccctttt tgcggcattt tgccttcct gtttttgctc acccagaaac    5820
gctggtgaaa gtaaaagatg ctgaagatca gttgggtgca cgagtgggtt acatcgaact    5880
ggatctcaac agcggtaaga tccttgagag ttttcgcccc gaagaacgtt ttccaatgat    5940
gagcactttt aaagttctgc tatgtggcgc ggtattatcc cgtattgacg ccgggcaaga    6000
gcaactcggt cgccgcatac actattctca gaatgacttg gttgagtact caccagtcac    6060
agaaaagcat cttacggatg gcatgacagt aagagaatta tgcagtgctg ccataaccat    6120
gagtgataac actgcggcca acttacttct gacaacgatc ggaggaccga aggagctaac    6180
cgcttttttg cacaacatgg gggatcatgt aactcgcctt gatcgttgga accgggagct    6240
gaatgaagcc ataccaaacg acgagcgtga ccacgatgct cctgtagcaa tggcaacaac    6300
gttgcgcaaa ctattaactg gcgaactact tactctagct tcccggcaac aattaataga    6360
ctggatggag gcggataaag ttgcaggacc acttctgcgc tcggcccttc cggctggctg    6420
gtttattgct gataaatctg gagccggtga gcgtgggtct cgcggtatca ttgcagcact    6480
ggggccagat ggtaagccct cccgtatcgt agttatctac acgacgggga gtcaggcaac    6540
tatgatgaa cgaaatagac agatcgctga gataggtgcc tcactgatta gcattggta    6600
actgtcagac caagtttact catatatact ttagattgat ttaaaacttc attttttaatt    6660
taaaaggatc taggtgaaga tccttttga taatctcatg accaaaatcc cttaacgtga    6720
gttttcgttc cactgagcgt cagacccccg agaaaagatc aaaggatctt cttgagatcc    6780
tttttttctg cgcgtaatct gctgcttgca acaaaaaaaa ccaccgctac cagcggtggt    6840
ttgtttgccg gatcaagagc taccaactct ttttccgaag gtaactggct tcagcagagc    6900
gcagatacca aatactgtcc ttctagtgta gccgtagtta ggccaccact tcaagaactc    6960
tgtagcaccg cctacatacc tcgctctgct aatcctgtta ccagtggctg ctgccagtgg    7020
cgataagtcg tgtcttaccg ggttggactc aagacgatag ttaccggata aggcgcagcg    7080
gtcgggctga acggggggtt cgtgcacaca gcccagcttg gagcgaacga cctacaccga    7140
actgagatac ctacagcgtg agctatgaga aagcgccacg cttcccgaag ggagaaaggc    7200
ggacaggtat ccggtaagcg gcagggtcgg aacaggagag cgcacgaggg agcttccagg    7260
gggaaacgcc tggtatcttt atagtcctgt cgggtttcgc cacctctgac ttgagcgtcg    7320
atttttgtga tgctcgtcag gggggcggag cctatggaaa aacgccagca acgcggcctt    7380
tttacggttc ctggcctttt gctggccttt tgctcacatg ttctttcctg cgttatccc    7440
tgattctgtg gataacgta ttaccgcctt tgagtgagct gataccgctc gccgcagccg    7500
aacgaccgag cgcagcgagt cagtgagcga ggaagcggaa gagcgcccaa tacgcaaacc    7560
gcctctcccc gcgcgttggc cgattcatta atg                                7593
```

SEQ ID NO: 53    moltype = DNA   length = 6718
FEATURE          Location/Qualifiers
misc_feature     1..6718
                 note = Synthesized rAAV PD-1 Exon1_MND-GFP construct
source           1..6718
                 mol_type = other DNA
                 organism = synthetic construct
SEQUENCE: 53

```
cagctgcgcg ctcgctcgct cactgaggcc gccccggcaa agcccgggcg tcgggcgacc      60
tttggtcgcc cggcctcagt gagcgagcga gcgcgcagag agggagtggc caactccatc    120
actaggggtt ccttgtagtt aatgattaac cgccatgct acttatctac gtaaggctgt    180
tgcaggcatc acacggtgga aagatctgga actgtgccca tggtgtgagg ccatccacaa    240
```

-continued

```
ggtggaagct ttgagggga gccgattagc catggacagt tgtcattcag tagggtcacc    300
tgtgccccag cgaaggggga tgggccggga aggcagaggc caggcacctg ccccagcag    360
gggcagaggc tgtgggcagc cgggaggctc ccagaggctc cgacagaatg ggagtggggt    420
tgagcccacc cctcactgca gcccaggaac ctgagcccag agggggccac ccaccttccc    480
caggcaggga ggcccggccc ccaggagagat gggggggatg gggaggaga agggcctgcc    540
cccaccggc agcctcagga ggggcagctc gggcgggata tggaaagagg ccacagcagt    600
gagcagagac acagaggagg aaggggccct gagctgggga gacccccacg gggtagggcg    660
tgggggccac gggcccacct cctccccatc tcctctgtct ccctgtctct gtctctctct    720
ccctcccca ccctctcccc agtcctaccc cctcctcacc cctcctcccc cagcactgc    780
tctgtcactc tcgcccacgt ggatgtggag gaagagggg cgggagcaag gggcgggcac    840
cctcccttca acctgacctg ggacagtttc ccttccgctc acctccgcct gagcagtgga    900
gaaggcggca ctctggtggg gctgctccaa cgcgtgaaca gagaaacagg agaatatggg    960
ccaaacagga tatctgtggt aagcagttcc tgccccggct caggggccaag aacagttgga   1020
acagcagaat atgggccaaa caggatatct gtggtaagca gttcctgccc cggctcaggg   1080
ccaagaacag atggtcccca gatgcggtcc cgccctcagc agtttctaga gaaccatcag   1140
atgtttccag ggtgccccaa ggacctgaaa tgacctgtg ccttatttga actaaccaat   1200
cagttcgctt ctcgcttctg ttcgcgcgct tctgctcccc gagctctata taagcagagc   1260
tcgtttagtg aaccgtcaga tcgccatcca cgctgttttg acttccatag               1320
aaggatctcg aggccaccat ggtgagcaag ggcgaggagc tgttcaccgg ggtggtgccc   1380
atcctggtcg agctggacgg cgacgtaaac ggccacaagt tcagcgtgtc cggcgagggc   1440
gagggcgatg ccacctacgg caagctgacc ctgaagttca tctgcaccac cggcaagctg   1500
cccgtgccct ggcccaccct cgtgaccacc ctgacctacg gcgtgcagtg cttcagccgc   1560
taccccgacc acatgaagca gcacgacttc ttcaagtccg ccatgcccga aggctacgtc   1620
caggagcgca ccatcttctt caaggacgac ggcaactaca agacccgcgc cgaggtgaag   1680
ttcgagggcg acaccctggt gaaccgcatc gagctgaagg gcatcgactt caaggaggac   1740
ggcaacatcc tggggcacaa gctggagtac aactacaaca gccacaacgt ctatatcatg   1800
gccgacaagc agaagaacgg catcaaggtg aacttcaaga tccgccacaa catcgaggac   1860
ggcagcgtgc agctcgccga ccactaccag cagaacaccc ccatcggcga cggccccgtg   1920
ctgctgcccg acaaccacta cctgagcacc cagtccgccc tgagcaaaga ccccaacgag   1980
aagcgcgatc acatggtcct gctggagttc gtgaccgccg ccgggatcac tctcggcatg   2040
gacgagctgt acaagtaagc ggccgcgctt tatttgtgaa atttgtgatg ctattgcttt   2100
atttgtaacc attataagct gcaataaaca agttaacaac aacaattgca ttcatttat   2160
gtttcaggtt caggggggaga tgtgggaggt tttttaaagc ctcaccggtt ctgggcggtg   2220
ctacaactgg gctggcggcc aggatggttc ttaggtaggg ggggtcggcg gtcaggtgtc   2280
ccagagccag gggtctggag ggaccttcca ccctcagtcc ctggcaggtc ggggggtgct   2340
gaggcgggcc tggccctggc agcccagggg tcccggagcg aggggtctgg agggaccttt   2400
cactctcagt ccctgggcagg tcgggggggtg ctgtggcagg cccagccttg gccccagct   2460
ctgcccctta ccctgagctg tgtggctttg ggcagctcga actcctgggt tcctctctgg   2520
gccccaactc ctccccctggc ccaagtcccc tcttttgctcc tgggcaggca ggacctctgt   2580
ccctctcag ccggtccttg gggctgcgtg tttctgtaga atgacgggtc aggctggcca   2640
gaaccccaaa ccttggccgt ggggagtctg cgtggcgggct ctgccttgcc caggcatcct   2700
tggtcctcac tcgagtttc ctaaggatgg gatgagcccc atgtgggact aaccttggct   2760
ttacgacgtc aaagtttaga tgagctggtg atatttttct cattatatcc aaagtgtacc   2820
tgttcgagtg aggacagttc ttctgtctcc aggatccctc ctgggtgggg attgtgcccg   2880
cctgggtctc tgcccagatt ccagggctct ccccgagccc tgttcagacc atccgtgggg   2940
gaggccttgg cctcactctt acgtagataa gtagcatggc gggttaatca ttaactacaa   3000
ggaacccta gtgatggagt tggccactcc ctctctgcgc gctcgctcgc tcactgaggc   3060
cgggcgacca aaggtcgccc gacgcccggg ctttgcccgg gcggcctcag tgagcgagcg   3120
agcgcgccag ctgcgtaat agcgaagagg cccgcaccga tcgcccttcc caacagttgc   3180
gcagcctgaa tggcgaatgg cgattccgtt gcaatggctg gcgtaatat tgttctggat   3240
attaccagca aggccgatag tttgagttct tctactcagg caagtgatgt tattactaat   3300
caaagaagta ttgcgacaac ggttaatttg cgtgatggac agactctttt actcggtggc   3360
ctcactgatt ataaaaacac ttctcaggat tctggcgtac cgttcctgtc taaaatccct   3420
ttaatcggcc tcctgtttag ctcccgctct gattctaacg aggaaagcac gttatacgtg   3480
ctcgtcaaag caaccatagt acgcgccctg tagcggcgca ttaagcgcgg cgggtgtggt   3540
ggttacgcgc agcgtgaccg ctacacttgc cagcgcccta gcgcccgctc ctttcgcttt   3600
cttcccttcc tttctcgcca cgttcgccgg cttcccccgt caagctctaa atcgggggct   3660
ccctttaggg ttccgattta gtgctttacg gcacctcgac cccaaaaaac ttgattaggg   3720
tgatggttca cgtagtgggc catcgccctg atagacggtt tttcgccctt tgacgttgga   3780
gtccacgttc tttaatagtg gactcttgtt ccaaactgga acaacactca accctatctc   3840
ggtctattct tttgatttat aagggatttt gccgatttcg gcctattggt taaaaaatga   3900
gctgatttaa caaaaattta acgcgaattt taacaaaata ttaacgttta caatttaaat   3960
atttgcttat acaatcttcc tgttttggg cttttctga ttatcaaccg ggtacatat   4020
gattgacatg ctagttttac gattaccgtt catcgattct ctgtttgct ccagactcc   4080
aggcaatgac ctgatagcct ttgtagagac ctctcaaaaa tagctaccc ctccggcatg   4140
aatttatcag ctagaacggt tgaatatcat attgatggtg atttgactgt ctccggcctt   4200
tctcacccgt ttgaatcttt acctacacat tactcaggca ttgcatttaa aatatatgag   4260
ggttctaaaa attttatcc ttgcgttgaa ataaaggctt ctcccgcaaa agtattacag   4320
gtcataatgt tttttggtac aaccgattta gctttatgct ctgaggcttt attgcttaat   4380
tttgctaatt ctttgccttg cctgtatgat ttattggatg ttggaatcgc ctgatgcggt   4440
atttctcct tacgcatctg tgcggtattt cacaccgcat atggtgcact ctcagtacaa   4500
tctgctctga tgccgcatag ttaagccagc ccgacaccc gccaacaccc gctgacgcgc   4560
cctgacgggc ttgtctgctc ccggcatccg cttacagaca agctgtgacc gtctccggga   4620
gctgcatgtg tcagaggttt tcaccgtcat caccgaaacg cgcgagacga aagggcctcg   4680
tgatacgcct atttttatag gttaatgtca tgataataat ggtttcttag acgtcaggtg   4740
gcacttttcg gggaaatgtg cgcggaaccc ctatttgttt attttctaa atacattcaa   4800
atatgtatcc gctcatgaga caataaccct gataaatgct tcaataatat tgaaaaagga   4860
agagtatgag tattcaacat ttccgtgtcg cccttattcc cttttttgcg cattttgcc   4920
ttcctgtttt tgctcaccca gaaacgctgg tgaaagtaaa agatgctgaa gatcagttgg   4980
```

```
gtgcacgagt gggttacatc gaactggatc tcaacagcgg taagatcctt gagagttttc   5040
gccccgaaga acgttttcca atgatgagca cttttaaagt tctgctatgt ggcgcggtat   5100
tatcccgtat tgacgccggg caagagcaac tcggtcgccg catacactat tctcagaatg   5160
acttggttga gtactcacca gtcacagaaa agcatcttac ggatggcatg acagtaagag   5220
aattatgcag tgctgccata accatgagtg ataaacactg ggccaactta cttctgacaa   5280
cgatcggagg accgaaggag ctaaccgctt ttttgcacaa catggggggat catgtaactc   5340
gccttgatcg ttgggaaccg gagctgaatg aagccatacc aaacgacgag cgtgacacca   5400
cgatgcctgt agcaatggca acaacgttgc gcaaactatt aactggcgaa ctacttactc   5460
tagcttcccg gcaacaatta atagactgga tggaggcgga taaagttgca ggaccacttc   5520
tgcgctcggc ccttccggct ggctggttta ttgctgataa atctgagcc ggtgagcgtg   5580
ggtctcgcgg tatcattgca gcactggggc cagatggtaa gccctcccgt atcgtagtta   5640
tctacacgac ggggagtcag gcaactatgg atgaacgaaa tagacagatc gctgagatag   5700
gtgcctcact gattaagcat tggtaactgt cagaccaagt ttactcatat atactttaga   5760
ttgatttaaa acttcatttt taatttaaaa ggatctaggt gaagatcctt tttgataatc   5820
tcatgaccaa aatcccttaa cgtgagtttt cgttccactg agcgtcagac cccgtagaaa   5880
agatcaaagg atcttcttga gatcctttt tctgcgcgt aatctgctgc ttgcaaacaa   5940
aaaaaccacc gctaccagcg gtggtttgtt tgccggatca agagctacca actcttttc   6000
cgaaggtaac tggcttcagc agagcgcaga taccaaatac tgtccttcta gtgtagccgt   6060
agttaggcca ccacttcaag aactctgtag caccgcctac atacctcgct ctgctaatcc   6120
tgttaccagt ggctgctgcc agtggcgata agtcgtgtct taccgggttg gactcaagac   6180
gatagttacc ggataaggcg cagcggtcgg gctgaacggg gggttcgtgc acacagccca   6240
gcttggagcg aacgacctac accgaactga gatacctaca gcgtgagcta tgagaaagcg   6300
ccacgcttcc cgaagggaga aaggcggaca ggtatccggt aagcggcagg gtcggaacag   6360
gagagcgcac gagggagctt ccaggggggaa acgcctggta tctttatagt cctgtcgggt   6420
ttcgccacct ctgacttgag cgtcgatttt tgtgatgctc gtcagggggg cggagcctat   6480
ggaaaaacgc cagcaacgcg gcctttttac ggttcctggc cttttgctgg ccttttgctc   6540
acatgttctt tcctgcgtta tcccctgatt ctgtggataa ccgtattacc gcctttgagt   6600
gagctgatac cgctcgccgc agccgaacga ccgagcgcag cgagtcagtg agcgaggaag   6660
cggaagagcg cccaatacgc aaaccgcctc tccccgcgcg ttggccgatt cattaatg    6718

SEQ ID NO: 54          moltype = DNA  length = 756
FEATURE                Location/Qualifiers
source                 1..756
                       mol_type = genomic DNA
                       organism = Homo sapiens
SEQUENCE: 54
aggctgttgc aggcatcaca cggtggaaag atctggaact gtggccatgg tgtgaggcca    60
tccacaaggt ggaagctttg aggggagcc gattagccat ggacagttgt cattcagtag    120
ggtcacctgt gccccagcga aggggatgg gccgggaagg caggccgg gcacctgccc     180
ccagcagggg cagaggctgt gggcagccgg gaggctccca gaggctccga cagaatggga    240
gtggggttga gcccacccct cactgcagcc caggaacctg agcccagagg gggccaccca    300
ccttccccag gcagggaggc ccggccccca gggagatggg ggggatgggg gagagaaggg    360
gcctgcccc accggccagc ctcaggaggg gcagctcggg gggatatgg aaagaggcca    420
cagcagtgag cagagacaca gaggaggaag gggccctgag ctggggagac cccacgggg    480
tagggcgtgg gggccacggg cccacctcct ccccatctcc tctgtctccc tgtctctgtc    540
tctctctccc tccccaccc tctcccagt cctacccct cctcaccct cctccccag     600
cactgcctct gtcactctcg cccacgtgga tgtggaggaa gggggggcgg gagcaagggg    660
cgggcaccct cccttcaacc tgacctggga cagtttccct tccgctcacc tccgcctgag    720
cagtggagaa ggcggcactc tggtggggct gctcca                              756

SEQ ID NO: 55          moltype = DNA  length = 750
FEATURE                Location/Qualifiers
source                 1..750
                       mol_type = genomic DNA
                       organism = Homo sapiens
SEQUENCE: 55
tctgggcggt gctacaactg gctggcggc caggatggtt cttaggtagg tggggtcggc    60
ggtcaggtgt cccagagcca ggggtctgga gggaccttcc accctcagtc cctggcaggt   120
cgggggggtgc tgaggcgggc ctggccctgg cagcccaggg gtcccggagc gagggtctg    180
gagggaccctt tcactctcag tccctggcag gtcggggggt gctgtggcag gcccagcctt   240
ggcccccagc tctgccccctt accctgagct gtgtggcttt gggcagctcg aactcctggg    300
ttcctctctg ggcccccaact cctccctgg cccaagtccc ctctttgctc ctgggcaggc    360
aggacctctg tcccctctca gccggtcctt ggggctgcgt gtttctgtag aatgacgggt    420
caggctggcc agaacccaa accttggccg tggggagtct gcgtggccgg tctgccttga    480
ccaggcatcc ttggtcctca ctcgagtttt cctaaggatg ggatgagccc catgtggggac    540
taaccttggc tttacgacgt caaagtttag atgagctggt gatattttc tcattatatc    600
caaagtgtac ctgttcgagt gaggacagtt cttctgtctc caggatccct cctgggtggg    660
gattgtgccc gcctgggtct ctgcccagat tccaggggct tccccgagcc ctgttcagac    720
catccgtggg ggaggccttg gcctcactct                                     750

SEQ ID NO: 56          moltype = DNA  length = 7609
FEATURE                Location/Qualifiers
misc_feature           1..7609
                       note = Synthesized rAAV PD-1 Exon1_MND-CD19CAR construct
source                 1..7609
                       mol_type = other DNA
                       organism = synthetic construct
SEQUENCE: 56
cagctgcgcg ctcgctcgct cactgaggcc gcccgggcaa agcccgggcg tcgggcgacc    60
```

```
tttggtcgcc cggcctcagt gagcgagcga gcgcgcagag agggagtggc caactccatc    120
actaggggtt ccttgtagtt aatgattaac ccgccatgct acttatctac gtaaggctgt    180
tgcaggcatc acacggtgga aagatctgga actgtggcca tggtgtgagg ccatccacaa    240
ggtggaagct tgagggggga gccgattagc catggacagt tgtcattcag tagggtcacc    300
tgtgccccag cgaaggggga tgggccggga aggcagagge caggcacctg cccccagcag    360
gggcagaggc tgtgggcagc cgggaggctc ccagaggctc cgacagaatg ggagtggggt    420
tgagcccacc cctcactgca gcccaggaac ctgagcccag aggggccac ccaccttccc     480
caggcaggga ggcccggccc ccaggagat gggggggatg ggggaggaga agggcctgcc     540
cccacccggc agcctcagga ggggcagctc gggcgggata tggaaagagg ccacagcagt    600
gagcagagac acagaggagg aagggggccct gagctgggga gaccccccacg gggtagggcg   660
tggggggccac gggcccacct cctccccatc tcctctgtct ccctgtctct gtctctctct    720
ccctcccca ccctctcccc agtcctaccc cctcctcacc cctcctcccc cagcactgcc     780
tctgtcactc tcgcccacgt ggatgtggag gaagaggggg cgggagcaag gggcgggcac    840
cctcccttca acctgacctg ggacagtttc ccttccgctc acctccgcct gagcagtgga    900
gaaggcggca ctctggtggg gctgctccaa cgcgtgatcc atcgattagt ccaatttgtt    960
aaagacagga tatcagtggt ccaggctcta gttttgactc aacaatatca ccagctgaag   1020
cctatagagt acgagccata gatagaataa aagatttat ttagtctcca gaaaaagggg   1080
ggaatgaaag accccacctg taggtttggc aagctaggat caaggttagg aacagagaga   1140
cagcagaata tgggccaaac aggatatctg tggtaagcag ttcctgcccc ggctcagggc   1200
caagaacagt tggaacagca gaatatgggc caaacaggat atctgtggta agcagttcct   1260
gccccggctc agggccaaga acagatggtc cccagatgcg gtcccgccct cagcagtttc   1320
tagagaacca tcagatgttt ccagggtgcc ccaaggacct gaaatgaccc tgtgccttat   1380
ttgaactaac caatcagttc gcttctcgct tctgttcgcg cgcttctgct ccccgagctc   1440
aataaaagag cccacaaccc ctcactcggc gcgacgcgtc atagccacca tggccttacc   1500
agtgaccgcc ttgctcctgc cgctggcctt gctgctccac gccgccaggc cggacatcca   1560
gatgacacag actacatcct ccctgtctgc tctctgggga gacagagtca ccatcagttg   1620
cagggcaagt caggacatta gtaaatattt aaattggtat cagcagaaac cagatgggaac  1680
tgttaaactc ctgatctacc atacatcaag attacactca ggagtcccat caaggttcag   1740
tggcagtggg tctggaacag attattctct caccattagc aacctggagc aagaagatat   1800
tgccacttac ttttgccaac agggtaatac gcttccgtac acgttcggag gggggaccaa   1860
gctggagatc acaggtggcg gtggctccgg cggtggtggg tctggtggcg gcggaagcga   1920
ggtgaaactg caggagtcag gacctggcct ggtggcgccc tcacagagcc tgtccgtcac   1980
atgcactgtc tcagggtgtct cattacccga ctatggtgta agctggattc gccagcctcc   2040
acgaaaggg ctggagtggc tgggagtaat atggggtagt gaaaccacat actataattc     2100
agctctcaaa tccagactga ccatcatcaa ggacaactcc aagagccaag ttttcttaaa   2160
aatgaacagt ctgcaaactg atgacacagc catttactac tgtgccaaac attattacta   2220
cggtggtagc tatgctatgg actactgggg tcaaggaacc tcggtcaccg tctcctcaac   2280
cacgacgcca gcgccgcgac caccaacacc ggcgcccacc atgcgtcgc agcccctgtc    2340
cctgcgccca gaggcgtgcc ggcagcggc gggggccgca gtgcacacga gggggctgca    2400
cttcgcctgt gatatctaca tctgggcgcc cttggccggg acttgtgggg tccttctcct   2460
gtcactggtg atcaccctt actgcaaacg gggcagaaag aaactcctgt atatattcaa    2520
acaaccattt atgagaccag tacaaactac tcaagaggaa gatggctgta gctgccgatt   2580
tccagaagaa gaagaaggag gatgtgaact gagagtcaag ttcagcagga gcgcagacgc   2640
cccccgcgtac cagcagggcc agaaccagct ctataacgag ctcaatctag gacgaagaga    2700
ggagtacgat gttttggaca agagacgtgg ccgggaccct gagatggggg gaaagccgag   2760
aaggaagaac cctcaggaag gcctgtacaa tgaactgcag aaagataaga tggcggaggc   2820
ctacagtgag attgggatga aggcgaagcg ccggagggc aaggggcacg atggccttta    2880
ccagggtctc agtacagcca ccaaggacac ctacgacgcc cttcacatgc aggccctgcc   2940
ccctcgctaa gcgccgcgc tttatttgtg aaatttgtga tgctattgct ttatttgtaa    3000
ccattataag ctgcaataaa caagttaaca acaacaattg cattcatttt atgtttcagg   3060
ttcagggga gatgtgggag gtttttaaa gctcaccgat tctgggcggt gctacaactg     3120
ggctggcggc caggatggtt cttaggtagg tggggtcggc ggtcaggtgt cccagagcca   3180
ggggtctgga gggaccttcc accctcagtc cctggcaggt cggggggtgc tgaggcgggc   3240
ctggccctgg cagcccaggg gtcccggagc gaggggtctg gagggacctt tcactctcag   3300
tccctggcag gtcggggggt gctgtggcag gcccagcctt ggccccagc tctgccctt    3360
accctgagct gtgtggcttt ggcagctcg aactcctggg ttcctctctg gcccccaact   3420
cctccctgg cccaagtccc ctctttgctc ctgggcaggc aggacctctg tcccctctca   3480
gccggtcctt ggggctgcgt gtttctgtag aatgacgggt caggctggcc agaaccccaa   3540
accttggccg tggggagtct gcgtggcggc tctgccttcc ccaggcatcc ttggtcctca   3600
ctcgagttttt cctaaggatg ggatgactg catgtgggac taaccttggc tttacgacgt   3660
caaagtttag atgagctggt gatatttttc tcattatatc caaagtgtac ctgttcgagt   3720
gaggacagtt cttctgtctc caggatccct cctgggtggg gattgtgccc gcctgggtct   3780
ctgcccagat tccagggctc tccccgagcc ctgttcagac catccgtggg ggaggccttg   3840
gcctcactct tacgtagata attagcatgg cgggttaatc attaactaca aggaaccct    3900
agtgatggag ttggccactc cctctctgcg cgctcgctcg ctcactgagg ccgggcgacc   3960
aaaggtcgcc cgacgcccgg gctttgcccg ggcggcctca gtgagcgagc gagcgcgcca   4020
gctggcgtaa tagcgaagag gcccgcaccg atcgcccttc ccaacagttg cgcagcctga   4080
atggcgaatg gcgattccgt tgcaatggct ggcggtaata ttgttctgga tattaccagc   4140
aaggccgata gtttgagttc ttactactcag tcaagtgatg tattactaa tcaaagaagt    4200
attgcgacaa cggttaattt gcgtgatgga cagactcttt tactcggtgg cctcactgat   4260
tataaaaaca cttctcagga ttctggcgta ccgttcctgt ctaaaatccc tttaatcggc   4320
ctcctgttta gctcccgctc tgattctaac gaggaaagca cgttatacgt gctcgtcaaa   4380
gcaaccatag tacgcgccct gtagcggcgc attaagcgcg gcgggtgtgg tggttacgcg   4440
cagcgtgacc gctacacttg ccagcgccct agcgcccgct cctttcgctt tcttcccttc   4500
ctttctcgcc acgttcgccg gctttccccg tcaagctcta aatcggggc tccctttagg    4560
gttccgattt agtgctttac ggcacctcga ccccaaaaaa cttgattagg gtgatggttc   4620
acgtagtggg ccatcgccct gatagacggt ttttcgccct ttgacgttgg agtccacgtt   4680
ctttaatagt ggactcttgt tccaaactgg aacaacactc aaccctatct cggtctattc   4740
ttttgattta agggatttt tgccgatttc ggcctattgg ttaaaaaatg agctgattta    4800
```

```
acaaaaattt aacgcgaatt ttaacaaaat attaacgttt acaatttaaa tatttgctta 4860
tacaatcttc ctgtttttgg ggcttttctg attatcaacc ggggtacata tgattgacat 4920
gctagtttta cgattaccgt tcatcgattc tcttgtttgc tccagactct caggcaatga 4980
cctgatagcc tttgtagaga cctctcaaaa atagctaccc tctccggcat gaatttatca 5040
gctagaaccg ttgaatatca tattgatggt gatttgactg tctccggcct ttctcacccg 5100
tttgaatctt tacctacaca ttactcaggc attgcattta aaatatatga gggttctaaa 5160
aattttatc cttgcgttga aataaaggct ctcccgcaa aagtattaca gggtcataat 5220
gttttttggta caaccgattt agctttatgc tctgaggctt tattgcttaa ttttgctaat 5280
tctttgcctt gcctgtatga tttattggat gttggaatcg cctgatgcgg tatttctctg 5340
ttacgcatct gtgcggtatt tcacaccgca tatggtgcac tctcagtaca atctgctctg 5400
atgccgcata gttaagccag ccccgacacc cgccaacacc cgctgacgcg ccctgacggg 5460
cttgtctgct cccggcatcc gcttacagac aagctgtgac cgtctccggg agctgcatgt 5520
gtcagaggtt ttcaccgtca tcaccgaaac gcgcgagacg aaagggcctc gtgatacgcc 5580
tatttttata ggttaatgtc atgataataa tggtttctta gacgtcaggt ggcacttttc 5640
ggggaaatgt gcgcggaacc cctatttgtt tatttttcta aatacattca aatatgtatc 5700
cgctcatgag acaataaccc tgataaatgc ttcaataata ttgaaaaagg aagagtatga 5760
gtattcaaca tttccgtgtc gcccttattc cctttttgc ggcattttgc cttcctgttt 5820
ttgctcaccc agaaacgctg tgaaagtaa aagatgctga agatcagttg ggtgcacgag 5880
tgggttacat cgaactggat ctcaacagcg gtaagatcct tgagagtttt cgccccgaag 5940
aacgttttcc aatgatgagc acttttaaag ttctgctatg tggcgcggta ttatcccgta 6000
ttgacgccgg gcaagagcaa ctcggtcgcc gcatacacta ttctcagaat gacttggttg 6060
agtactcacc agtcacagaa aagcatctta cggatggcat gacagtaaga attatgca 6120
gtgctgccat aaccatgagt gataacactg cggccaactt acttctgaca acgatcggag 6180
gaccgaagga gctaaccgct tttttgcaca acatggggga tcatgtaact cgccttgatc 6240
gttgggaacc ggagctgaat gaagccatac caaacgacga gcgtgacacc acgatgcctg 6300
tagcaatggc aacaacgttg cgcaaactat taactggcga actacttact ctagccttcc 6360
ggcaacaatt aatagactgg atggaggcgg ataaagttgc aggaccactt ctgcgctcgg 6420
cccttccggc tggctggttt attgctgata atctggagc cggtgagcgt gggtctcgcg 6480
gtatcattgc agcactgggg ccagatggta agccctcccg tatcgtagtt atctacacga 6540
cggggagtca ggcaactatg gatgaacgaa atagacagat cgctgagata ggtgcctcac 6600
tgattaagca ttggtaactg tcagaccaag tttactcata tatactttag attgatttaa 6660
aacttcattt taattttaaa aggatctagg tgaagatcct ttttgataat ctcatgacca 6720
aaatccctta acgtgagttt tcgttccact gagcgtcaga ccccgtagaa aagatcaaag 6780
gatcttcttg agatccttt tttctgcgcg taatctgctg cttgcaaaca aaaaaaccac 6840
cgctaccagc ggtggtttgt ttgccggatc aagagctacc aactctttt ccgaaggtaa 6900
ctggcttcag cagagcgcag ataccaaata ctgtccttct agtgtagccg tagttaggcc 6960
accacttcaa gaactctgta gcaccgccta catacctcgc tctgctaatc ctgttaccag 7020
tggctgctgc cagtggcgat aagtcgtgtc ttaccgggtt ggactcaaga cgatagttac 7080
cggataaggc gcagcggtcg ggctgaacgg ggggttcgtg cacacagccc agcttggagc 7140
gaacgaccta caccgaactg agatacctac agcgtgagct atgagaaagc gccacgcttc 7200
ccgaagggag aaaggcggac aggtatccgg taagcggcag ggtcggaaca ggagagcgca 7260
cgagggagct tccaggggga aacgcctggt atctttatag tcctgtcggg tttcgccacc 7320
tctgacttga gcgtcgattt ttgtgatgct cgtcaggggg gcggagccta tggaaaaacg 7380
ccagcaacgc ggcctttta cggttcctgg ccttttgctg gccttttgct cacatgttct 7440
ttcctgcgtt atccctgat tctgtggata accgtattac cgcctttgag tgagctgata 7500
ccgctcgccg cagccgaacg accgagcgca gcgagtcagt gagcgaggaa gcggaagagc 7560
gcccaatacg caaaccgcct ctccccgcgc gttggccgat tcattaatg 7609
```

SEQ ID NO: 57   moltype = DNA   length = 7492
FEATURE     Location/Qualifiers
misc_feature   1..7492
        note = Synthesized rAAV PD-1 Exon1_MND-BCMACAR construct
source      1..7492
        mol_type = other DNA
        organism = synthetic construct
SEQUENCE: 57

```
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac cgccatgct acttatctca gtaaggctgt 180
tgcaggcatc acacggtgga aagatctgga actgtggcca tggtgtgagg ccatccacaa 240
ggtggaagct ttgaggggga gccgattagc catggacagt tgtcattcag tagggtcacc 300
tgtgccccag cgaaggggga tgggccggga aggcagaggc caggcacctg cccccagcag 360
gggcagaggc tgtgggcagc cgggaggctc ccagaggctc cgacagaatg ggagtggggt 420
tgagcccacc cctcactgca gcccaggaac ctgagcccga aggggccac ccaccttccc 480
caggcaggga ggcccggccc caggggagat gggggggatg ggggaggaga agggcctgcc 540
cccaccggc agcctcagga ggggcagctc gggcgggata tggaaagagg ccacagcagt 600
gagcagagac acagaggagg aagggccct gagctgggga gacccccacg gggtagggcg 660
tgggggccac gggcccacct cctccccatc tcctctgtct ccctgtctct gtctctctct 720
cctcccccca cctctcccc agtcctaccc ctcctcacc ctctgctccc cagcactgtc 780
tctgtcactc tcgcccacgt ggatgtggag gaagagggg cggagcaag gggcgggcac 840
cctcccttca acctgacctg gacagttttc ccttccgctc acctccgcct gagcagtgga 900
gaaggcggca ctctggtggg gctgctccaa cgcgtaatga agaccccac ctgtaggttt 960
ggcaagctag gatcaaggtt aggaacagag agacagcaga atatgggcca aacaggatat 1020
ctgtggtaag cagttcctgc cccggctcag gccaagaac agttggaaca gcagaatatg 1080
ggccaaacag gatatctgtg gtaagcagtt cctgccccgg ctcagggcca agaacagatg 1140
gtccccagat gcgtcccgc cctcagcagt ttctagagaa ccatcagatg tttcagggt 1200
gccccaagga cctgaaatga ccctgtgcct tatttgaact aaccaatcag ttcgcttctc 1260
gcttctgttc gcgcgcttct gctccccgag ctcaataaaa gagcccacaa ccctctcactc 1320
ggcgcgattc acctgacgcg tctacgccac catggcactc ccgtcaccg ccttctctt 1380
```

```
gccctcgcc ctgctgctgc atgctgccag gcccgacatt gtgctcactc agtcacctcc  1440
cagcctggcc atgagcctgg gaaaaagggc caccatctcc tgtagagcca gtgagtccgt  1500
cacaatcttg gggagccatc ttattcactg gtatcagcag aagcccgggc agcctccaac  1560
ccttcttatt cagctcgcgt caaacgtcca gacgggtgta cctgccagat tttctggtag  1620
cgggtcccgc actgatttta cactgaccat agatccgatg gaagaagacg atgttggccgt  1680
gtattattgt ctgcagagca gaacgattcc tcgcacattt ggtggggggta ctaagctgga  1740
gattaaggga agcacgtccg gctcaggaa gccgggctcc ggcgagggaa gcacgaaggg  1800
gcaaattcag ctggtccaga gcggacctga gctgaaaaaa cccggcgaga ctgttaagat  1860
cagttgtaaa gcatctggct ataccttcac cgactacagc ataaattggg tgaaacgggc  1920
ccctggaaag ggcctcaaat ggatgggttg gatcaatacc gaaactaggg agcctgctta  1980
tgcatatgac ttccgcggga gattcgcctt tcactcgag acatctgcct ctactgctta  2040
cctccaaata aacaacctca agtatgaaga tacagccact tacttttgcg ccctcgacta  2100
tagttacgcc atggactact ggggacaggg aacctccgtt accgtcagtt ccgcggccgc  2160
aaccacaaca cctgctccaa ggccccccac acccgctcca actatagcca gccaaccatt  2220
gagcctcaga cctgaagctt gcaggccgc agcaggaggc gccgtccata cgcgaggcct  2280
ggacttcgcg tgtgatattt atatttgggc ccctttggcc ggaacatgtg gggtgttgct  2340
tctctcccctt gtgatcactc tgtattgtaa gcgcgggaga aagaagctcc tgtacatctc  2400
caagcagcct tttatgcgac ctgtgcaaac cactcaggaa gaagatgggt gttcatgccg  2460
cttccccgag gaggaagaag agggtgtga actgagggtg aaattttcta gaagcgccga  2520
tgctcccgca tatcagcagg gtcagaatca gctctacaat gaattgaatc tcggcaggcg  2580
agaagagtac gatgttctgg acaagagacg gggcagggat cccgagatgg ggggaaagcc  2640
ccggagaaaa aatcctcagg aggggttgta caatgagctg cagaaggaca agatggctga  2700
agcctatagc gagatcggaa tgaaaggcga aagacgcaga ggcaaggggc atgacggtct  2760
gtaccagggt ctctctacag ccaccaagga cactatgat gcgttgcata tgcaagcctt  2820
gccacccgc taagcggccg cgcttttattt gtgaaatttg tgatgctatt gctttatttg  2880
taaccattat aagctgcaat aaacaagtta acaacaacaa ttgcattcat tttatgtttc  2940
aggttcaggg ggagatgtgg gaggttttttt aaagctcacc ggttctgggc ggtgctacaa  3000
ctgggctggc ggccaggatg gttcttaggt aggtgggggtc ggcggtcagg tgtcccagag  3060
ccaggggtct ggagggacct tccacccctca gtccctggca ggtcgggggg tgctgaggcg  3120
ggcctggccc tggcagccca ggggtcccgg agcgaggggt ctggagggac cttcactct  3180
cagtccctgg caggtcgggg ggtgctgtgg caggcccagc cttggccccc agctctgccc  3240
cttaccctga gctgtgtggc tttgggcagc tcgaactcct gggttcctct ctgggcccca  3300
actcctcccc tggcccaagt cccctctttg ctcctgggca ggcaggacct ctgtcccctc  3360
tcagccggtc cttggggctg cgtgttctg tagaatgacg ggtcaggctg gccagaaccc  3420
caaaccttgg ccgtggggag tctgcgtggc ggctctgcct tgcccaggca tccttggtcc  3480
tcactcgagt tttcctaagg atgggatgag ccccatgtgg gactaacctt ggctttacga  3540
cgtcaaagtt tagatgagct ggtgatattt ttctcattat atccaaagtg tacctgttcg  3600
agtgaggaca gttcttctgt ctccaggatc cctcctgggt ggggattgtg cccgcctggg  3660
tctctgccca gattccaggg ctctccccga gcctgttca gaccatccgt gggaggaggcc  3720
ttggcctcac tcttacgtag ataagtagca tggcgggtta atcattaact acaaggaacc  3780
cctagtgatg gagttggcca ctccctctct gcgcgctcgc tcgctcactg aggccgggca  3840
accaaaggtc gcccgacgcc cgggctttgc ccgggcggcc tcagtgagcg agcgagcgcg  3900
ccagctggcg taatagcgaa gaggcccgca ccgatcgccc ttcccaacag ttgcgcagcc  3960
tgaatggcga atggcgattc cgttgcaatg ctggcggta atattgttct ggatattacc  4020
agcaaggccg atagtttgag ttcttctact caggcaagtg atgttattac taatcaaaga  4080
agtattgcga caacggttaa tttgcgtgat ggacagactc ttttactcgg tggcctcact  4140
gattataaaa acacttctca ggattctggc gtaccgttca tgtctaaaat cccttttaatc  4200
ggcctcctgt ttagctcccg ctctgattct aacgaggaaa gcacgttata cgtgctcgtc  4260
aaaagcaacca tagtacgcgc cctgtagcgg cgcattaagc gcggcgggtg tggtggttac  4320
gcgcagcgtg accgctacac ttgccagcgc cctagcgccc gctccttttcg ctttcttccc  4380
ttccttttctc gccacgttcg ccggctttcc ccgtcaagct ctaaatcggg ggctccctt  4440
agggttccga tttagtgctt tacggcacct cgaccccaaa aaacttgatt agggtgatgg  4500
ttcacgtagt gggccatcgc cctgatagac ggttttttcgc cctttgacgt tggagtccac  4560
gttctttaat agtggactct tgttccaaac tggaacaaca ctcaaccctat ctcggtcta  4620
ttcttttgat ttataaggga ttttgccgat ttcggcctat tggttaaaaa atgagctgat  4680
ttaacaaaaa tttaacgcga attttaacaa aatattaacg tttacaattt aaatatttgc  4740
ttatacaatc ttcctgtttt tggggctttt ctgattatca accggggtac atatgattga  4800
catgctagtt ttacgattac cgttcatcga ttctcttgtt tgctccagac tctcaggcaa  4860
tgacctgata gcctttgtag agacctctca aaaatagcta ccctctccgg catgaattta  4920
tcagctagaa cggttgaata tcatattgat ggtgatttga ctgtctccgg cctttctcac  4980
ccgtttgaat ctttacctac acattactca ggcattgcat ttaaaatata tgagggttct  5040
aaaaattttt atccttgcgt tgaaataag gcttctcccg caaaagtatt acagggtcat  5100
aatgtttttg gtacaaccga tttagcttta tgctctgagg ctttattgct taattttgct  5160
aattctttgc cttgcctgta tgatttattg gatgttggaa tcgcctgatg cggtatttc  5220
tccttacgca tctgtgcggt atttcacacc gcatatggtg cactctcagt acaatctgct  5280
ctgatgccgc atagttaagc cagccccgac acccgccaac acccgctgac gcgccctgac  5340
gggcttgtct gctcccggca tccgcttaca caagctgt gaccgtctcc gggagctgca  5400
tgtgtcagag gttttcaccg tcatcaccga aacgcgcgag acgaaagggc ctcgtgatac  5460
gcctattttt ataggttaat gtcatgataa taatggttca ttagacgtca ggtggcactt  5520
ttcggggaaa tgtgcgcgga acccctattt gtttattttt ctaaatacat tcaaatatgt  5580
atccgctcat gagacaataa ccctgataaa tgcttcaata atattgaaaa aggaagagta  5640
tgagtattca acatttccgt gtcgccctta ttcccttttt tgcggcattt tgccttcctg  5700
tttttgctca cccagaaacg ctggtgaaag taaaagatgc tgaagatcag ttgggtgcac  5760
gagtgggtta catcgaactg gatctcaaca gcggtaagat ccttgagagt tttcgccccg  5820
aagaacgttt tccaatgatg agcacttttta aagttctgct atgtggcgcg gtattatccc  5880
gtattgacgc cgggcaagag caactcggtc gccgcataca ctattctcag aatgacttgg  5940
ttgagtactc accagtcaca gaaaagcatc ttacggatgg catgacagta agagaattat  6000
gcagtgctgc cataaccatg agtgataaca ctgcggccaa cttacttctg acaacgatcg  6060
gaggaccgaa ggagctaacc gcttttttgc acaacatggg gatcatgta actcgccttg  6120
```

```
atcgttggga accggagctg aatgaagcca taccaaacga cgagcgtgac accacgatgc  6180
ctgtagcaat ggcaacaacg ttgcgcaaac tattaactgg cgaactactt actctagctt  6240
cccggcaaca attaatagac tggatggagg cggataaagt tgcaggacca cttctgcgct  6300
cggcccttcc ggctggctgg tttattgctg ataaatctgg agccggtgag cgtgggtctc  6360
gcggtatcat tgcagcactg gggccagatg gtaagccctc ccgtatcgta gttatctaca  6420
cgacggggag tcaggcaact atggatgaac gaaatagaca gatcgctgag ataggtgcct  6480
cactgattaa gcattggtaa ctgtcagacc aagtttactc atatatactt tagattgatt  6540
taaaacttca tttttaattt aaaaggatct aggtgaagat cctttttgat aatctcatga  6600
ccaaaatccc ttaacgtgag ttttcgttcc actgagcgtc agaccccgta gaaaagatca  6660
aaggatcttc ttgagatcct ttttttctgc gcgtaatctg ctgcttgcaa acaaaaaaac  6720
caccgctacc agcggtggtt tgtttgccgg atcaagagct accaactctt tttccgaagg  6780
taactggctt cagcagagcg cagataccaa atactgtcct tctagtgtag ccgtagttag  6840
gccaccactt caagaactct gtagcaccgc ctacatacct cgctctgcta atcctgttac  6900
cagtggctgc tgccagtggc gataagtcgt gtcttaccgg gttggactca agacgatagt  6960
taccggataa ggcgcagcgg tcgggctgaa cggggggttc gtgcacacag cccagcttgg  7020
agcgaacgac ctacaccgaa ctgagatacc tacagcgtga gctatgagaa agcgccacgc  7080
ttcccgaagg gagaaaggcg gacaggtatc cggtaagcgg cagggtcgga acaggagagc  7140
gcacgaggga gcttccaggg ggaaacgcct ggtatcttta gtcctgtc gggtttcgcc  7200
acctctgact tgagcgtcga ttttttgtgat gctcgtcagg ggggcggagc ctatggaaaa  7260
acgccagcaa cgcggccttt ttacggttcc tggccttttg ctggccttttt gctcacatgt  7320
tctttcctgc gttatcccct gattctgtgg ataaccgtat taccgccttt gagtgagctg  7380
ataccgctcg ccgcagccga acgaccgagc gcagcgagtc agtgagcgag gaagcggaag  7440
agcgcccaat acgcaaaccg cctctccccg cgcgttggcc gattcattaa tg            7492

SEQ ID NO: 58           moltype = DNA  length = 6147
FEATURE                 Location/Qualifiers
misc_feature            1..6147
                        note = Synthesized rAAV PD-1 Exon1_ATG-mCherry construct
source                  1..6147
                        mol_type = other DNA
                        organism = synthetic construct
SEQUENCE: 58
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc  120
actaggggtt ccttgtagtt aatgattaac ccgccatgct acttatctac gtaaggctgt  180
tgcaggcatc acacggtgga aagatctgga actgtggcca tggtgtgagg ccatccacaa  240
ggtggaagct ttgagggggga gccgattagc catggacagt tgtcattcag tagggtcacc  300
tgtgccccag cgaaggggga tgggccggga aggcagaggc caggcacctg cccgcagcag  360
gggcagagac tgtgggcagc cggagggctc ccagaggctc cgacagaatg ggagtggggt  420
tgagcccacc cctcactgca gcccaggaac ctgagcccag ggggggccac ccaccttccc  480
caggcaggga ggcccggccc caggggagat ggggggatg ggggaggaga agggcctgcc  540
cccacccggc agcctcagga ggggcagctc ggcgggata tggaaagagg ccacagcagt  600
gagcagagac acagaggagg aaggggcct gagctgggga gaccccccag gggtagggcg  660
tgggggccac gggcccacct cctccccatc tcctctgtct cctgtctct gtctctctct  720
ccctccccca ccctctcccc agtcctaccc ctcctcacc cctcctcccc cagcactgcc  780
tctgtcactc tcgcccacgt ggatgtggag gaagaggggg cgggagcaag gggcgggcac  840
cctcccttca acctgacctg ggacagtttt ccttccgctc acctccgctc gagcagtgga  900
gaaggcggca ctctggtggg gctgctccag gcatgcaggt gagcaagggc gaggaggata  960
actccgccat catcaaggag ttcctgcgct tcaaggtgca catggagggc tccgtgaacg 1020
gccacgagtt cgagatcgag ggcgagggcg agggccgccc ctacgagggc acccagaccg 1080
ccaagctgaa ggtgaccaag ggtggccccc tgcccttcgc ctggacatc tgtccctc   1140
agttcatgta cggctccaag gcctacgtga agcaccccgc cgacatcccc gactacttga 1200
agctgtcctt ccccgagggc ttcaagtggg agcgcgtgat gaacttcgag gacggcggcg 1260
tggtgaccgt gacccaggac tcctctctgc aggacgcga gttcatctac aaggtgaagc 1320
tgcgcggcac caacttcccc tccgacggcc ccgtaatgca gaagaagacc atgggctggg 1380
aggcctcctc cgagcggatg taccccgagg acggcgccct gaagggcgag atcaagcaga 1440
ggctgaagct gaaggacggc ggccactacg acgctgaggt caagaccacc tacaaggcca 1500
agaagcccgt gcagctgccc ggcgcctaca acgtcaacat caagttggac atcacctccc 1560
acaacgagga ctacaccatc gtggaacagt acgaacgcgc cgaggccgc cactccaccg 1620
gcggcatgga cgagctgtac aagtgatgaa agctttgctt tatttgtgatg atttgtgatg 1680
ctatgcttta tttgtaacca ttataagctg caataaacaa gttaacaac aacaattgca 1740
ttcattttat gtttcaggtt caggggggagg tgtgggaggt tttttaaagt aggtggggtc 1800
ggcggtcagg tgtcccagag ccaggggtct ggagggacct tccaccctca gtccctggca 1860
ggtcgggggg tgctgaggcg ggcctggccc tggcagccga agggtcccgg agcgagggcg 1920
ctggagggac ctttcactct cagtccctgg caggtcgggg ggtgctgtgg caggcccagc 1980
cttgccccc agctctgccc cttacccctga gctgtgtggc tttgggcagc tcgaactcct 2040
gggttcctct ctgggcccca actcctcccc tgcccaagt cccctctttg ctcctgggca 2100
ggcaggacct ctgtcccctc tcagccggtc cttgggctg cgtgttttctg tagaatgacg 2160
ggtcaggctg gccagaaccc caaaccttgg ccgtgggag tctgcgtgtg ggctctgctg 2220
tgccaggca tccttggtcc tcactcgagt tttcctaagg atgggatgac cccatgtgg 2280
gactaacctt ggctttacga cgtcaaagtt tagatgagct ggtgatattt ttctcattat 2340
atccaaagtg tacctgttcg agtgaggaca gttcttctgt ctccaggata cgtagataag 2400
tagcatggcg ggtaatcat taactacaag gaaccctag tgatggagtt ggccactccc 2460
tctctgtgcg ctcgctcgct cactgaggcc gggcgaccaa aggtcgcccg acgcccgggc 2520
tttgcccggg cggcctcagt gagcgagcga gcgcgccagc tggcgtaata gcgaagaggc 2580
ccgcaccgat cgcccttccc aacagttgcg cagcctgaat ggcgaatggc gattccgttg 2640
caatggctgg cggtaatatt gttctggata ttaccagcaa ggccgatagt ttgagttctt 2700
ctactcaggc aagtgatgtt attactaatc aaagaagtat tgcgacaacg gttaattttgc 2760
gtgatggaca gactcttta ctcggtggcc tcactgatta taaaaaacact tctcaggatt 2820
```

```
ctggcgtacc gttcctgtct aaaatcccttt taatcggcct cctgtttagc tcccgctctg 2880
attctaacga ggaaagcacg ttatacgtgc tcgtcaaagc aaccatagta cgcgccctgt 2940
agcggcgcat taagcgcggc gggtgtggtg gttacgcgca gcgtgaccgc tacacttgcc 3000
agcgccctag cgcccgctcc tttcgctttc ttcccttcct ttctcgccac gttcgccggc 3060
tttccccgtc aagctctaaa tcggggggctc cctttagttc tccgatttag tgctttacgg 3120
cacctcgacc ccaaaaaact tgattagggt gatggttcac gtagtgggcc atcgccctga 3180
tagacggttt tcgccctttt gacgttggag tccacgttct ttaatagtgg actcttgttc 3240
caaactggaa caacactcaa ccctatctcg gtctattctt ttgatttata agggattttg 3300
ccgatttcgg cctattggtt aaaaaatgag ctgatttaac aaaaaatttaa cgcgaatttt 3360
aacaaaatat taacgtttac aatttaaata tttgcttata caatcttcct gttttttgggg 3420
cttttctgat tatcaaccgg ggtacatatg attgacatgc tagttttacg attaccgttc 3480
atcgattctc ttgtttgctc cagactctca ggcaatgacc tgatagcctt tgtagagacc 3540
tctcaaaaat agctaccctc tccggcatga atttatcagc tagaacggtt gaatatcata 3600
ttgatggtga tttgactgtc tccggccttt ctcacccgtt tgaatcttta cctacacatt 3660
actcaggcat tgcatttaaa atatatgagg gttctaaaaa tttttatcct tgcgttgaaa 3720
taaaggcttc tcccgcaaaa gtattacagg gtcataatgt ttttggtaca accgatttag 3780
ctttatgctc tgaggcttta ttgcttaatt ttgctaattc tttgccttgc ctgtatgatt 3840
tattggatgt tggaatcgcc tgatgcggta ttttctcctt acgcatctgt gcggtatttc 3900
acaccgcata tggtgcactc tcagtacaat ctgctctgat gccgcatagt taagccagcc 3960
ccgacacccg ccaacacccg ctgacgcgcc ctgacgggct tgtctgctcc cggcatccgc 4020
ttacagacaa gctgtgaccg tctccgggag ctgcatgtgt cagaggtttt caccgtcatc 4080
accgaaacgc gcgagacgaa agggcctcgt gatacgccta ttttttatagg ttaatgtcat 4140
gataataatg gtttcttaga cgtcaggtgg cactttttcgg ggaaatgtgc gcggaacccc 4200
tatttgttta tttttctaaa tacattcaaa tatgtatccg ctcatgagac aataaccctg 4260
ataaatgctt caataatatt gaaaaggaa gagtatgagt attcaacatt tccgtgtcgc 4320
ccttattccc ttttttgcgg catttttgcct tcctgttttt gctcacccag aaacgctggt 4380
gaaagtaaaa gatgctgaag atcagttggg tgcacgagtg ggttacatcg aactggatct 4440
caacagcggt aagatccttg agagttttcg ccccgaagaa cgttttccaa tgatgagcac 4500
ttttaaagtt ctgctatgtg gcgcggtatt atcccgtatt gacgccgggc aagagcaact 4560
cggtcgccgc atacactatt ctcagaatga cttggttgag tactcaccag tcacagaaaa 4620
gcatcttacg gatggcatga cagtaagaga attatgcagt gctgccataa ccatgagtga 4680
taacactgcg gccaacttac ttctgacaac gatcggagga ccgaaggagc taaccgcttt 4740
tttgcacaac atgggggatc atgtaactcg ccttgatcgt tgggaaccgg agctgaatga 4800
agccatacca aacgacgagc gtgacaccac gatgcctgta gcaatggcaa caacgttgcg 4860
caaactatta actggcgaac tacttactct agcttcccgg caacaattaa tagactggat 4920
ggaggcggat aaagttgcag gaccacttct gcgctcggcc cttccggctg gctggtttat 4980
tgctgataaa tctggagccg gtgagcgtgg gtctcgcggt atcattgcag cactgggcc 5040
agatggtaag ccctcccgta tcgtagttat ctacacgacg gggagtcagg caactatgga 5100
tgaacgaaat agacagatcg ctgagatagg tgcctcactg attaagcatt ggtaactgtc 5160
agaccaagtt tactcatata ctttagat tgatttaaaa cttcattttt aatttaaaag 5220
gatctaggtg aagatccttt ttgataatct catgaccaaa atcccttaac gtgagttttc 5280
gttccactga gcgtcagacc ccgtagaaaa gatcaaagga tcttcttgag atcctttttt 5340
tctgcgcgta atctgctgct tgcaaacaaa aaaaccaccg ctaccagcgg tggtttgttt 5400
gccggatcaa gagctaccaa ctcttttttcc gaaggtaact ggcttcagca gagcgcagat 5460
accaaatact gtccttctag tgtagccgta gttaggccac cacttcaaga actctgtagc 5520
accgcctaca tacctcgctc tgctaatcct gttaccagtg gctgctgcca gtggcgataa 5580
gtcgtgtctt accgggttgg actcaagacg atagttaccg gataaggcgc agcggtcggg 5640
ctgaacgggg ggttcgtgca cacagcccag cttggagcga acgacctaca ccgaactgag 5700
atacctacag cgtgagctat gagaaagcgc cacgcttccc gaaggagaa aggcggacag 5760
gtatccggta agcggcaggg tcggaacagg agagcgcacg agggagcttc caggggggaaa 5820
cgcctggtat ctttatagtc ctgtcgggtt tcgccacctc tgacttgagc gtcgatttt 5880
gtgatgctcg tcaggggggc ggagcctatg gaaaaacgcc agcaacgcgg cctttttacg 5940
gttcctggcc ttttgctggc cttttgctca catgttcttt cctgcgttat cccctgattc 6000
tgtggataac cgtattaccg cctttgagtg agctgatacc gctcgccgca gccgaacgac 6060
cgagcgcagc gagtcagtga gcgaggaagc ggaagagcgc ccaatacgca aaccgcctct 6120
ccccgcgcgt tggccgattc attaatg 6147

SEQ ID NO: 59          moltype = AA  length = 232
FEATURE                Location/Qualifiers
REGION                 1..232
                       note = Made in Lab
source                 1..232
                       mol_type = protein
                       organism = synthetic construct
SEQUENCE: 59
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV IRSKRSRLLH SDYMNMTPRR PGPTRKHYQP YAPPRDFAAY RS           232

SEQ ID NO: 60          moltype = AA  length = 303
FEATURE                Location/Qualifiers
REGION                 1..303
                       note = Synthesized I-OnuI variant PD-1.ile3.exon1_RD2_B1G2
VARIANT                1..4
                       note = Any amino acid or absent
VARIANT                302..303
                       note = Any amino acid or absent
source                 1..303
```

```
                        mol_type = protein
                        organism = synthetic construct
SEQUENCE: 60
XXXXSRRESI NPWILTGFAD AEGSFQLEIR NVNPNIPRYK TRLRFEIDLH NKDKSILENI    60
QSTWKVGKIY NQGDSYVKLR VTRFEDLKVI IDHFEKYPLI TQKLGDYKLF KQAFSVMENK   120
EHLKENGIKE LVRIKAKMNW GLNDELKKAF PENISKERPL INKNIPNLKW LAGFTSGEGH   180
FGVILAKRRP ASPVQVRLRF AIGQHIRDKN LMNSLITYLG CGRIREKNIS EKSWLEFEVT   240
KFSDINDKII PVFQENTLIG VKLEDFEDWC KVAKLIEEKK HLTESGLDEI KKIKLNMNKG   300
RXX                                                                303

SEQ ID NO: 61           moltype = AA  length = 303
FEATURE                 Location/Qualifiers
REGION                  1..303
                        note = Synthesized I-OnuI variant PD-1.ile3.exon1_RD3_B1G2C4
VARIANT                 1..4
                        note = Any amino acid or absent
VARIANT                 302..303
                        note = Any amino acid or absent
source                  1..303
                        mol_type = protein
                        organism = synthetic construct
SEQUENCE: 61
XXXXSRRESI NPWILTGFAD AEGSFGLSIL NRNRGTARYH TRLSFTIMLH NKDKSILENI    60
QSTWKVGSIL NNGDHYVSLV VYRFEDLKVI IDHFEKYPLI TQKLGDYKLF KQAFSVMENK   120
EHLKENGIKE LVRIKAKMNW GLNDELKKAF PENISKERPL INKNIPNFKW LAGFTSGDGS   180
FFVRLRKSNV NARVRVQLVF EISQHIRDKN LMNSLITYLG CGHIYEGNKS ERSWLQFRVE   240
KFSDINDKII PVFQENTLIG VKLEDFEDWC KVAKLIEEKK HLTESGLDEI KKIKLNMNKG   300
RXX                                                                303

SEQ ID NO: 62           moltype = AA  length = 303
FEATURE                 Location/Qualifiers
REGION                  1..303
                        note = Synthesized I-OnuI variant PD-1.ile3.exon1_RD3_B1
                         G2C11
VARIANT                 1..4
                        note = Any amino acid or absent
VARIANT                 302..303
                        note = Any amino acid or absent
source                  1..303
                        mol_type = protein
                        organism = synthetic construct
SEQUENCE: 62
XXXXSRRESI NPWILTGFAD AEGSFGLSIL NRNRGTGRYH TRLSFTIMLH NKDKSILENI    60
QSTWKVGSIT NNGDHYVSLV VYRFEDLKVI IDHFEKYPLI TQKLGDYKLF KQAFSVMENK   120
EHLKENGIKE LVRIKAKMNW GLNDELKKAF PENISKERPL INKNIPNFKW LAGFTSGDGS   180
FFVRLRKSNV NARVRVQLVF EISQHIRDKN LMNSLITYLG CGHIYEGNKS ERSWLQFRVE   240
KFSDINDKII PVFQENTLIG VKLEDFEDWC KVAKLIEEKK HLTESGLDEI KKIKLNMNKG   300
RXX                                                                303

SEQ ID NO: 63           moltype = AA  length = 303
FEATURE                 Location/Qualifiers
REGION                  1..303
                        note = Synthesized I-OnuI variant PD-1.ile3.exon1_RD3_B1
                         G2C5
VARIANT                 1..4
                        note = Any amino acid or absent
VARIANT                 302..303
                        note = Any amino acid or absent
source                  1..303
                        mol_type = protein
                        organism = synthetic construct
SEQUENCE: 63
XXXXSRRESI NPWILTGFAD AEGSFGLSIL NRNRGTARYH TRLSFTIMLH NKDKSILENI    60
QSTWKVGSIY NNGDHYVSLE VFRFEDLKVI IDHFEKYPLI TQKLGDYKLF KQAFSVMENK   120
EHLKENGIKE LVRIKAKMNW GLNDELKKAF PENISKERPL INKNIPNFKW LAGFTSGDGS   180
FFVRLRKSNV NARVRVQLVF EISQHIRDKN LMNSLITYLG CGHIYEGNKS ERSWLQFRVE   240
KFSDINDKII PVFQENTLIG VKLEDFEDWC KVAKLIEEKK HLTESGLDEI KKIKLNMNKG   300
RXX                                                                303

SEQ ID NO: 64           moltype = AA  length = 943
FEATURE                 Location/Qualifiers
REGION                  1..943
                        note = Synthesized megaTAL PD-1.ile3.exon1_RD1_B1G2
                         construct
source                  1..943
                        mol_type = protein
                        organism = synthetic construct
SEQUENCE: 64
MGSAPPKKKR KVVDLRTLGY SQQQQEKIKP KVRSTVAQHH EALVGHGFTH AHIVALSQHP    60
```

```
AALGTVAVTY QHIITALPEA THEDIVGVGK QWSGARALEA LLTDAGELRG PPLQLDTGQL    120
VKIAKRGGVT AMEAVHASRN ALTGAPLNLT PDQVVAIASN NGGKQALETV QRLLPVLCQD    180
HGLTPDQVVA IASNNGGKQA LETVQRLLPV LCQDHGLTPD QVVAIASNGG KQALETVQR    240
LLPVLCQDHG LTPDQVVAIA SNNGGKQALE TVQRLLPVLC QDHGLTPDQV VAIASNNGGK    300
QALETVQRLL PVLCQDHGLT PDQVVAIASN NGGKQALETV QRLLPVLCQD HGLTPDQVVA    360
IASNNGGKQA LETVQRLLPV LCQDHGLTPD QVVAIASHDG GKQALETVQR LLPVLCQDHG    420
LTPDQVVAIA SNGGKQALE TVQRLLPVLC QDHGLTPDQV VAIASNNGGK QALETVQRLL    480
PVLCQDHGLT PDQVVAIASH DGGKQALETV QRLLPVLCQD HGLTPDQVVA IASNGGGKQA    540
LETVQRLLPV LCQDHGLTPD QVVAIASHDG GKQALESIVA QLSRPDPALA ALTNDHLVAL    600
ACLGGRPAMD AVKKGLPHAP ELIRRVNRRI GERTSHRVAI SRVGGSSRRE SINPWILTGF    660
ADAEGSFGLS ILNRNRGTAR YHTRLSFTIM LHNKDKSILE NIQSTWKVGI ITNNGDHYVT    720
LRVTRFEDLK VIIDHFEKYP LVTQKLGDYK LFKQAFSVME NKEHLKENGI KELVRIKAKM    780
NWGLNDELKK AFPENISKER PLINKNIPNF KWLAGFTSGD GSFFVRLRKS NVNARVRVQL    840
VFEISQHIRD KNLMNSLITY LGCGHIYEGN KSERSWLQFR VEKFSDINDK IIPVFQENTL    900
IGVKLEDFED WCKVAKLIEE KKHLTESGLD EIKKIKLNMN KGR                      943

SEQ ID NO: 65              moltype = RNA   length = 2832
FEATURE                    Location/Qualifiers
misc_feature               1..2832
                           note = Synthesized PD-1 Exon1 RD2_B1G2 megaTAL mRNA
                             construct
source                     1..2832
                           mol_type = other RNA
                           organism = synthetic construct
SEQUENCE: 65
atgggaagcg cgccacctaa gaagaaacgc aaagtcgtgg atctacgcac gctcggctac    60
agtcagcagc agcaagagaa gatcaaaccg aaggtgcgtt cgacagtggc gcagcaccac   120
gaggcactgg tgggccatgg gtttacacac gcgcacatcg ttgcgctcag ccaacacccg   180
gcagcgttag gaccgtcgc tgtcacgtat cagcacataa tcacggcgtt gccagaggcg   240
acacacgaag acatcgttgg cgtcggcaaa cagtggtccg gcgcacgcgc cctgaggcc   300
ttgctcacgg atgcgggga gttgagaggt ccgtccgttac agttggacac aggccaactt   360
gtgaagattg caaaacgtgg cggcgtgacc gcaatggagg cagtgcatgc atcgcgcaat   420
gcactgacgg gtgccccct gaacctaacc cctgatcagg tagtcgctat agcttcaaac   480
aacggggca agcaagcact ggagaccgtt caacgactcc tgccagtgct ctgccaagac   540
cacggactta cgccagatca ggtggttgct attgcctcca acaatggcgg gaaacaagcc   600
ttggaaactg tgcagagact gttacctgtc ttgtgtcaag accacggcct cacgccagat   660
caggtggtag ccatagcgtc gaatggaggt ggtaagcaag cccttgaaac ggtccagcgt   720
cttctgccgg tgttgtgcca ggaccacgga ctaacgccgg atcaggtcgt agccattgct   780
tcaaataacg gcggcaaaca ggcgctagag acagtccagc gcctcttgcc tgtgttatgc   840
caggatcacg gcttaacccc agaccaagtt gtggctattg catctaacaa tggtggcaaa   900
caagccttgg agacagtgca acgattactg cctgtcttat gtcaggatca tggcctgacg   960
cccgatcagg tagtggcaat cgcatctaat aatgaggta agcaagcact ggagactgtc   1020
cagagattgt tacccgtact atgtcaagat catggtttga cagttgttgcg                1080
atagccagca acaacggagg gaaacaggct cttgaaaccg tacagcgact tctcccagtc   1140
ttgtgccaag atcacgggct tactcctgat caagtcgtag ctatcgccag ccacgacggg   1200
gggaaacagg ccctggaaac cgtacaacgt ctcctcccag tactttgtca agaccacggg   1260
ttgactccgg atcaagtcgt cgcgatcgcg agcaatggag ggggaaagca ggcgctggaa   1320
actgttcaga gactgctgcc tgtactttgt caggaccatg gtctgacacc tgaccaagtt   1380
gtggcgatag ccagtaacaa tgggggaaaa caggcactag agacggttca aaggttgttg   1440
cccgttctgt gccaggacca cggcttgaca ccggatcagg tggtagctat cgcttcacac   1500
gatggcggaa aacaggcttt agaaacagtc caaagacttc tcccagtcct ttgtcaggac   1560
cacggattga ctccagatca agtcgttgct attgcaagta atggtggtgg taagcaagct   1620
ttagaaaccg tacagaggct tttgccagtg ctgtgccagg accatggact gaccctgat   1680
caagtggtag caattgcatc tcatgatgga ggaaaacaag ctctgaaag cattgtggcc   1740
cagctgagcc ggcctgatcc ggcgttggcc gcgttgacca acgaccacct cgtcgccttg   1800
gcctgcctcg gcggacgtcc tgccatggat gcagtgaaaa agggattgcc gcacgcgccg   1860
gaattgatca agagagtcaa tcgccgtatt ggcgaacgca cgtcccatcg cgttgcgata   1920
tctagagtgg gaggaagctc tcgcagagag tccatcaacc catggattct gactggtttc   1980
gctgatgccg aaggatcatt cgggctaagc atcctcaaca gaaacagagg tactgctaga   2040
taccacactc gactgtcatt cacaatcatg ctgcacaaca aggacaaatc gattctggaa   2100
aatatccagt cgacttggaa ggtcggcata atcaccaaca acggcgacca ctacgtcacc   2160
ctgcgcgtca cccgtttcga agatttgaaa gtgattatcg accacttcga gaaatatccg   2220
ctggtaacac agaaatttgg cgattacaag ttgtttaaac aggcattcag cgtcatggag   2280
aacaaagaac atcttaagga gaatgggatt aaggagctcg tacgaatcaa agctaagatg   2340
aattggggtc tcaatgacga attgaaaaaa gcatttccag agaacattag caaagagcgc   2400
ccccttatca ataagaacat tccgaatttc aaatggctgg ctggattcac atctggtgat   2460
ggctccttct cgtgcgcct aagaaagtct aatgttaatg ctagagtacg tgtgcaactg   2520
gtattcgaga tctcacagca catcagagac aagaacctga tgaattcatt gataacatac   2580
ctaggctgtg gtcacatcta cgagggaaac aaatctgagc gcagttggct ccaattcaga   2640
gtagaaaaat tcagcgatat caacgacaag atcattccgg tattccagga aaatactctg   2700
attggcgtca aactcgagga cttttgaagat tggtgcaagg ttgccaaatt gatcgaagag   2760
aagaaacacc tgaccgaatc cggtttggat gagattaaga aaatcaagct gaacatgaac   2820
aaaggtcgtt ga                                                       2832

SEQ ID NO: 66              moltype = RNA   length = 2832
FEATURE                    Location/Qualifiers
misc_feature               1..2832
                           note = Synthesized PD-1 Exon1 RD2_B1G2C4 megaTAL mRNA
                             construct
```

```
source                  1..2832
                        mol_type = other RNA
                        organism = synthetic construct
SEQUENCE: 66
atgggaagcg cgccacctaa gaagaaacgc aaagtcgtgg atctacgcac gctcggctac   60
agtcagcagc agcaagagaa gatcaaaccg aaggtgcgtt cgacagtggc gcagcaccac  120
gaggcactgg tgggccatgg gtttacacac gcgcacatcg ttgcgctcag ccaacacccg  180
gcagcgttag ggaccgtcgc tgtcacgtat cagcacataa tcacggcgtt gccagaggcg  240
acacacgaag acatcgttgg cgtcggcaaa cagtggtccg gcgcacgcgc cctggaggcg  300
ttgctcacgg atgcggggga gttgagaggt ccgccgttac agttggacac aggccaactt  360
gtgaagattg caaaacgtgg cggcgtgacc gcaatggagg cagtgcatgc atcgcgcaat  420
gcactgacgg gtgcccccct gaacctaacc cctgatcagg tagtcgctat agcttcaaac  480
aacgggggca agcaagcact ggagaccgtt caacgactcc tgccagtgct ctgccaagac  540
cacggactta cgccagatca ggtggttgct attgcctcca acaatggcgg gaaacaagcg  600
ttggaaactg tgcagagact gttacctgtc ttgtgtcaag accacggcct cacgccagat  660
caggtggtag ccatagcgtc gaatggaggt ggtaagcaag cccttgaaac ggtccagcgt  720
cttctgccgg tgttgtgcca ggaccacgga ctaacgccgg atcaggtcgt agccattgct  780
tcaaataacg gcggcaaaca ggcgctagag acagtccagc gcctcttgcc tgtgttatgc  840
caggatcacg gcttaacccc agaccaagtt gtggctattg catctaacaa tggtggcaaa  900
caagccttgg agacagtgca acgattactg cctgtcttat gtcaggatca tggcctgacg  960
cccgatcagg tagtggcaat cgcatctaat aatgaggta agcaagcact ggagactgtc 1020
cagagattgt tacccgtact atgtcaagat catggtttga ggttgttgcg 1080
atagccagca acaacggagg gaaacaggct cttgaaaccg tacagcgact tctcccagtc 1140
ttgtgccaag atcacgggct tactcctgat caagtcgtag ctatcgccag ccacgacggt 1200
gggaaacagg ccctggaaac cgtacaacgt ctcctcccag tactttgtca agaccacggg 1260
ttgactccgg atcaagtcgt cgcgatcgcg agcaatggaa gggggaagca ggcgctgaa  1320
actgttcaga gactgctgcc tgtactttgt caggaccatg gtctgacacc tgaccaagtt 1380
gtggcgatag ccagtaacaa tgggggaaaa caggcactag agacggttca aaggttgttg 1440
cccgttctgt gccaggacca cggcttgaca ccggatcagg tggtagctat cgcttcacac 1500
gatggcggaa aacaggcttt agaaacagtc caaagacttc tcccagtcct ttgtcaggac 1560
cacggattga ctccagatca agtcgttgct attgcaagta atggtggtgg taagcaagct 1620
ttagaaaccg tacagaggct tttgccagtg ctgtgccagg accatggact gacccctgat 1680
caagtggtag caattgcatc tcatgatgga ggaaaacaag ctctggaaag cattgtggcc 1740
cagctgagcc ggcctgatcc ggcgttggcc gcgttgacca acgaccacct cgtcgccttg 1800
gcctgcctcg gcggacgtcc tgccatggat gcagtgaaaa agggattgcc gcacgcgccg 1860
gaattgatca aagagtcaa tcgccgtatt ggcgaacgca cgtccatcg cgttgcgata 1920
tctagagtgg gaggaagctc tcgcagagag tccatcaacc catggattct gactggtttc 1980
gctgatgccg aaggatcatt cgggctaagc atcctcaaca gaaacagagg tactgctaga 2040
taccacactc gactgtcatt cacaatcatg ctgcacaaca aggacaaatc gattctggag 2100
aatatccagt cgacttggaa ggtcggcagc atcctcaaca atggcgacca ctacgtctcg 2160
ctggtggtct accgtttcga agatttgaaa gtgattatcg accacttcga gaatatccg  2220
ctgataacac agaaattggg cgattacaag ttgtttaaac aggcattcag cgtcatggag 2280
aacaaagaac atcttaagga gaatgggatt aaggagctcg tacgaatcaa agctaagatg 2340
aattggggtc tcaatgacga attgaaaaaa gcatttccag agaacattag caaagagcgc 2400
cccccttatca ataagaacat tccgaatttc aaatggctgg ctgattcac atctggtgat 2460
ggctccttct tcgtgcgcct aagaaagtct aatgttaatg ctagagtacg tgtgcaactg 2520
gtattcgaga tctcacagca catcagagac aagaacctga tgaattcatt gataacatac 2580
ctaggctgtg gtcacatcta cgagggaaac aaatctgagc gcagttggct ccaattcaga 2640
gtagaaaaat tcagcgatat caacgacaag atcattccgg tattccagga aaatactctg 2700
attggcgtca aactcgagga cttgaagat tggtgcaagg ttgccaaatt gatcgaagag 2760
aagaaacacc tgaccgaatc cggtttggat gagattaaga aaatcaagct gaacatgaac 2820
aaaggtcgtt ga                                                      2832

SEQ ID NO: 67           moltype = RNA  length = 2832
FEATURE                 Location/Qualifiers
misc_feature            1..2832
                        note = Synthesized PD-1 Exon1 RD2_B1G2C11 megaTAL mRNA
                        construct
source                  1..2832
                        mol_type = other RNA
                        organism = synthetic construct
SEQUENCE: 67
atgggaagcg cgccacctaa gaagaaacgc aaagtcgtgg atctacgcac gctcggctac   60
agtcagcagc agcaagagaa gatcaaaccg aaggtgcgtt cgacagtggc gcagcaccac  120
gaggcactgg tgggccatgg gtttacacac gcgcacatcg ttgcgctcag ccaacacccg  180
gcagcgttag ggaccgtcgc tgtcacgtat cagcacataa tcacggcgtt gccagaggcg  240
acacacgaag acatcgttgg cgtcggcaaa cagtggtccg gcgcacgcgc cctggaggcc  300
ttgctcacgg atgcggggga gttgagaggt ccgccgttac agttggacac aggccaactt  360
gtgaagattg caaaacgtgg cggcgtgacc gcaatggagg cagtgcatgc atcgcgcaat  420
gcactgacgg gtgcccccct gaacctaacc cctgatcagg tagtcgctat agcttcaaac  480
aacgggggca agcaagcact ggagaccgtt caacgactcc tgccagtgct ctgccaagac  540
cacggactta cgccagatca ggtggttgct attgcctcca acaatggcgg gaaacaagcg  600
ttggaaactg tgcagagact gttacctgtc ttgtgtcaag accacggcct cacgccagat  660
caggtggtag ccatagcgtc gaatggaggt ggtaagcaag cccttgaaac ggtccagcgt  720
cttctgccgg tgttgtgcca ggaccacgga ctaacgccgg atcaggtcgt agccattgct  780
tcaaataacg gcggcaaaca ggcgctagag acagtccagc gcctcttgcc tgtgttatgc  840
caggatcacg gcttaacccc agaccaagtt gtggctattg catctaacaa tggtggcaaa  900
caagccttgg agacagtgca acgattactg cctgtcttat gtcaggatca tggcctgacg  960
cccgatcagg tagtggcaat cgcatctaat aatgaggta agcaagcact ggagactgtc 1020
```

```
cagagattgt tacccgtact atgtcaagat catggtttga cgcctgatca ggttgttgcg  1080
atagccagca acaacggagg gaaacaggct cttgaaaccg tacagcgact tctcccagtc  1140
ttgtgccaag atcacgggct tactcctgat caagtcgtag ctatcgccag ccacgacggt  1200
gggaaacagg ccctggaaac cgtacaacgt ctcctcccag tactttgtca agaccacggg  1260
ttgactccgg atcaagtcgt cgcgatcgcg agcaatggag ggggaagca ggcgctggaa   1320
actgttcaga gactgctgcc tgtactttgt caggaccatg gtctgacacc tgaccaagtt  1380
gtggcgatag ccagtaacaa tgggggaaaa caggcactag agacggttca aaggttgttg  1440
cccgttctgt gccaggacca cggcttgaca ccggatcagg tggtagctat cgcttcacac  1500
gatggcggaa aacaggcttt agaaacagtc caaagacttc tcccagtcct ttgtcaggac  1560
cacggattga ctccagatca agtcgttgct attgcaagta atggtggtgg taagcaagct  1620
ttagaaaccg tacagaggct tttgccagtg ctgtgccagg accatggact gaccccctgat 1680
caagtggtag caattgcatc tcatgatgga ggaaaacaag ctctggaaag cattgtggcc  1740
cagctgagcc ggcctgatcc ggcgttggcc gcgttgacca acgaccacct cgtcgccttg  1800
gcctgcctcg gcggacgtcc tgccatggat gcagtgaaaa agggattgcc gcacgcgccg  1860
gaattgatca aagagtcaa tcgccgtatt ggcgaacgca cgtcccatcg cgttgcgata   1920
tctagagtgg gaggaagctc tcgcagagag tccatcaacc catggattct gactggtttc  1980
gctgatgccg aaggatcatt cgggctaagc atcctcaaca gaaacagagg tactggtaga  2040
taccacactc gactgtcatt cacaatcatg ctgcacaaca aggacaaatc gattctggag  2100
aatatccagt cgacttggaa ggtcggctcg atcacgaaca acggcgacca ctacgtcagc  2160
ctggtcgtct accgtttcga agatttgaaa gtgattatcg accacttcga gaaatatccg  2220
ctgataacac agaaattggg cgattacaag ttgtttaaac aggcattcag cgtcatggag  2280
aacaaagaac atcttaagga gaatgggatt aaggagctcg tacgaatcaa agctaagatg  2340
aattggggtc tcaatgacga attgaaaaaa gcatttccag agaacattag caaagagcgc  2400
cccttatca ataagaacat tccgaatttc aaatggctgg ctgggattcac atctggtgat  2460
ggctccttct tcgtgcgcct aagaaagtct aatgttaatg ctagagtacg tgtgcaactg  2520
gtattcgaga tctcacagca catcagagac aagaacctga tgaattcatt gataacatac  2580
ctaggctgtg gtcacatcta cgagggaaac aaatctgagc gcagttggct ccaattcaga  2640
gtagaaaaat tcagcgatat caacgacaag atcattccgg tattccagga aaatactctg  2700
attggcgtca aactcgagga ctttgaagat tggtgcaagg ttgccaaatt gatcgaagag  2760
aagaaacacc tgaccgaatc cggtttggat gagattaaga aaatcaagct gaacatgaac  2820
aaaggtcgtt ga                                                      2832

SEQ ID NO: 68          moltype = RNA  length = 2832
FEATURE                Location/Qualifiers
misc_feature           1..2832
                       note = Synthesized PD-1 Exon1 RD2_B1G2C5 megaTAL mRNA
                        construct
source                 1..2832
                       mol_type = other RNA
                       organism = synthetic construct
SEQUENCE: 68
atgggaagcg cgccacctaa gaagaaacgc aaagtcgtgg atctacgcac gctcggctac  60
agtcagcagc agcaagagaa gatcaaaccg aaggtgcgta cgacagtggc gcagcaccac  120
gaggcactgg tgggccatgg gtttacacac gcgcacatcg ttgcgctcag ccaacacccg  180
gcagcgttag ggaccgtcgc tgtcacgtat cagcacataa tcacggcgtt gccagaggcg  240
acacacgaag acatcgttgg cgtcggcaaa cagtggtccg cgcacgcgc cctggaggcc   300
ttgctcacgg atgcggggga gttgagaggt ccgccgttac agttggacac aggccaactt  360
gtgaagattg caaaacgtgg cggcgtgacc gcaatggagg cagtgcatgc atcgcgcaat  420
gcactgacgg gtgcccccct gaacctaacc cctgatcagg tagtcgctat agcttcaaac  480
aacggggca agcaagcact ggagaccgtt caacgactcc tgccagtgct ctgccaagac  540
cacggactta cgccagatca ggtggttgct attgcctcca acaatggcgg gaaacaagtg  600
ttggaaactg tgcagagact gttacctgtc ttgtgtcaag accacggcct acgccagat   660
caggtggtag ccatagcgtc gaatggaggt ggtaagcaag cccttgaaac ggtccagcgt  720
cttctgccgg tgttgtgcca ggaccacgga ctaacgccgg atcaggtcgt agccattgct  780
tcaaataacg gcggcaaaca ggcgctagag acagtccagg gcctcttgc tgtgttatgc  840
caggatcacg gcttaacccc agaccaagtt gtggctattg catctaacaa tggtggcaaa  900
caagccttgg agacagtgca acgattactg cctgtcttat gtcaggatca tggcctgacg  960
cccgatcagg tagtggcaat cgcatctaat aatggaggta agcaagcact ggagactgtc  1020
cagagattgt tacccgtact atgtcaagat catggtttga cgcctgatca ggttgttgcg  1080
atagccagca acaacggagg gaaacaggct cttgaaaccg tacagcgact tctcccagtc  1140
ttgtgccaag atcacgggct tactcctgat caagtcgtag ctatcgccag ccacgacggt  1200
gggaaacagg ccctggaaac cgtacaacgt ctcctcccag tactttgtca agaccacggg  1260
ttgactccgg atcaagtcgt cgcgatcgcg agcaatggag ggggaagca ggcgctggaa   1320
actgttcaga gactgctgcc tgtactttgt caggaccatg gtctgacacc tgaccaagtt  1380
gtggcgatag ccagtaacaa tgggggaaaa caggcactag agacggttca aaggttgttg  1440
cccgttctgt gccaggacca cggcttgaca ccggatcagg tggtagctat cgcttcacac  1500
gatggcggaa aacaggcttt agaaacagtc caaagacttc tcccagtcct ttgtcaggac  1560
cacggattga ctccagatca agtcgttgct attgcaagta atggtggtgg taagcaagct  1620
ttagaaaccg tacagaggct tttgccagtg ctgtgccagg accatggact gaccccctgat 1680
caagtggtag caattgcatc tcatgatgga ggaaaacaag ctctggaaag cattgtggcc  1740
cagctgagcc ggcctgatcc ggcgttggcc gcgttgacca acgaccacct cgtcgccttg  1800
gcctgcctcg gcggacgtcc tgccatggat gcagtgaaaa agggattgcc gcacgcgccg  1860
gaattgatca aagagtcaa tcgccgtatt ggcgaacgca cgtcccatcg cgttgcgata   1920
tctagagtgg gaggaagctc tcgcagagag tccatcaacc catggattct gactggtttc  1980
gctgatgccg aaggatcatt cgggctaagc atcctcaaca gaaacagagg tactgctaga  2040
taccacactc gactgtcatt cacaatcatg ctgcacaaca aggacaaatc gattctggag  2100
aatatccagt cgacttggaa ggtcggctcg atctacaaca acggcgacca ctacgtctcg  2160
ctggaggtct tccgtttcga agatttgaaa gtgattatcg accacttcga gaaatatccg  2220
ctgataacac agaaattggg cgattacaag ttgtttaaac aggcattcag cgtcatggag  2280
```

```
aacaaagaac atcttaagga gaatgggatt aaggagctcg tacgaatcaa agctaagatg   2340
aattggggtc tcaatgacga attgaaaaaa gcatttccag agaacattag caaagagcgc   2400
ccccttatca ataagaacat tccgaatttc aaatggctgg ctggattcac atctggtgat   2460
ggctccttct tcgtgcgcct aagaaagtct aatgttaatg ctagagtacg tgtgcaactg   2520
gtattcgaga tctcacagca catcagagac aagaacctga tgaattcatt gataacatac   2580
ctaggctgtg gtcacatcta cgagggaaac aaatctgagc gcagttggct ccaattcaga   2640
gtagaaaaat tcagcgatat caacgacaag atcattccgg tattccagga aaatactctg   2700
attggcgtca aactcgagga ctttgaagat tggtgcaagg ttgccaaatt gatcgaagag   2760
aagaaacacc tgaccgaatc cggtttggat gagattaaga aaatcaagct gaacatgaac   2820
aaaggtcgtt ga                                                      2832

SEQ ID NO: 69           moltype =    length =
SEQUENCE: 69
000

SEQ ID NO: 70           moltype = AA   length = 5
FEATURE                 Location/Qualifiers
REGION                  1..5
                        note = Exemplary linker sequence
source                  1..5
                        mol_type = protein
                        organism = synthetic construct
SEQUENCE: 70
DGGGS                                                                5

SEQ ID NO: 71           moltype = AA   length = 5
FEATURE                 Location/Qualifiers
REGION                  1..5
                        note = Exemplary linker sequence
source                  1..5
                        mol_type = protein
                        organism = synthetic construct
SEQUENCE: 71
TGEKP                                                                5

SEQ ID NO: 72           moltype = AA   length = 4
FEATURE                 Location/Qualifiers
REGION                  1..4
                        note = Exemplary linker sequence
source                  1..4
                        mol_type = protein
                        organism = synthetic construct
SEQUENCE: 72
GGRR                                                                 4

SEQ ID NO: 73           moltype = AA   length = 5
FEATURE                 Location/Qualifiers
REGION                  1..5
                        note = Exemplary linker sequence
source                  1..5
                        mol_type = protein
                        organism = synthetic construct
SEQUENCE: 73
GGGGS                                                                5

SEQ ID NO: 74           moltype = AA   length = 14
FEATURE                 Location/Qualifiers
REGION                  1..14
                        note = Exemplary linker sequence
source                  1..14
                        mol_type = protein
                        organism = synthetic construct
SEQUENCE: 74
EGKSSGSGSE SKVD                                                     14

SEQ ID NO: 75           moltype = AA   length = 18
FEATURE                 Location/Qualifiers
REGION                  1..18
                        note = Exemplary linker sequence
source                  1..18
                        mol_type = protein
                        organism = synthetic construct
SEQUENCE: 75
KESGSVSSEQ LAQFRSLD                                                 18

SEQ ID NO: 76           moltype = AA   length = 8
FEATURE                 Location/Qualifiers
REGION                  1..8
                        note = Exemplary linker sequence
```

```
source                      1..8
                            mol_type = protein
                            organism = synthetic construct
SEQUENCE: 76
GGRRGGGS                                                                          8

SEQ ID NO: 77               moltype = AA  length = 9
FEATURE                     Location/Qualifiers
REGION                      1..9
                            note = Exemplary linker sequence
source                      1..9
                            mol_type = protein
                            organism = synthetic construct
SEQUENCE: 77
LRQRDGERP                                                                         9

SEQ ID NO: 78               moltype = AA  length = 12
FEATURE                     Location/Qualifiers
REGION                      1..12
                            note = Exemplary linker sequence
source                      1..12
                            mol_type = protein
                            organism = synthetic construct
SEQUENCE: 78
LRQKDGGGSE RP                                                                    12

SEQ ID NO: 79               moltype = AA  length = 16
FEATURE                     Location/Qualifiers
REGION                      1..16
                            note = Exemplary linker sequence
source                      1..16
                            mol_type = protein
                            organism = synthetic construct
SEQUENCE: 79
LRQKDGGGSG GGSERP                                                                16

SEQ ID NO: 80               moltype =   length =
SEQUENCE: 80
000

SEQ ID NO: 81               moltype = AA  length = 7
FEATURE                     Location/Qualifiers
REGION                      1..7
                            note = Cleavage sequence by TEV protease
source                      1..7
                            mol_type = protein
                            organism = synthetic construct
SEQUENCE: 81
ENLYFQG                                                                           7

SEQ ID NO: 82               moltype = AA  length = 7
FEATURE                     Location/Qualifiers
REGION                      1..7
                            note = Cleavage sequence by TEV protease
source                      1..7
                            mol_type = protein
                            organism = synthetic construct
SEQUENCE: 82
ENLYFQS                                                                           7

SEQ ID NO: 83               moltype = AA  length = 22
FEATURE                     Location/Qualifiers
REGION                      1..22
                            note = Self-cleaving polypeptide comprising 2A site
source                      1..22
                            mol_type = protein
                            organism = synthetic construct
SEQUENCE: 83
GSGATNFSLL KQAGDVEENP GP                                                         22

SEQ ID NO: 84               moltype = AA  length = 19
FEATURE                     Location/Qualifiers
REGION                      1..19
                            note = Self-cleaving polypeptide comprising 2A site
source                      1..19
                            mol_type = protein
                            organism = synthetic construct
SEQUENCE: 84
ATNFSLLKQA GDVEENPGP                                                             19
```

```
SEQ ID NO: 85          moltype = AA  length = 14
FEATURE                Location/Qualifiers
REGION                 1..14
                       note = Self-cleaving polypeptide comprising 2A site
source                 1..14
                       mol_type = protein
                       organism = synthetic construct
SEQUENCE: 85
LLKQAGDVEE NPGP                                                         14

SEQ ID NO: 86          moltype = AA  length = 21
FEATURE                Location/Qualifiers
REGION                 1..21
                       note = Self-cleaving polypeptide comprising 2A site
source                 1..21
                       mol_type = protein
                       organism = synthetic construct
SEQUENCE: 86
GSGEGRGSLL TCGDVEENPG P                                                 21

SEQ ID NO: 87          moltype = AA  length = 18
FEATURE                Location/Qualifiers
REGION                 1..18
                       note = Self-cleaving polypeptide comprising 2A site
source                 1..18
                       mol_type = protein
                       organism = synthetic construct
SEQUENCE: 87
EGRGSLLTCG DVEENPGP                                                     18

SEQ ID NO: 88          moltype = AA  length = 13
FEATURE                Location/Qualifiers
REGION                 1..13
                       note = Self-cleaving polypeptide comprising 2A site
source                 1..13
                       mol_type = protein
                       organism = synthetic construct
SEQUENCE: 88
LLTCGDVEEN PGP                                                          13

SEQ ID NO: 89          moltype = AA  length = 23
FEATURE                Location/Qualifiers
REGION                 1..23
                       note = Self-cleaving polypeptide comprising 2A site
source                 1..23
                       mol_type = protein
                       organism = synthetic construct
SEQUENCE: 89
GSGQCTNYAL LKLAGDVESN PGP                                               23

SEQ ID NO: 90          moltype = AA  length = 20
FEATURE                Location/Qualifiers
REGION                 1..20
                       note = Self-cleaving polypeptide comprising 2A site
source                 1..20
                       mol_type = protein
                       organism = synthetic construct
SEQUENCE: 90
QCTNYALLKL AGDVESNPGP                                                   20

SEQ ID NO: 91          moltype = AA  length = 14
FEATURE                Location/Qualifiers
REGION                 1..14
                       note = Self-cleaving polypeptide comprising 2A site
source                 1..14
                       mol_type = protein
                       organism = synthetic construct
SEQUENCE: 91
LLKLAGDVES NPGP                                                         14

SEQ ID NO: 92          moltype = AA  length = 25
FEATURE                Location/Qualifiers
REGION                 1..25
                       note = Self-cleaving polypeptide comprising 2A site
source                 1..25
                       mol_type = protein
                       organism = synthetic construct
SEQUENCE: 92
```

```
GSGVKQTLNF DLLKLAGDVE SNPGP                                                     25

SEQ ID NO: 93           moltype = AA  length = 22
FEATURE                 Location/Qualifiers
REGION                  1..22
                        note = Self-cleaving polypeptide comprising 2A site
source                  1..22
                        mol_type = protein
                        organism = synthetic construct
SEQUENCE: 93
VKQTLNFDLL KLAGDVESNP GP                                                        22

SEQ ID NO: 94           moltype = AA  length = 14
FEATURE                 Location/Qualifiers
REGION                  1..14
                        note = Self-cleaving polypeptide comprising 2A site
source                  1..14
                        mol_type = protein
                        organism = synthetic construct
SEQUENCE: 94
LLKLAGDVES NPGP                                                                 14

SEQ ID NO: 95           moltype = AA  length = 19
FEATURE                 Location/Qualifiers
REGION                  1..19
                        note = Self-cleaving polypeptide comprising 2A site
source                  1..19
                        mol_type = protein
                        organism = synthetic construct
SEQUENCE: 95
LLNFDLLKLA GDVESNPGP                                                            19

SEQ ID NO: 96           moltype = AA  length = 19
FEATURE                 Location/Qualifiers
REGION                  1..19
                        note = Self-cleaving polypeptide comprising 2A site
source                  1..19
                        mol_type = protein
                        organism = synthetic construct
SEQUENCE: 96
TLNFDLLKLA GDVESNPGP                                                            19

SEQ ID NO: 97           moltype = AA  length = 14
FEATURE                 Location/Qualifiers
REGION                  1..14
                        note = Self-cleaving polypeptide comprising 2A site
source                  1..14
                        mol_type = protein
                        organism = synthetic construct
SEQUENCE: 97
LLKLAGDVES NPGP                                                                 14

SEQ ID NO: 98           moltype = AA  length = 17
FEATURE                 Location/Qualifiers
REGION                  1..17
                        note = Self-cleaving polypeptide comprising 2A site
source                  1..17
                        mol_type = protein
                        organism = synthetic construct
SEQUENCE: 98
NFDLLKLAGD VESNPGP                                                              17

SEQ ID NO: 99           moltype = AA  length = 20
FEATURE                 Location/Qualifiers
REGION                  1..20
                        note = Self-cleaving polypeptide comprising 2A site
source                  1..20
                        mol_type = protein
                        organism = synthetic construct
SEQUENCE: 99
QLLNFDLLKL AGDVESNPGP                                                           20

SEQ ID NO: 100          moltype = AA  length = 24
FEATURE                 Location/Qualifiers
REGION                  1..24
                        note = Self-cleaving polypeptide comprising 2A site
source                  1..24
                        mol_type = protein
                        organism = synthetic construct
```

```
SEQUENCE: 100
APVKQTLNFD LLKLAGDVES NPGP                                                      24

SEQ ID NO: 101          moltype = AA  length = 40
FEATURE                 Location/Qualifiers
REGION                  1..40
                        note = Self-cleaving polypeptide comprising 2A site
source                  1..40
                        mol_type = protein
                        organism = synthetic construct
SEQUENCE: 101
VTELLYRMKR AETYCPRPLL AIHPTEARHK QKIVAPVKQT                                      40

SEQ ID NO: 102          moltype = AA  length = 18
FEATURE                 Location/Qualifiers
REGION                  1..18
                        note = Self-cleaving polypeptide comprising 2A site
source                  1..18
                        mol_type = protein
                        organism = synthetic construct
SEQUENCE: 102
LNFDLLKLAG DVESNPGP                                                             18

SEQ ID NO: 103          moltype = AA  length = 40
FEATURE                 Location/Qualifiers
REGION                  1..40
                        note = Self-cleaving polypeptide comprising 2A site
source                  1..40
                        mol_type = protein
                        organism = synthetic construct
SEQUENCE: 103
LLAIHPTEAR HKQKIVAPVK QTLNFDLLKL AGDVESNPGP                                      40

SEQ ID NO: 104          moltype = AA  length = 33
FEATURE                 Location/Qualifiers
REGION                  1..33
                        note = Self-cleaving polypeptide comprising 2A site
source                  1..33
                        mol_type = protein
                        organism = synthetic construct
SEQUENCE: 104
EARHKQKIVA PVKQTLNFDL LKLAGDVESN PGP                                             33

SEQ ID NO: 105          moltype = DNA  length = 10
FEATURE                 Location/Qualifiers
misc_feature            1..10
                        note = Consensus Kozak sequence
source                  1..10
                        mol_type = other DNA
                        organism = synthetic construct
SEQUENCE: 105
gccrccatgg                                                                      10

SEQ ID NO: 106          moltype = AA  length = 8
FEATURE                 Location/Qualifiers
source                  1..8
                        mol_type = protein
                        organism = Homo sapiens
SEQUENCE: 106
EQTEYATI                                                                        8

SEQ ID NO: 107          moltype = DNA  length = 43
FEATURE                 Location/Qualifiers
source                  1..43
                        mol_type = genomic DNA
                        organism = Homo sapiens
SEQUENCE: 107
tgagcagacg gagtatgcca ccattgtctt tcctagcgga atg                                 43

SEQ ID NO: 108          moltype = DNA  length = 43
FEATURE                 Location/Qualifiers
misc_feature            1..43
                        note = Made in Lab
source                  1..43
                        mol_type = other DNA
                        organism = synthetic construct
SEQUENCE: 108
cattccgcta ggaaagacaa tggtggcata ctccgtctgc tca                                 43
```

```
SEQ ID NO: 109          moltype = DNA  length = 22
FEATURE                 Location/Qualifiers
misc_feature            1..22
                        note = Made in Lab
variation               14..22
                        note = n is A, C, G or T
source                  1..22
                        mol_type = other DNA
                        organism = synthetic construct
SEQUENCE: 109
aatggtggca tacnnnnnnn nn                                          22

SEQ ID NO: 110          moltype = DNA  length = 22
FEATURE                 Location/Qualifiers
misc_feature            1..22
                        note = Made in Lab
variation               1..9
                        note = n is a, c, g, or t
source                  1..22
                        mol_type = other DNA
                        organism = synthetic construct
SEQUENCE: 110
nnnnnnnnna tactccgtct gc                                          22

SEQ ID NO: 111          moltype = DNA  length = 22
FEATURE                 Location/Qualifiers
misc_feature            1..22
                        note = Made in Lab
source                  1..22
                        mol_type = other DNA
                        organism = synthetic construct
SEQUENCE: 111
aatggtggca tactccgtct gc                                          22

SEQ ID NO: 112          moltype = DNA  length = 43
FEATURE                 Location/Qualifiers
source                  1..43
                        mol_type = genomic DNA
                        organism = Homo sapiens
SEQUENCE: 112
attccgctag gaaagacaat ggtggcatac tccgtctgct cag                   43

SEQ ID NO: 113          moltype = DNA  length = 43
FEATURE                 Location/Qualifiers
misc_feature            1..43
                        note = Made in Lab
source                  1..43
                        mol_type = other DNA
                        organism = synthetic construct
SEQUENCE: 113
atttcgttag gaaagataat ggtggtatat tcgtttgtt tag                    43

SEQ ID NO: 114          moltype = AA  length = 7
FEATURE                 Location/Qualifiers
source                  1..7
                        mol_type = protein
                        organism = Homo sapiens
SEQUENCE: 114
MQIPQAP                                                            7

SEQ ID NO: 115          moltype = DNA  length = 44
FEATURE                 Location/Qualifiers
source                  1..44
                        mol_type = genomic DNA
                        organism = Homo sapiens
SEQUENCE: 115
ctctggtggg gctgctccag gcatgcagat cccacaggcg ccct                  44

SEQ ID NO: 116          moltype = DNA  length = 44
FEATURE                 Location/Qualifiers
misc_feature            1..44
                        note = Made in Lab
source                  1..44
                        mol_type = other DNA
                        organism = synthetic construct
SEQUENCE: 116
agggcgcctg tgggatctgc atccctggag cagccccacc agag                  44

SEQ ID NO: 117          moltype = AA  length = 8
```

```
FEATURE              Location/Qualifiers
source               1..8
                     mol_type = protein
                     organism = Homo sapiens
SEQUENCE: 117
NGRDFHMS                                                                         8

SEQ ID NO: 118       moltype = DNA  length = 43
FEATURE              Location/Qualifiers
source               1..43
                     mol_type = genomic DNA
                     organism = Homo sapiens
SEQUENCE: 118
gtgtcacaca actgcccaac gggcgtgact tccacatgag cgt                                  43

SEQ ID NO: 119       moltype = DNA  length = 43
FEATURE              Location/Qualifiers
misc_feature         1..43
                     note = Made in Lab
source               1..43
                     mol_type = other DNA
                     organism = synthetic construct
SEQUENCE: 119
acgctcatgt ggaagtcacg cccgttgggc agttgtgtga cac                                  43

SEQ ID NO: 120       moltype = DNA  length = 32
FEATURE              Location/Qualifiers
source               1..32
                     mol_type = genomic DNA
                     organism = Homo sapiens
SEQUENCE: 120
gctccaggca tgcagatccc acaggcgccc tg                                              32

SEQ ID NO: 121       moltype = DNA  length = 32
FEATURE              Location/Qualifiers
misc_feature         1..32
                     note = made in lab
source               1..32
                     mol_type = other DNA
                     organism = synthetic construct
SEQUENCE: 121
actccaaaca tacaaatccc acaaacaccc ta                                              32

SEQ ID NO: 122       moltype = DNA  length = 31
FEATURE              Location/Qualifiers
source               1..31
                     mol_type = genomic DNA
                     organism = Homo sapiens
SEQUENCE: 122
gcccaacggg cgtgacttcc acatgagcgt g                                               31

SEQ ID NO: 123       moltype = DNA  length = 31
FEATURE              Location/Qualifiers
misc_feature         1..31
                     note = Made in Lab
source               1..31
                     mol_type = other DNA
                     organism = synthetic construct
SEQUENCE: 123
acccaacgaa cgtaacttcc acataaacgt a                                               31
```

PD-1 HOMING ENDONUCLEASE VARIANTS, COMPOSITIONS, AND METHODS OF USE

CROSS REFERENCE TO RELATED APPLICATIONS

This application is a Continuation Application of U.S. patent application Ser. No. 17/738,484, filed on May 6, 2022, now U.S. Pat. No. 11,912,746, issued on Feb. 27, 2024, which is a Continuation Application of U.S. patent application Ser. No. 16/330,039, filed on Mar. 1, 2019, now U.S. Pat. No. 11,365,226, issued on Jun. 21, 2022, which is the National Stage of International Application No. PCT/US2017/050774, filed Sep. 8, 2017, which claims the benefit under 35 U.S.C. § 119 (e) of U.S. Provisional Application No. 62/414,279, filed Oct. 28, 2016, and U.S. Provisional Application No. 62/385,079, filed Sep. 8, 2016, each of which is incorporated by reference herein in its entirety.

STATEMENT REGARDING SEQUENCE LISTING

The Sequence Listing associated with this application is provided in XML format, and is hereby incorporated by reference into the specification. The name of the XML file containing the Sequence Listing is BLUE-076C2v2.xml. The XML file is 261,420 bytes, was created on Mar. 1, 2024, and is being submitted electronically, concurrent with the filing of the specification.

BACKGROUND

Technical Field

The present disclosure relates to improved genome editing compositions. More particularly, the disclosure relates to nuclease variants, compositions, and methods of using the same for editing the human program cell death 1 (PD-1) gene.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

The immune system has a key role in detecting and combating human cancer. The majority of transformed cells are quickly detected by immune sentinels and destroyed through the activation of antigen-specific T cells via clonally expressed T cell receptors (TCR). Accordingly, cancer can be considered an immunological disorder, a failure of immune system to mount the necessary anti-tumor response to durably suppress and eliminate the disease. In order to more effectively combat cancer, certain immunotherapy interventions developed over the last few decades have specifically focused on enhancing T cell immunity. These treatments have yielded only sporadic cases of disease remission, and have not had substantial overall success. More recent therapies that use monoclonal antibodies targeting molecules that inhibit T cell activation, such as CTLA-4 or PD-1, have shown a more substantial anti-tumor effect; however, these treatments are also associated with substantial toxicity due to systemic immune activation.

Most recently, adoptive cellular immunotherapy strategies, which are based on the isolation, modification, expansion and reinfusion of T cells, have been explored and tested in early stage clinical trials. T cells have often been the effector cells of choice for cancer immunotherapy due to their selective recognition and powerful effector mechanisms. These treatments have shown mixed rates of success, but a small number of patients have experienced durable remissions, highlighting the as-yet unrealized potential for T cell-based immunotherapies.

Successful recognition of tumor cell associated antigens by cytolytic T cells initiates targeted tumor lysis and underpins any effective cancer immunotherapy approach. Tumor-infiltrating T cells (TILs) express TCRs specifically directed tumor-associated antigens; however, substantial numbers of TILs are limited to only a few human cancers. Engineered T cell receptors (TCRs) and chimeric antigen receptors (CARs) potentially increase the applicability of T cell-based immunotherapy to many cancers and other immune disorders.

In addition, state of the art engineered T cells are still regulated by a complex immunosuppressive tumor microenvironment that consists of cancer cells, inflammatory cells, stromal cells and cytokines. Among these components, cancer cells, inflammatory cells and suppressive cytokines regulate T cell phenotype and function. Collectively, the tumor microenvironment drives T cells to terminally differentiate into exhausted T cells.

T cell exhaustion is a state of T cell dysfunction in a chronic environment marked by increased expression of, or increased signaling by inhibitory receptors; reduced effector cytokine production; and a decreased ability to persist and eliminate cancer. Exhausted T cells also show loss of function in a hierarchical manner: decreased IL-2 production and ex vivo killing capacity are lost at the early stage of exhaustion, TNF-α production is lost at the intermediate stage, and IFN-γ and GzmB production are lost at the advanced stage of exhaustion. Most T cells in the tumor microenvironment differentiate into exhausted T cells and lose the ability to eliminate cancer and are eventually cleared.

Program cell death 1 (PD-1) is expressed on T cells and mediates immunosuppression by binding to immunosuppressive factors, e.g., PD-L1 and PD-L2, present in the tumor microenvironment. The expression of PD-L1 and PD-L2 correlates with prognosis in some human malignancies. The PD-L1/PD-1 signaling pathway is one important regulatory pathway of T cell exhaustion. PD-L1 is abundantly expressed in cancer cells and stromal cells, and blockade of PD-L1/PD-1 using monoclonal antibodies enhances T cell anti-tumor function. PD-L2 also binds to PD-1 and negatively regulates T cell function.

BRIEF SUMMARY

The present disclosure generally relates, in part, to compositions comprising homing endonuclease variants and megaTALs that cleave a target site in the human PD-1 gene and methods of using the same.

In various embodiments, the present disclosure contemplates, in part, a polypeptide comprising a homing endonuclease (HE) variant that cleaves a target site in the human program cell death 1 (PD-1) gene.

In particular embodiments, the HE variant is an LAGLI-DADG homing endonuclease (LHE) variant.

In certain embodiments, the polypeptide comprises a biologically active fragment of the HE variant.

In some embodiments, the biologically active fragment lacks the 1, 2, 3, 4, 5, 6, 7, or 8 N-terminal amino acids compared to a corresponding wild type HE.

In additional embodiments, the biologically active fragment lacks the 4 N-terminal amino acids compared to a corresponding wild type HE.

In certain embodiments, the biologically active fragment lacks the 8 N-terminal amino acids compared to a corresponding wild type HE.

In particular embodiments, the biologically active fragment lacks the 1, 2, 3, 4, or 5 C-terminal amino acids compared to a corresponding wild type HE.

In particular embodiments, wherein the biologically active fragment lacks the C-terminal amino acid compared to a corresponding wild type HE.

In some embodiments, the biologically active fragment lacks the 2 C-terminal amino acids compared to a corresponding wild type HE.

In further embodiments, the HE variant is a variant of an LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I.

In particular embodiments, the HE variant is a variant of an LHE selected from the group consisting of: I-CpaMI, I-HjeMI, I-OnuI, I-PanMI, and SmaMI.

In further embodiments, the HE variant is an I-OnuI LHE variant.

In additional embodiments, the HE variant comprises one or more amino acid substitutions in the DNA recognition interface at amino acid positions selected from the group consisting of: 19, 24, 26, 28, 30, 32, 34, 35, 36, 37, 38, 40, 42, 44, 46, 48, 59, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 of an I-OnuI LHE amino acid sequence as set forth in SEQ ID NOs: 1-5, or a biologically active fragment thereof.

In particular embodiments, the HE variant comprises at least 5, at least 15, preferably at least 25, more preferably at least 35, or even more preferably at least 40 or more amino acid substitutions in the DNA recognition interface at amino acid positions selected from the group consisting of: 19, 24, 26, 28, 30, 32, 34, 35, 36, 37, 38, 40, 42, 44, 46, 48, 59, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 of an I-OnuI LHE amino acid sequence as set forth in SEQ ID NOs: 1-5, or a biologically active fragment thereof.

In particular embodiments, the HE variant cleaves a PD-1 exon 5 target site and comprises at least 5, at least 15, preferably at least 25, more preferably at least 35, or even more preferably at least 40 or more amino acid substitutions in at least one position selected from the position group consisting of positions: 26, 28, 32, 34, 35, 36, 37, 38, 40, 42, 44, 46, 48, 59, 68, 70, 72, 75, 76, 78, 80, 138, 143, 159, 168, 178, 180, 182, 184, 186, 188, 189, 190, 191, 192, 193, 197, 199, 201, 203, 207, 223, 224, 225, 227, 229, 232, 236, and 238 of any one of SEQ ID NOs: 1-5, or a biologically active fragment thereof.

In certain embodiments, the HE variant cleaves a PD-1 exon 5 target site and comprises at least 5, at least 15, preferably at least 25, more preferably at least 35, or even more preferably at least 40 or more of, or all of the following amino acid substitutions: L26Q, R28E, N32V, K34P, S35N, S36I, V37P, G38R, S40K, S40R, E42R, G44R, Q46E, T48D, N59D, V68K, A70Y, S72Q, S72R, N75S, A76Y, S78K, K80R, L138M, T143N, S159P, F168L, E178D, C180H, F182G, N184I, 186A, S188R, K189R, S190P, K191A, L192S, G193P, Q197R, V199R, S201A, S201M, T203G, K207R, Y223R, I224T, K225R, K229I, F232K, D236E, and V238E of any one of SEQ ID NOs: 1-5, or a biologically active fragment thereof.

In some embodiments, the HE variant cleaves a PD-1 exon 5 target site and comprises at least 5, at least 15, preferably at least 25, more preferably at least 35, or even more preferably at least 40 or more of, or all of the following amino acid substitutions: L26Q, R28E, N32V, K34P, S35N, S36I, V37P, G38R, S40K, E42R, G44R, Q46E, T48D, V68K, A70Y, S72Q, N75S, A76Y, S78K, K80R, L138M, T143N, S159P, F168L, C180H, F182G, N184I, I186A, S188R, K189R, S190P, K191A, L192S, G193P, Q197R, V199R, S201A, T203G, K207R, Y223R, K225R, K229I, F232K, D236E, and V238E of any one of SEQ ID NOs: 1-5, or a biologically active fragment thereof.

In particular embodiments, the HE variant cleaves a PD-1 exon 5 target site and comprises at least 5, at least 15, preferably at least 25, more preferably at least 35, or even more preferably at least 40 or more of, or all of the following amino acid substitutions: L26Q, R28E, N32V, K34P, S35N, S36I, V37P, G38R, S40R, E42R, G44R, Q46E, T48D, N59D, V68K, A70Y, S72R, N75S, A76Y, K80R, L138M, T143N, S159P, F168L, C180H, F182G, N184I, I186A, S188R, K189R, S190P, K191A, L192S, G193P, Q197R, V199R, S201A, T203G, K207R, Y223R, 1224T, K225R, K229I, F232K, D236E, and V238E of any one of SEQ ID NOs: 1-5, or a biologically active fragment thereof.

In additional embodiments, the HE variant cleaves a PD-1 exon 5 target site and comprises at least 5, at least 15, preferably at least 25, more preferably at least 35, or even more preferably at least 40 or more of, or all of the following amino acid substitutions: L26Q, R28E, N32V, K34P, S35N, S36I, V37P, G38R, S40R, E42R, G44R, Q46E, T48D, N59D, V68K, A70Y, S72Q, N75S, A76Y, K80R, L138M, T143N, S159P, F168L, E178D, C180H, F182G, N184I, I186A, S188R, K189R, S190P, K191A, L192S, G193P, Q197R, V199R, S201A, T203G, K207R, Y223R, 1224T, K225R, K229I, F232K, D236E, and V238E of any one of SEQ ID NOs: 1-5, or a biologically active fragment thereof.

In further embodiments, the HE variant cleaves a PD-1 exon 5 target site and comprises at least 5, at least 15, preferably at least 25, more preferably at least 35, or even more preferably at least 40 or more of, or all of the following amino acid substitutions: L26Q, R28E, N32V, K34P, S35N, S36I, V37P, G38R, S40R, E42R, G44R, Q46E, T48D, N59D, V68K, A70Y, S72Q, N75S, A76Y, K80R, L138M, T143N, S159P, F168L, E178D, C180H, F182G, N184I, I186A, S188R, K189R, S190P, K191A, L192S, G193P, Q197R, V199R, S201A, T203G, K207R, Y223R, K225R, F232K, D236E, and V238E of any one of SEQ ID NOs: 1-5, or a biologically active fragment thereof.

In particular embodiments, the HE variant cleaves a PD-1 exon 5 target site and comprises at least 5, at least 15, preferably at least 25, more preferably at least 35, or even more preferably at least 40 or more of, or all of the following amino acid substitutions: L26Q, R28E, N32V, K34P, S35N, S36I, V37P, G38R, S40R, E42R, G44R, Q46E, T48D, N59D, V68K, A70Y, S72Q, N75S, A76Y, K80R, L138M, T143N, S159P, F168L, E178D, C180H, F182G, N184I, I186A, S188R, K189R, S190P, K191A, L192S, G193P, Q197R, V199R, S201M, T203G, Y223R, K225R, F232K, D236E, and V238E of any one of SEQ ID NOs: 1-5, or a biologically active fragment thereof.

In particular embodiments, the HE variant cleaves a PD-1 exon 1 target site and comprises at least 5, at least 15, preferably at least 25, more preferably at least 35, or even more preferably at least 40 or more amino acid substitutions in at least one position selected from the position group consisting of positions: 26, 28, 30, 32, 34, 35, 36, 37, 38, 40, 42, 44, 46, 48, 68, 70, 72, 75, 76, 78, 80, 100, 132, 138, 143, 155, 159, 178, 180, 184, 186, 189, 190, 191, 192, 193, 195, 201, 203, 207, 223, 225, 227, 232, 236, 238, and 240 of any one of SEQ ID NOs: 1-5, or a biologically active fragment thereof.

In some embodiments, the HE variant cleaves a PD-1 exon 1 target site and comprises at least 5, at least 15, preferably at least 25, more preferably at least 35, or even more preferably at least 40 or more amino acid substitutions in at least one position selected from the position group consisting of positions: L26G, R28S, R30L, N32R, K34R, S35G, S36T, V37A, V37G, G38R, S40H, E42R, G44S, Q46A, Q46T, T48V, T48M, V68I, V68S, A70T, A70Y, A70L, S72D, S72N, N75R, N75H, A76Y, S78R, S78T, K80R, K80C, K80E, K80V, T82F, T82Y, I100V, V132A, L138M, T143N, S155G, S159P, E178D, C180S, N184R, I186R, K189N, S190V, K19 IN, L192A, G193R, Q195R, S201E, T203S, K207R, Y223H, K225Y, K227G, F232R, D236Q, V238R, and T240E of any one of SEQ ID NOs: 1-5, or a biologically active fragment thereof.

In further embodiments, the HE variant cleaves a PD-1 exon 1 target site and comprises at least 5, at least 15, preferably at least 25, more preferably at least 35, or even more preferably at least 40 or more of, or all of the following amino acid substitutions: L26G, R28S, R30L, N32R, K34R, S35G, S36T, V37A, G38R, S40H, E42R, G44S, Q46A, T48V, V68I, A70T, S72D, N75R, A76Y, S78R, K80R, I100V, L138M, T143N, S159P, E178D, C180S, N184R, I186R, K189N, S190V, K191N, L192A, G193R, Q195R, S201E, T203S, K207R, Y223H, K225Y, K227G, F232R, D236Q, V238R, and T240E of any one of SEQ ID NOs: 1-5, or a biologically active fragment thereof.

In certain embodiments, the HE variant cleaves a PD-1 exon 1 target site and comprises at least 5, at least 15, preferably at least 25, more preferably at least 35, or even more preferably at least 40 or more of, or all of the following amino acid substitutions: L26G, R28S, R30L, N32R, K34R, S35G, S36T, V37A, V37G, G38R, S40H, E42R, G44S, Q46T, T48V, V68I, A70T, S72D, N75R, A76Y, S78R, K80C, I100V, V132A, L138M, T143N, S155G, S159P, E178D, C180S, N184R, I186R, K189N, S190V, K191N, L192A, G193R, Q195R, S201E, T203S, K207R, Y223H, K225Y, K227G, F232R, D236Q, V238R, and T240E of any one of SEQ ID NOs: 1-5, or a biologically active fragment thereof.

In certain embodiments, the HE variant cleaves a PD-1 exon 1 target site and comprises at least 5, at least 15, preferably at least 25, more preferably at least 35, or even more preferably at least 40 or more of, or all of the following amino acid substitutions: L26G, R28S, R30L, N32R, K34R, S35G, S36T, V37A, G38R, S40H, E42R, G44S, Q46T, T48M, V68I, A70T, S72N, N75H, A76Y, S78T, K80R, I100V, L138M, T143N, S159P, E178D, C180S, N184R, I186R, K189N, S190V, K191N, L192A, G193R, Q195R, S201E, T203S, K207R, Y223H, K225Y, K227G, F232R, D236Q, V238R, and T240E of any one of SEQ ID NOs: 1-5, or a biologically active fragment thereof.

In certain embodiments, the HE variant cleaves a PD-1 exon 1 target site and comprises at least 5, at least 15, preferably at least 25, more preferably at least 35, or even more preferably at least 40 or more of, or all of the following amino acid substitutions: L26G, R28S, R30L, N32R, K34R, S35G, S36T, V37A, G38R, S40H, E42R, G44S, Q46T, T48M, V68S, A70Y, S72N, N75H, A76Y, K80E, T82F, L138M, T143N, S159P, E178D, C180S, N184R, I186R, K189N, S190V, K191N, L192A, G193R, Q195R, S201E, T203S, K207R, Y223H, K225Y, K227G, F232R, D236Q, V238R, and T240E of any one of SEQ ID NOs: 1-5, or a biologically active fragment thereof.

In certain embodiments, the HE variant cleaves a PD-1 exon 1 target site and comprises at least 5, at least 15, preferably at least 25, more preferably at least 35, or even more preferably at least 40 or more of, or all of the following amino acid substitutions: L26G, R28S, R30L, N32R, K34R, S35G, S36T, V37A, G38R, S40H, E42R, G44S, Q46T, T48M, V68S, A70L, S72N, N75H, A76Y, K80V, T82Y, L138M, T143N, S159P, E178D, C180S, N184R, I186R, K189N, S190V, K191N, L192A, G193R, Q195R, S201E, T203S, K207R, Y223H, K225Y, K227G, F232R, D236Q, V238R, and T240E of any one of SEQ ID NOs: 1-5, or a biologically active fragment thereof.

In certain embodiments, the HE variant cleaves a PD-1 exon 1 target site and comprises at least 5, at least 15, preferably at least 25, more preferably at least 35, or even more preferably at least 40 or more of, or all of the following amino acid substitutions: L26G, R28S, R30L, N32R, K34R, S35G, S36T, V37G, G38R, S40H, E42R, G44S, Q46T, T48M, V68S, A70T, S72N, N75H, A76Y, K80V, T82Y, L138M, T143N, S159P, E178D, C180S, N184R, I186R, K189N, S190V, K19 IN, L192A, G193R, Q195R, S201E, T203S, K207R, Y223H, K225Y, K227G, F232R, D236Q, V238R, and T240E of any one of SEQ ID NOs: 1-5, or a biologically active fragment thereof.

In particular embodiments, the HE variant cleaves a PD-1 exon 2 target site and comprises at least 5, at least 15, preferably at least 25, more preferably at least 35, or even more preferably at least 40 or more amino acid substitutions in at least one position selected from the position group consisting of positions: 24, 26, 28, 30, 32, 34, 35, 36, 37, 38, 40, 41, 42, 44, 46, 48, 68, 70, 72, 74, 75, 76, 78, 80, 82, 116, 138, 143, 159, 168, 178, 180, 182, 184, 186, 188, 189, 190, 191, 192, 193, 195, 199, 203, 207, 225, 227, 229, 232, 236, and 238 of any one of SEQ ID NOs: 1-5, or a biologically active fragment thereof.

In additional embodiments, the HE variant cleaves a PD-1 exon 2 target site and comprises at least 5, at least 15, preferably at least 25, more preferably at least 35, or even more preferably at least 40 or more amino acid substitutions in at least one position selected from the position group consisting of positions: S24C, L26Q, R28Y, R28H, R30S, N32V, N32L, K34N, K34R, S35N, S35T, S36R, V37S, V37T, G38R, G38K, S40R, T41A, E42R, G44S, G44R, Q46E, Q46A, T48E, V68I, A70N, S72I, D74N, N75T, N75R, A76S, A76R, S78R, K80S, T82G, T82R, V116L, L138M, T143N, S159P, F168L, E178D, C180N, F182Y, N184H, I186K, K189G, S190R, K191T, L192T, G193R, Q195Y, V199R, T203A, T203S, K207R, K225N, K225T, K227W, K227S, K229A, K229P, F232R, W234A, W234D, D236E, and V238R of any one of SEQ ID NOs: 1-5, or a biologically active fragment thereof.

In particular embodiments, the HE variant cleaves a PD-1 exon 2 target site and comprises at least 5, at least 15, preferably at least 25, more preferably at least 35, or even more preferably at least 40 or more of, or all of the following amino acid substitutions: L26Q, R28Y, R30S, N32V, K34N, S35N, S36R, V37S, G38R, S40R, T41A, E42R, G44R, Q46A, T48E, A70N, S72I, N75T, A76S, S78R, K80S, T82G, L138M, T143N, S159P, F168L, E178D, C180N, F182Y, N184H, I186K, K189G, S190R, K191T, L192T, G193R, Q195Y, V199R, T203A, K207R, K225N, K227W, K229A, F232R, W234A, D236E, and V238R of any one of SEQ ID NOs: 1-5, or a biologically active fragment thereof.

In some embodiments, the HE variant cleaves a PD-1 exon 2 target site and comprises at least 5, at least 15, preferably at least 25, more preferably at least 35, or even more preferably at least 40 or more of, or all of the following amino acid substitutions: S24C, R28H, N32L, K34R, S35T, V37T, G38K, S40R, E42R, G44S, Q46E, T48E, V68I, A70N, S72I, D74N, N75R, A76R, S78R, K80S, T82R, V116L, L138M, T143N, S159P, F168L, E178D, C180N, F182Y, N184H, I186K, K189G, S190R, K191T, L192T, G193R, Q195Y, V199R, T203S, K207R, K225T, K227S, K229P, F232R, W234D, D236E, and V238R of any one of SEQ ID NOs: 1-5, or a biologically active fragment thereof.

In additional embodiments, the HE variant comprises an amino acid sequence that is at least 80%, preferably at least 85%, more preferably at least 90%, or even more preferably at least 95% identical to the amino acid sequence set forth in any one of SEQ ID NOs: 6-14, 60-63, or a biologically active fragment thereof.

In particular embodiments, the HE variant comprises the amino acid sequence set forth in SEQ ID NO: 6, or a biologically active fragment thereof.

In particular embodiments, the HE variant comprises the amino acid sequence set forth in SEQ ID NO: 7, or a biologically active fragment thereof.

In some embodiments, the HE variant comprises the amino acid sequence set forth in SEQ ID NO: 8, or a biologically active fragment thereof.

In particular embodiments, the HE variant comprises the amino acid sequence set forth in SEQ ID NO: 9, or a biologically active fragment thereof.

In particular embodiments, the HE variant comprises the amino acid sequence set forth in SEQ ID NO: 10, or a biologically active fragment thereof.

In particular embodiments, the HE variant comprises the amino acid sequence set forth in SEQ ID NO: 11, or a biologically active fragment thereof.

In some embodiments, the HE variant comprises the amino acid sequence set forth in SEQ ID NO: 12, or a biologically active fragment thereof.

In particular embodiments, the HE variant comprises the amino acid sequence set forth in SEQ ID NO: 13, or a biologically active fragment thereof.

In some embodiments, the HE variant comprises the amino acid sequence set forth in SEQ ID NO: 14, or a biologically active fragment thereof.

In some embodiments, the HE variant comprises the amino acid sequence set forth in SEQ ID NO: 60, or a biologically active fragment thereof.

In some embodiments, the HE variant comprises the amino acid sequence set forth in SEQ ID NO: 61, or a biologically active fragment thereof.

In some embodiments, the HE variant comprises the amino acid sequence set forth in SEQ ID NO: 62, or a biologically active fragment thereof.

In some embodiments, the HE variant comprises the amino acid sequence set forth in SEQ ID NO: 63, or a biologically active fragment thereof.

In particular embodiments, the polypeptide binds the polynucleotide sequence set forth in SEQ ID NO: 25.

In particular embodiments, the polypeptide binds the polynucleotide sequence set forth in SEQ ID NO: 30.

In particular embodiments, the polypeptide binds the polynucleotide sequence set forth in SEQ ID NO: 35.

In further embodiments, the polypeptide further comprises a DNA binding domain.

In some embodiments, the DNA binding domain is selected from the group consisting of: a TALE DNA binding domain and a zinc finger DNA binding domain.

In certain embodiments, the TALE DNA binding domain comprises about 9.5 TALE repeat units to about 15.5 TALE repeat units.

In additional embodiments, the TALE DNA binding domain binds a polynucleotide sequence in the PD-1 gene.

In particular embodiments, the TALE DNA binding domain binds the polynucleotide sequence set forth in SEQ ID NO: 26.

In certain embodiments, the polypeptide binds and cleaves the polynucleotide sequence set forth in SEQ ID NO: 27.

In particular embodiments, the TALE DNA binding domain binds the polynucleotide sequence set forth in SEQ ID NO: 31.

In certain embodiments, the polypeptide binds and cleaves the polynucleotide sequence set forth in SEQ ID NO: 32.

In particular embodiments, the TALE DNA binding domain binds the polynucleotide sequence set forth in SEQ ID NO: 36.

In certain embodiments, the polypeptide binds and cleaves the polynucleotide sequence set forth in SEQ ID NO: 37.

In certain embodiments, the zinc finger DNA binding domain comprises 2, 3, 4, 5, 6, 7, or 8 zinc finger motifs.

In further embodiments, the polypeptide further comprises a peptide linker and an end-processing enzyme or biologically active fragment thereof.

In particular embodiments, the polypeptide further comprises a viral self-cleaving 2A peptide and an end-processing enzyme or biologically active fragment thereof.

In additional embodiments, the end-processing enzyme or biologically active fragment thereof has 5'-3' exonuclease, 5'-3' alkaline exonuclease, 3'-5' exonuclease, 5' flap endonuclease, helicase or template-independent DNA polymerase activity.

In particular embodiments, the end-processing enzyme comprises Trex2 or a biologically active fragment thereof.

In certain embodiments, the polypeptide comprises the amino acid sequence set forth in any one of SEQ ID NOs: 15-23 and 64, or a biologically active fragment thereof.

In further embodiments, the polypeptide comprises the amino acid sequence set forth in SEQ ID NO: 15, or a biologically active fragment thereof.

In particular embodiments, the polypeptide comprises the amino acid sequence set forth in SEQ ID NO: 16, or a biologically active fragment thereof.

In various embodiments, the polypeptide comprises the amino acid sequence set forth in SEQ ID NO: 17, or a biologically active fragment thereof.

In particular embodiments, the polypeptide comprises the amino acid sequence set forth in SEQ ID NO: 18, or a biologically active fragment thereof.

In particular embodiments, the polypeptide comprises the amino acid sequence set forth in SEQ ID NO: 19, or a biologically active fragment thereof.

In some embodiments, the polypeptide comprises the amino acid sequence set forth in SEQ ID NO: 20, or a biologically active fragment thereof.

In some embodiments, the polypeptide comprises the amino acid sequence set forth in SEQ ID NO: 21, or a biologically active fragment thereof.

In additional embodiments, the polypeptide comprises the amino acid sequence set forth in SEQ ID NO: 22, or a biologically active fragment thereof.

In additional embodiments, the polypeptide comprises the amino acid sequence set forth in SEQ ID NO: 23, or a biologically active fragment thereof.

In additional embodiments, the polypeptide comprises the amino acid sequence set forth in SEQ ID NO: 64, or a biologically active fragment thereof.

In additional embodiments, a polypeptide contemplated herein comprises the amino acid sequence set forth in SEQ ID NO: 24, or a biologically active fragment thereof.

In further embodiments, the polypeptide cleaves the human PD-1 gene at a polynucleotide sequence set forth in SEQ ID NOs: 25, 27, 30, 32, 35, or 37.

In various embodiments, the present disclosure contemplates, in part, a polynucleotide encoding a polypeptide contemplated herein.

In particular embodiments, the present disclosure contemplates, in part, an mRNA encoding a polypeptide contemplated herein.

In particular embodiments, the mRNA comprises the sequence set forth in SEQ ID NO: 40-42 and 65-68

In various embodiments, the present disclosure contemplates, in part, a cDNA encoding a polypeptide contemplated herein.

In certain embodiments, the present disclosure contemplates, in part, a vector comprising a polynucleotide encoding a polypeptide contemplated herein.

In various embodiments, the present disclosure contemplates, in part, a cell comprising a polypeptide contemplated herein.

In some embodiments, the present disclosure contemplates, in part, a cell comprising a polynucleotide encoding a polypeptide contemplated herein.

In various embodiments, the present disclosure contemplates, in part, a cell comprising a vector contemplated herein.

In additional embodiments, the present disclosure contemplates, in part, a cell comprising one or more genome modifications introduced by a polypeptide contemplated herein.

In particular embodiments, the cell comprises a polynucleotide encoding one or more of an immunopotency enhancer, an immunosuppressive signal damper, or an engineered antigen receptor.

In certain embodiments, the polynucleotide further comprises an RNA polymerase II promoter operably linked to the polynucleotide encoding the immunopotency enhancer, immunosuppressive signal damper, or engineered antigen receptor.

In particular embodiments, the RNA polymerase II promoter is selected from the group consisting of: a short EF1α promoter, a long EF1α promoter, a human ROSA 26 locus, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter.

In some embodiments, the polynucleotide further encodes one or more self-cleaving viral peptides operably linked to, interspersed between, and/or flanking the immunopotency enhancer, immunosuppressive signal damper, or engineered antigen receptor.

In some embodiments, the self-cleaving viral peptide is a 2A peptide.

In certain embodiments, the polynucleotide further comprises a heterologous polyadenylation signal.

In some embodiments, the immunosuppressive signal damper comprises an enzymatic function that counteracts an immunosuppressive factor.

In some embodiments, the immunosuppressive signal damper comprises kynureninase activity.

In particular embodiments, the immunosuppressive signal damper comprises: an exodomain that binds an immunosuppressive factor, optionally wherein the exodomain is an antibody or antigen binding fragment thereof; an exodomain that binds an immunosuppressive factor and a transmembrane domain; or an exodomain that binds an immunosuppressive factor, a transmembrane domain, and a modified endodomain that is unable to transduce immunosuppressive signals to the cell.

In certain embodiments, the immunosuppressive signal damper is a dominant negative TGFβRII receptor.

In some embodiments, the immunopotency enhancer is selected from the group consisting of: a bispecific T cell engager molecule (BiTE), an immunopotentiating factor, and a flip receptor.

In particular embodiments, the immunopotentiating factor is selected from the group consisting of: a cytokine, a chemokine, a cytotoxin, a cytokine receptor, and variants thereof.

In particular embodiments, the cytokine receptor is selected from the group consisting of an IL-2 receptor, an IL-7 receptor, an IL-12 receptor, an IL-15 receptor, an IL-18 receptor, and an IL-21 receptor.

In a preferred embodiment, the cell comprises a polynucleotide encoding a cytokine receptor selected from the group consisting of an IL-2 receptor, an IL-7 receptor, an IL-12 receptor, an IL-15 receptor, an IL-18 receptor, and an IL-21 receptor operably linked to the endogenous PD-1 promoter.

In another preferred embodiment, the cell comprises a polynucleotide encoding an IL-12 cytokine receptor operably linked to the endogenous PD-1 promoter.

In particular embodiments, the cytokine is selected from the group consisting of IL-2, IL-7, IL-12, IL-15, IL-18, and IL-21.

In a preferred embodiment, the cell comprises a polynucleotide encoding a cytokine selected from the group consisting of IL-2, IL-7, IL-12, IL-15, IL-18, and IL-21 operably linked to the endogenous PD-1 promoter.

In another preferred embodiment, the cell comprises a polynucleotide encoding IL-12 operably linked to the endogenous PD-1 promoter.

In additional embodiments, the flip receptor comprises a PD-1 exodomain and transmembrane domain; and an endodomain from CD28, CD134, CD137, CD278, and/or CD35 fused in frame to the C-terminal end of the PD-1 transmembrane domain.

In certain embodiments, the flip receptor comprises a PD-1 exodomain; a transmembrane domain isolated from a CD3 polypeptide, CD4, CD8a, CD28, CD134, or CD137; and an endodomain from CD28, CD134, CD137, CD278, and/or CD3ζ fused in frame to the C-terminal end of the PD-1 exodomain.

In particular embodiments, the flip receptor comprises a PD-1 exodomain; and a transmembrane domain and endodomain isolated from a CD3 polypeptide, CD4, CD8a, CD28, CD134, or CD137 fused in frame to the C-terminal end of the PD-1 exodomain.

In additional embodiments, the engineered antigen receptor is selected from the group consisting of: an engineered TCR, a CAR, a Daric, or a zetakine.

In particular embodiments, the engineered receptor is not integrated into the PD-1 gene.

In certain embodiments, the polynucleotide encoding one or more of an immunopotency enhancer, an immunosuppressive signal damper, or an engineered antigen receptor is integrated into the PD-1 gene.

In further embodiments, a donor repair template comprising the polynucleotide encoding one or more of an immunopotency enhancer, an immunosuppressive signal damper, or an engineered antigen receptor is integrated into the PD-1 gene at a DNA double stranded break site introduced by a polypeptide contemplated herein.

In particular embodiments, a donor repair template comprising a polynucleotide encoding a cytokine selected from the group consisting of IL-2, IL-7, IL-12, IL-15, IL-18, and IL-21, is integrated into the PD-1 gene at a DNA double stranded break site introduced by a polypeptide contemplated herein. In preferred embodiments, the cytokine is integrated into the PD-1 gene in operably linkage with the endogenous PD-1 promoter.

In particular embodiments, a donor repair template comprising a polynucleotide encoding IL-12 cytokine is integrated into the PD-1 gene at a DNA double stranded break site introduced by a polypeptide contemplated herein. In preferred embodiments, the IL-12 cytokine is integrated into the PD-1 gene in operably linkage with the endogenous PD-1 promoter.

In particular embodiments, a donor repair template comprising a polynucleotide encoding a cytokine receptor selected from the group consisting of an IL-2 receptor, an IL-7 receptor, an IL-12 receptor, an IL-15 receptor, an IL-18 receptor, and an IL-21 receptor, is integrated into the PD-1 gene at a DNA double stranded break site introduced by a polypeptide contemplated herein. In preferred embodiments, the cytokine receptor is integrated into the PD-1 gene in operably linkage with the endogenous PD-1 promoter.

In particular embodiments, a donor repair template comprising a polynucleotide encoding an IL-12 cytokine receptor is integrated into the PD-1 gene at a DNA double stranded break site introduced by a polypeptide contemplated herein. In preferred embodiments, the IL-12 cytokine receptor is integrated into the PD-1 gene in operably linkage with the endogenous PD-1 promoter.

In some embodiments, the cell is a hematopoietic cell.

In additional embodiments, the cell is a T cell.

In particular embodiments, the cell is a CD3+, CD4+, and/or CD8+ cell.

In particular embodiments, the cell is an immune effector cell.

In further embodiments, the cell is a cytotoxic T lymphocyte (CTL), a tumor infiltrating lymphocyte (TIL), or a helper T cell.

In certain embodiments, the cell is a natural killer (NK) cell or natural killer T (NKT) cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

In particular embodiments, the present disclosure contemplates, in part, a plurality of cells comprising one or more cells contemplated herein.

In various embodiments, the present disclosure contemplates, in part, a composition comprising one or more cells contemplated herein.

In certain embodiments, the present disclosure contemplates, in part, a composition comprising one or more cells contemplated herein and a physiologically acceptable carrier.

In various embodiments, the present disclosure contemplates, in part, a method of editing a human PD-1 gene in a cell comprising: introducing a polynucleotide encoding a polypeptide contemplated herein into the cell, wherein expression of the polypeptide creates a double strand break at a target site in a human PD-1 gene.

In some embodiments, the present disclosure contemplates, in part, a method of editing a human PD-1 gene in cell comprising: introducing a polynucleotide encoding a polypeptide contemplated herein into the cell, wherein expression of the polypeptide creates a double strand break at a target site in a human PD-1 gene, wherein the break is repaired by non-homologous end joining (NHEJ).

In various embodiments, the present disclosure contemplates, in part, a method of editing a human PD-1 gene in a cell comprising: introducing a polynucleotide encoding a polypeptide contemplated herein and a donor repair template into the cell, wherein expression of the polypeptide creates a double strand break at a target site in a human PD-1 gene and the donor repair template is incorporated into the human PD-1 gene by homology directed repair (HDR) at the site of the double-strand break (DSB).

In further embodiments, the cell is a hematopoietic cell.

In particular embodiments, the cell is a T cell.

In particular embodiments, the cell is a CD3+, CD4+, and/or CD8+ cell.

In certain embodiments, the cell is an immune effector cell.

In some embodiments, the cell is a cytotoxic T lymphocyte (CTL), a tumor infiltrating lymphocyte (TIL), or a helper T cell.

In particular embodiments, the cell is a natural killer (NK) cell or natural killer T (NKT) cell.

In certain embodiments, the source of the cell is peripheral blood mononuclear cells, bone marrow, lymph nodes tissue, cord blood, thymus issue, tissue from a site of infection, ascites, pleural effusion, spleen tissue, or tumors.

In particular embodiments, the polynucleotide encoding the polypeptide is an mRNA.

In additional embodiments, a polynucleotide encoding a 3'-5' exonuclease is introduced into the cell.

In some embodiments, a polynucleotide encoding Trex2 or a biologically active fragment thereof is introduced into the cell.

In further embodiments, the donor repair template encodes a PD-1 gene or portion thereof comprising one or more mutations compared to the wild type PD-1 gene.

In particular embodiments, the donor repair template encodes one or more of an immunopotency enhancer, an immunosuppressive signal damper, or an engineered antigen receptor.

In additional embodiments, the donor repair template further comprises an RNA polymerase II promoter operably linked to the immunopotency enhancer, immunosuppressive signal damper, or engineered antigen receptor.

In further embodiments, the RNA polymerase II promoter is selected from the group consisting of: a short EF1α promoter, a long EF1α promoter, a human ROSA 26 locus, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter.

In certain embodiments, the donor repair template further encodes one or more self-cleaving viral peptides operably linked to, interspersed between, and/or flanking the immunopotency enhancer, immunosuppressive signal damper, or engineered antigen receptor.

In additional embodiments, the self-cleaving viral peptide is a 2A peptide.

In some embodiments, the donor repair template further comprises a heterologous polyadenylation signal.

In certain embodiments, the immunosuppressive signal damper comprises an enzymatic function that counteracts an immunosuppressive factor.

In further embodiments, the immunosuppressive signal damper comprises kynureninase activity.

In particular embodiments, the immunosuppressive signal damper comprises: an exodomain that binds an immunosuppressive factor, optionally wherein the exodomain is an antibody or antigen binding fragment thereof; an exodomain that binds an immunosuppressive factor and a transmembrane domain; or an exodomain that binds an immunosuppressive factor, a transmembrane domain, and a modified endodomain that is unable to transduce immunosuppressive signals to the cell.

In additional embodiments, the immunosuppressive signal damper is a dominant negative TGFβRII receptor.

In certain embodiments, the immunopotency enhancer is selected from the group consisting of: a bispecific T cell engager molecule (BiTE), an immunopotentiating factor, and a flip receptor.

In further embodiments, the immunopotentiating factor is selected from the group consisting of: a cytokine, a chemokine, a cytotoxin, a cytokine receptor, and variants thereof.

In particular embodiments, the immunopotentiating factor is selected from the group consisting of: a cytokine, a chemokine, a cytotoxin, a cytokine receptor, and variants thereof.

In particular embodiments, the cytokine receptor is selected from the group consisting of an IL-2 receptor, an IL-7 receptor, an IL-12 receptor, an IL-15 receptor, an IL-18 receptor, and an IL-21 receptor.

In a preferred embodiment, the cell comprises a polynucleotide encoding a cytokine receptor selected from the group consisting of an IL-2 receptor, an IL-7 receptor, an IL-12 receptor, an IL-15 receptor, an IL-18 receptor, and an IL-21 receptor operably linked to the endogenous PD-1 promoter.

In another preferred embodiment, the cell comprises a polynucleotide encoding an IL-12 receptor operably linked to the endogenous PD-1 promoter.

In particular embodiments, the cytokine is selected from the group consisting of IL-2, IL-7, IL-12, IL-15, IL-18, and IL-21.

In a preferred embodiment, the cell comprises a polynucleotide encoding a cytokine selected from the group consisting of IL-2, IL-7, IL-12, IL-15, IL-18, and IL-21 operably linked to the endogenous PD-1 promoter.

In another preferred embodiment, the cell comprises a polynucleotide encoding IL-12 operably linked to the endogenous PD-1 promoter.

In particular embodiments, the flip receptor comprises a PD-1 exodomain and transmembrane domain; and an endodomain from CD28, CD134, CD137, CD278, and/or CD3ζ fused in frame to the C-terminal end of the PD-1 transmembrane domain.

In additional embodiments, the flip receptor comprises a PD-1 exodomain; a transmembrane domain isolated from a CD3 polypeptide, CD4, CD8α, CD28, CD134, or CD137; and an endodomain from CD28, CD134, CD137, CD278, and/or CD3ζ fused in frame to the C-terminal end of the PD-1 exodomain.

In further embodiments, the flip receptor comprises a PD-1 exodomain; and a transmembrane domain and endodomain isolated from a CD3 polypeptide, CD4, CD8α, CD28, CD134, or CD137 fused in frame to the C-terminal end of the PD-1 exodomain.

In additional embodiments, the engineered antigen receptor is selected from the group consisting of: an engineered TCR, a CAR, a Daric, or a zetakine.

In additional embodiments, the donor repair template comprises a 5' homology arm homologous to a human PD-1 gene sequence 5' of the DSB and a 3' homology arm homologous to a human PD-1 gene sequence 3' of the DSB.

In particular embodiments, the lengths of the 5' and 3' homology arms are independently selected from about 100 bp to about 2500 bp.

In some embodiments, the lengths of the 5' and 3' homology arms are independently selected from about 600 bp to about 1500 bp.

In some embodiments, the 5 homology arm is about 1500 bp and the 3' homology arm is about 1000 bp.

In certain embodiments, the 5 homology arm is about 600 bp and the 3' homology arm is about 600 bp.

In particular embodiments, a viral vector is used to introduce the donor repair template into the cell.

In additional embodiments, the viral vector is a recombinant adeno-associated viral vector (rAAV) or a retrovirus.

In further embodiments, the rAAV has one or more ITRs from AAV2.

In certain embodiments, the rAAV has a serotype selected from the group consisting of: AAV1, AAV2, AAV3, AAV4, AAV5, AAV6, AAV7, AAV8, AAV9, and AAV10.

In additional embodiments, the rAAV has an AAV2 or AAV6 serotype.

In some embodiments, the retrovirus is a lentivirus.

In particular embodiments, the lentivirus is an integrase deficient lentivirus (IDLV).

In various embodiments, the present disclosure contemplates, in part, a method of treating, preventing, or ameliorating at least one symptom of a cancer, infectious disease, autoimmune disease, inflammatory disease, and immunodeficiency, or condition associated therewith, comprising administering to the subject an effective amount of a composition contemplated herein.

In various embodiments, the present disclosure contemplates, in part, a method of treating a solid cancer comprising administering to the subject an effective amount of a composition contemplated herein.

In further embodiments, the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, or skin cancer.

In various embodiments, the present disclosure contemplates, in part, a method of treating a hematological malignancy comprising administering to the subject an effective amount of a composition contemplated herein.

In additional embodiments, the hematological malignancy is a leukemia, lymphoma, or multiple myeloma.

BRIEF DESCRIPTION OF SEVERAL VIEWS OF THE DRAWINGS

FIG. 3A shows the initial screening of the PD-1 exon 5 HE variant for activity in a chromosomal reporter assay.

FIG. 3B shows that the PD-1 HE variant (PD-1.ITSM.ex5_RD1_CV3-08) had moderate DNA binding affinity properties when measured by equilibrium substrate titration.

FIG. 12 further shows that PD-1.IgV.exon2_RD1_G5 efficiently cleaved both the unmethylated and methylated target sites (right upper and right lower panels, resp.).

FIG. 16B shows representative flow cytometry analyses to determine long-term expression of the chromosomally integrated cassettes in T cells treated with PD-1.ile3.exon1_RD2_B1H8 megaTAL and rAAV targeting vectors containing a GFP, anti-CD19 CAR, or anti-BCMA CAR expression cassette.

BRIEF DESCRIPTION OF THE SEQUENCE IDENTIFIERS

Figure 1A:
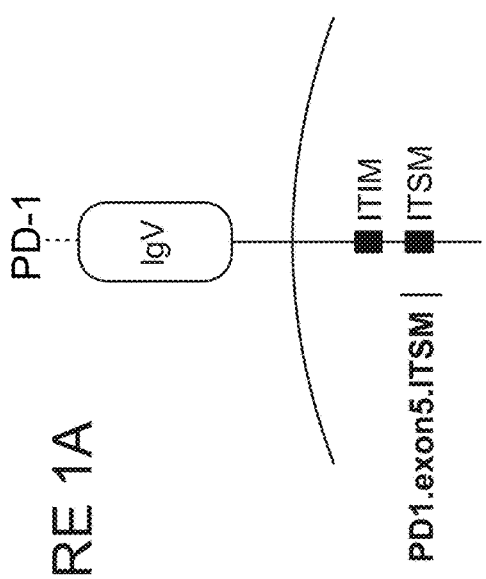
FIG. 1A shows a cartoon illustrating the positions of the IgV domain, and ITIM and ITSM motifs of PD-1 in relation to the position of the megaTAL target site in exon.

SEQ ID NO: 1 is an amino acid sequence of a wild type I-OnuI LAGLIDADG homing endonuclease (LHE).

SEQ ID NO: 2 is an amino acid sequence of a wild type I-OnuI LHE.

SEQ ID NO: 3 is an amino acid sequence of a biologically active fragment of a wild-type I-OnuI LHE.

SEQ ID NO: 4 is an amino acid sequence of a biologically active fragment of a wild-type I-OnuI LHE.

SEQ ID NO: 5 is an amino acid sequence of a biologically active fragment of a wild-type I-OnuI LHE.

SEQ ID NO: 6 is an amino acid sequence of an I-OnuI LHE variant reprogrammed to bind and cleave a target site in the human PD-1 gene.

SEQ ID NO: 7 is an amino acid sequence of an I-OnuI LHE variant reprogrammed to bind and cleave a target site in the human PD-1 gene.

SEQ ID NO: 8 is an amino acid sequence of an I-OnuI LHE variant reprogrammed to bind and cleave a target site in the human PD-1 gene.

SEQ ID NO: 9 is an amino acid sequence of an I-OnuI LHE variant reprogrammed to bind and cleave a target site in the human PD-1 gene.

SEQ ID NO: 10 is an amino acid sequence of an I-OnuI LHE variant reprogrammed to bind and cleave a target site in the human PD-1 gene.

SEQ ID NO: 11 is an amino acid sequence of an I-OnuI LHE variant reprogrammed to bind and cleave a target site in the human PD-1 gene.

SEQ ID NO: 12 is an amino acid sequence of an I-OnuI LHE variant reprogrammed to bind and cleave a target site in the human PD-1 gene.

SEQ ID NO: 13 is an amino acid sequence of an I-OnuI LHE variant reprogrammed to bind and cleave a target site in the human PD-1 gene.

SEQ ID NO: 14 is an amino acid sequence of an I-OnuI LHE variant reprogrammed to bind and cleave a target site in the human PD-1 gene.

SEQ ID NO: 15 is an amino acid sequence of a megaTAL that binds and cleaves a target site in a human PD-1 gene.

SEQ ID NO: 16 is an amino acid sequence of a megaTAL that binds and cleaves a target site in a human PD-1 gene.

SEQ ID NO: 17 is an amino acid sequence of a megaTAL that binds and cleaves a target site in a human PD-1 gene.

SEQ ID NO: 18 is an amino acid sequence of a megaTAL that binds and cleaves a target site in a human PD-1 gene.

SEQ ID NO: 19 is an amino acid sequence of a megaTAL that binds and cleaves a target site in a human PD-1 gene.

SEQ ID NO: 20 is an amino acid sequence of a megaTAL that binds and cleaves a target site in a human PD-1 gene.

SEQ ID NO: 21 is an amino acid sequence of a megaTAL that binds and cleaves a target site in a human PD-1 gene.

SEQ ID NO: 22 is an amino acid sequence of a megaTAL that binds and cleaves a target site in a human PD-1 gene.

SEQ ID NO: 23 is an amino acid sequence of a megaTAL that binds and cleaves a target site in a human PD-1 gene.

SEQ ID NO: 24 is an amino acid sequence encoding murine Trex2.

SEQ ID NO: 25 is an I-OnuI LHE variant target site in exon 5 of a human PD-1 gene.

SEQ ID NO: 26 is a TALE DNA binding domain target site in exon 5 of a human PD-1 gene.

SEQ ID NO: 27 is a megaTAL target site in exon 5 of a human PD-1 gene.

SEQ ID NO: 28 is an I-OnuI LHE variant N-terminal domain target site in exon 5 of a human PD-1 gene.

SEQ ID NO: 29 is an I-OnuI LHE variant C-terminal domain target site in exon 5 of a human PD-1 gene.

SEQ ID NO: 30 is an I-OnuI LHE variant target site in exon 1 of a human PD-1 gene.

SEQ ID NO: 31 is a TALE DNA binding domain target site in exon 1 of a human PD-1 gene.

SEQ ID NO: 32 is a megaTAL target site in exon 1 of a human PD-1 gene.

SEQ ID NO: 33 is an I-OnuI LHE variant N-terminal domain target site in exon 1 of a human PD-1 gene.

SEQ ID NO: 34 is an I-OnuI LHE variant C-terminal domain target site in exon 1 of a human PD-1 gene.

SEQ ID NO: 35 is an I-OnuI LHE variant target site in exon 2 of a human PD-1 gene.

SEQ ID NO: 36 is a TALE DNA binding domain target site in exon 2 of a human PD-1 gene.

SEQ ID NO: 37 is a megaTAL target site in exon 2 of a human PD-1 gene.

SEQ ID NO: 38 is an I-OnuI LHE variant N-terminal domain target site in exon 2 of a human PD-1 gene.

SEQ ID NO: 39 is an I-OnuI LHE variant C-terminal domain target site in exon 2 of a human PD-1 gene.

SEQ ID NO: 40 is an mRNA encoding a PD-1 megaTAL.

SEQ ID NO: 41 is an mRNA encoding a PD-1 megaTAL.

SEQ ID NO: 42 is an mRNA encoding a PD-1 megaTAL.

SEQ ID NO: 43 is an mRNA encoding a murine Trex2 protein.

SEQ ID NO: 44 is a polynucleotide sequence encoding a rAAV targeting vector with PD-1 homology arms, and a pMND-BFP-SV40polyA expression cassette.

SEQ ID NO: 45 is a polynucleotide encoding the 5' homology arm of SEQ ID NO: 44.

SEQ ID NO: 46 is a polynucleotide encoding the 3' homology arm of SEQ ID NO: 44.

SEQ ID NO: 47 is a polynucleotide sequence encoding a rAAV targeting vector with PD-1 homology arms, and a pMND-BFP-SV40polyA expression cassette. The 3' contains a single nucleotide polymorphism (SNP) relative to the wild type genomic sequence.

SEQ ID NO: 48 is a polynucleotide sequence encoding a rAAV targeting vector with PD-1 homology arms, and a pMND-BFP-SV40polyA expression cassette. The 5' contains a single nucleotide polymorphism (SNP) relative to the wild type genomic sequence.

SEQ ID NO: 49 is a polynucleotide encoding the 5' homology arm of SEQ ID NO: 48.

SEQ ID NO: 50 is a polynucleotide encoding the 3' homology arm of SEQ ID NO: 47.

SEQ ID NO: 51 is a polynucleotide sequence encoding a rAAV targeting vector with a pMND-PD-1.CD28 switch receptor.SV40polyA expression cassette.

SEQ ID NO: 52 is a polynucleotide sequence encoding a rAAV targeting vector with PD-1 homology arms, and a pMND-BFP.SV40polyA expression cassette with a 5' homology arm ~1.3 kb upstream of the ITSM motif in PD-1 exon 5.

SEQ ID NO: 53 is a polynucleotide sequence encoding a rAAV targeting vector with PD-1 homology arms, and a pMND-GFP-SV40polyA expression cassette.

SEQ ID NO: 54 is a polynucleotide encoding the 5' homology arm of SEQ ID NO: 53.

SEQ ID NO: 55 is a polynucleotide encoding the 3' homology arm of SEQ ID NO: 53.

SEQ ID NO: 56 is a polynucleotide sequence encoding a rAAV targeting vector with PD-1 homology arms, and a pMND-anti-CD19 CAR-SV40polyA expression cassette.

SEQ ID NO: 57 is a polynucleotide sequence encoding a rAAV targeting vector with PD-1 homology arms, and a pMND-anti-BCMA CAR-SV40polyA expression cassette.

SEQ ID NO: 58 is a polynucleotide sequence encoding a rAAV targeting vector with PD-1 homology arms, and a cDNA encoding mCherry.

SEQ ID NO: 60 is an amino acid sequence of an I-OnuI LHE variant reprogrammed to bind and cleave a target site in the human PD-1 gene SEQ ID NO: 61 is an amino acid sequence of an I-OnuI LHE variant reprogrammed to bind and cleave a target site in the human PD-1 gene SEQ ID NO: 62 is an amino acid sequence of an I-OnuI LHE variant reprogrammed to bind and cleave a target site in the human PD-1 gene SEQ ID NO: 63 is an amino acid sequence of an I-OnuI LHE variant reprogrammed to bind and cleave a target site in the human PD-1 gene SEQ ID NO: 64 is an amino acid sequence of a megaTAL that binds and cleaves a target site in a human PD-1 gene SEQ ID NO: 65 is an mRNA encoding a PD-1 megaTAL SEQ ID NO: 66 is an mRNA encoding a PD-1 megaTAL SEQ ID NO: 67 is an mRNA encoding a PD-1 megaTAL SEQ ID NO: 68 is an mRNA encoding a PD-1 megaTAL SEQ ID NOs: 69-79 set forth the amino acid sequences of various linkers.

SEQ ID NOs: 80-104 set forth the amino acid sequences of protease cleavage sites and self-cleaving polypeptide cleavage sites.

In the foregoing sequences, X, if present, refers to any amino acid or the absence of an amino acid.

DETAILED DESCRIPTION

A. Overview

The present disclosure generally relates to, in part, improved genome editing compositions and methods of use thereof. Without wishing to be bound by any particular theory, genome editing compositions contemplated in various embodiments can be used to prevent or treat a cancer, infectious disease, autoimmune disease, inflammatory disease, and immunodeficiency, or condition associated therewith, or ameliorates at least one symptom thereof. One limitation or problem that vexes existing adoptive cell therapy is hyporesponsiveness of immune effector cells due to exhaustion mediated by the tumor microenvironment. Exhausted T cells have a unique molecular signature that is markedly distinct from naive, effector or memory T cells. They are defined as T cells with decreased cytokine expression and effector function. PD-1 is a T cell exhaustion marker; increased PD-1 expression is associated with decreased T cell proliferation and reduced production of IL-2, TNF, and IFN-γ.

In particular embodiments, genome edited immune effector cells contemplated herein are made more resistant to exhaustion by eliminating, decreasing, or damping PD-1expression and/or signaling.

Genome editing compositions and methods contemplated in various embodiments comprise nuclease variants, designed to bind and cleave a target site in the human program cell death 1 (PD-1) gene. The nuclease variants contemplated in particular embodiments, can be used to introduce a double-strand break in a target polynucleotide sequence, which may be repaired by non-homologous end joining (NHEJ) in the absence of a polynucleotide template, e.g., a donor repair template, or by homology directed repair (HDR), i.e., homologous recombination, in the presence of a donor repair template. Nuclease variants contemplated in certain embodiments, can also be designed as nickases, which generate single-stranded DNA breaks that can be repaired using the cell's base-excision-repair (BER) machinery or homologous recombination in the presence of a donor repair template. NHEJ is an error-prone process that frequently results in the formation of small insertions and deletions that disrupt gene function. Homologous recombination requires homologous DNA as a template for repair and can be leveraged to create a limitless variety of modifications specified by the introduction of donor DNA containing the desired sequence at the target site, flanked on either side by sequences bearing homology to regions flanking the target site.

In one preferred embodiment, the genome editing compositions contemplated herein comprise a homing endonuclease variant or megaTAL that targets the human PD-1 gene.

In one preferred embodiment, the genome editing compositions contemplated herein comprise a homing endonuclease variant or megaTAL and an end-processing enzyme, e.g., Trex2.

In various embodiments, genome edited cells are contemplated. The genome edited cells comprise an edited PD-1 gene, wherein the editing strategy is designed to decrease or eliminate PD-1 expression, and/or co-opt PD-1 to act as a dominant negative by expressing the extracellular ligand binding domain of PD-1 but disrupting its ability to transduce immunosuppressive intracellular signals.

In various embodiments, a DNA break is generated in a target site of the PD-1 gene in a T cell, e.g., immune effector cell, and NHEJ of the ends of the cleaved genomic sequence may result in a cell with little or no PD-1 expression, and preferably a T cell that lacks or substantially lacks functional PD-1 expression and/or signaling, e.g., lacks the ability to increase T cell exhaustion. Without wishing to be bound by any particular theory, T cells that lack functional PD-1 expression are more resistant to immunosuppression and T cell exhaustion, and thus, are more persistent and therapeutically efficacious.

In various other embodiments, a donor template for repair of the cleaved PD-1 genomic sequence is provided. The PD-1 gene is repaired with the sequence of the template by homologous recombination at the DNA break-site. In particular embodiments, the repair template comprises a polynucleotide sequence that disrupts, and preferably substantially decreases or eliminates, functional PD-1 expression.

In particular embodiments, the PD-1 gene is repaired with a template that encodes a PD-1 exodomain with increased affinity to its ligands.

In particular embodiments, the PD-1 gene is repaired with a polynucleotide encoding an immunopotency enhancer, immunosuppressive signal damper, or engineered antigen receptor.

In particular embodiments, the PD-1 gene is repaired with a polynucleotide encoding an immunopotency enhancer, immunosuppressive signal damper, or engineered antigen receptor and is introduced into the PD-1 gene to coopt the endogenous PD-1 promoter to transcriptionally control the expression of the immunopotency enhancer, immunosuppressive signal damper, or engineered antigen receptor.

In preferred embodiments, the genome editing compositions and methods contemplated herein are used to edit the human PD-1 gene.

Accordingly, the methods and compositions contemplated herein represent a quantum improvement compared to existing adoptive cell therapies.

The practice of the particular embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, +9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism. In one embodiment, cellular genomes are engineered, edited, or modified in vivo.

By "enhance" or "promote" or "increase" or "expand" or "potentiate" refers generally to the ability of a nuclease variant, genome editing composition, or genome edited cell contemplated herein to produce, elicit, or cause a greater response (i.e., physiological response) compared to the response caused by either vehicle or control. A measurable response may include an increase in catalytic activity, binding affinity, persistence, cytolytic activity, and/or an increase in proinflammatory cytokines, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or control.

By "decrease" or "lower" or "lessen" or "reduce" or "abate" or "ablate" or "inhibit" or "dampen" refers generally to the ability of a nuclease variant, genome editing composition, or genome edited cell contemplated herein to produce, elicit, or cause a lesser response (i.e., physiological response) compared to the response caused by either vehicle or control. A measurable response may include a decrease in off-target binding affinity, off-target cleavage specificity, T cell exhaustion, and the like. A "decrease" or "reduced" amount is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, or control.

By "maintain," or "preserve," or "maintenance," or "no change," or "no substantial change," or "no substantial decrease" refers generally to the ability of a nuclease variant, genome editing composition, or genome edited cell contemplated herein to produce, elicit, or cause a substantially similar or comparable physiological response (i.e., downstream effects) in as compared to the response caused by either vehicle or control. A comparable response is one that is not significantly different or measurable different from the reference response.

The terms "specific binding affinity" or "specifically binds" or "specifically bound" or "specific binding" or "specifically targets" as used herein, describe binding of one molecule to another, e.g., DNA binding domain of a polypeptide binding to DNA, at greater binding affinity than background binding. A binding domain "specifically binds" to a target site if it binds to or associates with a target site with an affinity or $K_a$ (i.e., an equilibrium association constant of a particular binding interaction with units of 1/M) of, for example, greater than or equal to about $10^5$ $M^{-1}$. In certain embodiments, a binding domain binds to a target site with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_a$) of a particular binding interaction with units of M (e.g., $10^{-5}$ M to $10^{-13}$ M, or less). Affinities of nuclease variants comprising one or more DNA binding domains for DNA target sites contemplated in particular embodiments can be readily determined using conventional techniques, e.g., yeast cell surface display, or by binding association, or displacement assays using labeled ligands.

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, an HE or megaTAL selectively binds an on-target DNA binding site about 5, 10, 15, 20, 25, 50, 100, or 1000 times more frequently than the HE or megaTAL binds an off-target DNA target binding site.

"On-target" refers to a target site sequence.

"Off-target" refers to a sequence similar to but not identical to a target site sequence.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO. that references only one strand of a target site or target sequence, it would be understood that the target site or target sequence bound and/or cleaved by a nuclease variant is double-stranded and comprises the reference sequence and its complement. In a preferred embodiment, the target site is a sequence in a human PD-1 gene.

Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part of or all of the sequence of the donor polynucleotide is incorporated into the target polynucleotide.

"NHEJ" or "non-homologous end joining" refers to the resolution of a double-strand break in the absence of a donor repair template or homologous sequence. NHEJ can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, ligates ends back together with minimal processing and often leads to precise repair of the break. Alternative NHEJ pathways (altNHEJ) also are active in resolving dsDNA breaks, but these pathways are considerably more mutagenic and often result in imprecise repair of the break marked by insertions and deletions. While not wishing to be bound to any particular theory, it is contemplated that modification of dsDNA breaks by end-processing enzymes, such as, for example, exonucleases, e.g., Trex2, may increase the likelihood of imprecise repair.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and nuclease variants, e.g., homing endonuclease variants, megaTALs, etc. contemplated herein are used for targeted double-stranded DNA cleavage. Endonuclease cleavage recognition sites may be on either DNA strand.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extra-chromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression and/or function of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

An "immune disorder" refers to a disease that evokes a response from the immune system. In particular embodiments, the term "immune disorder" refers to a cancer, graft-versus-host disease, an autoimmune disease, or an immunodeficiency. In one embodiment, immune disorders encompass infectious disease.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood).

As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

"Graft-versus-host disease" or "GVHD" refers complications that can occur after cell, tissue, or solid organ transplant. GVHD can occur after a stem cell or bone marrow transplant in which the transplanted donor cells attack the transplant recipient's body. Acute GVHD in humans takes place within about 60 days post-transplantation and results in damage to the skin, liver, and gut by the action of cytolytic lymphocytes. Chronic GVHD occurs later and is a systemic autoimmune disease that affects primarily the skin, resulting in the polyclonal activation of B cells and the hyperproduction of Ig and autoantibodies. Solid-organ transplant graft-versus-host disease (SOT-GVHD) occurs in two forms. The more common type is antibody mediated, wherein antibodies from a donor with blood type O attack a recipient's red blood cells in recipients with blood type A, B, or AB, leading to mild transient, hemolytic anemias. The second form of SOT-GVHD is a cellular type associated with high mortality, wherein donor-derived T cells produce an immunological attack against immunologically disparate host tissue, most often in the skin, liver, gastrointestinal tract, and bone marrow, leading to complications in these organs.

"Graft-versus-leukemia" or "GVL" refer to an immune response to a person's leukemia cells by immune cells present in a donor's transplanted tissue, such as bone marrow or peripheral blood.

An "autoimmune disease" refers to a disease in which the body produces an immunogenic (i.e., immune system) response to some constituent of its own tissue. In other words, the immune system loses its ability to recognize some tissue or system within the body as "self" and targets and attacks it as if it were foreign. Illustrative examples of autoimmune diseases include, but are not limited to: arthritis, inflammatory bowel disease, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

An "immunodeficiency" means the state of a patient whose immune system has been compromised by disease or by administration of chemicals. This condition makes the system deficient in the number and type of blood cells needed to defend against a foreign substance. Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, Wiskott-Aldrich Syndrome (WAS), and diabetes.

An "infectious disease" refers to a disease that can be transmitted from person to person or from organism to organism, and is caused by a microbial or viral agent (e.g., common cold). Infectious diseases are known in the art and include, for example, hepatitis, sexually transmitted diseases (e.g., *Chlamydia*, gonorrhea), tuberculosis, HIV/AIDS, diphtheria, hepatitis B, hepatitis C, cholera, and influenza.

As used herein, the terms "individual" and "subject" are often used interchangeably and refer to any animal that exhibits a symptom of an immune disorder that can be treated with the nuclease variants, genome editing compositions, gene therapy vectors, genome editing vectors, genome edited cells, and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human subjects, are included. Typical subjects include human patients that have, have been diagnosed with, or are at risk of having an immune disorder.

As used herein, the term "patient" refers to a subject that has been diagnosed with an immune disorder that can be treated with the nuclease variants, genome editing compositions, gene therapy vectors, genome editing vectors, genome edited cells, and methods contemplated elsewhere herein.

As used herein "treatment" or "treating," includes any beneficial or desirable effect on the symptoms or pathology of a disease or pathological condition, and may include even minimal reductions in one or more measurable markers of the disease or condition being treated, e.g., cancer, GVHD, infectious disease, autoimmune disease, inflammatory disease, and immunodeficiency. Treatment can optionally involve delaying of the progression of the disease or condition. "Treatment" does not necessarily indicate complete eradication or cure of the disease or condition, or associated symptoms thereof.

As used herein, "prevent," and similar words such as "prevention," "prevented," "preventing" etc., indicate an approach for preventing, inhibiting, or reducing the likelihood of the occurrence or recurrence of, a disease or condition, e.g., cancer, GVHD, infectious disease, autoimmune disease, inflammatory disease, and immunodeficiency. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated, e.g., cancer, GVHD, infectious disease, autoimmune disease, inflammatory disease, and immunodeficiency. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

As used herein, the term "amount" refers to "an amount effective" or "an effective amount" of a nuclease variant, genome editing composition, or genome edited cell sufficient to achieve a beneficial or desired prophylactic or therapeutic result, including clinical results.

A "prophylactically effective amount" refers to an amount of a nuclease variant, genome editing composition, or genome edited cell sufficient to achieve the desired prophylactic result. Typically, but not necessarily, since a prophylactic dose is used in subjects prior to or at an earlier stage of disease, the prophylactically effective amount is less than the therapeutically effective amount.

A "therapeutically effective amount" of a nuclease variant, genome editing composition, or genome edited cell may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

C. Nuclease Variants

Nuclease variants contemplated in particular embodiments herein are suitable for genome editing a target site in the PD-1 gene and comprise one or more DNA binding domains and one or more DNA cleavage domains (e.g., one or more endonuclease and/or exonuclease domains), and optionally, one or more linkers contemplated herein. The terms "reprogrammed nuclease," "engineered nuclease," or "nuclease variant" are used interchangeably and refer to a nuclease comprising one or more DNA binding domains and one or more DNA cleavage domains, wherein the nuclease has been designed and/or modified from a parental or naturally occurring nuclease, to bind and cleave a double-stranded DNA target sequence in a PD-1 gene.

In particular embodiments, a nuclease variant binds and cleaves a target sequence in exon 5 of a PD-1 gene, preferably at SEQ ID NO: 25 in exon 5 of a PD-1 gene, and more preferably at the sequence "ATAC" in SEQ ID NO: 25 in exon 5 of a PD-1 gene.

In particular embodiments, a nuclease variant binds and cleaves a target sequence in exon 1 of a PD-1 gene, preferably at SEQ ID NO: 30 in exon 1 of a PD-1 gene, and more preferably at the sequence "ATCC" in SEQ ID NO: 30 in exon 1 of a PD-1 gene.

In particular embodiments, a nuclease variant binds and cleaves a target sequence in exon 2 of a PD-1 gene, preferably at SEQ ID NO: 35 in exon 2 of a PD-1 gene, and more preferably at the sequence "ACTT" in SEQ ID NO: 35 in exon 2 of a PD-1 gene.

The nuclease variant may be designed and/or modified from a naturally occurring nuclease or from a previous nuclease variant. Nuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5'exonuclease (e.g., Trex2), 5' flap endonuclease, helicase, template-dependent DNA polymerases or template-independent DNA polymerase activity.

Illustrative examples of nuclease variants that bind and cleave a target sequence in the PD-1 gene include, but are not limited to homing endonuclease (meganuclease) variants and megaTALs.

1. Homing Endonuclease (Meganuclease) Variants

In various embodiments, a homing endonuclease or meganuclease is reprogrammed to introduce a double-strand break (DSB) in a target site in a PD-1 gene. In particular embodiments, a homing endonuclease variant introduces a double strand break in exon 5 of a PD-1 gene, preferably at SEQ ID NO: 25 in exon 5 of a PD-1 gene, and more preferably at the sequence "ATAC" in SEQ ID NO: 25 in exon 5 of a PD-1 gene. In particular embodiments, a homing endonuclease variant introduces a double strand break in exon 1 of a PD-1 gene, preferably at SEQ ID NO: 30 in exon 1 of a PD-1 gene, and more preferably at the sequence "ATCC" in SEQ ID NO: 30 in exon 1 of a PD-1 gene. In particular embodiments, a homing endonuclease variant introduces a double strand break in exon 2 of a PD-1 gene, preferably at SEQ ID NO: 35 in exon 2 of a PD-1 gene, and more preferably at the sequence "ACTT" in SEQ ID NO: 35 in exon 2 of a PD-1 gene.

"Homing endonuclease" and "meganuclease" are used interchangeably and refer to naturally-occurring homing endonucleases that recognize 12-45 base-pair cleavage sites and are commonly grouped into five families based on sequence and structure motifs: LAGLIDADG, GIY-YIG, HNH, His-Cys box, and PD-(D/E)XK.

A "reference homing endonuclease" or "reference meganuclease" refers to a wild type homing endonuclease or a homing endonuclease found in nature. In one embodiment, a "reference homing endonuclease" refers to a wild type homing endonuclease that has been modified to increase basal activity.

An "engineered homing endonuclease," "reprogrammed homing endonuclease," "homing endonuclease variant," "engineered meganuclease," "reprogrammed meganuclease," or "meganuclease variant" refers to a homing endonuclease comprising one or more DNA binding domains and one or more DNA cleavage domains, wherein the homing endonuclease has been designed and/or modified from a parental or naturally occurring homing endonuclease, to bind and cleave a DNA target sequence in a PD-1 gene. The homing endonuclease variant may be designed and/or modified from a naturally occurring homing endonuclease or from another homing endonuclease variant. Homing endonuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template dependent DNA polymerase or template-independent DNA polymerase activity.

Homing endonuclease (HE) variants do not exist in nature and can be obtained by recombinant DNA technology or by random mutagenesis. HE variants may be obtained by making one or more amino acid alterations, e.g., mutating, substituting, adding, or deleting one or more amino acids, in a naturally occurring HE or HE variant. In particular embodiments, a HE variant comprises one or more amino acid alterations to the DNA recognition interface.

HE variants contemplated in particular embodiments may further comprise one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. In particular embodiments, HE variants are introduced into a T cell with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. The HE variant and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the HE amino acid residues that interact with nucleic acid target bases as well as those residues that are adjacent. For each HE, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or HE variant. By way of non-limiting example, a HE variant contemplated in particular embodiments may be derived by constructing libraries of HE variants in which one or more amino acid residues localized in the DNA recognition interface of the natural HE (or a previously generated HE variant) are varied. The libraries may be screened for target cleavage activity against each predicted PD-1 target site using cleavage assays (see e.g., Jarjour et al., 2009. *Nuc. Acids Res.* 37(20): 6871-6880).

LAGLIDADG homing endonucleases (LHE) are the most well studied family of homing endonucleases, are primarily encoded in archaea and in organellar DNA in green algae and fungi, and display the highest overall DNA recognition specificity. LHEs comprise one or two LAGLIDADG catalytic motifs per protein chain and function as homodimers or single chain monomers, respectively. Structural studies of LAGLIDADG proteins identified a highly conserved core structure (Stoddard 2005), characterized by an $\alpha\beta\beta\alpha\beta\beta\alpha$ fold, with the LAGLIDADG motif belonging to the first helix of this fold. The highly efficient and specific cleavage of LHE's represent a protein scaffold to derive novel, highly specific endonucleases. However, engineering LHEs to bind and cleave a non-natural or non-canonical target site requires selection of the appropriate LHE scaffold, examination of the target locus, selection of putative target sites, and extensive alteration of the LHE to alter its DNA contact points and cleavage specificity, at up to two-thirds of the base-pair positions in a target site.

In one embodiment, LHEs from which reprogrammed LHEs or LHE variants may be designed include, but are not limited to I-CreI and I-SceI.

Illustrative examples of LHEs from which reprogrammed LHEs or LHE variants may be designed include, but are not limited to I-AabMI, I-AacMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I.

In one embodiment, the reprogrammed LHE or LHE variant is selected from the group consisting of: an I-CpaMI variant, an I-HjeMI variant, an I-OnuI variant, an I-PanMI variant, and an I-SmaMI variant.

In one embodiment, the reprogrammed LHE or LHE variant is an I-OnuI variant. See e.g., SEQ ID NOs: 6-14 and 60-63.

In one embodiment, reprogrammed I-OnuI LHEs or I-OnuI variants targeting the PD-1 gene were generated from a natural I-OnuI or biologically active fragment thereof (SEQ ID NOs: 1-5). In a preferred embodiment, reprogrammed I-OnuI LHEs or I-OnuI variants targeting the human PD-1 gene were generated from an existing I-OnuI variant. In one embodiment, reprogrammed I-OnuI LHEs were generated against a human PD-1 gene target site set forth in SEQ ID NO: 25. In one embodiment, reprogrammed I-OnuI LHEs were generated against a human PD-1 gene target site set forth in SEQ ID NO: 30. In one embodiment, reprogrammed I-OnuI LHEs were generated against a human PD-1 gene target site set forth in SEQ ID NO: 35.

In a particular embodiment, the reprogrammed I-OnuI LHE or I-OnuI variant that binds and cleaves a human PD-1 gene comprises one or more amino acid substitutions in the DNA recognition interface. In particular embodiments, the I-OnuI LHE that binds and cleaves a human PD-1 gene comprises at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the DNA recognition interface of I-OnuI (Taekuchi et al. 2011. *Proc Natl Acad Sci U.S.A* 2011 Aug. 9; 108(32): 13077-13082) or an I-OnuI LHE variant as set forth in any one of SEQ ID NOs: 6-14, and 60-63, biologically active fragments thereof, and/or further variants thereof.

In one embodiment, the I-OnuI LHE that binds and cleaves a human PD-1 gene comprises at least 70%, more preferably at least 80%, more preferably at least 85%, more preferably at least 90%, more preferably at least 95%, more preferably at least 97%, more preferably at least 99% sequence identity with the DNA recognition interface of I-OnuI (Tackuchi et al. 2011. *Proc Natl Acad Sci U.S.A* 2011 Aug. 9; 108(32): 13077-13082) or an I-OnuI LHE variant as set forth in any one of SEQ ID NOs: 6-14 and 60-63, biologically active fragments thereof, and/or further variants thereof.

In a particular embodiment, an I-OnuI LHE variant that binds and cleaves a human PD-1 gene comprises one or more amino acid substitutions or modifications in the DNA recognition interface of an I-OnuI as set forth in any one of SEQ ID NOs: 1-14 and 60-63, biologically active fragments thereof, and/or further variants thereof.

In a particular embodiment, an I-OnuI LHE variant that binds and cleaves a human PD-1 gene comprises one or more amino acid substitutions or modifications in the DNA recognition interface, particularly in the sub-motifs situated from positions 24-50, 68 to 82, 180 to 203 and 223 to 240 of I-OnuI (SEQ ID NOs: 1-5) or an I-OnuI variant as set forth in any one of SEQ ID NOs: 6-14 and 60-63, biologically active fragments thereof, and/or further variants thereof.

In a particular embodiment, an I-OnuI LHE that binds and cleaves a human PD-1 gene comprises one or more amino acid substitutions or modifications in the DNA recognition interface at amino acid positions selected from the group consisting of: 19, 24, 26, 28, 30, 32, 34, 35, 36, 37, 38, 40, 42, 44, 46, 48, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 of I-OnuI (SEQ ID NOs: 1-5) or an I-OnuI variant as set forth in any one of SEQ ID NOs: 6-14 and 60-63, biologically active fragments thereof, and/or further variants thereof.

In a particular embodiment, an I-OnuI LHE variant that binds and cleaves a human PD-1 gene comprises 5, 10, 15, 20, 25, 30, 35, or 40 or more amino acid substitutions or modifications in the DNA recognition interface, particularly in the sub-motifs situated from positions 24-50, 68 to 82, 180 to 203 and 223 to 240 of I-OnuI (SEQ ID NOs: 1-5) or an I-OnuI variant as set forth in any one of SEQ ID NOs: 6-14 and 60-63, biologically active fragments thereof, and/or further variants thereof.

In a particular embodiment, an I-OnuI LHE variant that binds and cleaves a human PD-1 gene comprises 5, 10, 15, 20, 25, 30, 35, or 40 or more amino acid substitutions or modifications in the DNA recognition interface at amino acid positions selected from the group consisting of: 19, 24, 26, 28, 30, 32, 34, 35, 36, 37, 38, 40, 42, 44, 46, 48, 59, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 of I-OnuI (SEQ ID NOs: 1-5) or an I-OnuI variant as set forth in any one of SEQ ID NOs: 6-14 and 60-63, biologically active fragments thereof, and/or further variants thereof.

In one embodiment, an I-OnuI LHE variant that binds and cleaves a human PD-1 gene comprises one or more amino acid substitutions or modifications at additional positions situated anywhere within the entire I-OnuI sequence. The residues which may be substituted and/or modified include but are not limited to amino acids that contact the nucleic acid target or that interact with the nucleic acid backbone or with the nucleotide bases, directly or via a water molecule. In one non-limiting example, an I-OnuI LHE variant contemplated herein that binds and cleaves a human PD-1 gene comprises one or more substitutions and/or modifications, preferably at least 5, preferably at least 10, preferably at least 15, preferably at least 20, more preferably at least 25, more preferably at least 30, even more preferably at least 35, or even more preferably at least 40 or more amino acid substitutions in at least one position selected from the position group consisting of positions: 26, 28, 32, 34, 35, 36, 37, 38, 40, 42, 44, 46, 48, 59, 68, 70, 72, 75, 76, 78, 80, 138, 143, 159, 168, 178, 180, 182, 184, 186, 188, 189, 190, 191, 192, 193, 197, 199, 201, 203, 207, 223, 224, 225, 227, 229, 232, 236, and 238 of I-OnuI (SEQ ID NOs: 1-5) or an I-OnuI variant as set forth in any one of SEQ ID NOs: 6-14 and 60-63, biologically active fragments thereof, and/or further variants thereof.

In certain embodiments, the HE variant cleaves a PD-1 exon 5 target site and comprises at least 5, at least 15, preferably at least 25, more preferably at least 35, or even more preferably at least 40 or more of the following amino acid substitutions: L26Q, R28E, N32V, K34P, S35N, S36I, V37P, G38R, S40K, S40R, E42R, G44R, Q46E, T48D, N59D, V68K, A70Y, S72Q, S72R, N75S, A76Y, S78K, K80R, L138M, T143N, S159P, F168L, E178D, C180H, F182G, N184I, I186A, S188R, K189R, S190P, K191A, L192S, G193P, Q197R, V199R, S201A, S201M, T203G, K207R, Y223R, I224T, K225R, K229I, F232K, D236E, and V238E of I-OnuI (SEQ ID NOs: 1-5) or an I-OnuI variant as set forth in any one of SEQ ID NOs: 6-10, biologically active fragments thereof, and/or further variants thereof.

In some embodiments, the HE variant cleaves a PD-1 exon 5 target site and comprises at least 5, at least 15, preferably at least 25, more preferably at least 35, or even more preferably at least 40 or more of the following amino acid substitutions: L26Q, R28E, N32V, K34P, S35N, S36I, V37P, G38R, S40K, E42R, G44R, Q46E, T48D, V68K, A70Y, S72Q, N75S, A76Y, S78K, K80R, L138M, T143N, S159P, F168L, C180H, F182G, N184I, I186A, S188R, K189R, S190P, K191A, L192S, G193P, Q197R, V199R, S201A, T203G, K207R, Y223R, K225R, K229I, F232K, D236E, and V238E of I-OnuI (SEQ ID NOs: 1-5) or an I-OnuI variant as set forth in any one of SEQ ID NOs: 6-10, biologically active fragments thereof, and/or further variants thereof.

In particular embodiments, the HE variant cleaves a PD-1 exon 5 target site and comprises at least 5, at least 15, preferably at least 25, more preferably at least 35, or even more preferably at least 40 or more of the following amino acid substitutions: L26Q, R28E, N32V, K34P, S35N, S36I, V37P, G38R, S40R, E42R, G44R, Q46E, T48D, N59D, V68K, A70Y, S72R, N75S, A76Y, K80R, L138M, T143N, S159P, F168L, C180H, F182G, N184I, I186A, S188R, K189R, S190P, K191A, L192S, G193P, Q197R, V199R, S201A, T203G, K207R, Y223R, I224T, K225R, K229I, F232K, D236E, and V238E of I-OnuI (SEQ ID NOs: 1-5) or an I-OnuI variant as set forth in any one of SEQ ID NOs: 6-10, biologically active fragments thereof, and/or further variants thereof.

In additional embodiments, the HE variant cleaves a PD-1 exon 5 target site and comprises at least 5, at least 15, preferably at least 25, more preferably at least 35, or even more preferably at least 40 or more of the following amino acid substitutions: L26Q, R28E, N32V, K34P, S35N, S36I, V37P, G38R, S40R, E42R, G44R, Q46E, T48D, N59D, V68K, A70Y, S72Q, N75S, A76Y, K80R, L138M, T143N, S159P, F168L, E178D, C180H, F182G, N184I, I186A, S188R, K189R, S190P, K191A, L192S, G193P, Q197R, V199R, S201A, T203G, K207R, Y223R, I224T, K225R, K229I, F232K, D236E, and V238E of I-OnuI (SEQ ID NOs: 1-5) or an I-OnuI variant as set forth in any one of SEQ ID NOs: 6-10, biologically active fragments thereof, and/or further variants thereof.

In further embodiments, the HE variant cleaves a PD-1 exon 5 target site and comprises at least 5, at least 15, preferably at least 25, more preferably at least 35, or even more preferably at least 40 or more of the following amino acid substitutions: L26Q, R28E, N32V, K34P, S35N, S36I, V37P, G38R, S40R, E42R, G44R, Q46E, T48D, N59D, V68K, A70Y, S72Q, N75S, A76Y, K80R, L138M, T143N, S159P, F168L, E178D, C180H, F182G, N184I, I186A, S188R, K189R, S190P, K191A, L192S, G193P, Q197R, V199R, S201A, T203G, K207R, Y223R, K225R, F232K, D236E, and V238E of I-OnuI (SEQ ID NOs: 1-5) or an I-OnuI variant as set forth in any one of SEQ ID NOs: 6-10, biologically active fragments thereof, and/or further variants thereof.

In particular embodiments, the HE variant cleaves a PD-1 exon 5 target site and comprises at least 5, at least 15, preferably at least 25, more preferably at least 35, or even more preferably at least 40 or more of the following amino acid substitutions: L26Q, R28E, N32V, K34P, S35N, S36I, V37P, G38R, S40R, E42R, G44R, Q46E, T48D, N59D, V68K, A70Y, S72Q, N75S, A76Y, K80R, L138M, T143N, S159P, F168L, E178D, C180H, F182G, N184I, I186A, S188R, K189R, S190P, K191A, L192S, G193P, Q197R, V199R, S201M, T203G, Y223R, K225R, F232K, D236E, and V238E of I-OnuI (SEQ ID NOs: 1-5) or an I-OnuI variant as set forth in any one of SEQ ID NOs: 6-10, biologically active fragments thereof, and/or further variants thereof.

In particular embodiments, the HE variant cleaves a PD-1 exon 1 target site and comprises at least 5, at least 15, preferably at least 25, more preferably at least 35, or even more preferably at least 40 or more amino acid substitutions in at least one position selected from the position group consisting of positions: 26, 28, 30, 32, 34, 35, 36, 37, 38, 40, 42, 44, 46, 48, 68, 70, 72, 75, 76, 78, 80, 100, 132, 138, 143, 155, 159, 178, 180, 184, 186, 189, 190, 191, 192, 193, 195, 201, 203, 207, 223, 225, 227, 232, 236, 238, and 240 of I-OnuI (SEQ ID NOs: 1-5) or an I-OnuI variant as set forth in any one of SEQ ID NOs: 11-12 and 60-63, biologically active fragments thereof, and/or further variants thereof.

In some embodiments, the HE variant cleaves a PD-1 exon 1 target site and comprises at least 5, at least 15, preferably at least 25, more preferably at least 35, or even more preferably at least 40 or more of the following amino acid substitutions: L26G, R28S, R30L, N32R, K34R, S35G, S36T, V37A, G38R, S40H, E42R, G44S, Q46A, Q46T, T48V, V68I, A70T, S72D, N75R, A76Y, S78R, K80R, K80C, I100V, V132A, L138M, T143N, S155G, S159P, E178D, C180S, N184R, I186R, K189N, S190V, K19 IN, L192A, G193R, Q195R, S201E, T203S, K207R, Y223H, K225Y, K227G, F232R, D236Q, V238R, and T240E of I-OnuI (SEQ ID NOs: 1-5) or an I-OnuI variant as set forth in any one of SEQ ID NOs: 11-12 and 60-63, biologically active fragments thereof, and/or further variants thereof.

In further embodiments, the HE variant cleaves a PD-1 exon 1 target site and comprises at least 5, at least 15, preferably at least 25, more preferably at least 35, or even more preferably at least 40 or more of the following amino acid substitutions: L26G, R28S, R30L, N32R, K34R, S35G, S36T, V37A, G38R, S40H, E42R, G44S, Q46A, T48V, V68I, A70T, S72D, N75R, A76Y, S78R, K80R, I100V, L138M, T143N, S159P, E178D, C180S, N184R, I186R, K189N, S190V, K191N, L192A, G193R, Q195R, S201E, T203S, K207R, Y223H, K225Y, K227G, F232R, D236Q, V238R, and T240E of I-OnuI (SEQ ID NOs: 1-5) or an I-OnuI variant as set forth in any one of SEQ ID NOs: 11-12 and 60-63, biologically active fragments thereof, and/or further variants thereof.

In certain embodiments, the HE variant cleaves a PD-1 exon 1 target site and comprises at least 5, at least 15, preferably at least 25, more preferably at least 35, or even more preferably at least 40 or more of the following amino acid substitutions: L26G, R28S, R30L, N32R, K34R, S35G, S36T, V37A, G38R, S40H, E42R, G44S, Q46T, T48V, V68I, A70T, S72D, N75R, A76Y, S78R, K80C, I100V, V132A, L138M, T143N, S155G, S159P, E178D, C180S, N184R, I186R, K189N, S190V, K19 IN, L192A, G193R, Q195R, S201E, T203S, K207R, Y223H, K225Y, K227G, F232R, D236Q, V238R, and T240E of I-OnuI (SEQ ID NOs: 1-5) or an I-OnuI variant as set forth in any one of SEQ ID NOs: 11-12 and 60-63, biologically active fragments thereof, and/or further variants thereof.

In certain embodiments, the HE variant cleaves a PD-1 exon 1 target site and comprises at least 5, at least 15, preferably at least 25, more preferably at least 35, or even more preferably at least 40 or more of the following amino acid substitutions: L26G, R28S, R30L, N32R, K34R, S35G, S36T, V37A, G38R, S40H, E42R, G44S, Q46T, T48M, V68I, A70T, S72N, N75H, A76Y, S78T, K80R, I100V, L138M, T143N, S159P, E178D, C180S, N184R, I186R, K189N, S190V, K191N, L192A, G193R, Q195R, S201E, T203S, K207R, Y223H, K225Y, K227G, F232R, D236Q, V238R, and T240E of I-OnuI (SEQ ID NOs: 1-5) or an I-OnuI variant as set forth in any one of SEQ ID NOs: 11-12 and 60-63, biologically active fragments thereof, and/or further variants thereof.

In certain embodiments, the HE variant cleaves a PD-1 exon 1 target site and comprises at least 5, at least 15, preferably at least 25, more preferably at least 35, or even more preferably at least 40 or more of the following amino acid substitutions: L26G, R28S, R30L, N32R, K34R, S35G, S36T, V37A, G38R, S40H, E42R, G44S, Q46T, T48M, V68S, A70L, S72N, N75H, A76Y, K80V, T82Y, L138M, T143N, S159P, E178D, C180S, N184R, I186R, K189N, S190V, K191N, L192A, G193R, Q195R, S201E, T203S, K207R, Y223H, K225Y, K227G, F232R, D236Q, V238R, and T240E of I-OnuI (SEQ ID NOs: 1-5) or an I-OnuI variant as set forth in any one of SEQ ID NOs: 11-12 and 60-63, biologically active fragments thereof, and/or further variants thereof.

In certain embodiments, the HE variant cleaves a PD-1 exon 1 target site and comprises at least 5, at least 15, preferably at least 25, more preferably at least 35, or even more preferably at least 40 or more of the following amino acid substitutions: L26G, R28S, R30L, N32R, K34R, S35G, S36T, V37G, G38R, S40H, E42R, G44S, Q46T, T48M, V68S, A70T, S72N, N75H, A76Y, K80V, T82Y, L138M, T143N, S159P, E178D, C180S, N184R, I186R, K189N, S190V, K19 IN, L192A, G193R, Q195R, S201E, T203S, K207R, Y223H, K225Y, K227G, F232R, D236Q, V238R, and T240E of I-OnuI (SEQ ID NOs: 1-5) or an I-OnuI variant as set forth in any one of SEQ ID NOs: 11-12 and 60-63, biologically active fragments thereof, and/or further variants thereof.

In certain embodiments, the HE variant cleaves a PD-1 exon 1 target site and comprises at least 5, at least 15, preferably at least 25, more preferably at least 35, or even more preferably at least 40 or more of the following amino acid substitutions: L26G, R28S, R30L, N32R, K34R, S35G, S36T, V37A, G38R, S40H, E42R, G44S, Q46T, T48M, V68S, A70Y, S72N, N75R, A76Y, K80E, T82F, L138M, T143N, S159P, E178D, C180S, N184R, I186R, K189N, S190V, K19 IN, L192A, G193R, Q195R, S201E, T203S, K207R, Y223H, K225Y, K227G, F232R, D236Q, V238R, and T240E of I-OnuI (SEQ ID NOs: 1-5) or an I-OnuI variant as set forth in any one of SEQ ID NOs: 11-12 and 60-63, biologically active fragments thereof, and/or further variants thereof.

In particular embodiments, the HE variant cleaves a PD-1 exon 2 target site and comprises at least 5, at least 15, preferably at least 25, more preferably at least 35, or even more preferably at least 40 or more amino acid substitutions in at least one position selected from the position group consisting of positions: 24, 26, 28, 30, 32, 34, 35, 36, 37, 38, 40, 41, 42, 44, 46, 48, 68, 70, 72, 74, 75, 76, 78, 80, 82, 116, 138, 143, 159, 168, 178, 180, 182, 184, 186, 188, 189, 190, 191, 192, 193, 195, 199, 203, 207, 225, 227, 229, 232, 236, and 238 of I-OnuI (SEQ ID NOs: 1-5) or an I-OnuI variant as set forth in any one of SEQ ID NOs: 13-14, biologically active fragments thereof, and/or further variants thereof.

In additional embodiments, the HE variant comprises at least 5, at least 15, preferably at least 25, more preferably at least 35, or even more preferably at least 40 or more of the following amino acid substitutions: S24C, L26Q, R28Y, R28H, R30S, N32V, N32L, K34N, K34R, S35N, S35T, S36R, V37S, V37T, G38R, G38K, S40R, T41A, E42R, G44S, G44R, Q46E, Q46A, T48E, V68I, A70N, S72I, D74N, N75T, N75R, A76S, A76R, S78R, K80S, T82G, T82R, V116L, L138M, T143N, S159P, F168L, E178D, C180N, F182Y, N184H, I186K, K189G, S190R, K191T, L192T, G193R, Q195Y, V199R, T203A, T203S, K207R, K225N, K225T, K227W, K227S, K229A, K229P, F232R, W234A, W234D, D236E, and V238R of I-OnuI (SEQ ID NOs: 1-5) or an I-OnuI variant as set forth in any one of SEQ ID NOs: 13-14, biologically active fragments thereof, and/or further variants thereof.

In particular embodiments, the HE variant comprises at least 5, at least 15, preferably at least 25, more preferably at least 35, or even more preferably at least 40 or more of the following amino acid substitutions: L26Q, R28Y, R30S, N32V, K34N, S35N, S36R, V37S, G38R, S40R, T41A, E42R, G44R, Q46A, T48E, A70N, S72I, N75T, A76S, S78R, K80S, T82G, L138M, T143N, S159P, F168L, E178D, C180N, F182Y, N184H, I186K, K189G, S190R, K19IT, L192T, G193R, Q195Y, V199R, T203A, K207R, K225N, K227W, K229A, F232R, W234A, D236E, and V238R of I-OnuI (SEQ ID NOs: 1-5) or an I-OnuI variant as set forth in any one of SEQ ID NOs: 13-14, biologically active fragments thereof, and/or further variants thereof.

In some embodiments, the HE variant comprises at least 5, at least 15, preferably at least 25, more preferably at least 35, or even more preferably at least 40 or more of the following amino acid substitutions: S24C, R28H, N32L, K34R, S35T, V37T, G38K, S40R, E42R, G44S, Q46E, T48E, V68I, A70N, S72I, D74N, N75R, A76R, S78R, K80S, T82R, V116L, L138M, T143N, S159P, F168L, E178D, C180N, F182Y, N184H, I186K, K189G, S190R, K19IT, L192T, G193R, Q195Y, V199R, T203S, K207R, K225T, K227S, K229P, F232R, W234D, D236E, and V238R of I-OnuI (SEQ ID NOs: 1-5) or an I-OnuI variant as set forth in any one of SEQ ID NOs: 13-14, biologically active fragments thereof, and/or further variants thereof.

In particular embodiments, an I-OnuI LHE variant that binds and cleaves a human PD-1 gene comprises an amino acid sequence that is at least 80%, preferably at least 85%, more preferably at least 90%, or even more preferably at least 95% identical to the amino acid sequence set forth in any one of SEQ ID NOs: 6-14 and 60-63, or a biologically active fragment thereof.

In particular embodiments, an I-OnuI LHE variant comprises an amino acid sequence set forth in any one of SEQ ID NOs: 6-14 and 60-63, or a biologically active fragment thereof.

In particular embodiments, an I-OnuI LHE variant comprises an amino acid sequence set forth in SEQ ID NO: 6, or a biologically active fragment thereof.

In particular embodiments, an I-OnuI LHE variant comprises an amino acid sequence set forth in SEQ ID NO: 7, or a biologically active fragment thereof.

In particular embodiments, an I-OnuI LHE variant comprises an amino acid sequence set forth in SEQ ID NO: 8, or a biologically active fragment thereof.

In particular embodiments, an I-OnuI LHE variant comprises an amino acid sequence set forth in SEQ ID NO: 9, or a biologically active fragment thereof.

In particular embodiments, an I-OnuI LHE variant comprises an amino acid sequence set forth in SEQ ID NO: 10, or a biologically active fragment thereof.

In particular embodiments, an I-OnuI LHE variant comprises an amino acid sequence set forth in SEQ ID NO: 11, or a biologically active fragment thereof.

In particular embodiments, an I-OnuI LHE variant comprises an amino acid sequence set forth in SEQ ID NO: 12, or a biologically active fragment thereof.

In particular embodiments, an I-OnuI LHE variant comprises an amino acid sequence set forth in SEQ ID NO: 13, or a biologically active fragment thereof.

In particular embodiments, an I-OnuI LHE variant comprises an amino acid sequence set forth in SEQ ID NO: 14, or a biologically active fragment thereof.

In particular embodiments, an I-OnuI LHE variant comprises an amino acid sequence set forth in SEQ ID NO: 60, or a biologically active fragment thereof.

In particular embodiments, an I-OnuI LHE variant comprises an amino acid sequence set forth in SEQ ID NO: 61, or a biologically active fragment thereof.

In particular embodiments, an I-OnuI LHE variant comprises an amino acid sequence set forth in SEQ ID NO: 62, or a biologically active fragment thereof.

In particular embodiments, an I-OnuI LHE variant comprises an amino acid sequence set forth in SEQ ID NO: 63, or a biologically active fragment thereof.

2. MEGATALS

In various embodiments, a megaTAL comprising a homing endonuclease variant is reprogrammed to introduce a double-strand break (DSB) in a target site in a PD-1 gene. In particular embodiments, a megaTAL introduces a DSB in exon 5 of a PD-1 gene, preferably at SEQ ID NO: 27 in exon 5 of a PD-1 gene, and more preferably at the sequence "ATAC" in SEQ ID NO: 27 in exon 5 of a PD-1 gene. In particular embodiments, a megaTAL introduces a double strand break in exon 1 of a PD-1 gene, preferably at SEQ ID NO: 32 in exon 1 of a PD-1 gene, and more preferably at the sequence "ATCC" in SEQ ID NO: 32 in exon 1 of a PD-1 gene. In particular embodiments, a megaTAL introduces a double strand break in exon 2 of a PD-1 gene, preferably at SEQ ID NO: 37 in exon 2 of a PD-1 gene, and more preferably at the sequence "ACTT" in SEQ ID NO: 37 in exon 2 of a PD-1 gene.

A "megaTAL" refers to a polypeptide comprising a TALE DNA binding domain and a homing endonuclease variant that binds and cleaves a DNA target sequence in a PD-1 gene, and optionally comprises one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase or template-independent DNA polymerase activity.

In particular embodiments, a megaTAL can be introduced into a cell along with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase, or template-independent DNA polymerase activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. Science 318:648-651). TALE DNA binding domains contemplated in particular embodiments are engineered de novo or from naturally occurring TALEs, e.g., AvrBs3 from *Xanthomonas campestris* pv. *vesicatoria*, *Xanthomonas gardneri*, *Xanthomonas translucens*, *Xanthomonas axonopodis*, *Xanthomonas perforans*, *Xanthomonas alfalfa*, *Xanthomonas citri*, *Xanthomonas euvesicatoria*, and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S*for recognition of A or T or G or C, wherein (*) means that the amino acid at position 13 is absent. Additional illustrative examples of RVDs suitable for use in particular megaTALs contemplated in particular embodiments further include those disclosed in U.S. U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-15 repeat units, more preferably 7-15 repeat units, more preferably 9-15 repeat units, and more preferably 9, 10, 11, 12, 13, 14, or 15 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids −20 to −1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-15.5 repeat units, more preferably 7.5-15.5 repeat units, more preferably 9.5-15.5 repeat units, and more preferably 9.5, 10.5, 11.5, 12.5, 13.5, 14.5, or 15.5 repeat units.

In particular embodiments, a megaTAL comprises a TAL effector architecture comprising an "N-terminal domain (NTD)" polypeptide, one or more TALE repeat domains/units, a "C-terminal domain (CTD)" polypeptide, and a homing endonuclease variant. In some embodiments, the NTD, TALE repeats, and/or CTD domains are from the same species. In other embodiments, one or more of the NTD, TALE repeats, and/or CTD domains are from different species.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids+1 to +122 to at least about +1 to +137 of a *Xanthomonas* TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a *Xanthomonas* TALE protein. In one embodiment, a megaTAL contemplated herein comprises an NTD polypeptide of at least amino acids+1 to +121 of a *Ralstonia* TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a *Ralstonia* TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain. In one embodiment, a megaTAL contemplated herein comprises a CTD polypeptide of at least about amino acids −20 to −1 of a *Xanthomonas* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Xanthomonas* TALE protein. In one embodiment, a megaTAL contemplated herein comprises a CTD polypeptide of at least about amino acids −20 to −1 of a *Ralstonia* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Ralstonia* TALE protein.

In particular embodiments, a megaTAL contemplated herein, comprises a fusion polypeptide comprising a TALE DNA binding domain engineered to bind a target sequence, a homing endonuclease reprogrammed to bind and cleave a target sequence, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to a homing endonuclease variant. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the homing endonuclease variant. In this way, the megaTALs contemplated herein, increase the specificity and efficiency of genome editing.

In one embodiment, a megaTAL comprises a homing endonuclease variant and a TALE DNA binding domain that binds a nucleotide sequence that is within about 2, 3, 4, 5, or 6 nucleotides, preferably, 2 or 4 nucleotides upstream of the binding site of the reprogrammed homing endonuclease.

In one embodiment, a megaTAL comprises a homing endonuclease variant and a TALE DNA binding domain that binds the nucleotide sequence set forth in SEQ ID NO: 26, which is 5 nucleotides upstream of the nucleotide sequence bound and cleaved by the homing endonuclease variant (SEQ ID NO: 25). In preferred embodiments, the megaTAL target sequence is SEQ ID NO: 27.

In one embodiment, a megaTAL comprises a homing endonuclease variant and a TALE DNA binding domain that binds the nucleotide sequence set forth in SEQ ID NO: 31, which is 2 nucleotides upstream of the nucleotide sequence bound and cleaved by the homing endonuclease variant (SEQ ID NO: 30). In preferred embodiments, the megaTAL target sequence is SEQ ID NO: 32.

In one embodiment, a megaTAL comprises a homing endonuclease variant and a TALE DNA binding domain that binds the nucleotide sequence set forth in SEQ ID NO: 36, which is 5 nucleotides upstream of the nucleotide sequence bound and cleaved by the homing endonuclease variant (SEQ ID NO: 35). In preferred embodiments, the megaTAL target sequence is SEQ ID NO: 37.

In particular embodiments, a megaTAL contemplated herein, comprises one or more TALE DNA binding repeat units and an LHE variant designed or reprogrammed from an LHE selected from the group consisting of: I-AabMI, I-AacMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-Ncrl, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, I-Vdi141I and variants thereof, or preferably I-CpaMI, I-HjeMI, I-OnuI, I-PanMI, SmaMI and variants thereof, or more preferably I-OnuI and variants thereof.

In particular embodiments, a megaTAL contemplated herein, comprises an NTD, one or more TALE DNA binding repeat units, a CTD, and an LHE variant selected from the group consisting of: I-AabMI, I-AacMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-Ncrl, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, I-Vdi141I and variants thereof, or preferably I-CpaMI, I-HjeMI, I-OnuI, I-PanMI, SmaMI and variants thereof, or more preferably I-OnuI and variants thereof.

In particular embodiments, a megaTAL contemplated herein, comprises an NTD, about 9.5 to about 15.5 TALE DNA binding repeat units, and an LHE variant selected from the group consisting of: I-AabMI, I-AacMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-Ncrl, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, I-Vdi141I and variants thereof, or preferably I-CpaMI, I-HjeMI, I-OnuI, I-PanMI, SmaMI and variants thereof, or more preferably I-OnuI and variants thereof.

In particular embodiments, a megaTAL contemplated herein, comprises an NTD of about 122 amino acids to 137 amino acids, about 9.5, about 10.5, about 11.5, about 12.5, about 13.5, about 14.5, or about 15.5 binding repeat units, a CTD of about 20 amino acids to about 85 amino acids, and an I-OnuI LHE variant. In particular embodiments, any one of, two of, or all of the NTD, DNA binding domain, and CTD can be designed from the same species or different species, in any suitable combination.

In particular embodiments, a megaTAL contemplated herein, comprises the amino acid sequence set forth in any one of SEQ ID NOs: 15-23 and 64.

In certain embodiments, a megaTAL contemplated herein, is encoded by an mRNA sequence set forth in any one of SEQ ID NOs: 40-42 and 65-68.

In particular embodiments, a megaTAL-Trex2 fusion protein contemplated herein, comprises the amino acid sequence set forth in SEQ ID NO: 24.

In certain embodiments, a megaTAL comprises a TALE DNA binding domain and an I-OnuI LHE variant binds and cleaves the nucleotide sequence set forth in SEQ ID NO: 27. In particular embodiments, the megaTAL that binds and cleaves the nucleotide sequence set forth in SEQ ID NO: 27 comprises the amino acid sequence set forth in any one of SEQ ID NOS: 15-19.

In certain embodiments, a megaTAL comprises a TALE DNA binding domain and an I-OnuI LHE variant binds and cleaves the nucleotide sequence set forth in SEQ ID NO: 32. In particular embodiments, the megaTAL that binds and cleaves the nucleotide sequence set forth in SEQ ID NO: 32 comprises the amino acid sequence set forth in any one of SEQ ID NOs: 20-21 and 64.

In certain embodiments, a megaTAL comprises a TALE DNA binding domain and an I-OnuI LHE variant binds and cleaves the nucleotide sequence set forth in SEQ ID NO: 37. In particular embodiments, the megaTAL that binds and cleaves the nucleotide sequence set forth in SEQ ID NO: 37 comprises the amino acid sequence set forth in any one of SEQ ID NOS: 22-23.

3. End-Processing Enzymes

Genome editing compositions and methods contemplated in particular embodiments comprise editing cellular genomes using a nuclease variant and one or more copies of an end-processing enzyme. In particular embodiments, a single polynucleotide encodes a homing endonuclease variant and an end-processing enzyme, separated by a linker, a self-cleaving peptide sequence, e.g., 2A sequence, or by an IRES sequence. In particular embodiments, genome editing compositions comprise a polynucleotide encoding a nuclease variant and a separate polynucleotide encoding an end-processing enzyme. In particular embodiments, genome editing compositions comprise a polynucleotide encoding a homing endonuclease variant end-processing enzyme single polypeptide fusion in addition to a tandem copy of the end-processing enzyme separated by a self-cleaving peptide.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using a homing endonuclease variant or megaTAL and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include, but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), Apel, Mung Bean nuclease, Hex1, TTRAP (TDP2), Sgs1, Sac2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising a homing endonuclease variant or megaTAL and an exonuclease. The term "exonuclease" refers to enzymes that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, E. coli ExoI, hTREX2, mouse TREX2, rat TREX2, hTREX1, mouse TREX1, rat TREX1, and Rat TREX1.

In particular embodiments, the DNA end-processing enzyme is a 3' to 5' exonuclease, preferably Trex 1 or Trex2, more preferably Trex2, and even more preferably human or mouse Trex2.

D. Target Sites

Nuclease variants contemplated in particular embodiments can be designed to bind to any suitable target sequence and can have a novel binding specificity, compared to a naturally-occurring nuclease. In particular embodiments, the target site is a regulatory region of a gene including, but not limited to promoters, enhancers, repressor elements, and the like. In particular embodiments, the target site is a coding region of a gene or a splice site. In certain embodiments, nuclease variants are designed to down-regulate or decrease expression of a gene. In particular embodiments, a nuclease variant and donor repair template can be designed to repair or delete a desired target sequence.

In various embodiments, nuclease variants bind to and cleave a target sequence in a program death receptor 1 (PD-1) gene. PD-1 is also referred to as programmed cell death 1 (PDCD1), systemic lupus erythematosus susceptibility 2 (SLEB2), CD279, HPD1, PD1, HPD-L, and HSLE1. PD-1 is a member of the B7/CD28 family of costimulatory receptors. The PD-1 molecule consists of an extracellular ligand binding IgV domain, a transmembrane domain, and an intracellular domain which has potential phosphorylation sites located with immune tyrosine-based inhibitory motif (ITIM) and immune receptor inhibitory tyrosine-based switch motif (ITSM). PD-1 is an inhibitory co-receptor expressed on T cells, Tregs, exhausted T cells, B cells, activated monocytes, dendritic cells (DCs), natural killer (NK) cells and natural killer T (NKT) cells. PD-1 negatively regulates T-cell activation through binding to its ligands, programmed death ligand 1 (PD-L1) and programmed death ligand 2 (PD-L2). PD-1 binding inhibits T-cell proliferation, and interferon-γ (IFN-γ), tumor necrosis factor-α, and IL-2 production, and reduces T-cell survival. PD-1 expression is a hallmark of "exhausted" T cells that have experienced high levels of stimulation. This state of exhaustion, which occurs during chronic infections and cancer, is characterized by T-cell dysfunction, resulting in suboptimal control of infections and tumors.

In particular embodiments, a homing endonuclease variant or megaTAL introduces a double-strand break (DSB) in a target site in a PD-1 gene. In particular embodiments, a homing endonuclease variant or megaTAL introduces a DSB in exon 5 of a PD-1 gene, preferably at SEQ ID NO: 25 (or SEQ ID NO: 27) in exon 5 of a PD-1 gene, and more preferably at the sequence "ATAC" in SEQ ID NO: 25 (or SEQ ID NO: 27) in exon 5 of a PD-1 gene.

In a preferred embodiment, a homing endonuclease variant or megaTAL cleaves double-stranded DNA and introduces a DSB into the polynucleotide sequence set forth in SEQ ID NO: 25 or 27.

In particular embodiments, a homing endonuclease variant or megaTAL introduces a DSB in exon 1 of a PD-1 gene, preferably at SEQ ID NO: 30 (or SEQ ID NO: 32) in exon 1 of a PD-1 gene, and more preferably at the sequence "ATCC" in SEQ ID NO: 30 (or SEQ ID NO: 32) in exon 1 of a PD-1 gene.

In a preferred embodiment, a homing endonuclease variant or megaTAL cleaves double-stranded DNA and introduces a DSB into the polynucleotide sequence set forth in SEQ ID NO: 30 or 32.

In particular embodiments, a homing endonuclease variant or megaTAL introduces a DSB in exon 2 of a PD-1 gene, preferably at SEQ ID NO: 35 (or SEQ ID NO: 37) in exon 2 of a PD-1 gene, and more preferably at the sequence "ACTT" in SEQ ID NO: 35 (or SEQ ID NO: 37) in exon 2 of a PD-1 gene.

In a preferred embodiment, a homing endonuclease variant or megaTAL cleaves double-stranded DNA and introduces a DSB into the polynucleotide sequence set forth in SEQ ID NO: 35 or 37.

In a preferred embodiment, the PD-1 gene is a human PD-1 gene.

E. Donor Repair Templates

Nuclease variants may be used to introduce a DSB in a target sequence; the DSB may be repaired through homology directed repair (HDR) mechanisms in the presence of one or more donor repair templates.

In various embodiments, the donor repair template comprises one or more polynucleotides encoding an immunopotency enhancer, an immunosuppressive signal damper, or an engineered antigen receptor.

In various embodiments, it is contemplated that providing a cell an engineered nuclease in the presence of a plurality of donor repair templates independently encoding immunopotency enhancers and/or immunosuppressive signal dampers targeting different immunosuppressive pathways, yields genome edited T cells with increased therapeutic efficacy and persistence. For example, immunopotency enhancers or immunosuppressive signal targeting combinations of PD-1, LAG-3, CTLA-4, TIM3, IL-10R, TIGIT, and TGFβRII pathways may be preferred in particular embodiments.

In particular embodiments, the donor repair template is used to insert a sequence into the genome. In particular preferred embodiments, the donor repair template is used to repair or modify a sequence in the genome.

In various embodiments, a donor repair template is introduced into a hematopoietic cell, e.g., a T cell, by transducing the cell with an adeno-associated virus (AAV), retrovirus, e.g., lentivirus, IDLV, etc., herpes simplex virus, adenovirus, or vaccinia virus vector comprising the donor repair template.

In particular embodiments, the donor repair template comprises one or more homology arms that flank the DSB site.

As used herein, the term "homology arms" refers to a nucleic acid sequence in a donor repair template that is identical, or nearly identical, to DNA sequence flanking the DNA break introduced by the nuclease at a target site. In one embodiment, the donor repair template comprises a 5' homology arm that comprises a nucleic acid sequence that is identical or nearly identical to the DNA sequence 5' of the DNA break site. In one embodiment, the donor repair template comprises a 3' homology arm that comprises a nucleic acid sequence that is identical or nearly identical to the DNA sequence 3' of the DNA break site. In a preferred embodiment, the donor repair template comprises a 5' homology arm and a 3' homology arm. The donor repair template may comprise homology to the genome sequence immediately adjacent to the DSB site, or homology to the genomic sequence within any number of base pairs from the DSB site. In one embodiment, the donor repair template comprises a nucleic acid sequence that is homologous to a genomic sequence about 5 bp, about 10 bp, about 25 bp, about 50 bp, about 100 bp, about 250 bp, about 500 bp, about 1000 bp, about 2500 bp, about 5000 bp, about 10000 bp or more, including any intervening length of homologous sequence.

Illustrative examples of suitable lengths of homology arms contemplated in particular embodiments, may be independently selected, and include but are not limited to: about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, or longer homology arms, including all intervening lengths of homology arms.

Additional illustrative examples of suitable homology arm lengths include, but are not limited to: about 100 bp to about 3000 bp, about 200 bp to about 3000 bp, about 300 bp to about 3000 bp, about 400 bp to about 3000 bp, about 500 bp to about 3000 bp, about 500 bp to about 2500 bp, about 500 bp to about 2000 bp, about 750 bp to about 2000 bp, about 750 bp to about 1500 bp, or about 1000 bp to about 1500 bp, including all intervening lengths of homology arms.

In a particular embodiment, the lengths of the 5' and 3' homology arms are independently selected from about 500 bp to about 1500 bp. In one embodiment, the 5'homology arm is about 1500 bp and the 3' homology arm is about 1000 bp. In one embodiment, the 5'homology arm is between about 200 bp to about 600 bp and the 3' homology arm is between about 200 bp to about 600 bp. In one embodiment, the 5'homology arm is about 200 bp and the 3' homology arm is about 200 bp. In one embodiment, the 5'homology arm is about 300 bp and the 3' homology arm is about 300 bp. In one embodiment, the 5'homology arm is about 400 bp and the 3' homology arm is about 400 bp. In one embodiment, the 5'homology arm is about 500 bp and the 3' homology arm is about 500 bp. In one embodiment, the 5' homology arm is about 600 bp and the 3' homology arm is about 600 bp.

Donor repair templates may further comprises one or more polynucleotides such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, contemplated elsewhere herein.

In one embodiment, the donor repair template comprises a polynucleotide comprising a PD-1 gene or portion thereof and is designed to introduce one or more mutations in a genomic PD-1 sequence such that a mutant PD-1 gene product is expressed. In one embodiment, the mutant PD-1 has decreased ligand binding and/or a reduction in intracellular signaling.

In various embodiments, the donor repair template comprises a 5' homology arm, an RNA polymerase II promoter, one or more polynucleotides encoding an immunopotency enhancer, an immunosuppressive signal damper, or an engineered antigen receptor, and a 3' homology arm.

In various embodiments, a target site is modified with a donor repair template comprising a 5' homology arm, one or more polynucleotides encoding self-cleaving viral peptide, e.g., T2A, an immunopotency enhancer, an immunosuppressive signal damper, or an engineered antigen receptor, optionally a poly(A) signal or self-cleaving peptide, and a 3' homology arm, wherein expression of the one or more polynucleotides is governed by the endogenous PD-1 promoter.

1. Immunopotency Enhancers

In particular embodiments, the genome edited immune effector cells contemplated herein are made more potent and/or resistant to immunosuppressive factors by introducing a DSB in the PD-1 gene in the presence of a donor repair template encoding an immunopotency enhancer. As used herein, the term "immunopotency enhancer" refers to non-naturally occurring molecules that stimulate and/or potentiate T cell activation and/or function, immunopotentiating factors, and non-naturally occurring polypeptides that convert the immunosuppressive signals from the tumor microenvironment to an immunostimulatory signal in a T cell or other immune cells.

In particular embodiments, the immunopotency enhancer is selected from the group consisting of: a bispecific T cell engager (BiTE) molecule; an immunopotentiating factor including, but not limited to, cytokines, chemokines, cytotoxins, and/or cytokine receptors; and a flip receptor.

In some embodiments, the immunopotency enhancer, immunopotentiating factor, or flip receptor are fusion polypeptides comprising a protein destabilization domain.

a. Bispecific T Cell Engager (BITE) Molecules

In particular embodiments, the genome edited immune effector cells contemplated herein are made more potent by introducing a DSB in the PD-1 gene in the presence of a donor repair template encoding a bispecific T cell engager (BiTE) molecules. BiTE molecules are bipartite molecules comprising a first binding domain that binds a target antigen, a linker or spacer as contemplated elsewhere herein, and a second binding domain that binds a stimulatory or costimulatory molecule on an immune effector cell. The first and second binding domains may be independently selected from ligands, receptors, antibodies or antigen binding fragments thereof, lectins, and carbohydrates.

In particular embodiments, the first and second binding domains are antigen binding domains.

In particular embodiments, the first and second binding domains are antibodies or antigen binding fragments thereof. In one embodiment, the first and second binding domains are single chain variable fragments (scFv).

Illustrative examples of target antigens that may be recognized and bound by the first binding domain in particular embodiments include, but are not limited to: alpha folate receptor, 5T4, $\alpha v\beta 6$ integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRVIII, EGP2, EGP40, EPCAM, EphA2, EpCAM, FAP, fetal AchR, FR$\alpha$, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11R$\alpha$, IL-13R$\alpha$2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

Other illustrative embodiments of target antigens include MHC-peptide complexes, optionally wherein the peptide is processed from: alpha folate receptor, 5T4, $\alpha v\beta 6$ integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRVIII, EGP2, EGP40, EPCAM, EphA2, EpCAM, FAP, fetal AchR, FR$\alpha$, GD2, GD3, Glypican-3 (GPC3), MAGE1, NY-ESO-1, IL-11R$\alpha$, IL-13R$\alpha$2, Lambda, Lewis-Y, Kappa, Mesothelin, Muc1, Muc16, NCAM, NKG2D Ligands, PRAME, PSCA, PSMA, ROR1, SSX, Survivin, TAG72, TEMs, VEGFR2, and WT-1.

Illustrative examples of stimulatory or co-stimulatory molecules on immune effector cells recognized and bound by the second binding domain in particular embodiments include, but are not limited to: CD3$\gamma$, CD3$\delta$, CD3$\epsilon$, CD3$\zeta$, CD28, CD134, CD137, and CD278.

In particular embodiments, a DSB is induced in a PD-1 gene by an engineered nuclease, and a donor repair template comprising a BiTE is introduced into the cell and is inserted into the PD-1 gene by homologous recombination.

b. Immunopotentiating Factors

In particular embodiments, the genome edited immune effector cells contemplated herein are made more potent by increasing immunopotentiating factors either in the genome edited cells or cells in the tumor microenvironment. Immunopotentiating factors refer to particular cytokines, chemokines, cytotoxins, and cytokine receptors that potentiate the immune response in immune effector cells. In one embodiment, T cells are engineered by introducing a DSB in the PD-1 gene in the presence of a donor repair template encoding a cytokine, chemokine, cytotoxin, or cytokine receptor.

In particular embodiments, the donor repair template encodes a cytokine selected from the group consisting of: IL-2, insulin, IFN-γ, IL-7, IL-21, IL-10, IL-12, IL-15, and TNF-α.

In a preferred embodiment, the donor repair template encodes a cytokine selected from the group consisting of IL-2, IL-7, IL-12, IL-15, IL-18, and IL-21, that when integrated at a target site in the PD-1 gene, operably links the cytokine to the endogenous PD-1 promoter, thereby placing transcriptional control of the cytokine under the control of the endogenous PD-1 promoter.

In another preferred embodiment, the donor repair template encodes IL-12 that when integrated at a target site in the PD-1 gene, operably links the cytokine to the endogenous PD-1 promoter, thereby placing transcriptional control of the cytokine under the control of the endogenous PD-1 promoter.

In particular embodiments, the donor repair template encodes a chemokine selected from the group consisting of: MIP-1α, MIP-1β, MCP-1, MCP-3, and RANTES.

In particular embodiments, the donor repair template encodes a cytotoxin selected from the group consisting of: Perforin, Granzyme A, and Granzyme B.

In particular embodiments, the donor repair template encodes a cytokine receptor selected from the group consisting of: an IL-2 receptor, an IL-7 receptor, an IL-12 receptor, an IL-15 receptor, and an IL-21 receptor.

In a preferred embodiment, the donor repair template encodes a cytokine receptor selected from the group consisting of an IL-2 receptor, an IL-7 receptor, an IL-12 receptor, an IL-15 receptor, an IL-18 receptor, and an IL-21 receptor, that when integrated at a target site in the PD-1 gene, operably links the cytokine receptor to the endogenous PD-1 promoter, thereby placing transcriptional control of the cytokine receptor under the control of the endogenous PD-1 promoter.

In another preferred embodiment, the donor repair template encodes an IL-12 receptor that when integrated at a target site in the PD-1 gene, operably links the cytokine receptor to the endogenous PD-1 promoter, thereby placing transcriptional control of the cytokine receptor under the control of the endogenous PD-1 promoter.

c. Flip Receptors

In further embodiments, the donor repair template encodes a flip receptor or portion thereof. As used herein, the term "flip receptor" refers to a non-naturally occurring polypeptide that converts the immunosuppressive signals from the tumor microenvironment to an immunostimulatory signal in a T cell. In particular embodiments, a PD-1 flip receptor refers to a polypeptide that comprises a PD-1 exodomain or ligand binding domain or variant thereof, a transmembrane domain, and an endodomain that transduces an immunostimulatory signal to a T cell. In particular embodiments, a PD-1 flip receptor refers to a polypeptide that comprises a PD-1 exodomain or ligand binding domain or variant thereof, a transmembrane domain, and an endodomain that transduces an immunostimulatory signal to a T cell. In particular embodiments, a PD-1 flip receptor refers to a polypeptide that comprises a PD-1 exodomain or ligand binding domain or variant thereof and a transmembrane domain and endodomain from a protein that transduces an immunostimulatory signal to a T cell. In certain embodiments, the PD-1 exodomain variant has increased binding affinity for PD-L1 and/or PD-L2.

In one embodiment, the transmembrane is isolated from CD3ζ, CD3ε, CD3γ, CD3ζ, CD4, CD5, CD8α, CD9, CD 16, CD22, CD27, CD28, CD33, CD37, CD45, CD64, CD80, CD86, CD134, CD137, CD152, CD154, AMN, and PD-1.

In one embodiment, the transmembrane is isolated from CD4, CD8α, CD8β, CD27, CD28, CD134, CD137, a CD3 polypeptide, IL-2 receptor, IL-7 receptor, IL-12 receptor, IL-15 receptor, or IL-21 receptor.

In one embodiment, the endodomain is isolated from an IL-2 receptor, IL-7 receptor, IL-12 receptor, IL-15 receptor, or IL-21 receptor.

In one embodiment, the donor repair template comprises a PD-1 flip receptor comprises a PD-1 exodomain or ligand binding domain, a transmembrane domain, and one or more intracellular co-stimulatory signaling domains and/or primary signaling domains. The transmembrane and endodomains may be isolated from the same protein or different proteins.

In one embodiment, the donor repair template comprises a PD-1 flip receptor comprises a PD-1 exodomain or ligand binding domain, a PD-1 transmembrane domain, and one or more intracellular co-stimulatory signaling domains and/or primary signaling domains.

2. Immunosuppressive Signal Dampers

One limitation or problem that vexes existing adoptive cell therapy is hyporesponsiveness of immune effector cells due to exhaustion mediated by the tumor microenvironment. Exhausted T cells have a unique molecular signature that is markedly distinct from naive, effector or memory T cells. They are defined as T cells with decreased cytokine expression and effector function.

In particular embodiments, genome edited immune effector cells contemplated herein are made more resistant to exhaustion by decreasing or damping signaling by immunosuppressive factors. In one embodiment, T cells are engineered by introducing a DSB in the PD-1 gene in the presence of a donor repair template encoding an immunosuppressive signal damper.

As used herein, the term "immunosuppressive signal damper" refers to a non-naturally occurring polypeptide that decreases the transduction of immunosuppressive signals from the tumor microenvironment to a T cell. In one embodiment, the immunosuppressive signal damper is an antibody or antigen binding fragment thereof that binds an immunosuppressive factor. In preferred embodiments, an immunosuppressive signal damper refers to a polypeptide that elicits a suppressive, dampening, or dominant negative effect on a particular immunosuppressive factor or signaling pathway because the damper comprises and exodomain that binds an immunosuppressive factor, and optionally, a transmembrane domain, and optionally, a modified endodomain (e.g., intracellular signaling domain).

In particular embodiments, the exodomain is an extracellular binding domain that recognizes and binds and immunosuppressive factor.

In particular embodiments, the modified endodomain is mutated to decrease or inhibit immunosuppressive signals. Suitable mutation strategies include, but are not limited to amino acid substitution, addition, or deletion. Suitable mutations further include, but are not limited to endodomain truncation to remove signaling domains, mutating endodomains to remove residues important for signaling motif activity, and mutating endodomains to block receptor cycling. In particular embodiments, the endodomain, when present does not transduce immunosuppressive signals, or has substantially reduced signaling.

Thus, in some embodiments, an immunosuppressive signal damper acts as a sink for one or more immunosuppressive factors from the tumor microenvironment and inhibits the corresponding immunosuppressive signaling pathways in the T cell.

One immunosuppressive signal is mediated by tryptophan catabolismryptophan catabolismby indoleamine 2,3-dioxygenase (IDO) in cancer cells leads to the production of kynurenines which have been shown to have an immunosuppressive effect on T cells in the tumor microenvironment. See e.g., Platten et al. (2012) Cancer Res. 72(21):5435-40.

In one embodiment, a donor repair template comprises an enzyme with kynureninase activity.

Illustrative examples of enzymes having kynureninase activity suitable for use in particular embodiments include, but are not limited to, L-Kynurenine hydrolase.

In one embodiment, the donor repair template comprises one or more polynucleotides that encodes an immunosuppressive signal damper that decrease or block immunosuppressive signaling mediated by an immunosuppressive factor.

Illustrative examples of immunosuppressive factors targeted by the immunosuppressive signal dampers contemplated in particular embodiments include, but are not limited to: programmed death ligand 1 (PD-L1), programmed death ligand 2 (PD-L2), transforming growth factor β (TGFβ), macrophage colony-stimulating factor 1 (M-CSF1), tumor necrosis factor related apoptosis inducing ligand (TRAIL), receptor-binding cancer antigen expressed on SiSo cells ligand (RCAS1), Fas ligand (FasL), CD47, interleukin-4 (IL-4), interleukin-6 (IL-6), interleukin-8 (IL-8), interleukin-10 (IL-10), and interleukin-13 (IL-13).

In various embodiments, the immunosuppressive signal damper comprises an antibody or antigen binding fragment thereof that binds an immunosuppressive factor.

In various embodiments, the immunosuppressive signal damper comprises an exodomain that binds an immunosuppressive factor.

In particular embodiments, the immunosuppressive signal damper comprises an exodomain that binds an immunosuppressive factor and a transmembrane domain.

In another embodiment, the immunosuppressive signal damper comprises an exodomain that binds an immunosuppressive factor, a transmembrane domain, and a modified endodomain that does not transduce or that has substantially reduced ability to transduce immunosuppressive signals.

As used herein, the term "exodomain" refers to an antigen binding domain. In one embodiment, the exodomain is an extracellular ligand binding domain of an immunosuppressive receptor that transduces immunosuppressive signals from the tumor microenvironment to a T cell. In particular embodiments, an exodoum refers to an extracellular ligand binding domain of a receptor that comprises an immunoreceptor tyrosine inhibitory motif (ITIM) and/or an immunoreceptor tyrosine switch motif (ITSM).

Illustrative examples of exodomains suitable for use in particular embodiments of immunosuppressive signal dampers include, but are not limited to antibodies or antigen binding fragments thereof, or extracellular ligand binding domains isolated from the following polypeptides: programmed cell death protein 1 (PD-1), lymphocyte activation gene 3 protein (LAG-3), T cell immunoglobulin domain and mucin domain protein 3 (TIM3), cytotoxic T lymphocyte antigen-4 (CTLA-4), band T lymphocyte attenuator (BTLA), T cell immunoglobulin and immunoreceptor tyrosine-based inhibitory motif domain (TIGIT), transforming growth factor β receptor II (TGFβRII), macrophage colony-stimulating factor 1 receptor (CSF1R), interleukin 4 receptor (IL4R), interleukin 6 receptor (IL6R), chemokine (C-X-C motif) receptor 1 (CXCR1), chemokine (C-X-C motif) receptor 2 (CXCR2), interleukin receptor subunit alpha (IL10R), interleukin 13 receptor subunit alpha 2 (IL13Rα2), tumor necrosis factor related apoptosis inducing ligand (TRAILR1), receptor-binding cancer antigen expressed on SiSo cells (RCAS1R), and Fas cell surface death receptor (FAS).

In one embodiment, the exodomain comprises an extracellular ligand binding domain of a receptor selected from the group consisting of: PD-1, LAG-3, TIM3, CTLA-4, IL10R, TIGIT, CSF1R, and TGFβRII.

A number of transmembrane domains may be used in particular embodiments. Illustrative examples of transmembrane domains suitable for use in particular embodiments of immunosuppressive signal dampers contemplated in particular embodiments include, but are not limited to transmembrane domains of the following proteins: alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD80, CD86, CD 134, CD137, CD152, CD154, and PD-1.

In particular embodiments, the adoptive cell therapies contemplated herein comprise an immunosuppressive signal damper that inhibits or blocks the transduction of immunosuppressive TGFβ signals from the tumor microenvironment through TGFβRII. In one embodiment, the immunosuppressive signal damper comprises an exodomain that comprises a TGFβRII extracellular ligand binding, a TGFβRII transmembrane domain, and a truncated, non-functional TGFβRII endodomain. In another embodiment, the immunosuppressive signal damper comprises an exodomain that comprises a TGFβRII extracellular ligand binding, a TGFβRII transmembrane domain, and lacks an endodomain.

3. Engineered Antigen Receptors

In particular embodiments, the genome edited immune effector cells contemplated herein comprise an engineered antigen receptor. In one embodiment, T cells are engineered by introducing a DSB in one or more PD-1 genes in the presence of a donor repair template encoding an engineered antigen receptor.

In particular embodiments, the engineered antigen receptor is an engineered T cell receptor (TCR), a chimeric antigen receptor (CAR), a Daric receptor or components thereof, or a chimeric cytokine receptor.

a. Engineered TCRs

In particular embodiments, the genome edited immune effector cells contemplated herein comprise an engineered TCR. In one embodiment, T cells are engineered by introducing a DSB in one or more PD-1 genes in the presence of a donor repair template encoding an engineered TCR. In a particular embodiment, an engineered TCR is inserted at a DSB in a single PD-1 gene. Another embodiment, the alpha chain of an engineered TCR is inserted into a DSB in one PD-1 gene and the beta chain of the engineered TCR is inserted into a DSB in the other PD-1 gene.

In one embodiment, the engineered T cells contemplated herein comprise an engineered TCR that is not inserted at a PD-1 gene and one or more of an immunosuppressive signal damper, a flip receptor, an alpha and/or beta chain of an engineered T cell receptor (TCR), a chimeric antigen receptor (CAR), a Daric receptor or components thereof, or a chimeric cytokine receptor is inserted into a DSB in one or more PD-1 genes.

Naturally occurring T cell receptors comprise two subunits, an alpha chain and a beta chain subunit, each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy.

In one embodiment, T cells are modified by introducing donor repair template comprising a polynucleotide encoding a subunit of a TCR at a DSB in one or more PD-1 genes, wherein the TCR subunit has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the inventive alpha chain or beta chain of a TCR so long as the attached additional polypeptide does not interfere with the ability of the alpha chain or beta chain to form a functional T cell receptor and the MHC dependent antigen recognition.

Antigens that are recognized by the engineered TCRs contemplated in particular embodiments include, but are not limited to cancer antigens, including antigens on both hematological cancers and solid tumors. Illustrative antigens include, but are not limited to alpha folate receptor, alpha folate receptor, 5T4, αvβ6 integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRVIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In one embodiment, a donor repair template comprises a polynucleotide encoding an RNA polymerase II promoter or a first self-cleaving viral peptide and a polynucleotide encoding the alpha chain and/or the beta chain of the engineered TCR integrated into one modified and/or non-functional PD-1 gene.

In one embodiment, a donor repair template comprises a polynucleotide encoding an RNA polymerase II promoter or a first self-cleaving viral peptide and a polynucleotide encoding the alpha chain and the beta chain of the engineered TCR integrated into one modified and/or non-functional PD-1 gene.

In a particular embodiment, the donor repair template comprises from 5' to 3', a polynucleotide encoding a first self-cleaving viral peptide, a polynucleotide encoding the alpha chain of the engineered TCR, a polynucleotide encoding a second self-cleaving viral peptide, and a polynucleotide encoding the beta chain of the engineered TCR integrated into one modified and/or non-functional PD-1 gene. In such a case, the other PD-1 gene may be functional or may have decreased function or been rendered non-functional by a DSB and repair by NHEJ. In one embodiment, the other PD-1 gene has been modified by an engineered nuclease contemplated herein and may have decreased function or been rendered non-functional.

In a certain embodiment, both PD-1 genes are modified and have decreased function or are non-functional: the first modified PD-1 gene comprises a nucleic acid comprising a polynucleotide encoding a first self-cleaving viral peptide and a polynucleotide encoding the alpha chain of the engineered TCR, and the second modified PD-1 gene comprises a polynucleotide encoding a second self-cleaving viral peptide and a polynucleotide encoding the beta chain of the engineered TCR.

b. Chimeric Antigen Receptors (CARs)

In particular embodiments, the engineered immune effector cells contemplated herein comprise one or more chimeric antigen receptors (CARs). In one embodiment, T cells are engineered by introducing a DSB in one or more PD-1 genes in the presence of a donor repair template encoding a CAR. In a particular embodiment, a CAR is inserted at a DSB in a single PD-1 gene.

In one embodiment, the engineered T cells contemplated herein a CAR that is not inserted at a PD-1 gene and one or more of an immunosuppressive signal damper, a flip receptor, an alpha and/or beta chain of an engineered T cell receptor (TCR), a chimeric antigen receptor (CAR), a Daric receptor or components thereof, or a chimeric cytokine receptor is inserted into a DSB in one or more PD-1 genes.

In various embodiments, the genome edited T cells express CARs that redirect cytotoxicity toward tumor cells. CARs are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

In various embodiments, a CAR comprises an extracellular domain that binds to a specific target antigen (also referred to as a binding domain or antigen-specific binding domain), a transmembrane domain and an intracellular signaling domain. The main characteristics of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, CARs comprise an extracellular binding domain that specifically binds to a target polypeptide, e.g., target antigen, expressed on tumor cell. As used herein, the terms, "binding domain," "extracellular domain," "extracellular binding domain," "antigen binding domain," "antigen-specific binding domain," and "extracellular antigen specific binding domain," are used interchangeably and provide a chimeric receptor, e.g., a CAR or Daric, with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In particular embodiments, the extracellular binding domain comprises an antibody or antigen binding fragment thereof.

An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the CAR comprises an extracellular domain that binds an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRVIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In particular embodiments, the CARs comprise an extracellular binding domain, e.g., antibody or antigen binding fragment thereof that binds an antigen, wherein the antigen is an MHC-peptide complex, such as a class I MHC-peptide complex or a class II MHC-peptide complex.

In certain embodiments, the CARs comprise linker residues between the various domains. A "variable region linking sequence," is an amino acid sequence that connects a heavy chain variable region to a light chain variable region and provides a spacer function compatible with interaction of the two binding domains so that the resulting polypeptide retains a specific binding affinity to the same target molecule as an antibody that comprises the same light and heavy chain variable regions. In particular embodiments, CARs comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 of IgG1, IgG4, or IgD.

In one embodiment, the binding domain of the CAR is linked to one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8α, and CD4, which may be wild-type hinge regions from these molecules or may be altered. In another embodiment, the hinge domain comprises a CD8α hinge region.

In one embodiment, the hinge is a PD-1 hinge or CD152 hinge.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a CAR comprises a TM domain derived from CD8α. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In particular embodiments, a CAR comprises an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. In preferred embodiments, a CAR comprises an intracellular signaling domain that comprises one or more "costimulatory signaling domains" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain.

In particular embodiments, a CAR comprises one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule.

Illustrative examples of such costimulatory molecules suitable for use in CARs contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a CAR comprises one or more costimulatory signaling domains selected from the group consisting of CD28, CD137, and CD134, and a CD3ζ primary signaling domain.

In various embodiments, the CAR comprises: an extracellular domain that binds an antigen selected from the group consisting of: BCMA, CD19, CSPG4, PSCA, ROR1, and TAG72; a transmembrane domain isolated from a polypeptide selected from the group consisting of: CD4, CD8α, CD154, and PD-1; one or more intracellular costimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

c. Daric Receptors

In particular embodiments, the engineered immune effector cells comprise one or more Daric receptors. As used herein, the term "Daric receptor" refers to a multichain engineered antigen receptor. In one embodiment, T cells are engineered by introducing a DSB in one or more PD-1 genes in the presence of a donor repair template encoding one or more components of a Daric. In a particular embodiment, a Daric or one or more components thereof is inserted at a DSB in a single PD-1 gene.

In one embodiment, the engineered T cells comprise a Daric that is not inserted at a PD-1 gene and one or more of an immunosuppressive signal damper, a flip receptor, an alpha and/or beta chain of an engineered T cell receptor (TCR), a chimeric antigen receptor (CAR), or a Daric receptor or components thereof is inserted into a DSB in one or more PD-1 genes.

Illustrative examples of Daric architectures and components are disclosed in PCT Publication No. WO2015/017214 and U.S. Patent Publication No. 20150266973, each of which is incorporated here by reference in its entirety.

In one embodiment, a donor repair template comprises the following Daric components: a signaling polypeptide comprising a first multimerization domain, a first transmembrane domain, and one or more intracellular co-stimulatory signaling domains and/or primary signaling domains; and a binding polypeptide comprising a binding domain, a second multimerization domain, and optionally a second transmembrane domain. A functional Daric comprises a bridging factor that promotes the formation of a Daric receptor complex on the cell surface with the bridging factor associated with and disposed between the multimerization domains of the signaling polypeptide and the binding polypeptide.

In particular embodiments, the first and second multimerization domains associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, and any combination thereof.

Illustrative examples of rapamycin analogs (rapalogs) include those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. In one embodiment, "substantially reduced immunosuppressive effect" refers to a rapalog having an EC50 value in such an in vitro assay that is at least 10 to 250 times larger than the EC50 value observed for rapamycin in the same assay.

Other illustrative examples of rapalogs include, but are not limited to, everolimus, novolimus, pimecrolimus, ridaforolimus, tacrolimus, temsirolimus, umirolimus, and zotarolimus.

In certain embodiments, multimerization domains will associate with a bridging factor being a rapamycin or rapalog thereof. For example, the first and second multimerization domains are a pair selected from FKBP and FRB. FRB domains are polypeptide regions (protein "domains") that are capable of forming a tripartite complex with an FKBP protein and rapamycin or rapalog thereof. FRB domains are present in a number of naturally occurring proteins, including mTOR proteins (also referred to in the literature as FRAP, RAPT1, or RAFT) from human and other species; yeast proteins including Tor1 and Tor2; and a *Candida* FRAP homolog. Information concerning the nucleotide sequences, cloning, and other aspects of these proteins is already known in the art. For example, a protein sequence accession number for a human mTOR is GenBank Accession No. L34075.1 (Brown et al., Nature 369:756, 1994).

FRB domains suitable for use in particular embodiments contemplated herein generally contain at least about 85 to about 100 amino acid residues. In certain embodiments, an FRB amino acid sequence for use in fusion proteins of this disclosure will comprise a 93 amino acid sequence Ile-2021 through Lys-2113 and a mutation of T2098L, based the amino acid sequence of GenBank Accession No. L34075.1. An FRB domain for use in Darics contemplated in particular embodiments will be capable of binding to a complex of an FKBP protein bound to rapamycin or a rapalog thereof. In certain embodiments, a peptide sequence of an FRB domain comprises (a) a naturally occurring peptide sequence spanning at least the indicated 93 amino acid region of human mTOR or corresponding regions of homologous proteins; (b) a variant of a naturally occurring FRB in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide encoded by a nucleic acid molecule capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides, such as FK506, FK520 and rapamycin, and are highly conserved across species lines. FKBPs are proteins or protein domains that are capable of binding to rapamycin or to a rapalog thereof and further forming a tripartite complex with an FRB-containing protein or fusion protein. An FKBP domain may also be referred to as a "rapamycin binding domain." Information concerning the nucleotide sequences, cloning, and other aspects of various FKBP species is known in the art (see, e.g., Staendart et al., Nature 346:671, 1990 (human FKBP12); Kay, Biochem. J. 314:361, 1996). Homologous FKBP proteins in other mammalian species, in yeast, and in other organisms are also known in the art and may be used in the fusion proteins disclosed herein. An FKBP domain contemplated in particular embodiments will be capable of binding to rapamycin or a rapalog thereof and participating in a tripartite complex with an FRB-containing protein (as may be determined by any means, direct or indirect, for detecting such binding).

Illustrative examples of FKBP domains suitable for use in a Daric contemplated in particular embodiments include, but are not limited to: a naturally occurring FKBP peptide sequence, preferably isolated from the human FKBP12 protein (GenBank Accession No. AAA58476.1) or a peptide sequence isolated therefrom, from another human FKBP, from a murine or other mammalian FKBP, or from some other animal, yeast or fungal FKBP; a variant of a naturally occurring FKBP sequence in which up to about ten amino acids, or about 1 to about 5 amino acids or about 1 to about 3 amino acids, or in some embodiments just one amino acid, of the naturally-occurring peptide have been deleted, inserted, or substituted; or a peptide sequence encoded by a nucleic acid molecule capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

Other illustrative examples of multimerization domain pairs suitable for use in a Daric contemplated in particular embodiments include, but are not limited to include from FKBP and FRB, FKBP and calcineurin, FKBP and cyclophilin, FKBP and bacterial DHFR, calcineurin and cyclophilin, PYL1 and ABI1, or GIBI and GAI, or variants thereof.

In yet other embodiments, an anti-bridging factor blocks the association of a signaling polypeptide and a binding polypeptide with the bridging factor. For example, cyclosporin or FK506 could be used as anti-bridging factors to titrate out rapamycin and, therefore, stop signaling since only one multimerization domain is bound. In certain embodiments, an anti-bridging factor (e.g., cyclosporine, FK506) is an immunosuppressive agent. For example, an immunosuppressive anti-bridging factor may be used to block or minimize the function of the Daric components contemplated in particular embodiments and at the same time inhibit or block an unwanted or pathological inflammatory response in a clinical setting.

In one embodiment, the first multimerization domain comprises FRB T2098L, the second multimerization domain comprises FKBP12, and the bridging factor is rapalog AP21967.

In another embodiment, the first multimerization domain comprises FRB, the second multimerization domain comprises FKBP12, and the bridging factor is Rapamycin, temsirolimus or everolimus.

In particular embodiments, a signaling polypeptide a first transmembrane domain and a binding polypeptide comprises a second transmembrane domain or GPI anchor. Illustrative examples of the first and second transmembrane domains are isolated from a polypeptide independently selected from the group consisting of: CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a signaling polypeptide comprises one or more intracellular co-stimulatory signaling domains and/or primary signaling domains.

Illustrative examples of primary signaling domains suitable for use in Daric signaling components contemplated in particular embodiments include those derived from FcRγ, FcRβ, CD3γ, CD3δ, CD3ε, CD3ζ, CD22, CD79a, CD79b, and CD66d. In particular preferred embodiments, a Daric signaling component comprises a CD3ζ primary signaling domain and one or more costimulatory signaling domains. The intracellular primary signaling and costimulatory signaling domains may be linked in any order in tandem to the carboxyl terminus of the transmembrane domain.

Illustrative examples of such costimulatory molecules suitable for use in Daric signaling components contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a Daric signaling component comprises one or more costimulatory signaling domains selected from the group consisting of CD28, CD137, and CD134, and a CD3ζ primary signaling domain.

In particular embodiments, a Daric binding component comprises a binding domain. In one embodiment, the binding domain is an antibody or antigen binding fragment thereof.

The antibody or antigen binding fragment thereof comprises at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the Daric binding component comprises an extracellular domain that binds an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRVIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In one embodiment, the Daric binding component comprises an extracellular domain, e.g., antibody or antigen binding fragment thereof that binds an MHC-peptide complex, such as a class I MHC-peptide complex or class II MHC-peptide complex.

In particular embodiments, the Daric components contemplated herein comprise a linker or spacer that connects two proteins, polypeptides, peptides, domains, regions, or motifs. In certain embodiments, a linker comprises about two to about 35 amino acids, or about four to about 20 amino acids or about eight to about 15 amino acids or about 15 to about 25 amino acids. In other embodiments, a spacer may have a particular structure, such as an antibody CH2CH3 domain, hinge domain or the like. In one embodiment, a spacer comprises the CH2 and CH3 domains of IgG1, IgG4, or IgD.

In particular embodiments, the Daric components contemplated herein comprise one or more "hinge domains," which plays a role in positioning the domains to enable proper cell/cell contact, antigen binding and activation. A Daric may comprise one or more hinge domains between the binding domain and the multimerization domain and/or the transmembrane domain (TM) or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region. In particular embodiment, the hinge is a CD8α hinge or a CD4 hinge.

In one embodiment, a Daric comprises a signaling polypeptide comprises a first multimerization domain of FRB T2098L, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is rapalog AP21967.

In one embodiment, a Daric comprises a signaling polypeptide comprises a first multimerization domain of FRB, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is Rapamycin, temsirolimus or everolimus.

d. Zetakines

In particular embodiments, the engineered immune effector cells contemplated herein comprise one or more chimeric cytokine receptors. In one embodiment, T cells are engineered by introducing a DSB in one or more PD-1 genes in the presence of a donor repair template encoding a CAR. In a particular embodiment, a chimeric cytokine receptor is inserted at a DSB in a single PD-1 gene.

In one embodiment, the engineered T cells contemplated herein a chimeric cytokine receptor that is not inserted at a PD-1 gene and one or more of an immunosuppressive signal damper, a flip receptor, an alpha and/or beta chain of an engineered T cell receptor (TCR), a chimeric antigen receptor (CAR), a Daric receptor or components thereof, or a chimeric cytokine receptor is inserted into a DSB in one or more PD-1 genes.

In various embodiments, the genome edited T cells express chimeric cytokine receptor that redirect cytotoxicity toward tumor cells. Zetakines are chimeric transmembrane immunoreceptors that comprise an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors redirect the antigen specificity of T cells, with application to treatment of a variety of cancers, particularly via the autocrine/paracrine cytokine systems utilized by human malignancy.

In particular embodiments, the chimeric cytokine receptor comprises an immunosuppressive cytokine or cytokine receptor binding variant thereof, a linker, a transmembrane domain, and an intracellular signaling domain.

In particular embodiments, the cytokine or cytokine receptor binding variant thereof is selected from the group consisting of: interleukin-4 (IL-4), interleukin-6 (IL-6), interleukin-8 (IL-8), interleukin-10 (IL-10), and interleukin-13 (IL-13).

In certain embodiments, the linker comprises a CH2CH3 domain, hinge domain, or the like. In one embodiment, a linker comprises the CH2 and CH3 domains of IgG1, IgG4, or IgD. In one embodiment, a linker comprises a CD8α or CD4 hinge domain.

In particular embodiments, the transmembrane domain is selected from the group consisting of: the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In particular embodiments, the intracellular signaling domain is selected from the group consisting of: an ITAM containing primary signaling domain and/or a costimulatory domain.

In particular embodiments, the intracellular signaling domain is selected from the group consisting of: FcRγ, FcRβ, CD3γ, CD3δ, CD3ε, CD3ζ, CD22, CD79a, CD79b, and CD66d.

In particular embodiments, the intracellular signaling domain is selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In one embodiment, a chimeric cytokine receptor comprises one or more costimulatory signaling domains selected from the group consisting of CD28, CD137, and CD134, and a CD3ζ primary signaling domain.

F. Polypeptides

Various polypeptides are contemplated herein, including, but not limited to, homing endonuclease variants, megaTALs, and fusion polypeptides. In preferred embodiments, a polypeptide comprises the amino acid sequence set forth in SEQ ID NOs: 1-24 and 60-64. "Polypeptide," "polypeptide fragment," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances.

Illustrative examples of polypeptides contemplated in particular embodiments include, but are not limited to homing endonuclease variants, megaTALs, end-processing nucleases, fusion polypeptides and variants thereof.

Polypeptides include "polypeptide variants." Polypeptide variants may differ from a naturally occurring polypeptide in one or more amino acid substitutions, deletions, additions and/or insertions. Such variants may be naturally occurring or may be synthetically generated, for example, by modifying one or more amino acids of the above polypeptide sequences. For example, in particular embodiments, it may be desirable to improve the biological properties of a homing endonuclease, megaTAL or the like that binds and cleaves a target site in the human PD-1 gene by introducing one or more substitutions, deletions, additions and/or insertions into the polypeptide. In particular embodiments, polypeptides include polypeptides having at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to any of the reference sequences contemplated herein, typically where the variant maintains at least one biological activity of the reference sequence.

Polypeptides variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity.

In preferred embodiments, the biological activity is binding affinity and/or cleavage activity for a target sequence. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long. In particular embodiments, a polypeptide comprises a biologically active fragment of a homing endonuclease variant. In particular embodiments, the polypeptides set forth herein may comprise one or more amino acids denoted as "X." "X" if present in an amino acid SEQ ID NO, refers to any amino acid. One or more "X" residues may be present at the N- and C-terminus of an amino acid sequence set forth in particular SEQ ID NOs contemplated herein. If the "X" amino acids are not present the remaining amino acid sequence set forth in a SEQ ID NO may be considered a biologically active fragment.

In particular embodiments, a polypeptide comprises a biologically active fragment of a homing endonuclease variant, e.g., SEQ ID NOs: 3-14, and 60-63, or a megaTAL (SEQ ID NOs: 15-23 and 64). The biologically active fragment may comprise an N-terminal truncation and/or C-terminal truncation. In a particular embodiment, a biologically active fragment lacks or comprises a deletion of the 1, 2, 3, 4, 5, 6, 7, or 8 N-terminal amino acids of a homing endonuclease variant compared to a corresponding wild type homing endonuclease sequence, more preferably a deletion of the 4 N-terminal amino acids of a homing endonuclease variant compared to a corresponding wild type homing endonuclease sequence. In a particular embodiment, a biologically active fragment lacks or comprises a deletion of the 1, 2, 3, 4, or 5 C-terminal amino acids of a homing endonuclease variant compared to a corresponding wild type homing endonuclease sequence, more preferably a deletion of the 2 C-terminal amino acids of a homing endonuclease variant compared to a corresponding wild type homing endonuclease sequence. In a particular preferred embodiment, a biologically active fragment lacks or comprises a deletion of the 4 N-terminal amino acids and 2 C-terminal amino acids of a homing endonuclease variant compared to a corresponding wild type homing endonuclease sequence.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1, 2, 3, 4, or 5 C-terminal amino acids: R, G, S, F, V.

In a particular embodiment, an I-OnuI variant comprises a deletion or substitution of 1, 2, 3, 4, 5, 6, 7, or 8 the following N-terminal amino acids: M, A, Y, M, S, R, R, E; and/or a deletion or substitution of the following 1, 2, 3, 4, or 5 C-terminal amino acids: R, G, S, F, V.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1 or 2 C-terminal amino acids: F, V.

In a particular embodiment, an I-OnuI variant comprises a deletion or substitution of 1, 2, 3, 4, 5, 6, 7, or 8 the following N-terminal amino acids: M, A, Y, M, S, R, R, E; and/or a deletion or substitution of the following 1 or 2 C-terminal amino acids: F, V.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene,* Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure (Natl. Biomed. Res. Found.,* Washington, D.C.).

In certain embodiments, a variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons |
|---|---|---|---|
| Alanine | A | Ala | GCA GCC GCG GCU |
| Cysteine | C | Cys | UGC UGU |
| Aspartic acid | D | Asp | GAC GAU |
| Glutamic acid | E | Glu | GAA GAG |
| Phenylalanine | F | Phe | UUC UUU |
| Glycine | G | Gly | GGA GGC GGG GGU |
| Histidine | H | His | CAC CAU |
| Isoleucine | I | Iso | AUA AUC AUU |
| Lysine | K | Lys | AAA AAG |
| Leucine | L | Leu | UUA UUG CUA CUC CUG CUU |
| Methionine | M | Met | AUG |
| Asparagine | N | Asn | AAC AAU |
| Proline | P | Pro | CCA CCC CCG CCU |
| Glutamine | Q | Gln | CAA CAG |
| Arginine | R | Arg | AGA AGG CGA CGC CGG CGU |
| Serine | S | Ser | AGC AGU UCA UCC UCG UCU |
| Threonine | T | Thr | ACA ACC ACG ACU |
| Valine | V | Val | GUA GUC GUG GUU |
| Tryptophan | W | Trp | UGG |
| Tyrosine | Y | Tyr | UAC UAU |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p. 224).

In one embodiment, where expression of two or more polypeptides is desired, the polynucleotide sequences encoding them can be separated by and IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

In one embodiment, a fusion protein contemplated herein comprises one or more DNA binding domains and one or more nucleases, and one or more linker and/or self-cleaving polypeptides.

In one embodiment, a fusion protein contemplated herein comprises nuclease variant; a linker or self-cleaving peptide; and an end-processing enzyme including but not limited to a 5'-3' exonuclease, a 5'-3' alkaline exonuclease, and a 3'-5' exonuclease (e.g., Trex2).

Fusion polypeptides can comprise one or more polypeptide domains or segments including, but are not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers $(G)_n$; glycine-serine polymers $(G_{1-5}S_{1-5})_n$, where n is an integer of at least one, two, three, four, or five; glycine-alanine polymers; alanine-serine polymers; GGG (SEQ ID NO: 69); DGGGS (SEQ ID NO: 70); TGEKP (SEQ ID NO: 71) (see e.g., Liu et al., PNAS 5525-5530 (1997)); GGRR (SEQ ID NO: 72) (Pomerantz et al. 1995, supra); $(GGGGS)_n$ wherein n=1, 2, 3, 4 or 5 (SEQ ID NO: 73) (Kim et al., *PNAS* 93, 1156-1160 (1996).); EGKSSGSGSESKVD (SEQ ID NO: 74) (Chaudhary et al., 1990, *Proc. Natl. Acad. Sci. U.S.A.* 87:1066-1070); KESGSVSSEQLAQFRSLD (SEQ ID NO: 75) (Bird et al., 1988, *Science* 242:423-426), GGRRGGGS (SEQ ID NO: 76); LRQRDGERP (SEQ ID NO: 77); LRQKDGGGSERP (SEQ ID NO: 78); LRQKD (GGGS)¿ERP (SEQ ID NO: 79). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods.

Fusion polypeptides may further comprise a polypeptide cleavage signal between each of the polypeptide domains described herein or between an endogenous open reading frame and a polypeptide encoded by a donor repair template. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) *Nature Biotech.* 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 80), for example, ENLYFQG (SEQ ID NO: 81) and ENLYFQS (SEQ ID NO: 82), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 2.

TABLE 2

Exemplary 2A sites include the following sequences:

| SEQ ID NO: 83 | GSGATNFSLLKQAGDVEENPGP |
| SEQ ID NO: 84 | ATNFSLLKQAGDVEENPGP |
| SEQ ID NO: 85 | LLKQAGDVEENPGP |
| SEQ ID NO: 86 | GSGEGRGSLLTCGDVEENPGP |
| SEQ ID NO: 87 | EGRGSLLTCGDVEENPGP |
| SEQ ID NO: 88 | LLTCGDVEENPGP |
| SEQ ID NO: 89 | GSGQCTNYALLKLAGDVESNPGP |
| SEQ ID NO: 90 | QCTNYALLKLAGDVESNPGP |
| SEQ ID NO: 91 | LLKLAGDVESNPGP |
| SEQ ID NO: 92 | GSGVKQTLNFDLLKLAGDVESNPGP |
| SEQ ID NO: 93 | VKQTLNFDLLKLAGDVESNPGP |
| SEQ ID NO: 94 | LLKLAGDVESNPGP |
| SEQ ID NO: 95 | LLNFDLLKLAGDVESNPGP |
| SEQ ID NO: 96 | TLNFDLLKLAGDVESNPGP |
| SEQ ID NO: 97 | LLKLAGDVESNPGP |
| SEQ ID NO: 98 | NFDLLKLAGDVESNPGP |
| SEQ ID NO: 99 | QLLNFDLLKLAGDVESNPGP |
| SEQ ID NO: 100 | APVKQTLNFDLLKLAGDVESNPGP |
| SEQ ID NO: 101 | VTELLYRMKRAETYCPRPLLAIHPTEARHKQKIVAPVKQT |

TABLE 2-continued

Exemplary 2A sites include the following sequences:

| SEQ ID NO: 102 | LNFDLLKLAGDVESNPGP |
| SEQ ID NO: 103 | LLAIHPTEARHKQKIVAPVKQTLNFDLLKLAGDVESNPGP |
| SEQ ID NO: 104 | EARHKQKIVAPVKQTLNFDLLKLAGDVESNPGP |

G. Polynucleotides

In particular embodiments, polynucleotides encoding one or more homing endonuclease variants, megaTALs, end-processing enzymes, and fusion polypeptides contemplated herein are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x)

systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, Nucleic Acids Res. 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, Nucleic Acids Res. 22, 2183-2196).

Illustrative examples of polynucleotides include, but are not limited to polynucleotides encoding SEQ ID NOs: 1-24 and 60-64, and polynucleotide sequences set forth in SEQ ID NOs: 25-59 and 65-68.

In various illustrative embodiments, polynucleotides contemplated herein include, but are not limited to polynucleotides encoding homing endonuclease variants, megaTALs, end-processing enzymes, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant polynucleotide, a synthetic polynucleotide, or other polynucleotide that does not exist in nature and that has been made by the hand of man.

In various embodiments, a polynucleotide comprises an mRNA encoding a polypeptide contemplated herein including, but not limited to, a homing endonuclease variant, a megaTAL, and an end-processing enzyme. In certain embodiments, the mRNA comprises a cap, one or more nucleotides, and a poly(A) tail.

As used herein, the terms "5' cap" or "5' cap structure" or "5' cap moiety" refer to a chemical modification, which has been incorporated at the 5' end of an mRNA. The 5' cap is involved in nuclear export, mRNA stability, and translation.

In particular embodiments, a mRNA contemplated herein comprises a 5' cap comprising a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue.

Illustrative examples of 5' cap suitable for use in particular embodiments of the mRNA polynucleotides contemplated herein include, but are not limited to: unmethylated 5' cap analogs, e.g., G(5)ppp(5')G, G(5')ppp(5')C, G(5)ppp(5')A; methylated 5' cap analogs, e.g., m$^7$G(5')ppp(5')G, m$^7$G(5')ppp(5')C, and m$^7$G(5')ppp(5')A; dimethylated 5' cap analogs, e.g., m$^{2,7}$G(5')ppp(5')G, m$^{2,7}$G(5')ppp(5')C, and m$^{2,7}$G(5')ppp(5')A; trimethylated 5' cap analogs, e.g., m$^{2,2,7}$G(5)ppp(5')G, m$^{2,2,7}$G(5')ppp(5')C, and m$^{2,2,7}$G(5')ppp(5')A; dimethylated symmetrical 5' cap analogs, e.g., m$^7$G(5')pppm$^7$(5')G, m$^7$G(5')pppm$^7$(5')C, and m$^7$G(5')pppm$^7$(5')A; and anti-reverse 5' cap analogs, e.g., Anti-Reverse Cap Analog (ARCA) cap, designated 3'O-Me-m$^7$G(5')ppp(5')G, 2'O-Me-m$^7$G(5')ppp(5')G, 2'O-Me-m$^7$G(5')ppp(5')C, 2'O-Me-m$^7$G(5')ppp(5')A, m$^{7 2'}$d(5')ppp(5')G, m$^7$2'd(5')ppp(5')C, m$^7$2'd(5')ppp(5')A, 3'O-Me-m$^7$G(5')ppp(5')C, 3'O-Me-m$^7$G(5')ppp(5')A, m$^7$3'd(5')ppp(5')G, m$^7$3'd(5')ppp(5')C, m$^7$3'd(5')ppp(5')A and their tetraphosphate derivatives) (see, e.g., Jemielity et al., RNA, 9: 1108-1122 (2003)).

In particular embodiments, mRNAs comprise a 5' cap that is a 7-methyl guanylate ("m$^7$G") linked via a triphosphate bridge to the 5'-end of the first transcribed nucleotide, resulting in m$^7$G(5')ppp(5')N, where N is any nucleoside.

In some embodiments, mRNAs comprise a 5' cap wherein the cap is a Cap0 structure (Cap0 structures lack a 2'-O-methyl residue of the ribose attached to bases 1 and 2), a Cap1 structure (Cap1 structures have a 2'-O-methyl residue at base 2), or a Cap2 structure (Cap2 structures have a 2'-O-methyl residue attached to both bases 2 and 3).

In one embodiment, an mRNA comprises a m$^7$G(5')ppp(5')G cap.

In one embodiment, an mRNA comprises an ARCA cap.

In particular embodiments, an mRNA contemplated herein comprises one or more modified nucleosides.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In one embodiment, an mRNA comprises one or more modified nucleosides selected from the group consisting of:

5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In one embodiment, an mRNA comprises one or more modified nucleosides selected from the group consisting of: 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In one embodiment, an mRNA comprises one or more modified nucleosides selected from the group consisting of: inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more pseudouridines, one or more 5-methyl-cytosines, and/or one or more 5-methyl-cytidines.

In one embodiment, an mRNA comprises one or more pseudouridines.

In one embodiment, an mRNA comprises one or more 5-methyl-cytidines.

In one embodiment, an mRNA comprises one or more 5-methyl-cytosines.

In particular embodiments, an mRNA contemplated herein comprises a poly(A) tail to help protect the mRNA from exonuclease degradation, stabilize the mRNA, and facilitate translation. In certain embodiments, an mRNA comprises a 3' poly(A) tail structure.

In particular embodiments, the length of the poly(A) tail is at least about 10, 25, 50, 75, 100, 150, 200, 250, 300, 350, 400, 450, or at least about 500 or more adenine nucleotides or any intervening number of adenine nucleotides. In particular embodiments, the length of the poly(A) tail is at least about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275 or more adenine nucleotides.

In particular embodiments, the length of the poly(A) tail is about 10 to about 500 adenine nucleotides, about 50 to about 500 adenine nucleotides, about 100 to about 500 adenine nucleotides, about 150 to about 500 adenine nucleotides, about 200 to about 500 adenine nucleotides, about 250 to about 500 adenine nucleotides, about 300 to about 500 adenine nucleotides, about 50 to about 450 adenine nucleotides, about 50 to about 400 adenine nucleotides, about 50 to about 350 adenine nucleotides, about 100 to about 500 adenine nucleotides, about 100 to about 450 adenine nucleotides, about 100 to about 400 adenine nucleotides, about 100 to about 350 adenine nucleotides, about 100 to about 300 adenine nucleotides, about 150 to about 500 adenine nucleotides, about 150 to about 450 adenine nucleotides, about 150 to about 400 adenine nucleotides, about 150 to about 350 adenine nucleotides, about 150 to about 300 adenine nucleotides, about 150 to about 250 adenine nucleotides, about 150 to about 200 adenine nucleotides, about 200 to about 500 adenine nucleotides, about 200 to about 450 adenine nucleotides, about 200 to about 400 adenine nucleotides, about 200 to about 350 adenine nucleotides, about 200 to about 300 adenine nucleotides, about 250 to about 500 adenine nucleotides, about 250 to about 450 adenine nucleotides, about 250 to about 400 adenine nucleotides, about 250 to about 350 adenine nucleotides, or about 250 to about 300 adenine nucleotides or any intervening range of adenine nucleotides.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3" sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' AGTCATG3' is 3'TCAGTAC5'. The latter sequence is often written as the reverse complement with the 5' end on the left and the 3' end on the right, 5'CATGA CT 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

Moreover, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In one embodiment, polynucleotides comprising particular allelic sequences are provided. Alleles are endogenous polynucleotide sequences that are altered as a result of one or more mutations, such as deletions, additions and/or substitutions of nucleotides.

In a certain embodiment, a polynucleotide-of-interest comprises a donor repair template.

In a certain embodiment, a polynucleotide-of-interest comprises an inhibitory polynucleotide including, but not limited to, an siRNA, an miRNA, an shRNA, a ribozyme or another inhibitory RNA.

In one embodiment, a donor repair template comprising an inhibitory RNA comprises one or more regulatory sequences, such as, for example, a strong constitutive pol III, e.g., human or mouse U6 snRNA promoter, the human and mouse H1 RNA promoter, or the human tRNA-val promoter, or a strong constitutive pol II promoter, as described elsewhere herein.

The polynucleotides contemplated in particular embodiments, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, as disclosed elsewhere herein or as known in the art, such that their overall length may vary considerably. It is therefore contemplated in particular embodiments that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector-origin of replication, selection cassettes, promoters, enhancers, translation initiation signals (Shine Dalgarno sequence or Kozak sequence) introns, post-transcriptional regulatory elements, a polyadenylation sequence, 5' and 3' untranslated regions-which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, a short elongation factor 1-alpha (EF1a-short) promoter, a long elongation factor 1-alpha (EF1a-long) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter (Challita et al., *J Virol.* 69(2):748-55 (1995)).

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

Conditional expression can also be achieved by using a site specific DNA recombinase. According to certain embodiments, polynucleotides comprise at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, six, seven, eight, nine, ten or more.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m$^2$ (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), F4. F5 (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

In one embodiment, a polynucleotide contemplated herein comprises a donor repair template polynucleotide flanked by a pair of recombinase recognition sites. In particular embodiments, the repair template polynucleotide is flanked by LoxP sites, FRT sites, or att sites.

In particular embodiments, polynucleotides contemplated herein, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. RNA 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Hucz et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO: 105), where R is a purine (A or G) (Kozak, 1986. *Cell.* 44(2):283-92, and Kozak, 1987. *Nucleic Acids Res.* 15(20): 8125-48).

Elements directing the efficient termination and polyadenylation of the heterologous nucleic acid transcripts increase heterologous gene expression. Transcription termination signals are generally found downstream of the polyadenylation signal. In particular embodiments, vectors comprise a polyadenylation sequence 3' of a polynucleotide encoding a polypeptide to be expressed. The terms "polyA site," "polyA sequence," "poly(A) site" or "poly(A) sequence" as used herein denote a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Efficient polyadenylation of the recombinant transcript is desirable as transcripts lacking a poly(A) tail are unstable and are rapidly degraded. Illustrative examples of poly(A) signals that can be used in a vector, includes an ideal poly(A) sequence (e.g., AATAAA, ATTAAA, AGTAAA), a bovine growth hormone poly(A) sequence (BGHpA), a rabbit β-globin poly(A) sequence (rβgpA), or another suitable heterologous or endogenous poly(A) sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the genetically modified cells contemplated herein to be susceptible to negative selection in vivo. "Negative selection" refers to an infused cell that can be eliminated as a result of a change in the in vivo condition of the individual. The negative selectable phenotype may result from the insertion of a gene that confers sensitivity to an administered agent, for example, a compound. Negative selection genes are known in the art, and include, but are not limited to: the Herpes simplex virus type I thymidine kinase (HSV-I TK) gene which confers ganciclovir sensitivity; the cellular hypoxanthine phosphribosyltransferase (HPRT) gene, the cellular adenine phosphoribosyltransferase (APRT) gene, and bacterial cytosine deaminase.

In some embodiments, genetically modified cells comprise a polynucleotide further comprising a positive marker that enables the selection of cells of the negative selectable phenotype in vitro. The positive selectable marker may be a gene, which upon being introduced into the host cell, expresses a dominant phenotype permitting positive selection of cells carrying the gene. Genes of this type are known in the art, and include, but are not limited to hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, the positive selectable marker and the negative selectable element are linked such that loss of the negative selectable element necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, nco, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include, but are not limited to genes wherein the positive selectable marker is derived from hph or neo, and the negative selectable marker is derived from cytosine deaminase or a TK gene or selectable marker.

In particular embodiments, polynucleotides encoding one or more nuclease variants, megaTALs, end-processing enzymes, or fusion polypeptides may be introduced into hematopoietic cells, e.g., T cells, by both non-viral and viral methods. In particular embodiments, delivery of one or more polynucleotides encoding nucleases and/or donor repair templates may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated herein include, but are not limited to those provided by Amaxa Biosystems, Maxcyte, Inc., BTX Molecular Delivery Systems, ThermoFisher Scientific, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising nuclease variants and/or donor repair templates are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated herein include, but are not limited to adeno-associated virus (AAV), retrovirus, herpes simplex virus, adenovirus, and vaccinia virus vectors.

In various embodiments, one or more polynucleotides encoding a nuclease variant and/or donor repair template are introduced into a hematopoietic cell, e.g., a T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. rAAV vectors comprising two ITRs have a payload capacity of about 4.4 kB.

Self-complementary rAAV vectors contain a third ITR and package two strands of the recombinant portion of the vector leaving only about 2.1 kB for the polynucleotides contemplated herein. In one embodiment, the AAV vector is an scAAV vector.

Extended packaging capacities that are roughly double the packaging capacity of an rAAV(about 9 kB) have been achieved using dual rAAV vector strategies. Dual vector strategies useful in producing rAAV contemplated herein include, but are not limited to splicing (trans-splicing), homologous recombination (overlapping), or a combination of the two (hybrid). In the dual AAV trans-splicing strategy, a splice donor (SD) signal is placed at the 3' end of the 5'-half vector and a splice acceptor (SA) signal is placed at the 5' end of the 3'-half vector. Upon co-infection of the same cell by the dual AAV vectors and inverted terminal repeat (ITR)-mediated head-to-tail concatemerization of the two halves, trans-splicing results in the production of a mature mRNA and full-size protein (Yan et al, 2000). Trans-splicing has been successfully used to express large genes in muscle and retina (Reich et al, 2003; Lai et al, 2005). Alternatively, the two halves of a large transgene expression cassette contained in dual AAV vectors may contain homologous overlapping sequences (at the 3' end of the 5'-half vector and at the 5' end of the 3'-half vector, dual AAV overlapping), which will mediate reconstitution of a single large genome by homologous recombination (Duan et al, 2001). This strategy depends on the recombinogenic properties of the transgene overlapping sequences (Ghosh et al, 2006). A third dual AAV strategy (hybrid) is based on adding a highly recombinogenic region from an exogenous gene (i.e., alkaline phosphatase; Ghosh et al, 2008, Ghosh et al, 2011)) to the trans-splicing vectors. The added region is placed downstream of the SD signal in the 5'-half vector and upstream of the S A signal in the 3'-half vector in order to increase recombination between the dual AAVs.

A "hybrid AAV," "hybrid rAAV," "chimeric AAV," or "chimeric rAAV" refers to an rAAV genome packaged with a capsid of a different AAV serotype (and preferably, of a different serotype from the one or more AAV ITRs), and may otherwise be referred to as a pseudotyped rAAV. For example, an rAAV type 1, 2, 3, 4, 5, 6, 7, 8, 9, 10, 11, 12, 13, 14, 15, or 16 genome may be encapsidated within an AAV type 1, 2, 3, 4, 5, 6, 7, 8, 9, 10, 11, 12, 13, 14, 15, or 16 capsid or variants thereof, provided that the AAV capsid and genome (and preferably, the one or more AAV ITRs) are of different serotypes. In certain embodiments, a pseudotyped rAAV particle may be referred to as being of the type "x/y", where "x" indicates the source of ITRs and "y" indicates the serotype of capsid, for example a 2/5 rAAV particle has ITRs from AAV2 and a capsid from AAV6.

In particular embodiments, the rAAV comprises ITRs and capsid sequences isolated from AAV1, AAV2, AAV3, AAV4, AAV5, AAV6, AAV7, AAV8, AAV9, AAV10, AAV11, AAV 12, AAV13, AAV 14, AAV15, and AAV16.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides encoding a nuclease variant and/or donor repair template are introduced into a hematopoietic cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (Ψ) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81R, D41A, K42A, H51A, Q53C, D55V, D64E, D64V, E69A, K71A, E85A, E87A, D116N, D116I, D116A, N120G, N120I, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

In one embodiment, the HIV-1 integrase deficient pol gene comprises a D64V, D116I, D116A, E152G, or E152A mutation; D64V, D116I, and E152G mutations; or D64V, D116A, and E152A mutations.

In one embodiment, the HIV-1 integrase deficient pol gene comprises a D64V mutation.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173. In another embodiment, a lentiviral vector contains a FLAP element with one or more mutations in the cPPT and/or CTS elements. In yet another embodiment, a lentiviral vector comprises either a cPPT or CTS element. In yet another embodiment, a lentiviral vector does not comprise a cPPT or CTS element.

As used herein, the term "packaging signal" or "packaging sequence" refers to psi [Ψ] sequences located within the retroviral genome which are required for insertion of the viral RNA into the viral capsid or particle, see e.g., Clever et al., 1995. *J. of Virology*, Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zuffercy et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., in which the right (3') LTR enhancer-promoter region, known as the U3 region, has been modified (e.g., by deletion or substitution) to prevent viral transcription beyond the first round of viral replication. An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides encoding a nuclease variant and/or donor repair template are introduced into a hematopoietic cell by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides encoding nuclease variant and/or donor repair template are introduced into a hematopoietic cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

H. Genome Edited Cells

The genome edited cells manufactured by the methods contemplated in particular embodiments comprise one or more gene edits in a PD-1 gene and provide improved cell-based therapeutics for the prevention, treatment, or amelioration of at least one symptom, of a cancer, GVHD, infectious disease, autoimmune disease, immunodeficiency or condition associated therewith. Without wishing to be bound to any particular theory, it is believed that the compositions and methods contemplated herein increase the efficacy of adoptive cell therapies, in part, by making the therapeutic cells more resistant to immunosuppressive signals and exhaustion.

Genome edited cells contemplated in particular embodiments may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

An "isolated cell" refers to a non-naturally occurring cell, e.g., a cell that does not exist in nature, a modified cell, an engineered cell, a recombinant cell etc., that has been obtained from an in vivo tissue or organ and is substantially free of extracellular matrix.

As used herein, the term "population of cells" refers to a plurality of cells that may be made up of any number and/or combination of homogenous or heterogeneous cell types, as described elsewhere herein. For example, for transduction of T cells, a population of cells may be isolated or obtained from peripheral blood. A population of cells may comprise about 10%, about 20%, about 30%, about 40%, about 50%, about 60%, about 70%, about 80%, about 90%, or about 100% of the target cell type to be edited. In certain embodiments, T cells may be isolated or purified from a population of heterogeneous cells using methods known in the art.

Illustrative examples of cell types whose genome can be edited using the compositions and methods contemplated herein include, but are not limited to, cell lines, primary cells, stem cells, progenitor cells, and differentiated cells, and mixtures thereof.

In a preferred embodiment, the genome editing compositions and methods are used to edit hematopoietic cells, more preferably immune cells, and even more preferably T cells.

The terms "T cell" or "T lymphocyte" are art-recognized and are intended to include thymocytes, immune effector cells, regulatory T cells, naïve T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8$^+$ T cell), a tumor infiltrating cytotoxic T cell (TIL; CD8$^+$ T cell), CD4$^+$CD8$^+$ T cell, CD4CD8$^-$ T cell, or any other subset of T cells. In one embodiment, the T cell is an immune effector cell. In one embodiment, the T cell is an NKT cell. Other illustrative populations of T cells suitable for use in particular embodiments include naïve T cells and memory T cells.

In various embodiments, genome edited cells comprise immune effector cells comprising a PD-1 gene edited by the compositions and methods contemplated herein. An "immune effector cell," is any cell of the immune system that has one or more effector functions (e.g., cytotoxic cell killing activity, secretion of cytokines, induction of ADCC and/or CDC). Illustrative immune effector cells contemplated in particular embodiments are T lymphocytes, in particular cytotoxic T cells (CTLs; CD8$^+$ T cells), TILs, and helper T cells (HTLs; CD4$^+$ T cells). In one embodiment, immune effector cells include natural killer (NK) cells. In one embodiment, immune effector cells include natural killer T (NKT) cells.

"Potent T cells," and "young T cells," are used interchangeably in particular embodiments and refer to T cell phenotypes wherein the T cell is capable of proliferation and a concomitant decrease in differentiation. In particular embodiments, the young T cell has the phenotype of a "naïve T cell." In particular embodiments, young T cells comprise one or more of, or all of the following biological markers: CD62L, CCR7, CD28, CD27, CD122, CD127, CD197, and CD38. In one embodiment, young T cells comprise one or more of, or all of the following biological markers: CD62L, CD127, CD197, and CD38. In one embodiment, the young T cells lack expression of CD57, CD244, CD160, PD-1, CTLA4, PD-1, and LAG3.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors.

In particular embodiments, a population of cells comprising immune effector cells or T cells comprises an edited PD-1 gene, wherein the edit is a DSB repaired by NHEJ. In particular embodiments, an immune effector cell or T cell comprises an edited PD-1 gene, wherein the edit is a DSB repaired by NHEJ. In particular embodiments, the edit is an insertion or deletion (INDEL) of about 1, 2, 3, 4, 5, 6, 7, 8, 9, 10, 11, 12, 13, 14 15, 16, 17, 18, 19, 20, 21, 22, 23, 24, 25 or more nucleotides in a coding sequence of the PD-1 gene, preferably in exon 5, exon 1, or exon 2 of the PD-1 gene, more preferably at SEQ ID NO: 25 (or SEQ ID NO: 27) in exon 5 of the PD-1 gene, at SEQ ID NO: 30 (or SEQ ID NO: 32) in exon 1 of the PD-1 gene, or at SEQ ID NO: 35 (or SEQ ID NO: 37) in exon 2 of the PD-1 gene.

In a particular embodiment, the edit is a deletion of +1, −1, −2, −3, or −4 nucleotides in the coding sequence of the PD-1 gene, preferably in exon 5, exon 1, or exon 2 of the PD-1 gene, more preferably at SEQ ID NO: 25 (or SEQ ID NO: 27) in exon 5 of the PD-1 gene, at SEQ ID NO: 30 (or SEQ ID NO: 32) in exon 1 of the PD-1 gene, or at SEQ ID NO: 35 (or SEQ ID NO: 37) in exon 2 of the PD-1 gene.

In particular embodiments, a population of cells comprising immune effector cells or T cells comprises an edited PD-1 gene comprising a donor repair template incorporated at a DSB repaired by HDR.

In particular embodiments, a population of cells comprising immune effector cells or T cells comprises an edited PD-1 gene comprising a donor repair template comprising a PD-1 gene or portion thereof and is designed to introduce one or more mutations in a genomic PD-1 sequence to modify PD-1 expression or signaling, and preferably, to decrease or eliminate PD-1 expression and/or signaling.

In various embodiments, a genome edited cell comprises an edit in the PD-1 gene and further comprises a polynucleotide encoding PD-1 flip receptor, a bispecific T cell engager (BiTE) molecule; a cytokine (e.g., IL-2, insulin, IFN-γ, IL-7, IL-21, IL-10, IL-12, IL-15, and TNF-α), a chemokine (e.g., MIP-1α, MIP-1β, MCP-1, MCP-3, and RANTES), a cytotoxin (e.g., Perforin, Granzyme A, and Granzyme B), a cytokine receptor (e.g., an IL-2 receptor, an IL-7 receptor, an IL-12 receptor, an IL-15 receptor, and an IL-21 receptor), or an engineered antigen receptor (e.g., an engineered T cell receptor (TCR), a chimeric antigen receptor (CAR), a Daric receptor or components thereof, or a chimeric cytokine receptor). In one embodiment, a donor repair template comprising the polynucleotide and a nuclease variant are introduced into the cell and the polynucleotide is incorporated into the cell's genome at the DSB site in the PD-1 gene by HDR repair. The polynucleotide may also be introduced into the cell at a site other than the PD-1 gene, e.g., by transducing the cell with a vector comprising the polynucleotide.

I. Compositions and Formulations

The compositions contemplated in particular embodiments may comprise one or more polypeptides, polynucleotides, vectors comprising same, and genome editing compositions and genome edited cell compositions, as contemplated herein. The genome editing compositions and methods contemplated in particular embodiments are useful for editing a target site in the human program cell death 1 (PD-1) gene in a cell or a population of cells. In preferred embodiments, a genome editing composition is used to edit a PD-1 gene in a hematopoietic cell, e.g., a T cell or an immune effector cell.

In various embodiments, the compositions contemplated herein comprise a nuclease variant, and optionally an end-processing enzyme, e.g., a 3'-5' exonuclease (Trex2). The nuclease variant may be in the form of an mRNA that is introduced into a cell via polynucleotide delivery methods disclosed supra, e.g., electroporation, lipid nanoparticles, etc. In one embodiment, a composition comprising an mRNA encoding a homing endonuclease variant or megaTAL, and optionally a 3'-5' exonuclease, is introduced in a cell via polynucleotide delivery methods disclosed supra. The composition may be used to generate a genome edited cell or population of genome edited cells by error prone NHEJ.

In various embodiments, the compositions contemplated herein comprise a donor repair template. The composition may be delivered to a cell that expresses or will express nuclease variant, and optionally an end-processing enzyme. In one embodiment, the composition may be delivered to a cell that expresses or will express a homing endonuclease variant or megaTAL, and optionally a 3'-5' exonuclease. Expression of the gene editing enzymes in the presence of the donor repair template can be used to generate a genome edited cell or population of genome edited cells by HDR.

In particular embodiments, the compositions contemplated herein comprise a population of cells, a nuclease variant, and optionally, a donor repair template. In particular embodiments, the compositions contemplated herein comprise a population of cells, a nuclease variant, an end-processing enzyme, and optionally, a donor repair template. The nuclease variant and/or end-processing enzyme may be in the form of an mRNA that is introduced into the cell via polynucleotide delivery methods disclosed supra.

In particular embodiments, the compositions contemplated herein comprise a population of cells, a homing endonuclease variant or megaTAL, and optionally, a donor repair template. In particular embodiments, the compositions contemplated herein comprise a population of cells, a homing endonuclease variant or megaTAL, a 3'-5' exonuclease, and optionally, a donor repair template. The homing endonuclease variant, megaTAL, and/or 3'-5' exonuclease may be in the form of an mRNA that is introduced into the cell via polynucleotide delivery methods disclosed supra.

In particular embodiments, the population of cells comprise genetically modified immune effector cells.

Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the composition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the genome edited T cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of genome edited T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In a preferred embodiment, the compositions comprising genome edited T cells are formulated in PlasmaLyte.

In various embodiments, compositions comprising genome edited T cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of polynucleotides are contemplated including, but not limited to, one or more mRNAs encoding one or more reprogrammed nucleases, and optionally end-processing enzymes.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. 22$^{nd}$ Edition. Edited by Loyd V. Allen Jr. Philadelphia, PA: Pharmaceutical Press; 2012, which is incorporated by reference herein, in its entirety.

J. Genome Edited Cell Therapies

Genome edited cells manufactured by the compositions and methods contemplated herein provide improved drug products for use in the prevention, treatment, or amelioration of at least one symptom of a cancer, GVHD, an infectious disease, an autoimmune disease, an inflammatory disease, or an immunodeficiency. As used herein, the term "drug product" refers to genetically modified cells produced using the compositions and methods contemplated herein. In particular embodiments, the drug product comprises genetically edited immune effector cells or T cells. Moreover, the genome edited T cells contemplated in particular embodiments provide safer and more efficacious adoptive cell therapies because they are resistant to T cell exhaustion and display increased durability and persistence in the tumor microenvironment that can lead to sustained therapy.

In particular embodiments, an effective amount of genome edited immune effector cells or T cells comprising an edited PD-1 gene are administered to a subject to prevent, treat, or ameliorate at least one symptom of a cancer, GVHD, an infectious disease, an autoimmune disease, an inflammatory disease, or an immunodeficiency.

In particular embodiments, the PD-1 edited cells do not substantially express, or lack expression of, PD-1 and therefore lack or substantially lack functional PD-1 expression, e.g., lack the ability to increase T cell exhaustion and to inhibit expression of proinflammatory cytokines. In particular embodiments, genome edited immune effector cells that lack PD-1 are more resistant to immunosuppressive signals from the tumor microenvironment and display increased persistence and resistance to T cell exhaustion.

In particular embodiments, a method of preventing, treating, or ameliorating at least one symptom of a cancer comprises administering the subject an effective amount of genome edited immune effector cells or T cells comprising an edited PD-1 gene and an engineered TCR, CAR, or Daric, or other therapeutic transgene to redirect the cells to a tumor or cancer. The genetically modified cells are a more durable and persistent drug product because the cells are more resistant to immunosuppressive signals from the tumor microenvironment by virtue of editing the PD-1 gene to decrease or eliminate PD-1 expression.

In particular embodiments, genome edited cells contemplated herein are used in the treatment of solid tumors or cancers.

In particular embodiments, genome edited cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pincaloma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, genome edited cells contemplated herein are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, genome edited cells contemplated herein are used in the treatment of various cancers including but not limited to pancreatic, bladder, and lung.

In particular embodiments, genome edited cells contemplated herein are used in the treatment of liquid cancers or hematological cancers.

In particular embodiments, genome edited cells contemplated herein are used in the treatment of B-cell malignancies, including but not limited to: leukemias, lymphomas, and multiple myeloma.

In particular embodiments, genome edited cells contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, nonsecretory myeloma, IgD myeloma, osteosclerotic myeloma, solitary plasmacytoma of bone, and extramedullary plasmacytoma.

Preferred cells for use in the genome editing methods contemplated herein include autologous/autogeneic ("self") cells, preferably hematopoietic cells, more preferably T cells, and more preferably immune effector cells or Treg cells.

In particular embodiments, methods comprising administering a therapeutically effective amount of genome edited cells contemplated herein or a composition comprising the same, to a patient in need thereof, alone or in combination with one or more therapeutic agents, are provided. In certain embodiments, the cells are used in the treatment of patients at risk for developing a cancer, GVHD, an infectious disease, an autoimmune disease, an inflammatory disease, or an immunodeficiency. Thus, particular embodiments comprise the treatment or prevention or amelioration of at least one symptom of a cancer, an infectious disease, an autoimmune disease, an inflammatory disease, or an immunodeficiency comprising administering to a subject in need thereof, a therapeutically effective amount of the genome edited cells contemplated herein.

In one embodiment, a method of treating a cancer, GVHD, an infectious disease, an autoimmune disease, an inflammatory disease, or an immunodeficiency in a subject in need thereof comprises administering an effective amount, e.g., therapeutically effective amount of a composition comprising genome edited cells contemplated herein. The quantity and frequency of administration will be determined by such factors as the condition of the patient, and the type and severity of the patient's disease, although appropriate dosages may be determined by clinical trials.

In one illustrative embodiment, the effective amount of genome edited cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of genome edited cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of genome edited cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

One of ordinary skill in the art would recognize that multiple administrations of the compositions contemplated in particular embodiments may be required to effect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

The administration of the compositions contemplated in particular embodiments may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a method of treating a subject diagnosed with a cancer, comprises removing immune effector cells from the subject, editing the genome of said immune effector cells and producing a population of genome edited immune effector cells, and administering the population of genome edited immune effector cells to the same subject. In a preferred embodiment, the immune effector cells comprise T cells.

The methods for administering the cell compositions contemplated in particular embodiments include any method which is effective to result in reintroduction of ex vivo genome edited immune effector cells or on reintroduction of the genome edited progenitors of immune effector cells that on introduction into a subject differentiate into mature immune effector cells. One method comprises genome editing peripheral blood T cells ex vivo and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily

EXAMPLES

Example 1

Figure 1B:
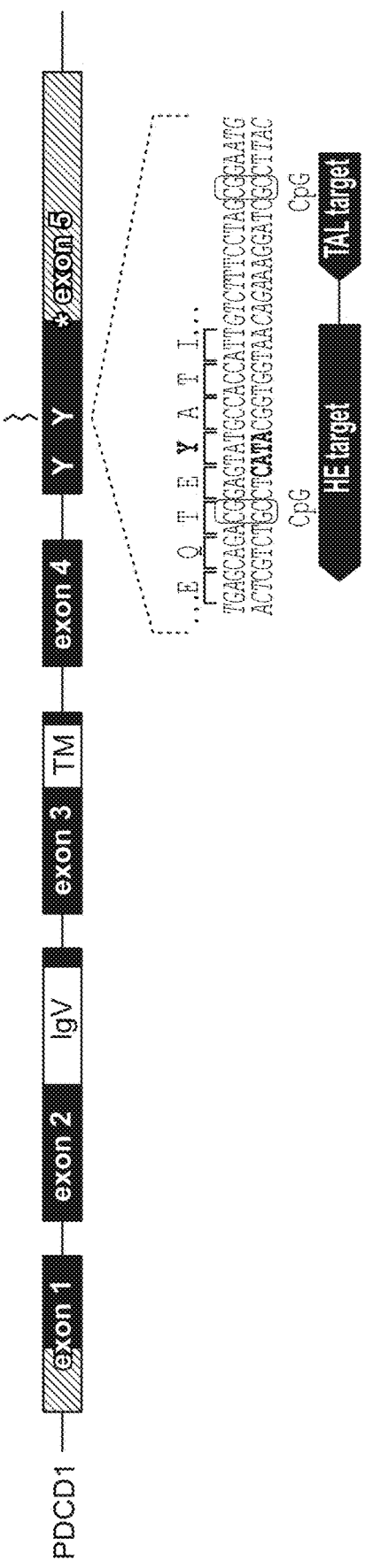
FIG. 1B shows the PD-1 gene and the sequence of the target site in the ITSM motif encoded by exon 5 (SEQ ID NOS: 106-108), highlighting the HE central-4 motif located at the codon for the ITSM phosphotyrosine residue at position 248.

Reprogramming I-OnuI to Disrupt the Intracellular Signaling Motif within the Programmed Death Receptor-1 (PD-1) Gene PD-1 is expressed on the T cell plasma membrane following antigen receptor stimulation and activation. PD-1 comprises a signal peptide, an extracellular IgV-like domain, a transmembrane spanning domain, and an intracellular tail that contains both an immunoreceptor tyrosine-based inhibition motif (ITIM, consensus sequence S/V/V/LxYxxI/V/L) and an immunoreceptor tyrosine-based switch motif (ITSM, consensus sequence TxYxxV/I). FIG. 1A. The tyrosine at amino acid position 248 within the PD-1 ITSM becomes phosphorylated upon PD-L1/2 ligand binding concomitant with T cell activation, establishing a binding substrate for the SH2 domain-containing protein tyrosine phosphatase-2 (SHP2, see Chemnitz J M et. al. *J Immunol.* 2004 Jul. 15; 173(2):945-54.). The recruitment of SHP2 to the plasma membrane counteracts phospho-tyrosine driven activation signals in T cells (Yokosuka T et. al., *J Exp Med.* 2012 Jun. 4; 209(6): 1201-17) and suppresses the duration of T cell's activated state. The codon for the phosphorylated ITSM tyrosine is encompassed by a canonical I-OnuI "central-4" cleavage motif, ATAC. FIG. 1B. A homing endonuclease variant targeting the 22 bp target sequence (SEQ ID NO: 25) centered upon this central-4 motif in exon 5 of the PD-1 gene was developed.

Without wishing to be bound to any particular theory, it is contemplated that all putative insertion/deletion events ('indels') in and proximal to the ATAC central-4 sequence would fully abolish one or more essential features the ITSM motif, with most plausible indels disrupting the tyrosine-248 codon itself. These indels are likely to generate dominant negative PD-1 proteins comprising a normal extracellular domain and a non-functional intracellular signaling domain. The dominant negative PD-1 proteins may act as a 'sink' for PD-1 ligands thereby reducing or eliminating immunosuppressive signaling. In addition, because activated T cells upregulate expression of PD-L1; because PD-1:PD-L1 interactions happen amongst T cells, either in cis or trans; and because these interactions are important for T cell function, gene editing to disrupt PD-1 signaling without impacting expression may retain putative PD-LI driven functions.

Figure 2:
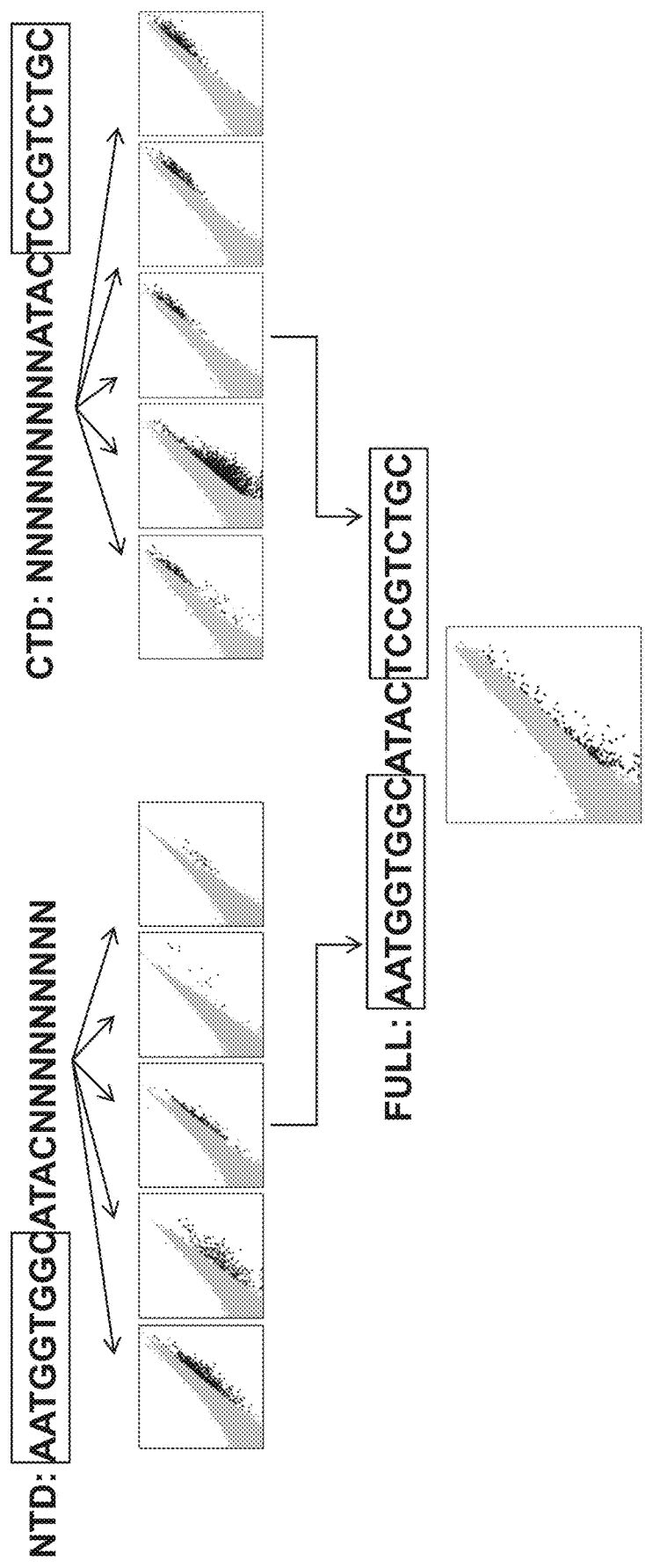
FIG. 2 shows how I-OnuI was reprogrammed via engineering of the NTD and CTD against chimeric "half-sites" (SEQ ID NOS: 109 and 110) through two rounds of sorting, followed by fusion of the reprogrammed domains (SEQ ID NO: 111) and screening against the complete PD-1 exon 5 target site to isolate a fully reprogrammed HE.

I-OnuI was thus reprogrammed to target the ITSM coding region by constructing modular libraries containing variable amino acid residues in the DNA recognition interface. To construct the variants, degenerate codons were incorporated into I-OnuI DNA binding domains using oligonucleotides. The oligonucleotides encoding the degenerate codons were used as PCR templates to generate variant libraries by gap recombination in the yeast strain *S. cerevisiae*. Each variant library spanned either the N- or C-terminal I-OnuI DNA recognition domain and contained ~$10^7$ to $10^8$ unique transformants. The resulting surface display libraries were screened by flow cytometry for cleavage activity against target sites comprising the corresponding domains' "half-sites" (SEQ ID NOs: 28-29), as shown in FIG. 2.

Yeast displaying the N- and C-terminal domain reprogrammed I-OnuI HEs were purified and the plasmid DNA was extracted. PCR reactions were performed to amplify the reprogrammed domains, which were subsequently transformed into *S. cerevisiae* to create a library of reprogrammed domain combinations. Fully reprogrammed I-OnuI variants that recognize the complete target site (SEQ ID NO: 25) present in the ITSM coding region in exon 5 of the PD-1 gene were identified from this library and purified.

The activity of reprogrammed I-OnuI HEs that target the PD-1 ITSM coding region in exon 5 was measured using a chromosomally integrated fluorescent reporter system (Certo et. al., 2011). Fully reprogrammed I-OnuI HEs that bind and cleave the PD-1 ITSM target sequence were cloned into mammalian expression plasmids and then individually transfected into a HEK 293T fibroblast cell line that was containing the PD-1 exon 5 target sequence upstream of an out-of-frame gene encoding the fluorescent mCherry protein. Cleavage of the embedded target site by the HE and the accumulation of indels following DNA repair via the non-homologous end joining (NHEJ) pathway results in approximately one out of three repaired loci placing the fluorescent reporter gene back "in-frame". The percentage of mCherry fluorescing HEK 293T cells is therefore used a readout of endonuclease activity at the chromosomally embedded target sequence. The fully reprogrammed I-OnuI HE (PD-1.ITSM.ex5_RD1_CV3-08, SEQ ID NO: 6) targeting the PD-1 exon 5 site showed a very moderate efficiency of mCherry expression in a cellular chromosomal context. FIG. 3A. The HE variant had moderate DNA affinity properties when measured by equilibrium substrate titration (FIG. 3B).

Figure 4:
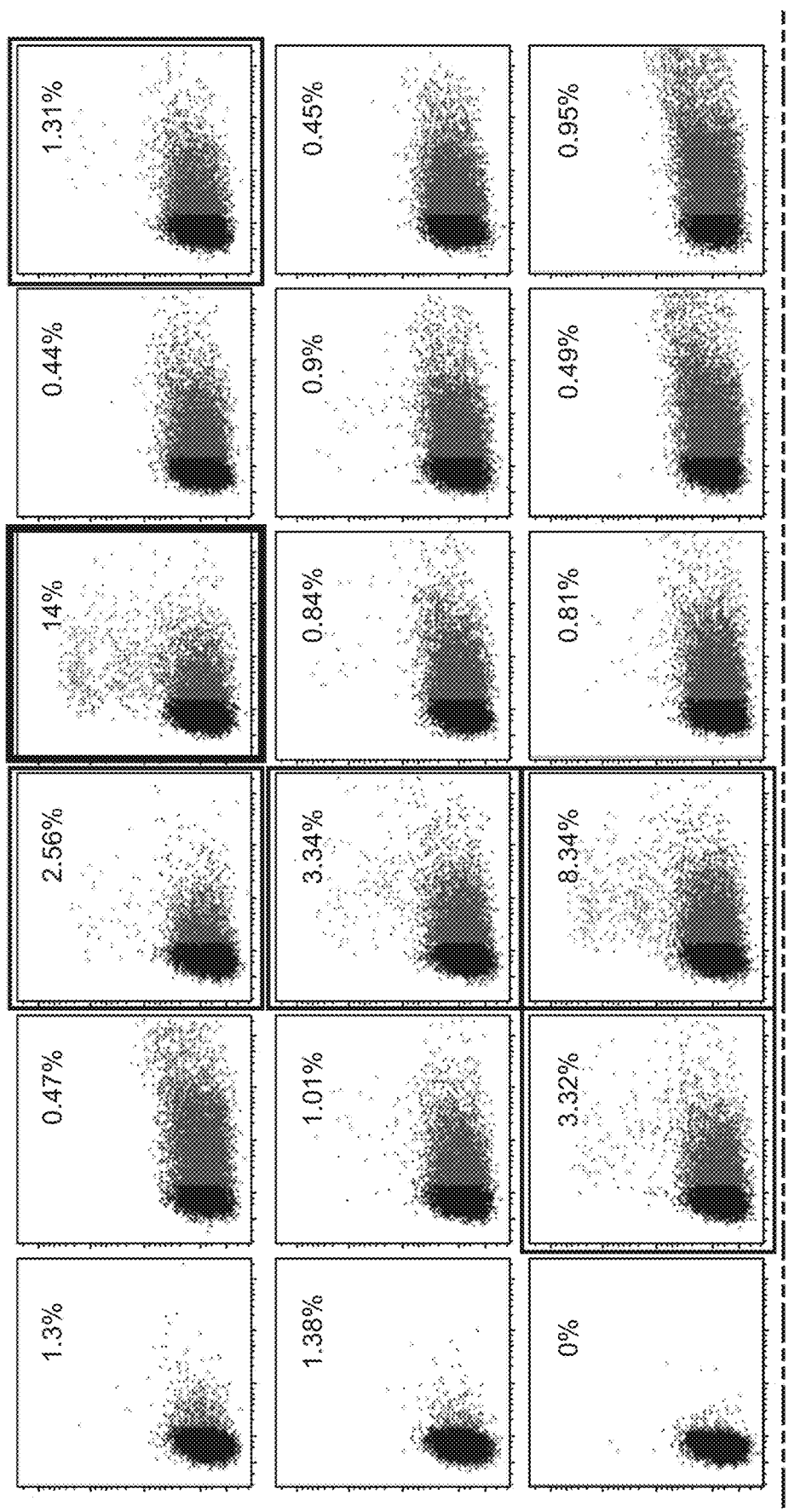
FIG. 4 shows the secondary screening of PD-1 HE for activity in a chromosomal reporter assay following the isolation of enhanced variants from display-based flow sorting of a randomly mutagenized library of variants of PD-1.ITSM.ex5_RD1_CV3-08 performed under more stringent cleavage and affinity conditions to isolate variants with improved activity.
Figure 4:
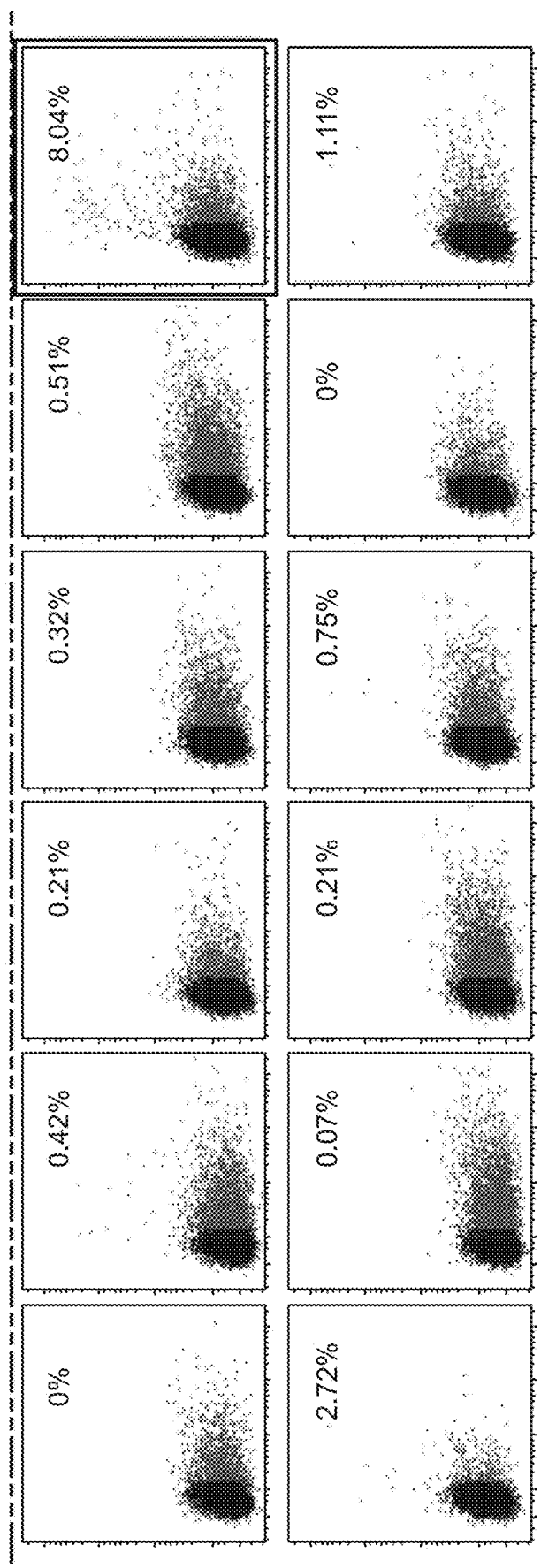

A secondary I-OnuI variant library was next generated by performing random mutagenesis on the PD-1.ITSM.ex5_RD1_CV3-08 HE variant. Display-based flow sorting was performed under more stringent cleavage conditions in an effort to isolate variants with improved catalytic efficiency. This process identified an I-OnuI variant PD-1.ITSM.ex5_RD2_73, SEQ ID NO: 7), which contained four amino acid mutations relative to the RD1 variant, and has a several-fold higher rate of mCherry expressing cells versus the RD1 variant. FIG. 4. Three additional rounds of activity refinement screens were performed to increase the gene editing efficiency at the exon 5 target site (PD-1.ITSM.ex5_RD3_03, SEQ ID NO: 8; PD-1.ITSM.ex5_RD4_CV23, SEQ ID NO: 9; and PD-1.ITSM.ex5_RD5_CV23MK, SEQ ID NO: 10).

Example 2

Characterization of an I-OnuI Variant and a MegaTAL Targeting PD-1 Exon 5

Figure 5:
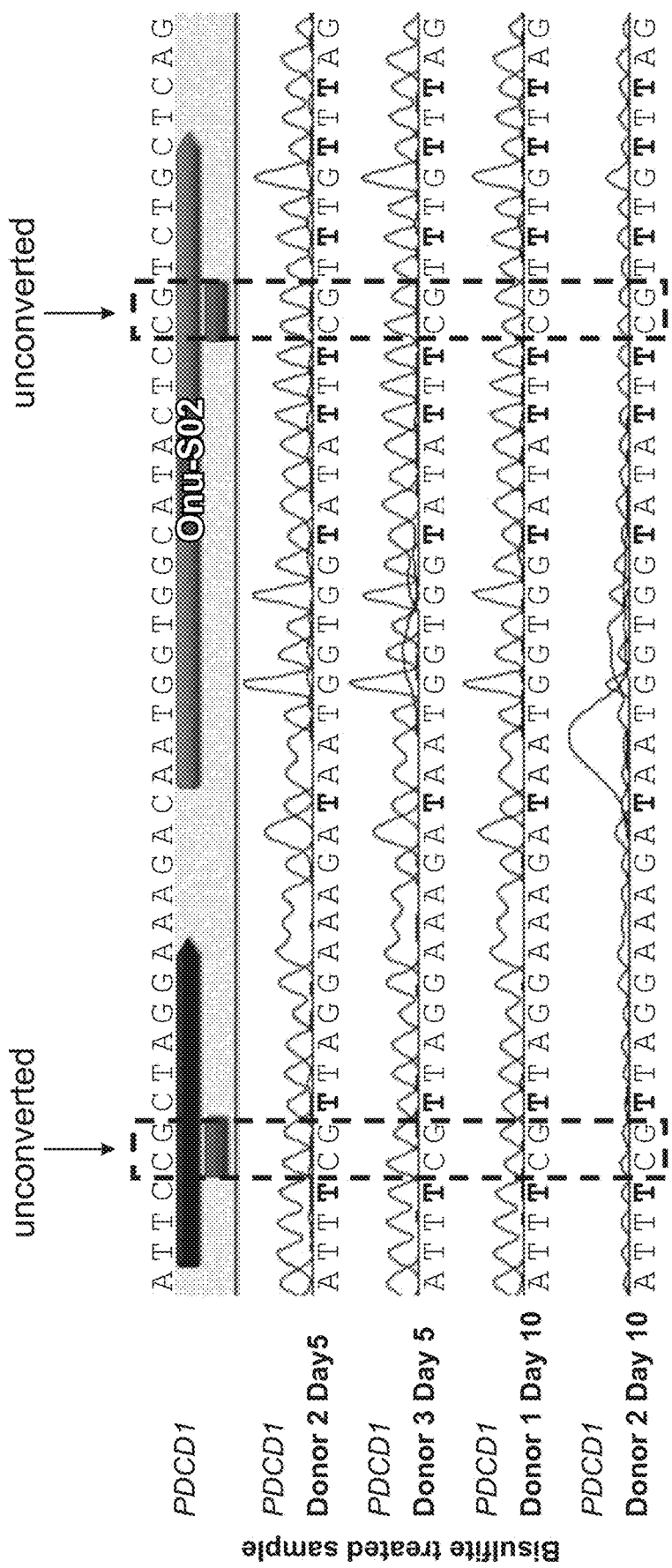
FIG. 5 shows the results of a bisulfite sequencing assay of PD-1 exon 5 (SEQ ID NO: 112) in activated primary human T cells to determine the methylation status of CpG motifs (SEQ ID NO: 113) present within the PD-1 exon 5 HE.

The PD-1 exon 5 target site comprises CpG dinucleotide motifs in both the meganuclease binding site and adjacent TAL array binding site (FIG. 1B). Methylation status of these dinucleotides was evaluated by bisulfite sequencing in primary human T cells activated with CD3 and CD28 and cultured in complete media supplemented with IL-2. After 3 days, genomic DNA was isolated and treated with bisulfite to convert any unmethylated cytosine bases to uracil. The exon 5 target site was then sequenced to reveal unmethylated (converted to Thymine) versus methylated (remained Cytosine) status of each cytosine. The results show that both of the CpG motif cytosines in the target site were predominantly methylated (FIG. 5), consistent with typical 'gene body' methylation patterns.

Figure 6:
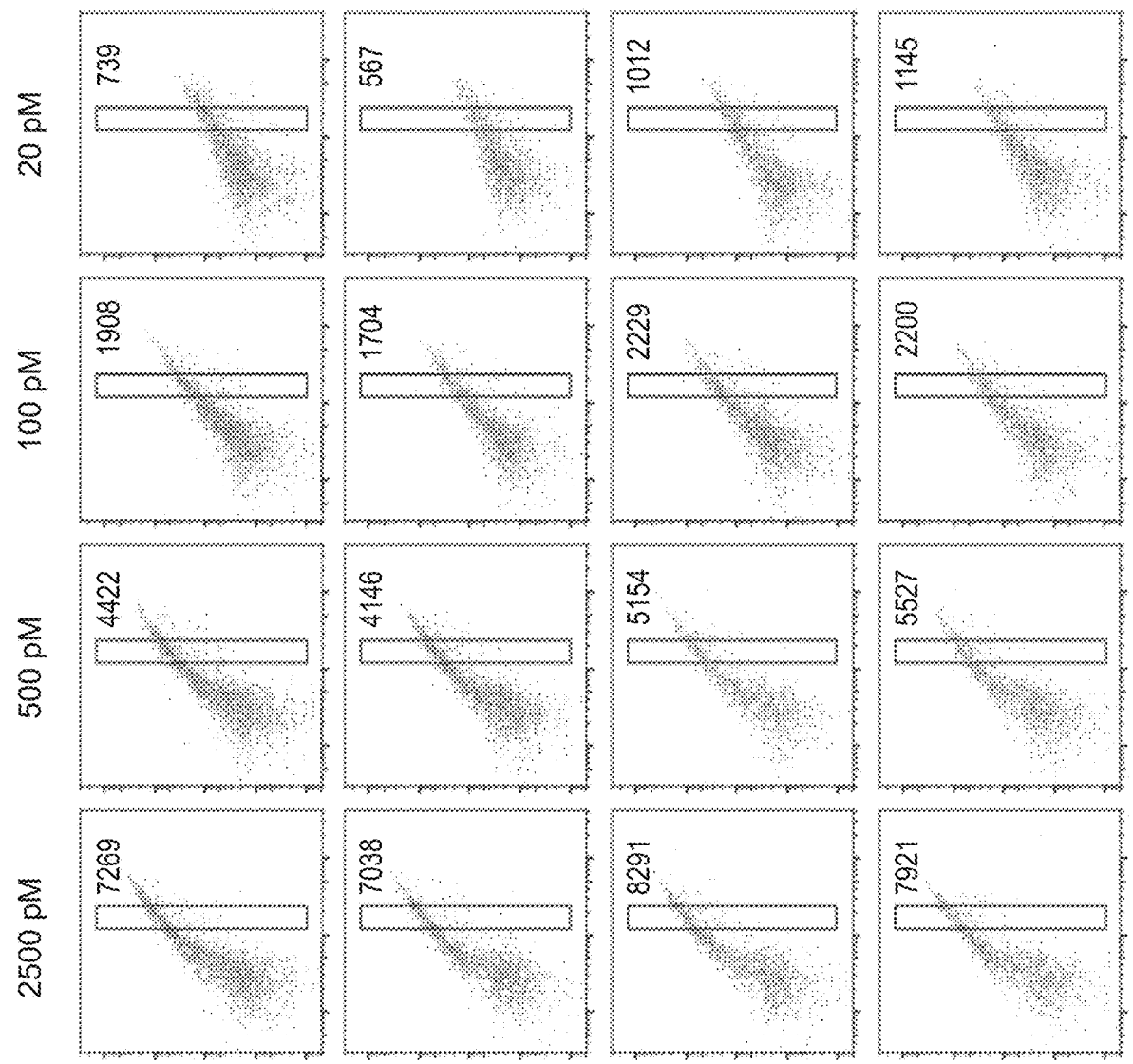
FIG. 6 shows the results of a DNA binding affinity and cleavage analysis of the PD-1.ITSM.ex5_RD5_CV23MK HE variant against partially and fully methylated PD-1 exon 5 substrates.
Figure 6:
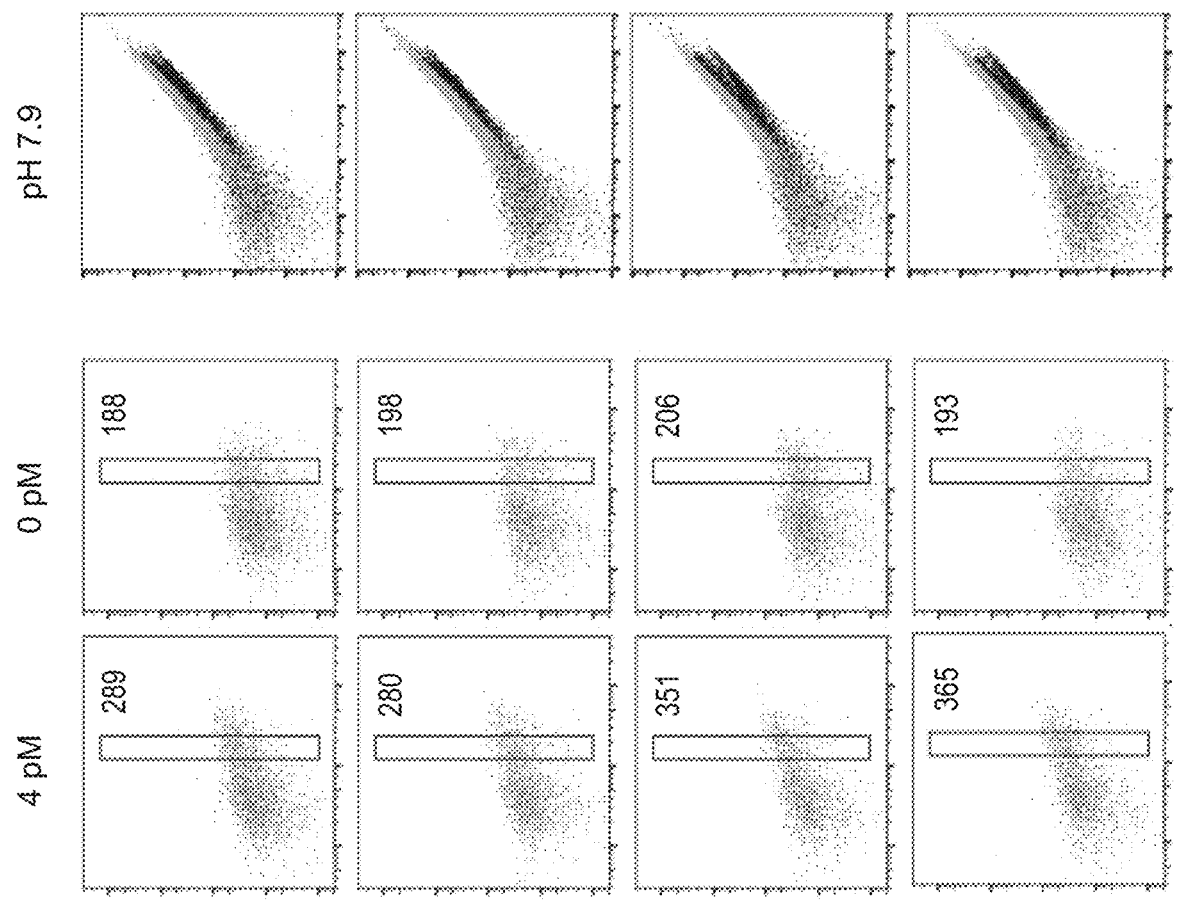

To confirm that the PD-1.ITSM.ex5_RD5_CV23MK HE variant recognized and cleaved the methylated exon 5 target site, DNA binding affinity and cleavage analyses were performed using substrates containing 5-methylcytosine at target site position p5, or on the reverse complement of the guanine base at p6, or on both strands of the target sequence, which is representative of the methylation status of the target site in activated T cells. FIG. 6. The HE variant bound and cleaved the methylated DNA substrates and unmodified substrate similarly.

The PD-1.ITSM.ex5_RD5_CV23MK HE variant was formatted as a megaTAL (SEQ ID NO: 19) by appending the 5-methylcytosine tolerant 10.5 unit TAL array, corresponding to an 11 base pair TAL array target site (SEQ ID NO: 26), to the N-terminus of the meganuclease domain (as described in Boissel et al., 2013). The megaTAL target site sequence is set forth in SEQ ID NO: 27. The megaTAL was tested against the methylated CpG dinucleotide present in the target site of the TAL array. The TAL array was designed to tolerate the methylated base by incorporating an 'N*' RVD at the corresponding array position.

The megaTAL editing efficiency was assessed by pre-stimulating primary human T cells with anti-CD3 and anti-CD28 antibodies in cytokine-supplemented media for 48-72 hours, and then electroporating the cells with in vitro transcribed (IVT), capped, and polyadenylated mRNA (SEQ ID NO: 40) encoding the PD-1.ITSM.ex5_RD5_CV23MK megaTAL. Additionally, IVT-mRNA encoding the 3' to 5' exonuclease Trex2 was added to enhance break processing by the non-homologous end-joining (NHEJ) pathway (see Certo et al., 2012). Post-electroporation, cells were cultured for 7-10 days in cytokine-supplemented media, during which time aliquots were removed for genomic DNA isolation followed by PCR amplification across the PD-1 exon 5 target site.

Figure 7A:
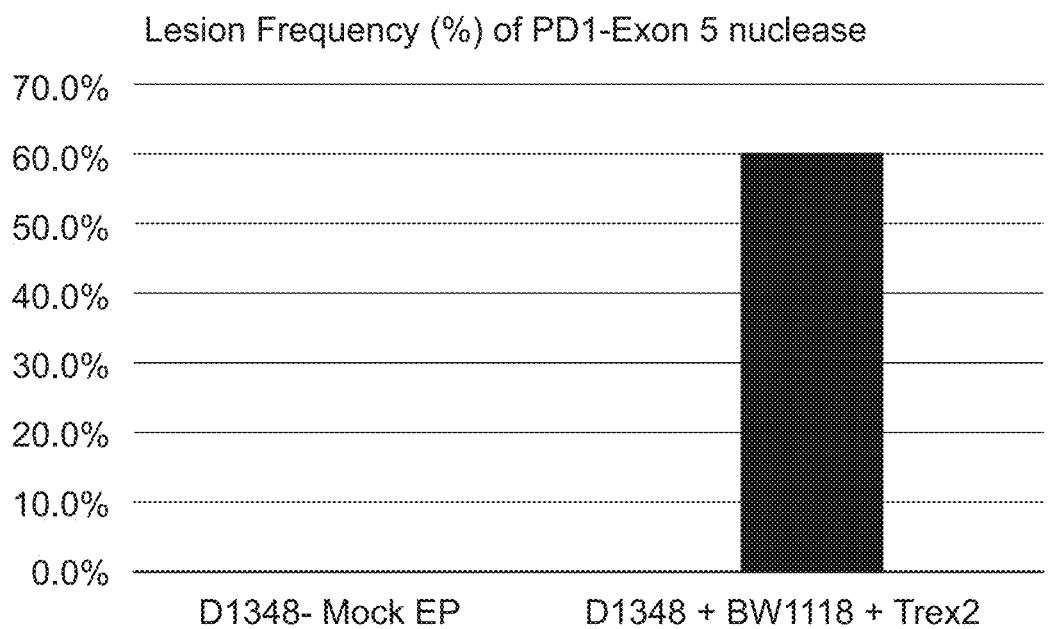
FIG. 7A shows that the co-delivery of the PD-1.ITSM.ex5_RD5_CV23MK megaTAL into T cells along with TREX2 edits the target locus at a rate of about 60% as measured by TIDE analysis.
Figure 7B:
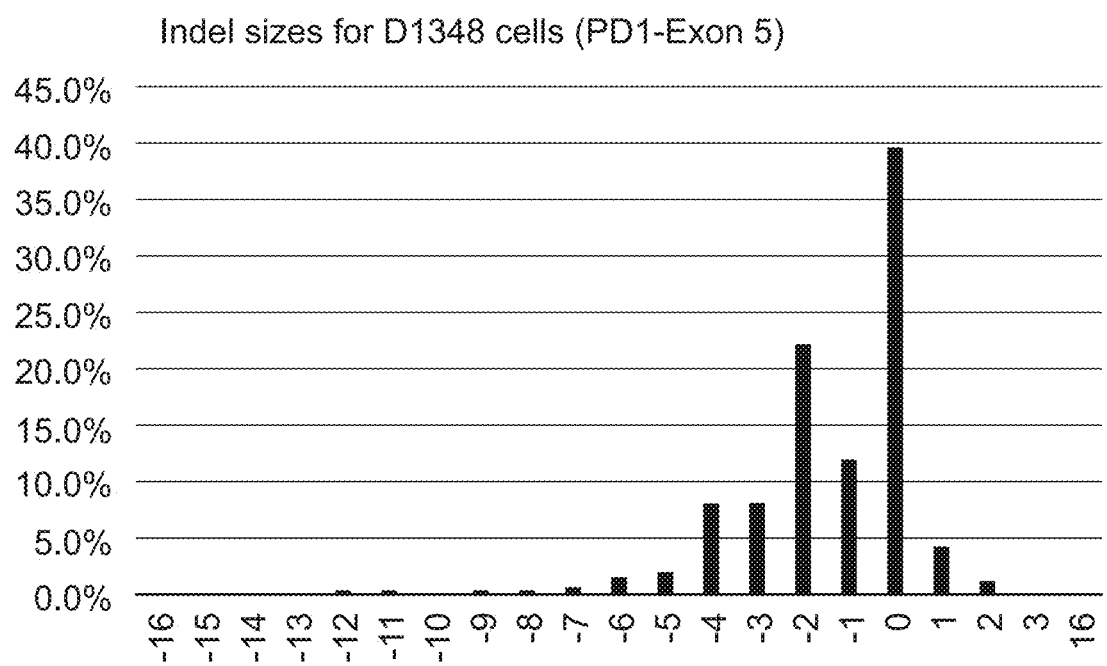
FIG. 7B shows the indel distribution at the PD-1 ITSM consensus motif when cleaved by the PD-1.ITSM.ex5_RD5_CV23MK megaTAL in the presence of Trex2.

The frequency of indels was measured using Tracking of Indels by DEcomposition (TIDE, see Brinkman et al., 2014) or high throughput sequencing. The editing efficiency of the PD-1.ITSM.ex5_RD5_CV23MK megaTAL in the presence of Trex2 was approximately 60%. FIG. 7A. The predominant indel types observed at the target site were +1, -1, -2, -3, or -4 nucleotides. FIG. 7B. This analysis confirmed that the PD-1.ITSM.ex5_RD5_CV23MK variant disrupted the PD-1 ITSM consensus motif in a significant portion of megaTAL treated human T cells.

Example 3

Figure 8:
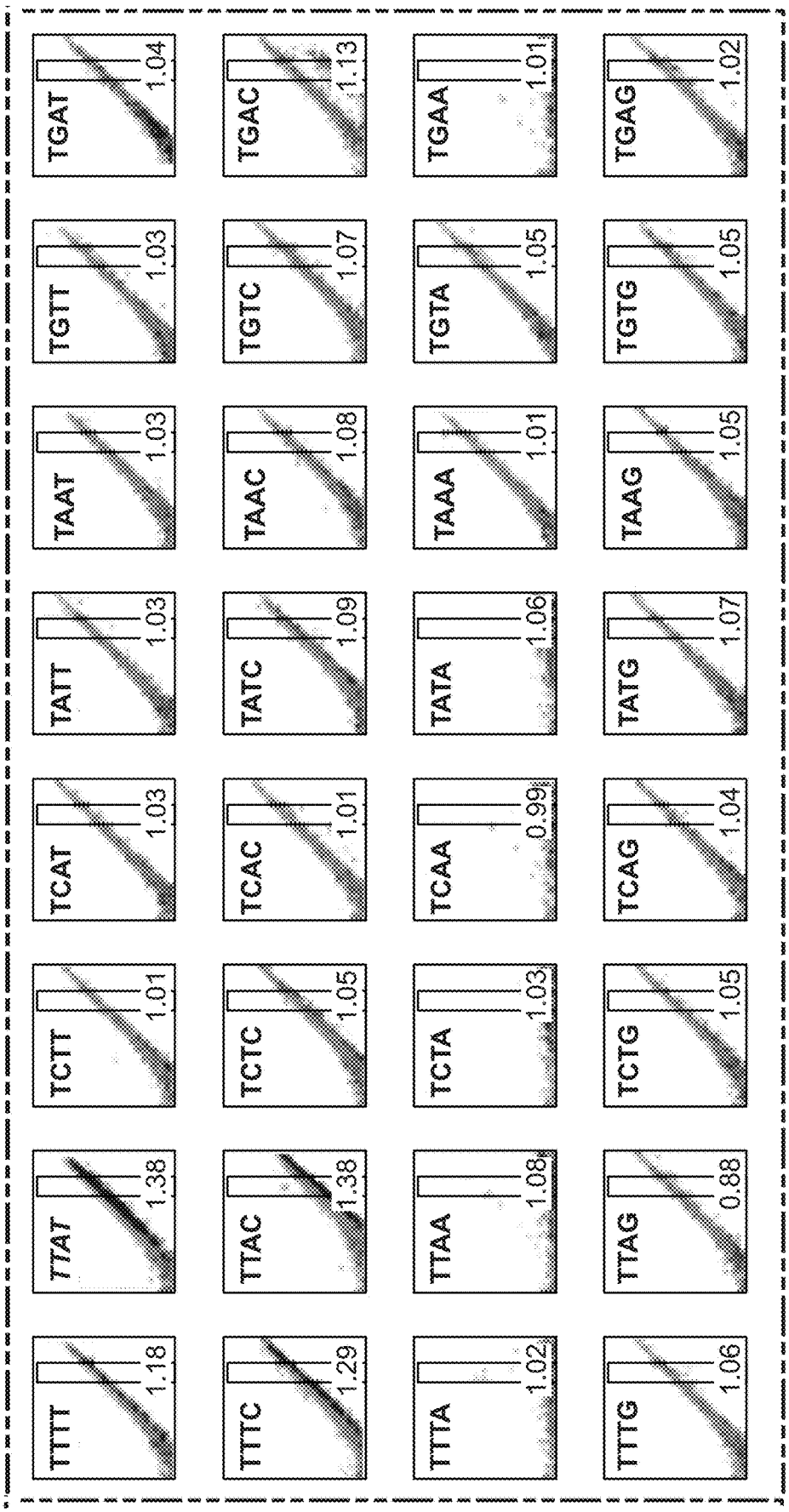
FIG. 8 shows the results from profiling the central-4 specificity of the PD-1 exon 5 HE.
Figure 8:
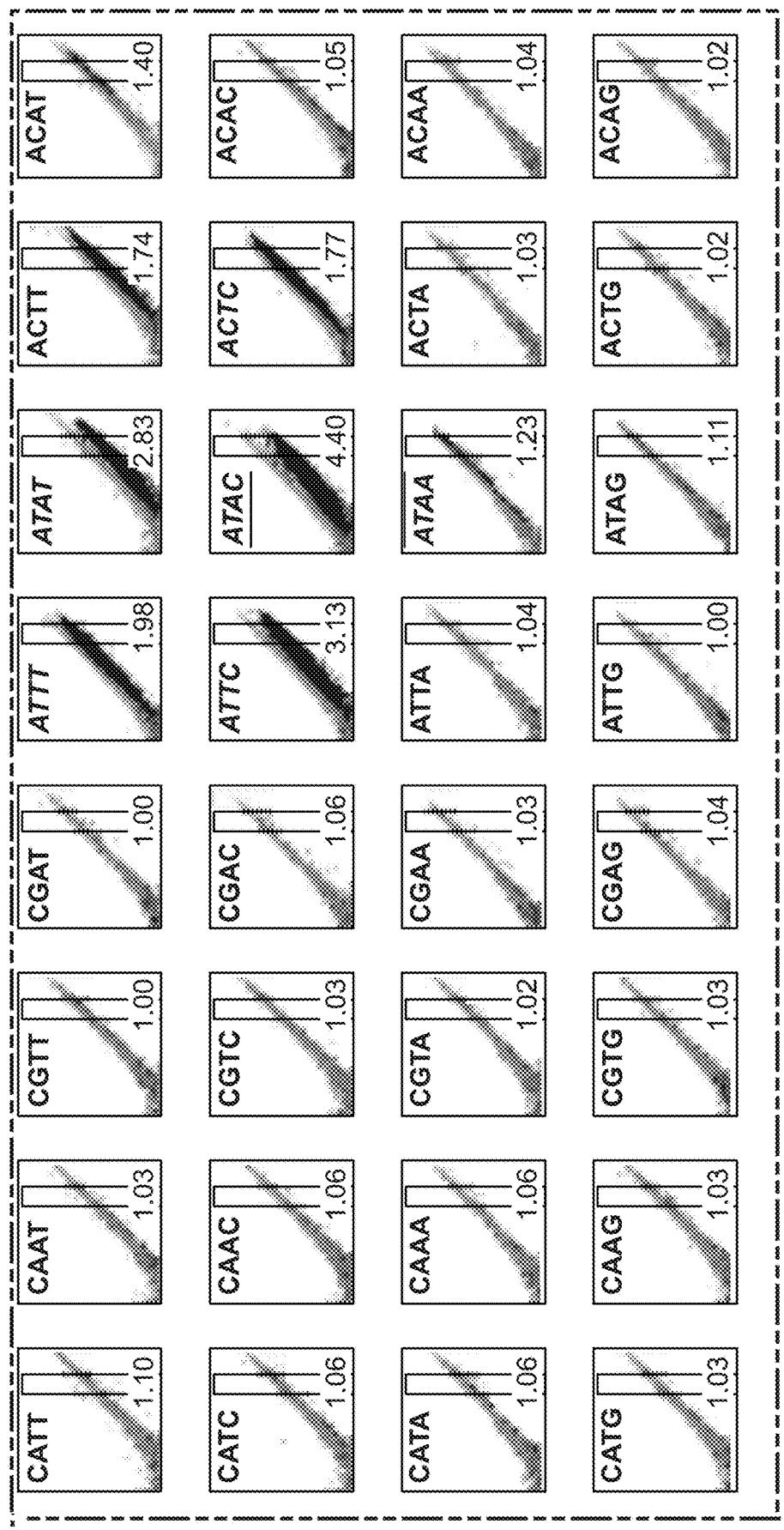
Figure 8:
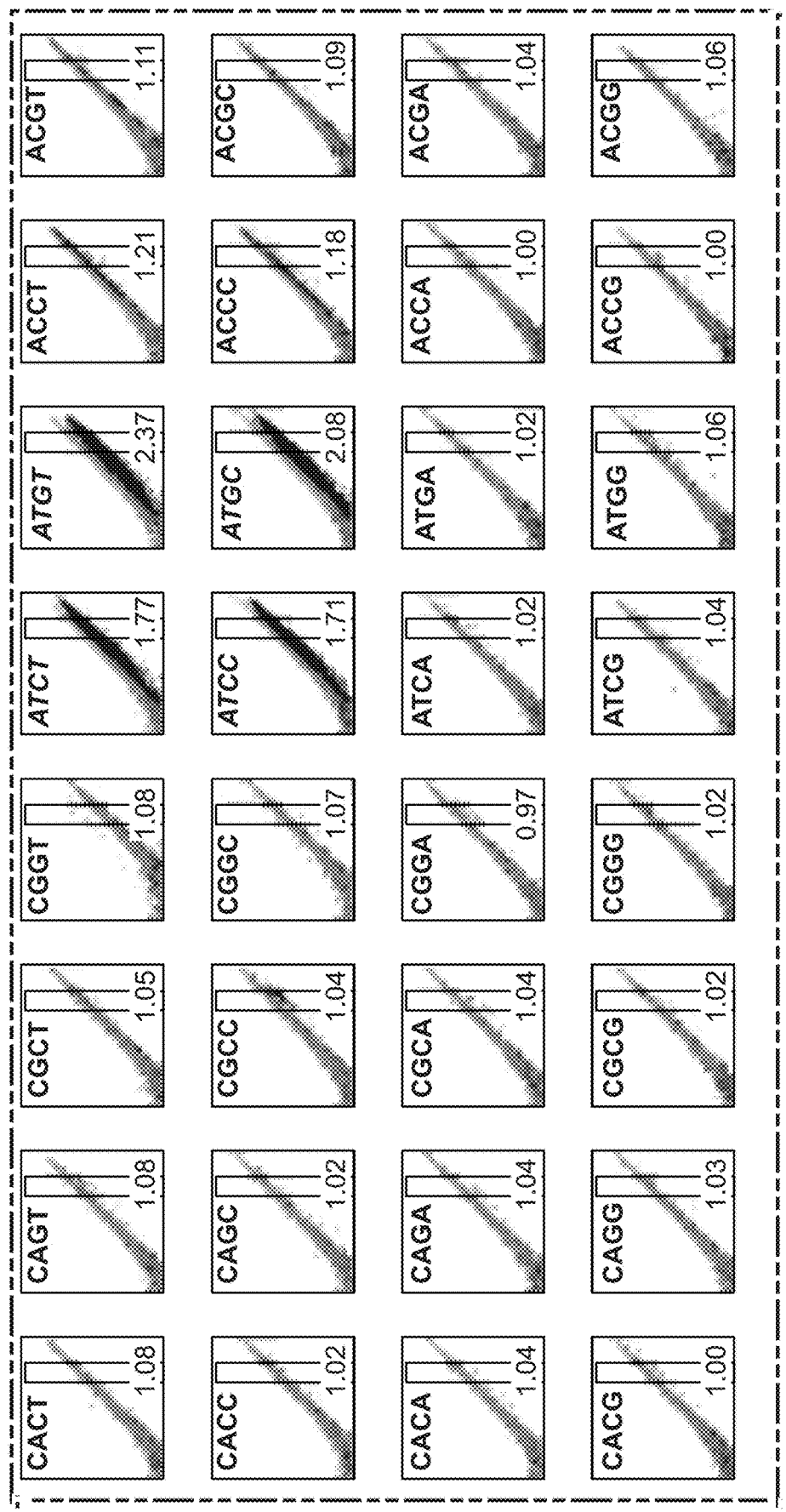
Figure 8:
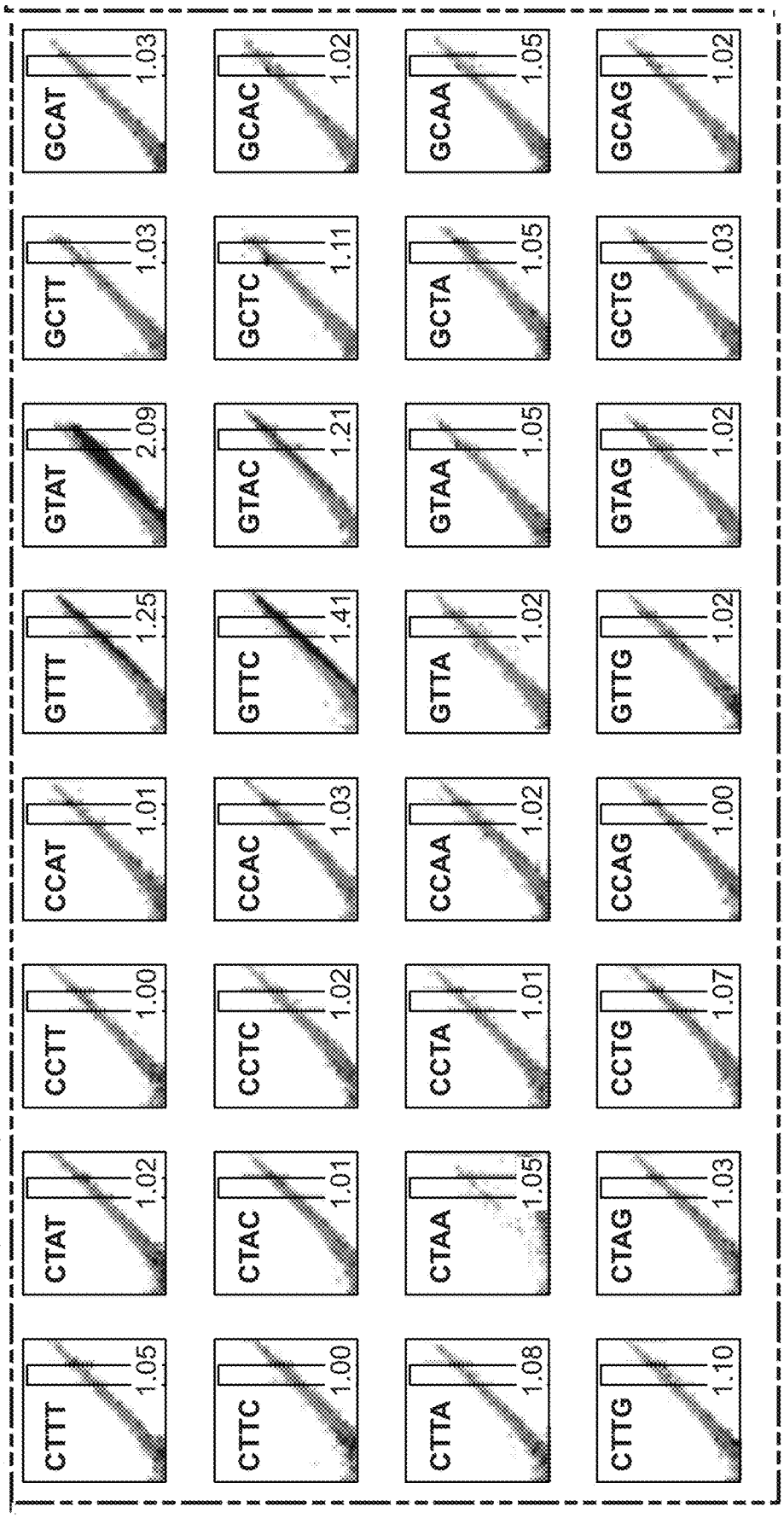
Figure 8:
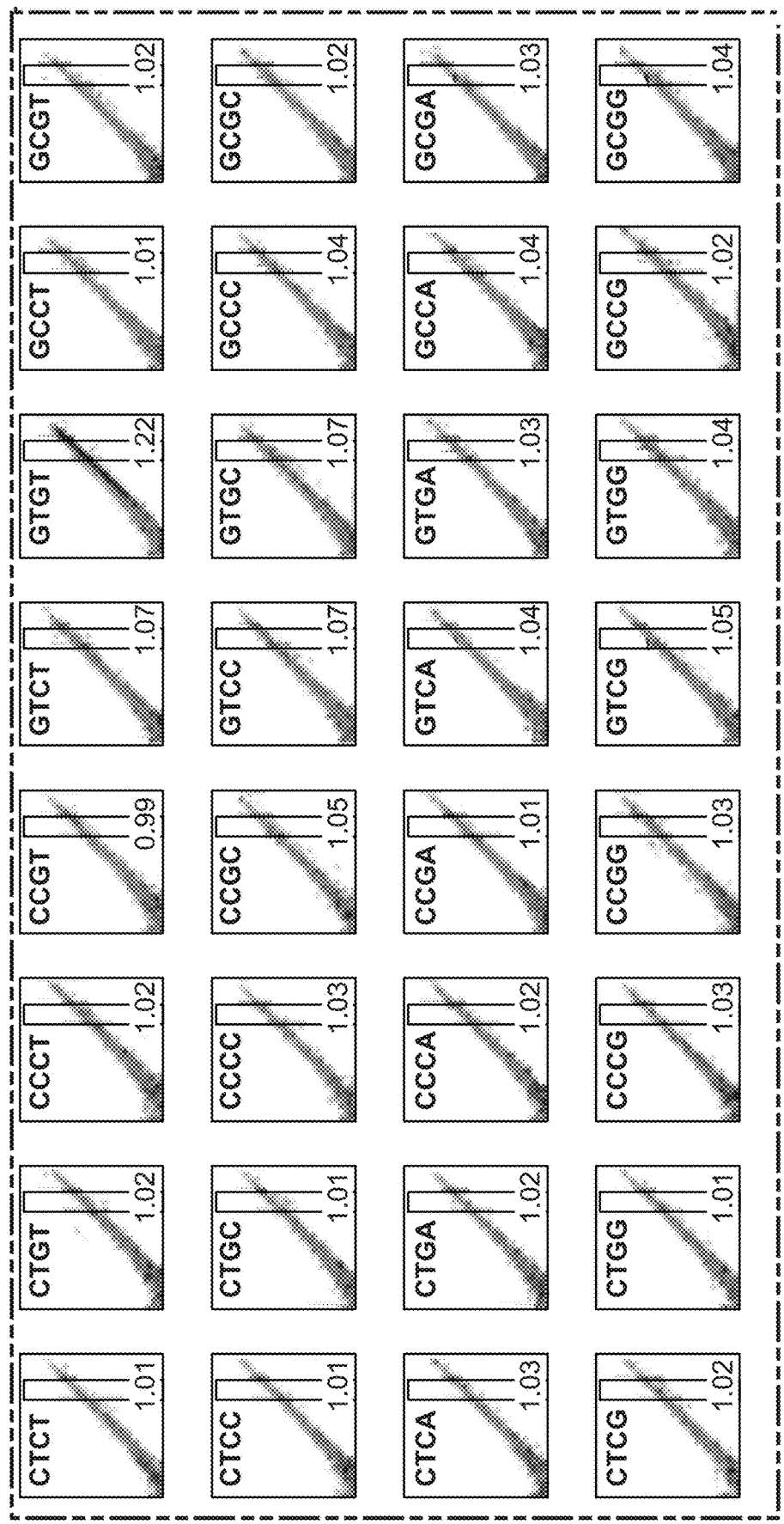
Figure 8:
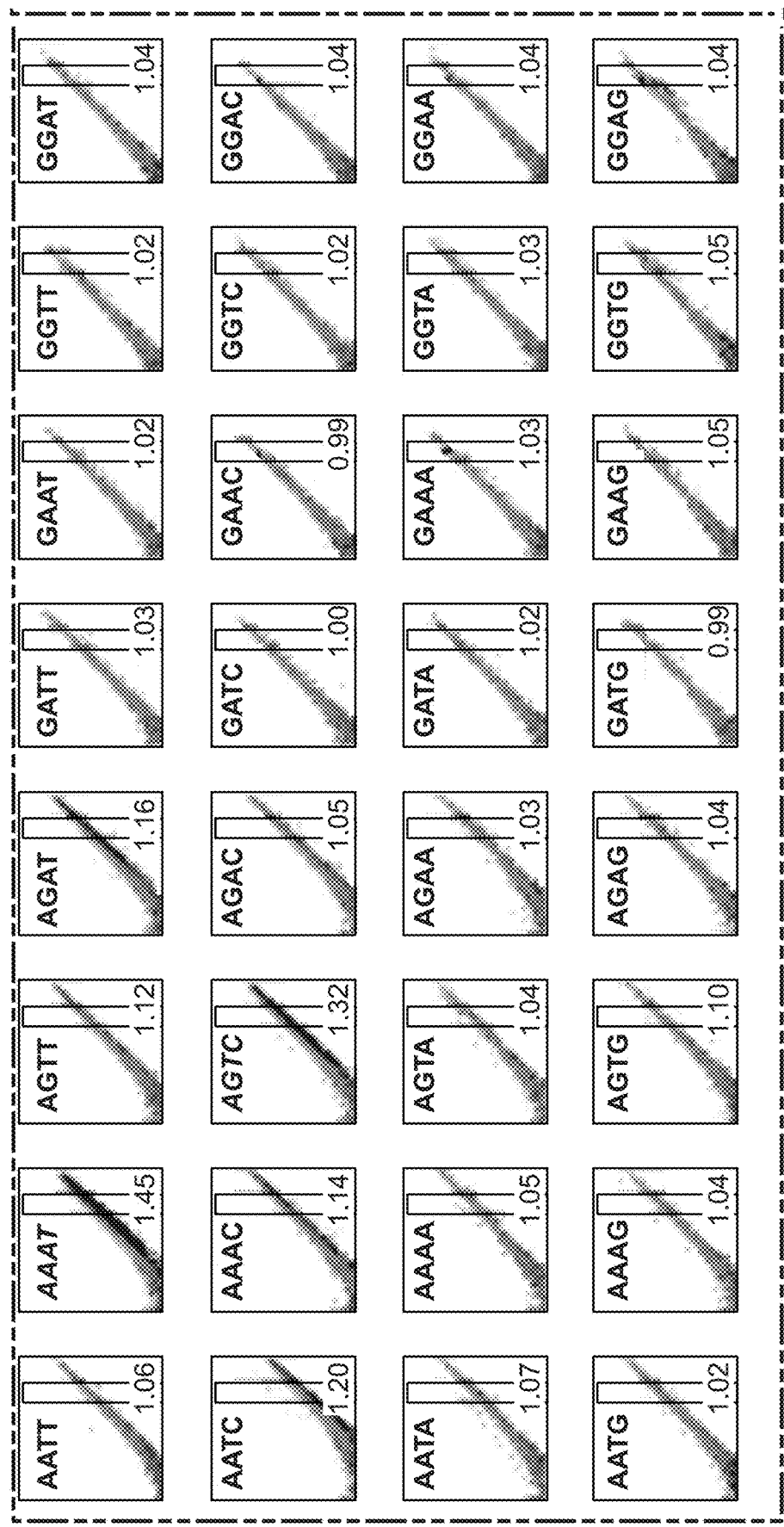
Figure 8:
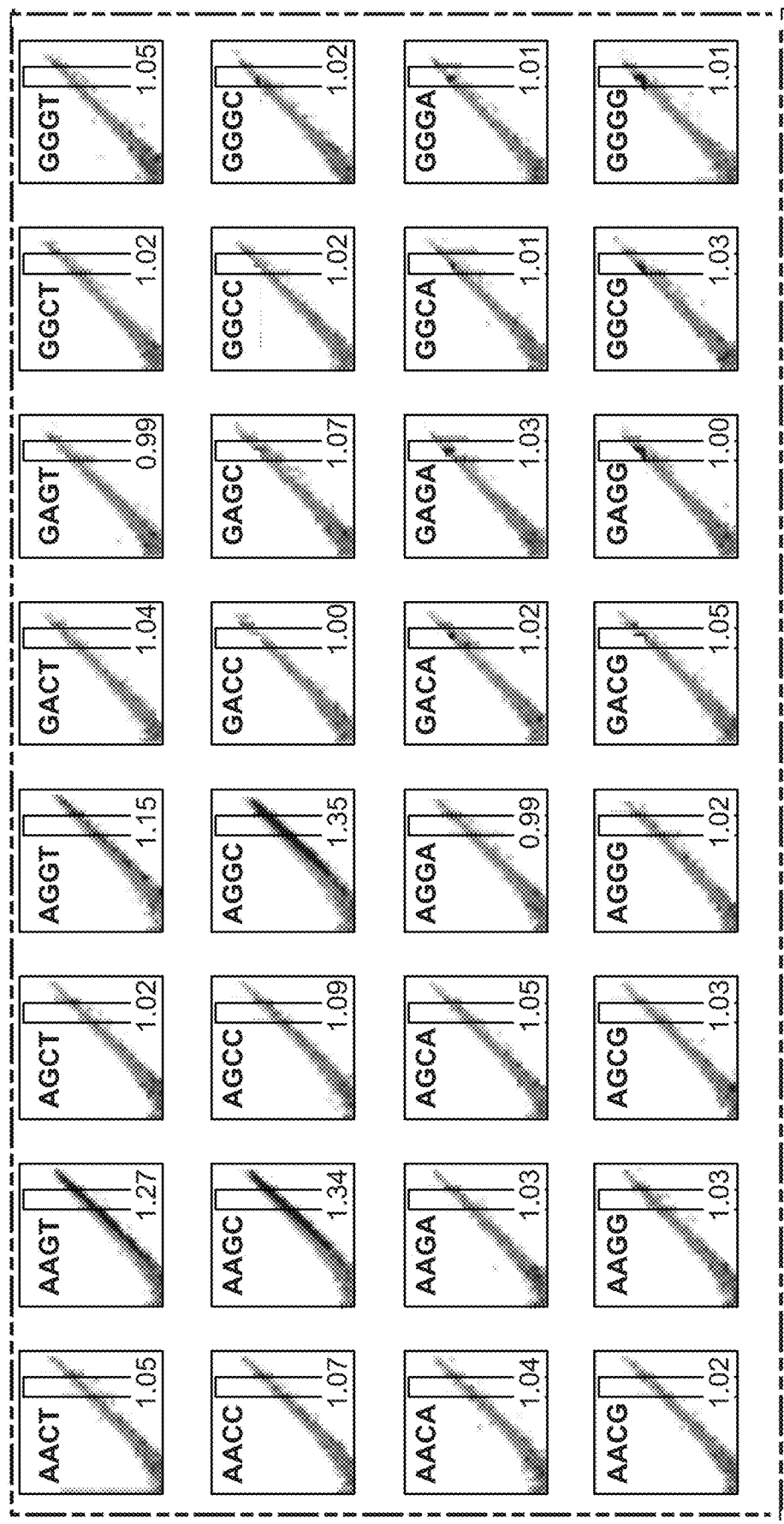

Reprogramming I-OnuI Meganuclease Domains to Disrupt the Extracellular Domains within the Programmed Death Receptor-1 (PD-1) Gene The central-4 specificity of an I-OnuI variant HE that targets the PD-1 exon 5 target site (SEQ ID NO: 25) was profiled using high throughput yeast surface display in vitro endonuclease assays (Jarjour, West-Foyle et al., 2009). A plasmid encoding an HE variant that targets PD-1 exon 5 was transformed into S. cerevisiae for surface display, then tested for cleavage activity against PCR-generated double-stranded DNA substrates comprising the PD-1 exon 5 target site DNA sequence that contains each of the 256 possible central-4 sequences. The specificity profile showed that this reprogrammed I-OnuI is highly selective for central-4 target targets sites (FIG. 8), but can also cleave additional non-canonical central-4 target sites. Since there are very few canonical I-OnuI central-4 target sites located elsewhere in the PD-1 gene, non-canonical central-4 target sites in PD-1 exon 1 and exon 2 were used to reprogram additional homing endonucleases.

These non-canonical central-4 target sites in PD-1 exon 1 and exon 2 are in regions that encode the signal peptide and IgV domain, respectively. Without wishing to be bound to any particular theory, it is contemplated that targeting these regions by gene editing indels abolishes or destabilizes PD-1 protein expression to create a clean knock-out phenotype. In addition, accessing these sites for more advanced gene editing operations including, but not limited to, targeted insertion of transgene cassettes, could create phenotypes that are under unique regulatory control.

Figure 9A:
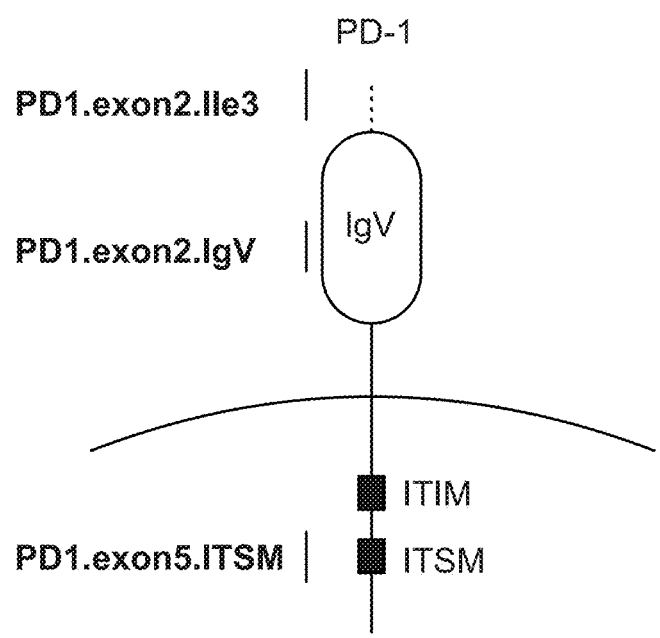
FIG. 9A shows a cartoon illustrating the positions of the IgV, ITIM, and ITSM domains of PD-1 in relation to the position of exons 1, 2, and 5.
Figure 9B:
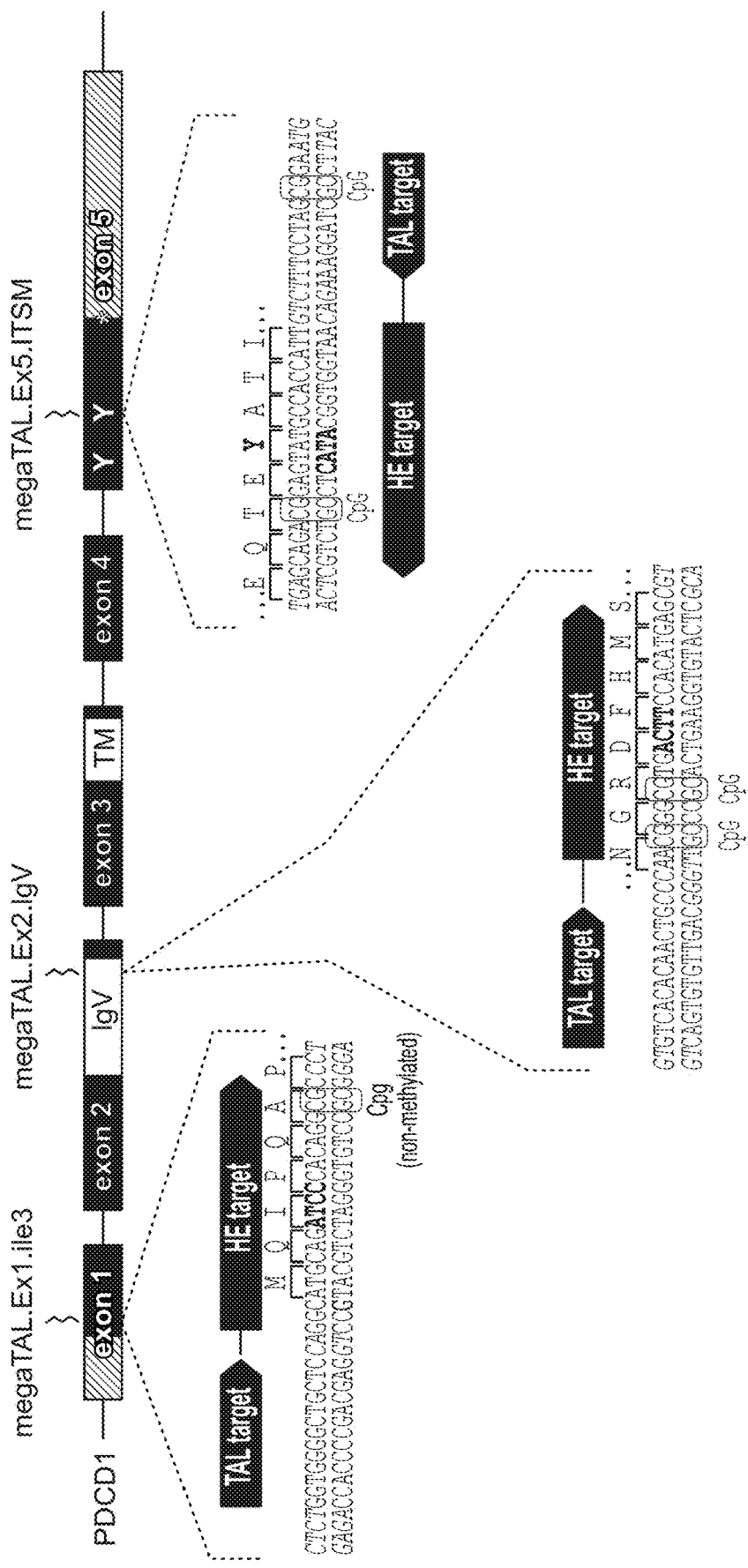
FIG. 9B shows the PD-1 gene and the location of the target sites in exons 1 (SEQ ID NOS: 114-116), 2 (SEQ ID NOS: 117-119), and 5 (SEQ ID NOS: 106-108).

I-OnuI was reprogrammed to target two non-canonical central-4 containing target sites (SEQ ID NOs: 30 and 35), one in each of these two exons/motifs, and extending to the corresponding TAL array target sites (SEQ ID NOs: 26 and 31) and full megaTAL target sites (SEQ ID NOs: 31 and 37). FIGS. 9A and 9B. I-OnuI was reprogrammed to target exon 1 or exon 2 of the PD-1 gene by constructing modular libraries containing variable amino acid residues in the DNA recognition interface. To construct the variants, degenerate codons were incorporated into I-OnuI DNA binding domains using oligonucleotides. The oligonucleotides encoding the degenerate codons were used as PCR templates to generate variant libraries by gap recombination in the yeast strain S. cerevisiae. Each variant library spanned either the N- or C-terminal I-OnuI DNA recognition domain and contained ~ $10^7$ to $10^8$ unique transformants. The resulting surface display libraries were screened by flow cytometry for cleavage activity against target sites comprising the corresponding domains' "half-sites" (exon 1: SEQ ID NOs: 34 and 35; exon 2: SEQ ID NOs: 38 and 39).

Yeast displaying the N- and C-terminal domain reprogrammed I-OnuI HEs were purified and the plasmid DNA was extracted. PCR reactions were performed to amplify the reprogrammed domains, which were subsequently transformed into S. cerevisiae to create libraries of reprogrammed domain combinations. Fully reprogrammed I-OnuI variants active against the complete target site in the region encoding the signal peptide in PD-1 exon 1 and in the region encoding the IgV domain in PD-1 exon 2 were identified and purified from these libraries.

The reprogrammed I-OnuI HEs targeting the PD-1 exon 1 and exon 2 target sites were cloned into mammalian expression plasmids and then individually transfected into a HEK 293T fibroblast cell line containing the corresponding target sequences upstream of an out-of-frame gene encoding the fluorescent iRFP protein.

Figure 10:
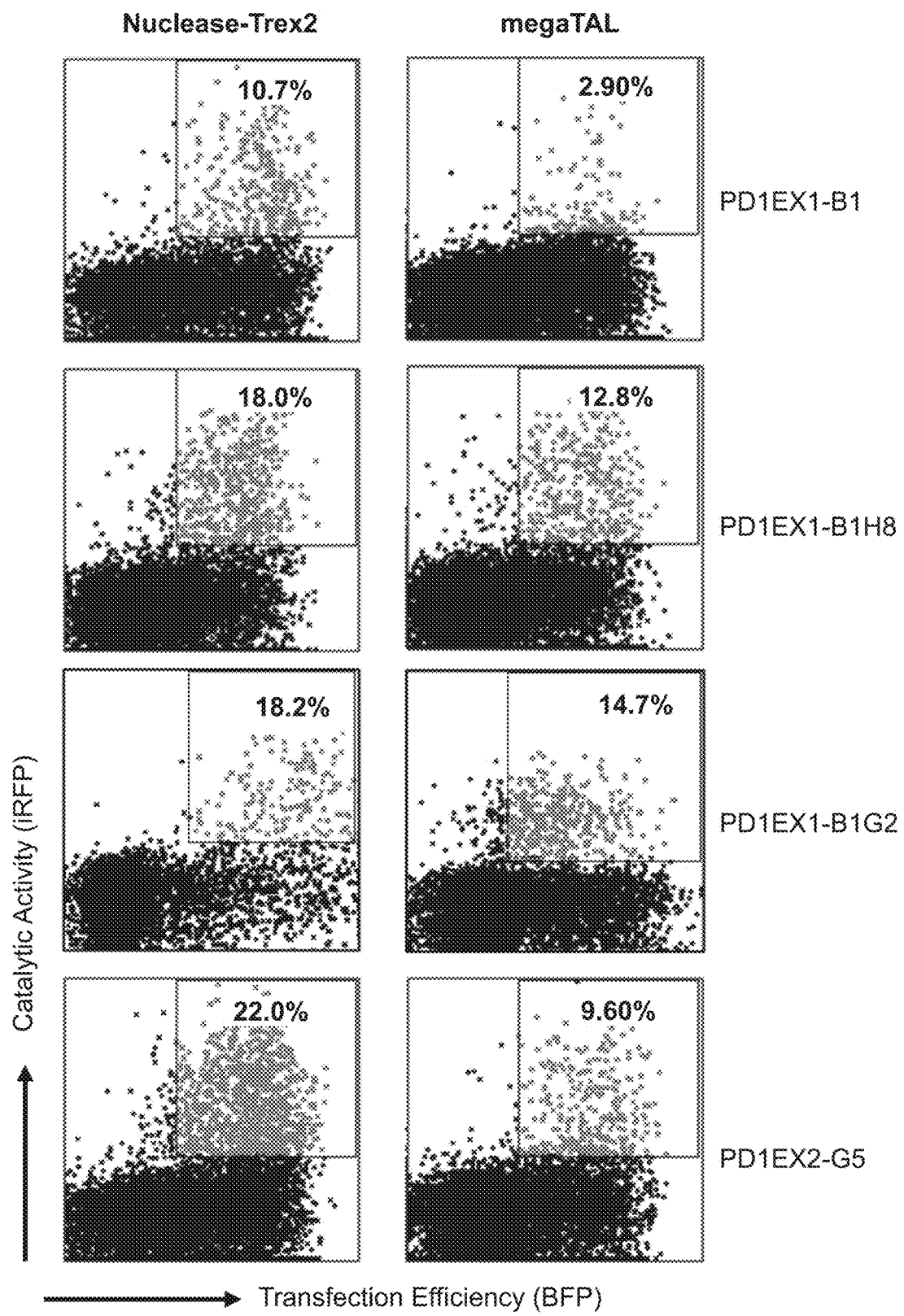
FIG. 10 shows results from chromosomal reporter assays following display-based flow sorting of catalytic activity for an initially reprogrammed I-OnuI that targets PD-1 exon 1 (PD-1.ile3.exon1_RD1_B1, top panel); refinement of PD-1.ile3.exon1_RD1_B1 by mutagenizing and screening under more stringent catalytic conditions to identify mutations that assist target cleavage to identify a more active variants (PD-1.ile3.exon1_RD2_B1H8, and PD-1.ile3.exon1_RD2_B1G2 middle panels); and an initially reprogrammed I-OnuI that targets PD-1 exon 2 (PD-1.IgV.exon2_RD1_G5, lower panel). Results are shown for the nuclease in the presence of Trex2 (left panels) and formatted as megaTALs (right panels).

A reprogrammed I-OnuI HE targeting the PD-1 exon 1 site (PD-1.ile3.exon1_RD1_B1, SEQ ID NO: 11) showed a moderate efficiency of iRFP expression in a cellular chromosomal context, either as a stand-alone HE variant or, after formatting as a megaTAL (SEQ ID NO: 20). A secondary I-OnuI variant library was generated by performing random mutagenesis over the PD-1 exon 1 RD1 variant identified in the initial library screening process. Display-based flow sorting was performed under more stringent cleavage conditions in an effort to isolate variants with improved catalytic efficiency. This process identified two I-OnuI variants (PD-1.ile3.exon1_RD2_B1H8, PD-1.ile3.exon1_RD2_B1G2, SEQ ID NOs: 12 and 60 respectively). The variants contained four (PD-1.ile3.exon1_RD2_B1H8) or five (PD-1.ile3.exon1_RD2_B1G2) amino acid mutations relative to the RD1 variant, and had a significantly higher rate of iRFP expressing cells compared to the PD-1 exon 1 RD1 variant, both as a stand-alone HE variant and after formatting as a megaTAL (SEQ ID NO: 21 and SEQ ID NO: 64). FIG. 10.

A reprogrammed I-OnuI HE targeting the PD-1 exon 2 site (PD-1.IgV.exon2_RD1_G5; SEQ ID NO: 13) showed a high efficiency of iRFP expression when delivered either as a stand-alone HE variant or, after formatting as a megaTAL (SEQ ID NO: 22)

Figure 11A:
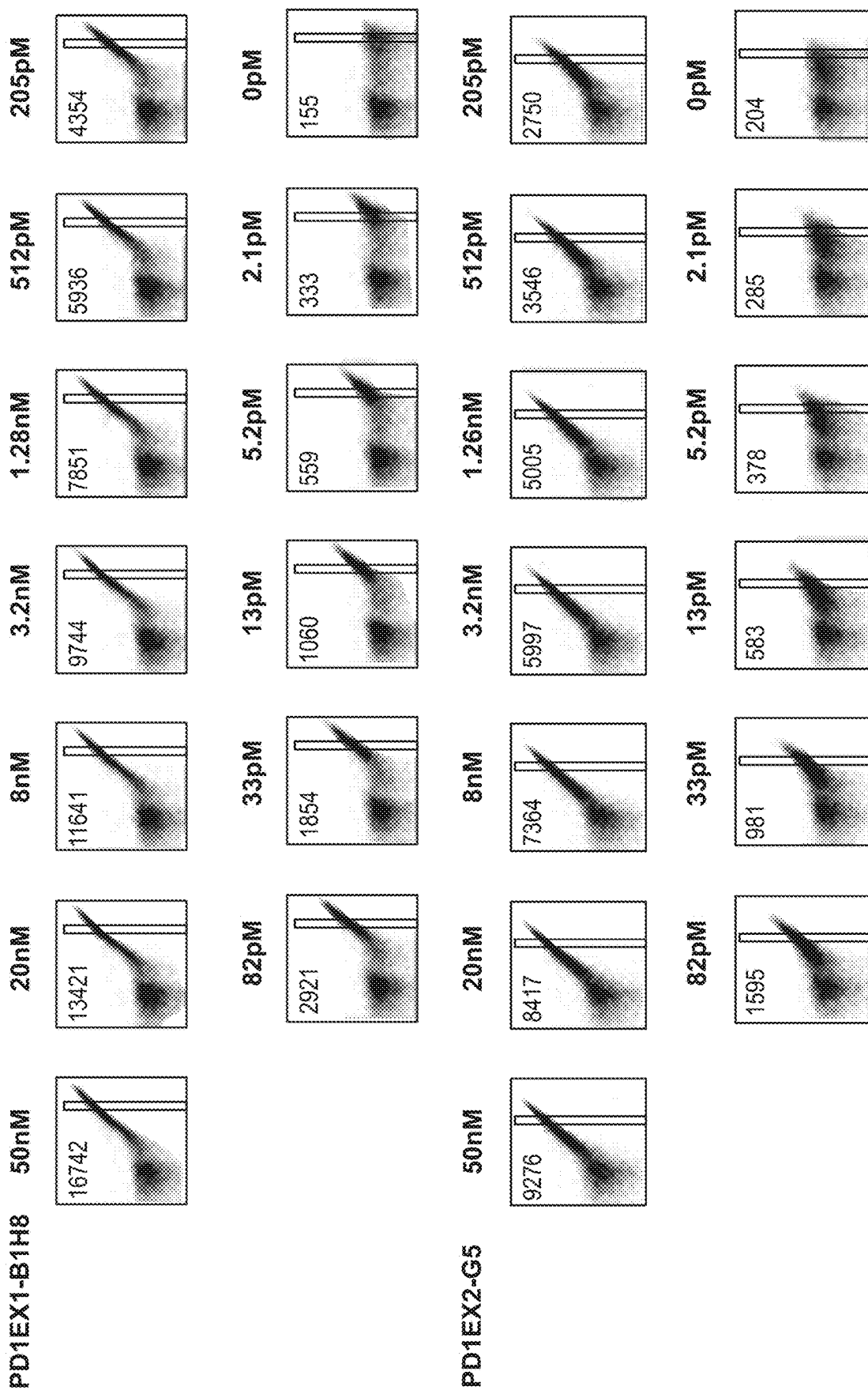
FIG. 11A shows the DNA binding affinities of PD-1.ile3.exon1_RD2_B1H8 and PD-1.IgV.exon2_RD1_G5 when measured by equilibrium substrate titration using their respective target sequences.

The exon 1 and exon 2 targeting HE variants displayed strong DNA affinity properties when measured by equilibrium substrate titration using their respective target sequences. FIG. 11A.

Figure 11B:
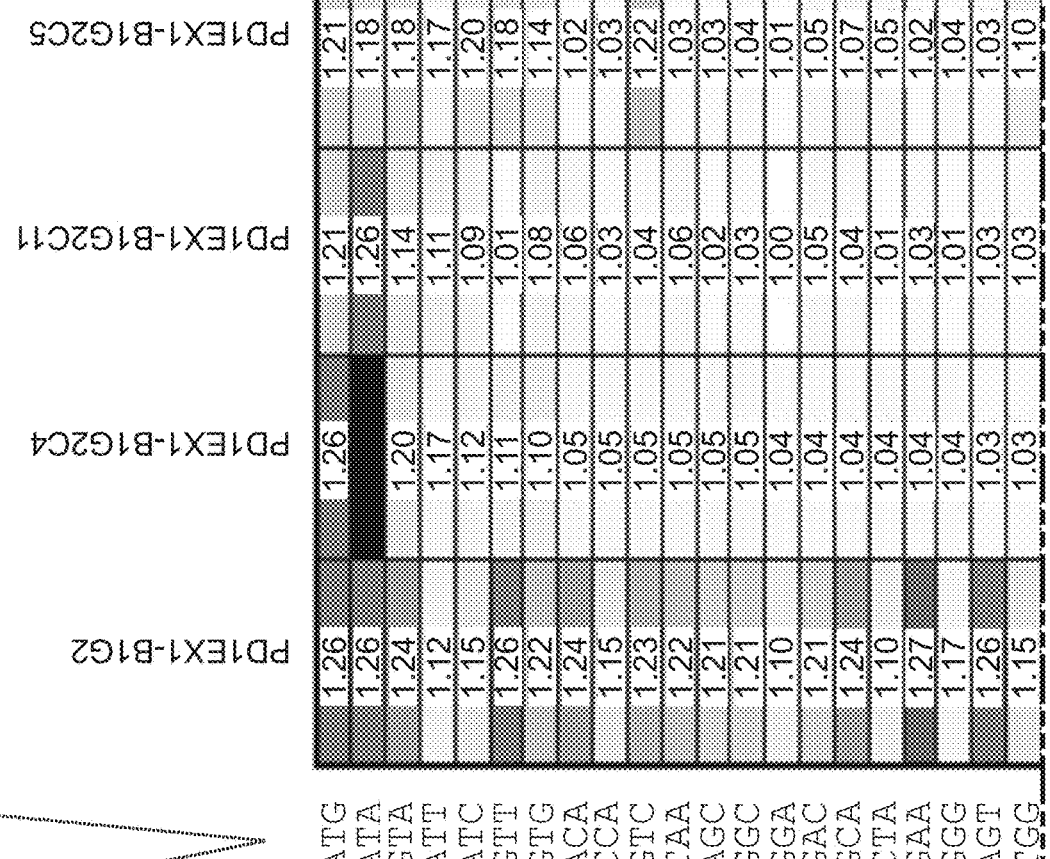
FIG. 11B shows a comparison of DNA cleaving activity among specificity refined nucleases of PD-1.ile3.exon1 (SEQ ID NO: 30) (i.e., nucleases RD2_B1G2, RD3_B1G2C4, RD3_B1G2C11, RD3_B1G2C5) against 64 DNA targets varied at base pairs −8, −7 and −6. Heat map represents ratio of non-cleaving: cleaving median values obtained from dot plots.
Figure 11B:
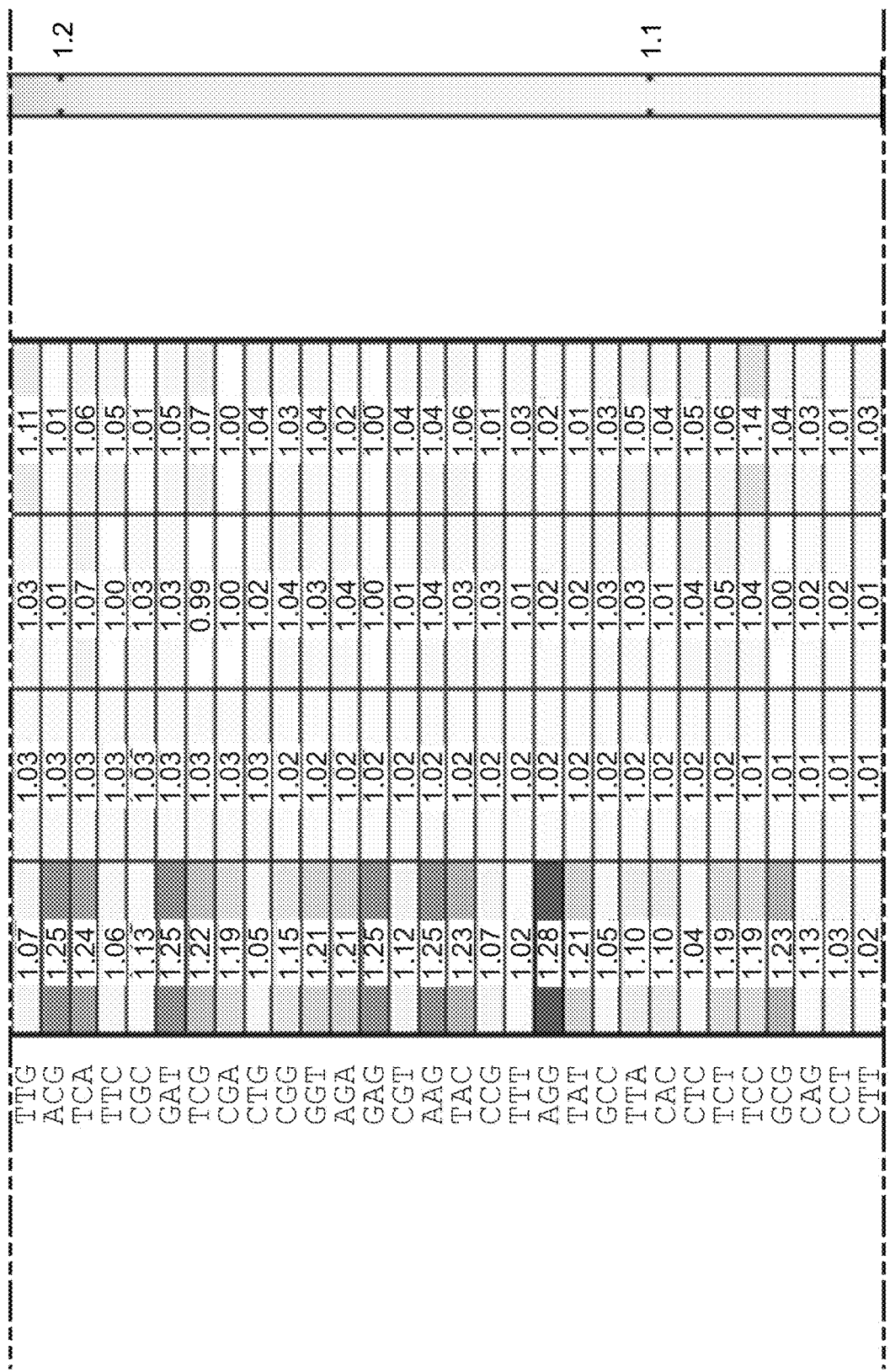

The exon 1 nuclease was further refined to improve its specificity at the region contacting the base pair −8, −7, and −6. Micro-libraries were built by randomizing amino acid residues 68, 70, 78, 80 and 82, and after 6 rounds of sorting by flow cytometer, three clones (PD-1.ile3.exon1_RD2_B1G2C4, PD-1.ile3.exon1_RD2_B1G2C11, and PD-1.ile3.exon1_RD2_B1G2C5; SEQ ID NOs: 61, 62, and 63, respectively) showed higher specificity than the parental nuclease (PD-1.ile3.exon1_RD2_B1G2; SEQ ID No: 60). FIG. 11B.

Figure 12:
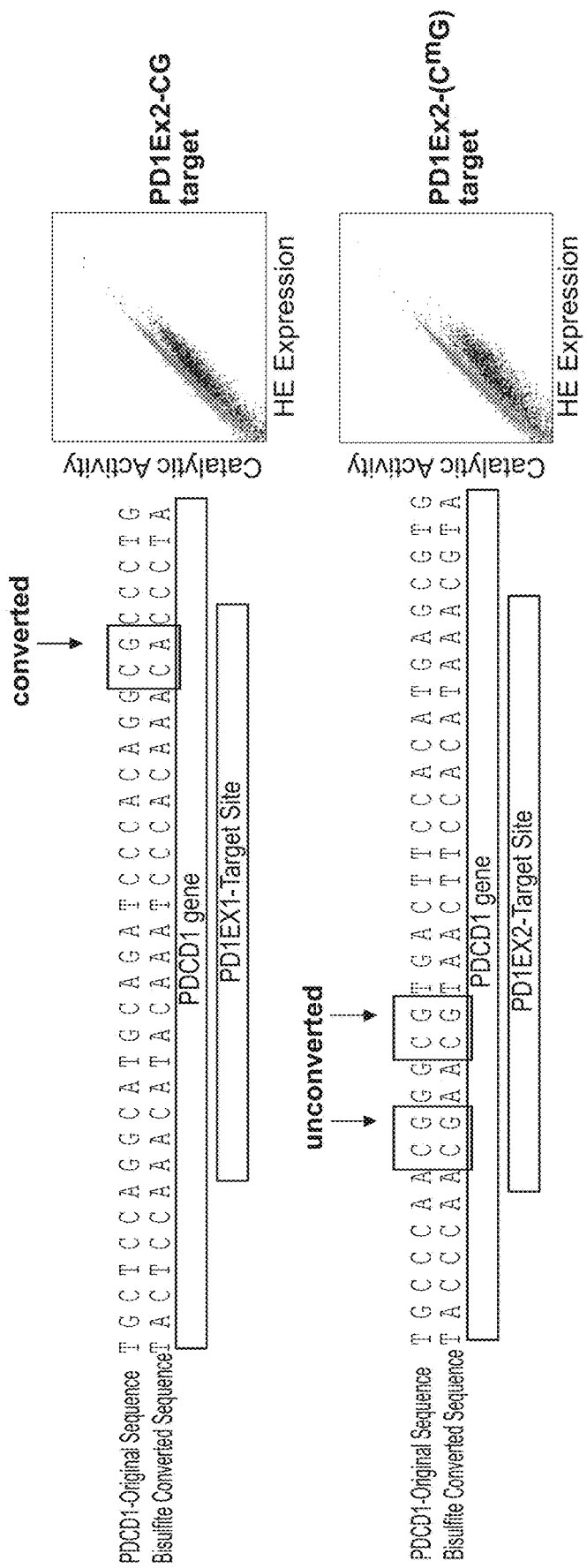
FIG. 12 shows the results of a bisulfite sequencing assay of PD-1 exon 1 (SEQ ID NO: 120) and exon 2 (SEQ ID NO: 122) in activated primary human T cells (left panels), demonstrating that the PD-1 exon 1 CpG motif (SEQ ID NO: 121) remains unmethylated while the PD-1 exon 2 CpG motifs (SEQ ID NO: 123) are methylated.

Bisulfite sequencing was used to evaluate the methylation status of the CpG motifs present within the PD-1 exon 1 and exon 2 target sites. FIG. 12. The CpG motif in PD-1 exon 1 target site was shown to be non-methylated in activated T cells, whereas both CpG motifs in the PD-1 exon 2 target were methylated. Display based activity analysis was performed to confirm that the fully CpG methylated PD-1 exon 2 target sequence was efficiently cleaved by the corresponding HE variant.

In addition, the fully CpG methylated exon 2 target site was used to identify an I-OnuI variant (PD-1.IgV.exon2_RD1_PS3, SEQ ID NO: 14) with improved binding and cleavage activity against the CpG methylated target site.

Example 4

Figure 13A:
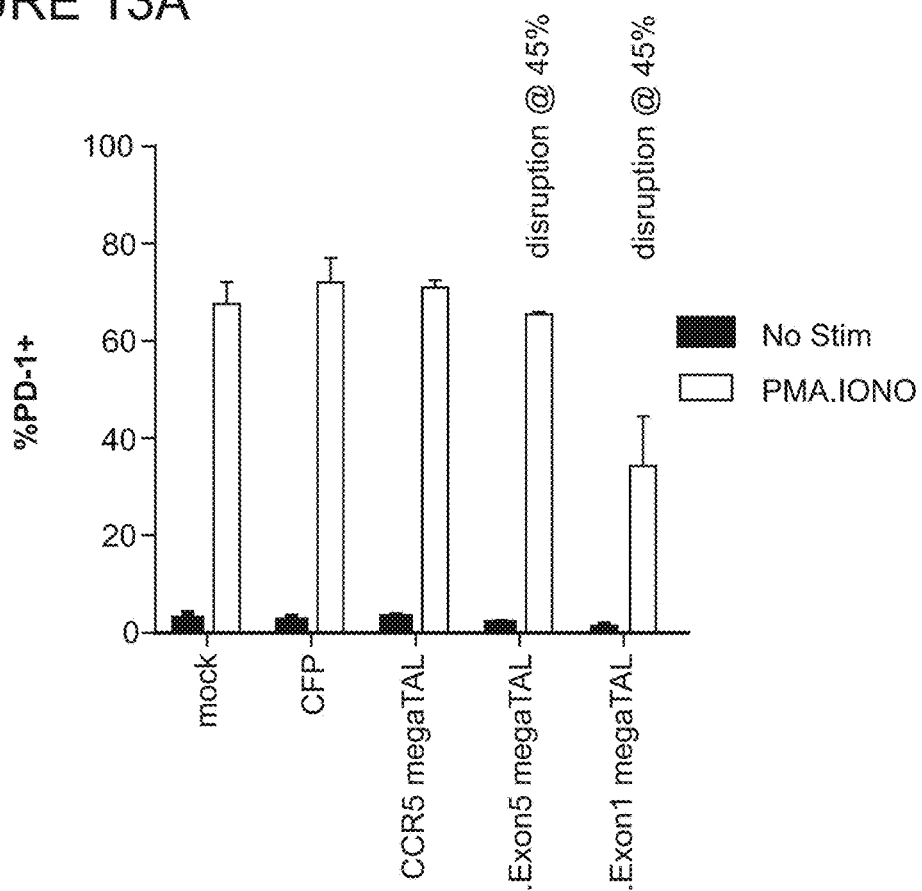
FIG. 13A shows the PD-1 surface expression in CAR T cells electroporated with vehicle, CFP, a CCR5 megaTAL, PD-1.ITSM.ex5_RD5_CV23MK megaTAL, or PD-1.ile3.exon1_RD2_B1H8 megaTAL and subsequently stimulated with vehicle or phorbol 12-myristate 13-acetate (PMA)/Ionomycin (P/I).
Figure 13B:
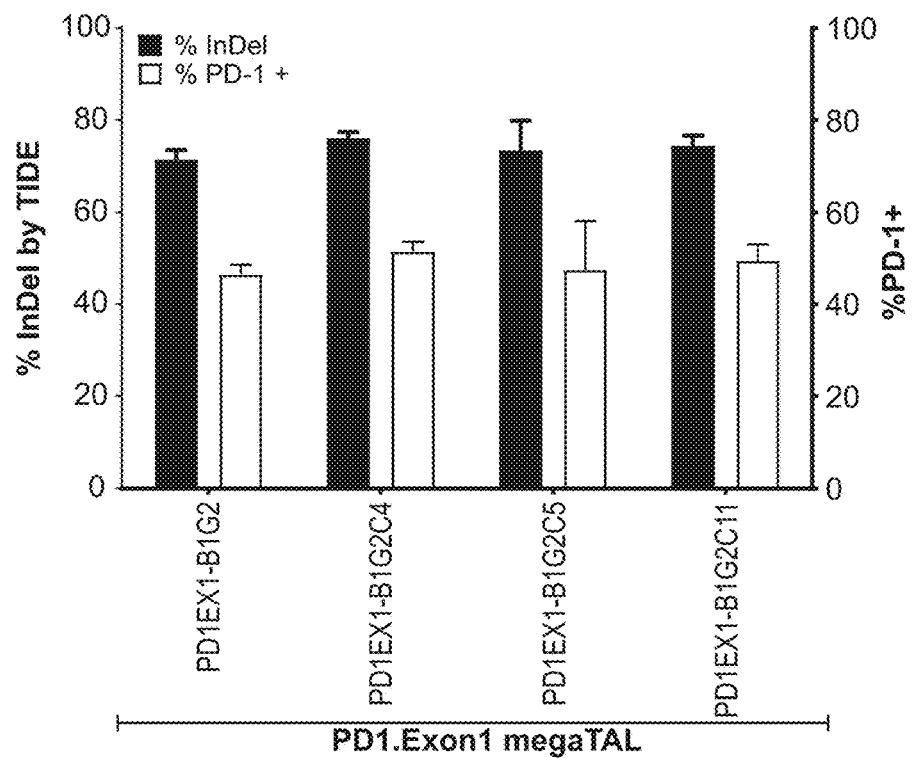
FIG. 13B shows the PD-1 surface expression in T cells electroporated with refined versions of PD-1.ile3.exon1 (RD2_B1G2, RD3_B1G2C4, RD3_B1G2C11, RD3_B1G2C5) megaTALs
Figure 14:
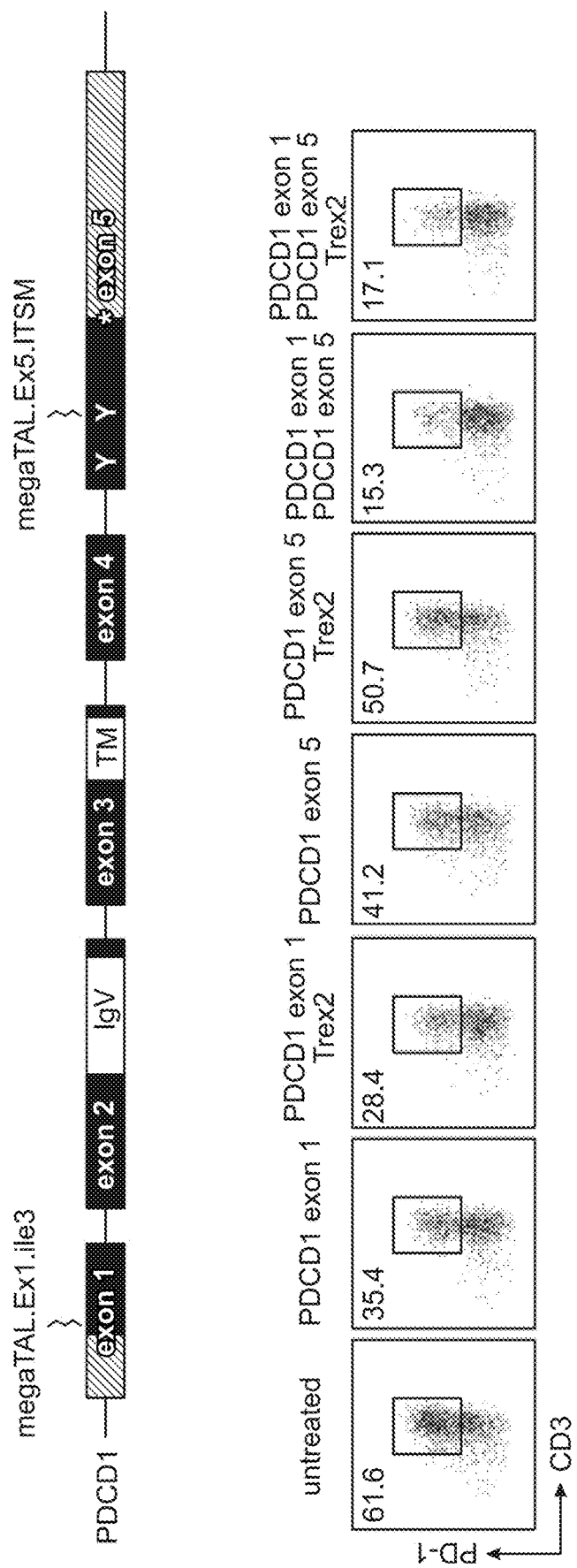
FIG. 14 shows that simultaneous delivery of PD-1.ITSM.ex5_RD5_CV23MK megaTAL and PD-1.ile3.exon1_RD2_B1H8 megaTAL with or without Trex2 significantly decreases PD-1 cell surface expression.

Targeted Disruption of the PD-1 Gene in Primary Human T Cells Rescues PD-L1 Mediated Suppression of T Cell Function The functional impact of the megaTALs reprogrammed to cleave various target sequences in the PD-1 gene was evaluated in primary human T cells activated with CD3 and CD28 and cultured in complete media supplemented with IL-2. Activated PBMCs were transduced with a lentiviral vector encoding an anti-BCMA CAR. Anti-BCMA CAR T cells were electroporated with in vitro transcribed mRNA encoding either the PD-1 exon 5 or PD-1 exon 1 targeting megaTALs (SEQ ID NOs: 40 and 41, resp.) and mRNA encoding Trex2 (SEQ ID NO: 43). Controls included untreated T cells or T cells treated with mRNA encoding cyan fluorescent protein (CFP) or a CCR5-targeting megaTAL (see Sather et. al., *Sci Transl Med.* 2015 Sep. 30; 7(307):307ra156). Following a 10 day expansion, T cells were stimulated with a polyclonal activation reagent phorbol 12-myristate 13-acetate (PMA)/Ionomycin (P/I). PD-1 is naturally upregulated on the cell surface following T cell activation. PD-1 upregulation was suppressed following transfection of PD-1 exon 1 megaTAL mRNA, indicating that indels in this region disrupt normal production of the PD-1 protein. In contrast, treatment with mRNA encoding a control CCR5 megaTAL or the PD-1 exon 5 targeting megaTAL had no impact on PD-1 surface expression despite the high rate of indels induced in the ITSM by this megaTAL. FIG. 13A. Further experiments repeated under similar conditions with specificity refined versions of PD-1 exon 1 megaTAL mRNA (SEQ ID NOS: 65, 66, 67 and 68) also showed similar PD-1 expression disruption in T-cells. FIG. 13B Simultaneous delivery of both the PD-1 exon 1 and exon 5 megaTALs significantly improved disruption of PD-1 cell surface expression, independent of the delivery of the Trex2 exonuclease. FIG. 14. This indicates that simultaneous proximal DNA break formation is a mechanism to promote large gene deletion events with high efficiency independent of exonuclease-driven indel enhancement.

Figure 15A:
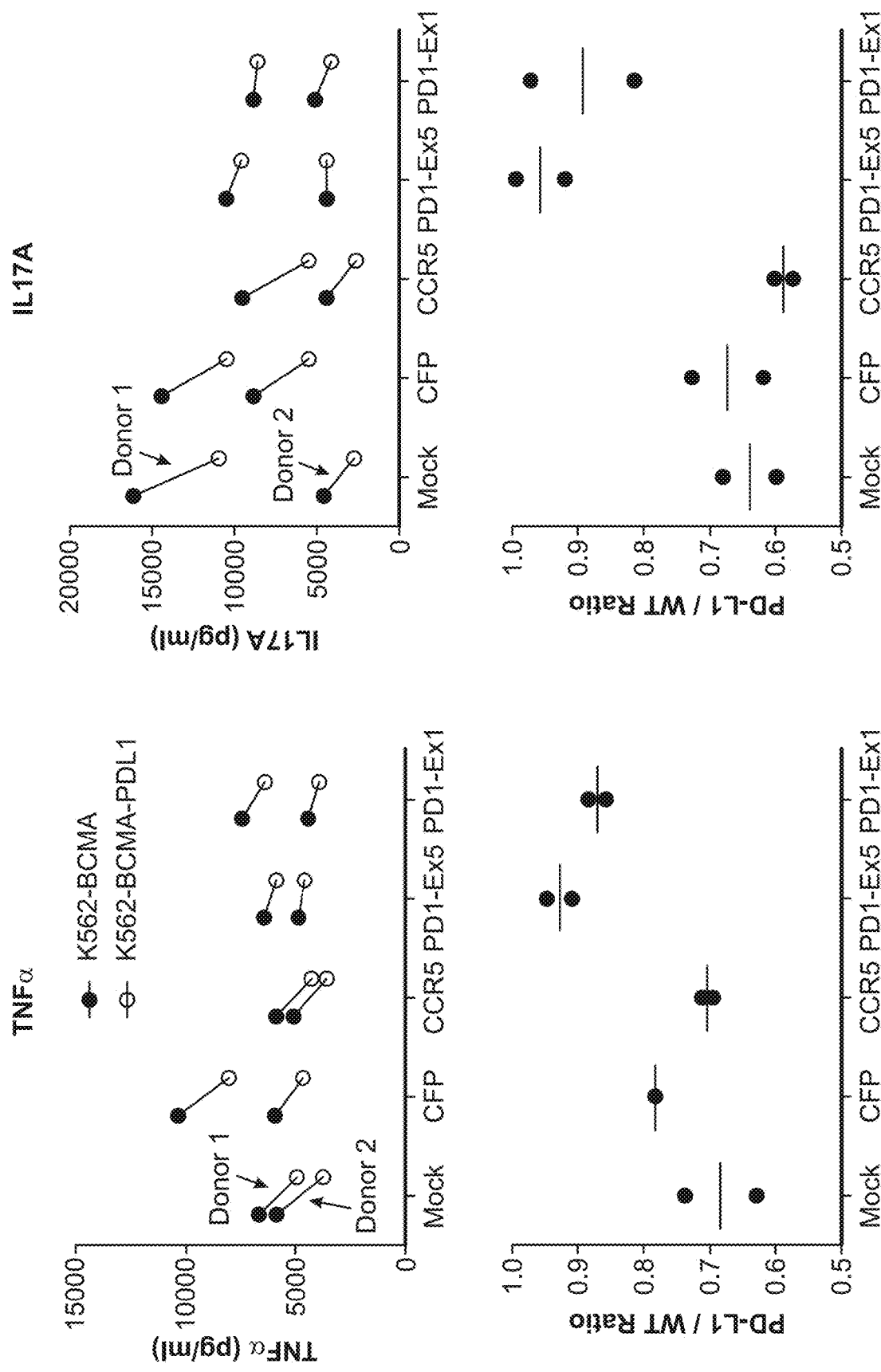
FIG. 15A shows that anti-BCMA CAR T cells electroporated with mRNA encoding PD-1.ITSM.ex5_RD5_CV23MK or PD-1.ile3.exon1_RD2_B1H8 megaTALs show reduced PD-L1 mediated cytokine suppression compared to anti-BCMA CAR T cells electroporated with vehicle, or mRNA encoding CFP or a CCR5 megaTAL.

The impact of disrupting PD-1 signaling in T cells by targeting either its expression or its signaling functions was analyzed by CAR-T cell cytokine production in response to tumor cells engineered to express the PD-1 ligand, PD-L1. Co-culture of anti-BCMA CAR T cells with BCMA expressing tumor cell lines resulted in T cell activation and subsequent inflammatory cytokine secretion, exemplified by high levels of TNFα and IL-17A measured in the supernatant. Co-expression of PD-L1 on BCMA expressing tumor cells suppressed inflammatory cytokine production. However, transfection of the anti-BCMA CAR T cells with mRNA encoding either the PD-1 exon 1 or exon 5 megaTALs reduces PD-L1 mediated cytokine suppression, as inflammatory cytokine production is rescued to baseline levels in these samples. FIG. 15A.

Example 5

Homologous Recombination of a Transgene into Exon 1 of the PD-1 Gene

Figure 16A:
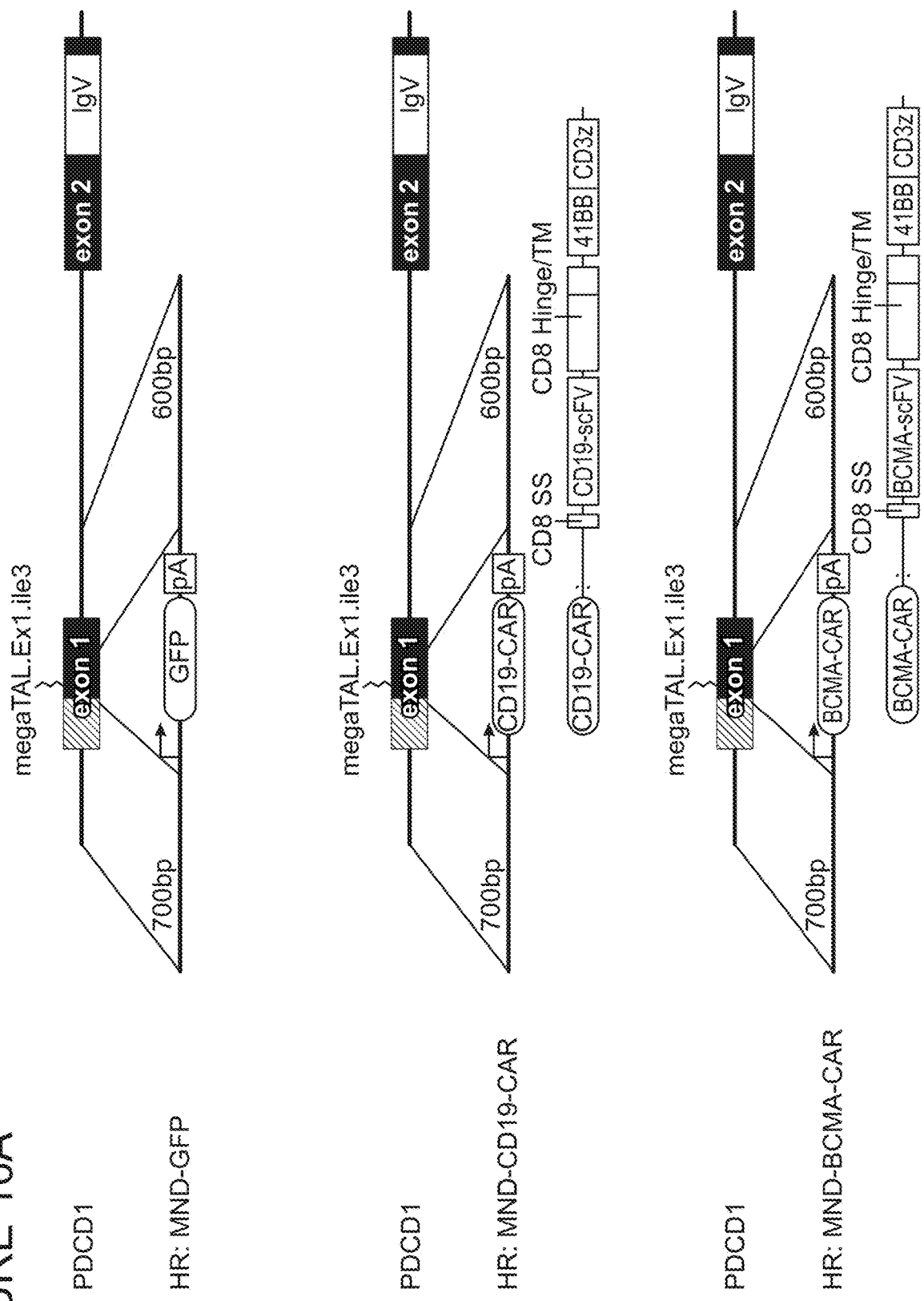
FIG. 16A shows strategies for introducing various expression cassettes (GFP, top panel; anti-CD19 CAR, middle panel; and anti-BCMA CAR, lower panel) into PD-1 exon 1 by homologous recombination.

A recombinant adeno-associated virus (rAAV) plasmid containing a promoter-transgene cassette comprising, a heterologous promoter, a transgene encoding a fluorescent protein, and a polyadenylation signal, situated between gene targeting homology regions, was designed and constructed. The integrity of AAV ITR elements was verified with XmaI digest. The transgene cassette was placed between two homology regions, approximately 600-700 bp in length, flanking the PD-1 exon1 megaTAL cleavage site (SEQ ID NO: 27). The 5' homology arm (SEQ ID NO: 54) contained a portion of the first PD-1 exon and other sequences upstream of the megaTAL cleavage site. The 3' homology arm (SEQ ID NO: 55) contained a portion of the PD-1 exon and other sequences downstream of the megaTAL cleavage site. Neither homology region contained the complete megaTAL target site. This exemplary expression cassette contained the myeloproliferative sarcoma virus enhancer, negative control region deleted, d1587rev primer-binding site substituted (MND) promoter operably linked to a polynucleotide encoding a fluorescent polypeptide, e.g., blue fluorescent protein (BFP), red fluorescent protein (RFP), cyan fluorescent protein (CFP), green fluorescent protein (GFP), etc. Additionally, the expression cassette contained the SV40 late polyadenylation signal placed downstream of the transgene termination codon. FIG. 16A. Recombinant AAV (rAAV) was prepared by transiently co-transfecting HEK 293T cells with plasmids providing the replication, capsid, and adenoviral helper elements necessary for viral production. rAAV was purified from the co-transfected HEK 293T cell culture using ultracentrifugation in an iodixanol-based gradient.

MegaTAL-induced homologous recombination was evaluated in primary human T cells activated with CD3 and CD28 and cultured in complete media supplemented with IL-2. After 3 days in culture, T cells were washed and electroporated with in vitro transcribed PD-1 exon 1 mega- TAL mRNA (SEQ ID NO: 41), and subsequently transduced with purified recombinant AAV encoding MND-GFP transgene cassette (SEQ ID NO: 53). Controls included T cells treated with either megaTAL mRNA or rAAV targeting vector. Flow cytometry was used at multiple time points to measure the frequency of T cells expressing the fluorescent protein and to differentiate transient expression of the fluorescent protein from the episomal rAAV targeting vector from long-term expression of the chromosomally integrated cassette. FIG. 16B. MegaTAL mediated disruption of the PD-1 gene was detected by sequencing and by the loss of PD-1 expression following polyclonal T cell activation.

Long-term transgene expression was observed in 20-60% of the T cells that were treated with both the megaTAL and the rAAV targeting vector. In control samples, rAAV treatment alone produced variable levels of transient fluorescent protein expression and very low levels (<1%) of long-term fluorescent protein expression in treated T cells, consistent with a lack of integration into the genome. Results were confirmed in experiments performed on T cells isolated from several independent donors.

Example 6

Homologous Recombination of a Transgene Encoding a Chimeric Antigen Receptor (CAR) into the PD-1 Gene Recombinant adeno-associated virus (rAAV) plasmids were designed, constructed, and verified as described above, except that a transgene cassette encoding an anti-CD19 CAR (SEQ ID NO: 56) or anti-BCMA CAR (SEQ ID NO: 57) was placed between the PD-1 exon 1 targeting homology regions. The CAR expression cassettes contained an MND promoter operable linked to a polynucleotide encoding a CAR comprising a CD8α-derived signal peptide, a single-chain variable fragment (scFv) targeting either the CD19 antigen or B cell maturation antigen (BCMA), a CD8α derived hinge region and transmembrane domain, an intracellular 4-1BB co-stimulatory domain, a CD3 zeta signaling domain, and homology arms designed to target the PDCD1 exon 1 target site (SEQ ID NOs: 54 and 55).

Primary human T cells were activated with CD3 and CD28 and grown in cytokine supplemented media as described above. Homologous recombination of the CAR transgenes into the PD-1 exon 1 target site was evaluated using activated primary human T cells electroporated with in vitro transcribed PD-1 exon 1 megaTAL mRNA (SEQ ID NO: 41) and then subsequently transduced with rAAV encoding the anti-CD19 or anti-BCMA CAR. Flow cytometry to detect CAR expression was performed at the 10 day time point, 7 days after electroporation and transduction. Control samples included T cells treated with either mega-TAL mRNA or rAAV targeting vector. CD19-CAR and BCMA-CAR expression was analyzed using recombinant PE-conjugated CD19-Fc or PE-conjugated BCMA-Fc staining reagents. T cells treated with megaTAL mRNA and rAAV-CARs showed CD19-CAR expression in 30-60% of T cells and BCMA-CAR expression in 10-20% of T cells. FIG. 16B. Similar rates of T cell expansion and indistinguishable T cell phenotypes were observed between untreated, rAAV-treated, and megaTAL/rAAV CAR-treated T cells.

Example 7

Homologous Recombination of a Promoter-Less Transgene into the PD-1 Gene

Figure 17:
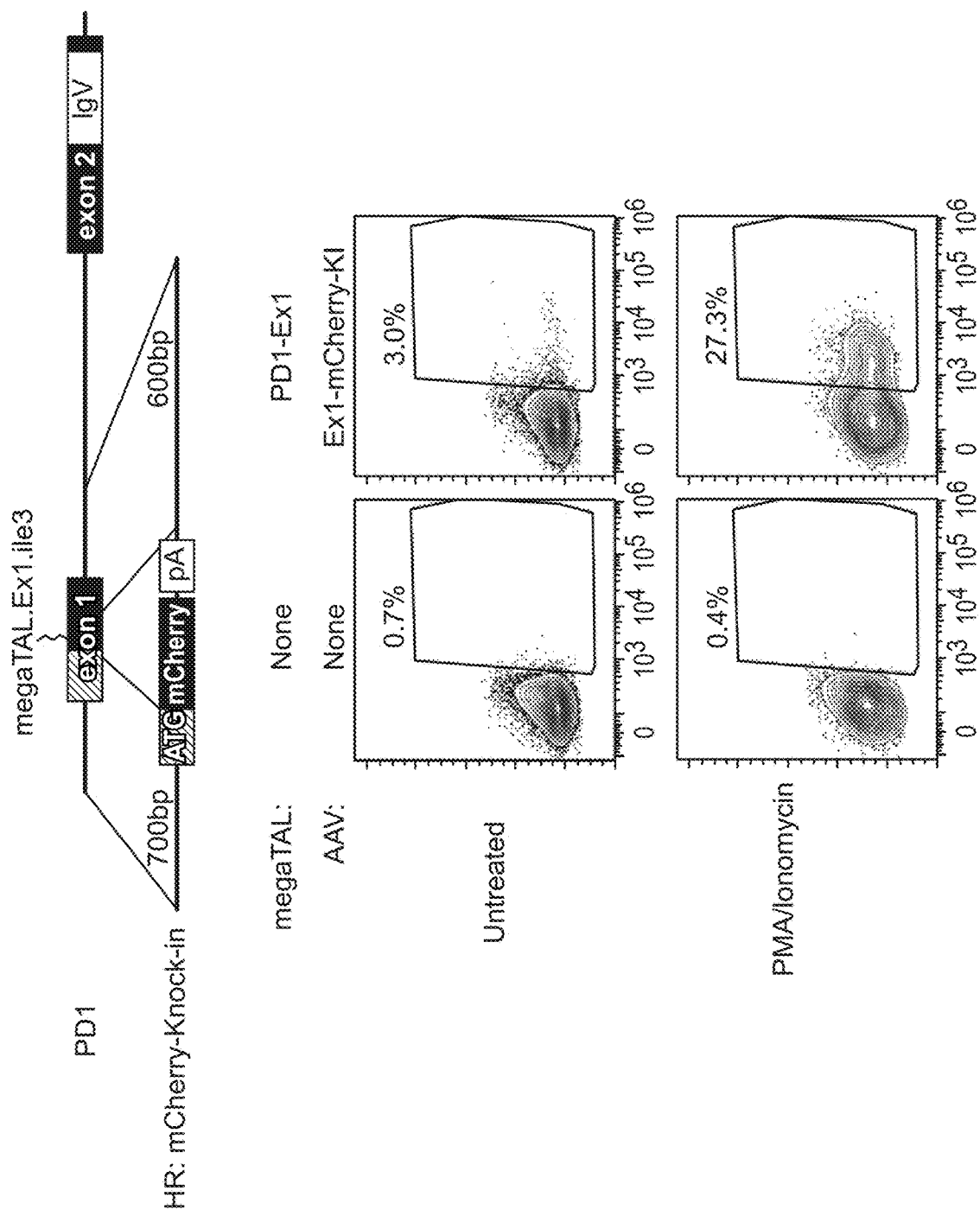
FIG. 17 shows a strategy for introducing an mCherry reporter gene at the PD-1 start codon in exon 1, and a flow cytometry analysis of mCherry expression in T cells electroporated with vehicle or PD-1.ile3.exon1_RD2_B1H8 megaTAL and transduced with vehicle or an rAAV targeting vector encoding mCherry both in the presence and absence of 24 hours of PMA/Ionomycin treatment.

A recombinant adeno-associated virus (rAAV) plasmid containing a fluorescent reporter (mCherry) transgene and a polyadenylation signal, but lacking an exogenous promoter, was designed, constructed, and verified (SEQ ID NO: 58). FIG. 17. The mCherry start codon merges and overlaps with the endogenous PD-1 start codon, while replacing the remainder of PD-1 exon 1 with a cDNA encoding the mCherry protein. This strategy drives expression of the fluorescent protein from the endogenous PD-1 promoter while also disrupting the normal expression of the PD-1 protein.

Primary human T cells were activated, electroporated with in vitro transcribed megaTAL mRNA, and transduced with rAAV as described above. Control samples included T cells treated with either megaTAL mRNA or rAAV targeting vector. Fluorescent reporter expression was analyzed by flow cytometry at various times post-transfection, in the presence or absence of polyclonal T cell activation using phorbol 12-myristate 13-acetate (PMA)/Ionomycin (P/I). Reporter expression was not observed in T cells treated with megaTAL mRNA or rAAV targeting vector alone. Similar rates of megaTAL activity were observed with or without rAAV transduction. Low-level fluorescent reporter expression was observed in T cells that received both megaTAL and rAAV targeting vector and activated with P/I for 48 hours. Fluorescent reporter expression driven by the endogenous PD-1 promoter was lower compared to a heterologous promoter-driven receptor expression (~5 fold reduction in fluorescence intensity).

Example 8

Figure 18:
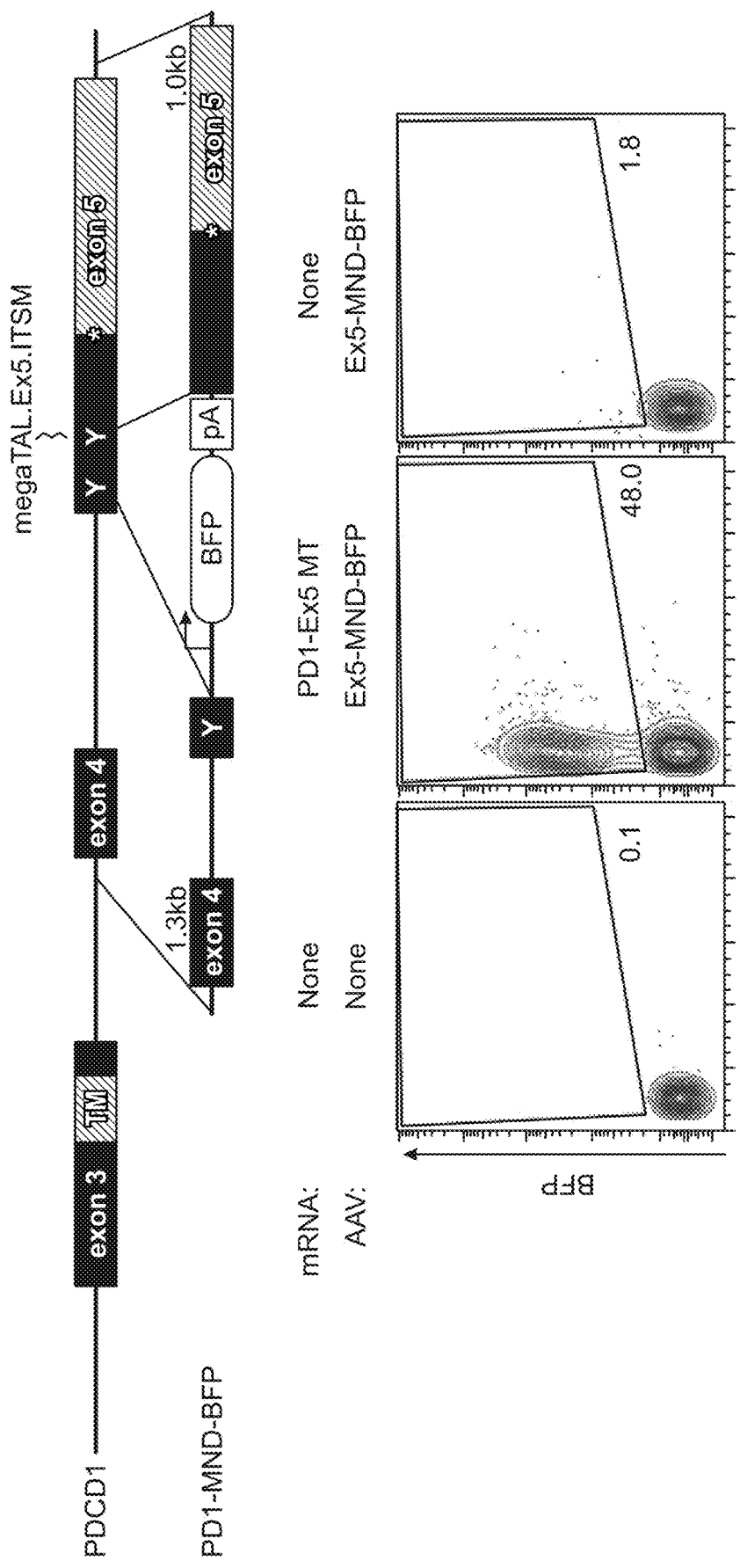
FIG. 18 shows a strategy for introducing an MND promoter-BFP expression cassette at the ITSM motif in PD-1 exon 5, and a flow cytometry analysis of BFP expression in T cells electroporated with vehicle or PD-1.ITSM.ex5_RD5_CV23MK megaTAL and transduced with vehicle or an rAAV targeting vector containing the pMND-BFP expression cassette.

Constitutive PD-1 Expression Following Homologous Recombination of A Transgene Encoding a Fluorescent Protein into Exon 5 of the PD-1 Gene A recombinant adeno-associated virus (rAAV) plasmid containing a heterologous promoter, a blue fluorescent protein (BFP) transgene, and a polyadenylation signal was designed, constructed, and verified (SEQ ID NO: 44) for introducing into PD-1 exon 5. The transgene cassette was placed between 1.3 kb and 1.0 kb homology arms flanking the PD-1 exon 5 megaTAL cleavage site. The 5' homology arm (SEQ ID NO: 45) included portion of PD-1 exon 5 upstream of the megaTAL cleavage site and other upstream sequences. The 3' homology arm (SEQ ID NO: 46) contained the terminal coding sequence of PD-1 exon 5 and other downstream sequences. Neither homology region contained the complete megaTAL target site. FIG. 18.

Primary human T cells were activated with CD3 and CD28, electroporated with in vitro transcribed PD-1 exon 5 megaTAL mRNA (SEQ ID NO: 40), then transduced with rAAV encoding the fluorescent reporter transgene. Controls included untreated T cells and T cells treated with rAAV targeting vector alone. Fluorescent reporter expression was analyzed by flow cytometry at various time points post-transfection. Cells treated with rAAV alone exhibited transient BFP expression which decreased to background levels during cell expansion. T cells that received both the PD-1 exon 5 megaTAL mRNA and rAAV vector exhibited a stable population of BFP expressing T cells that persisted throughout the course of ex vivo culture.

Figure 19:
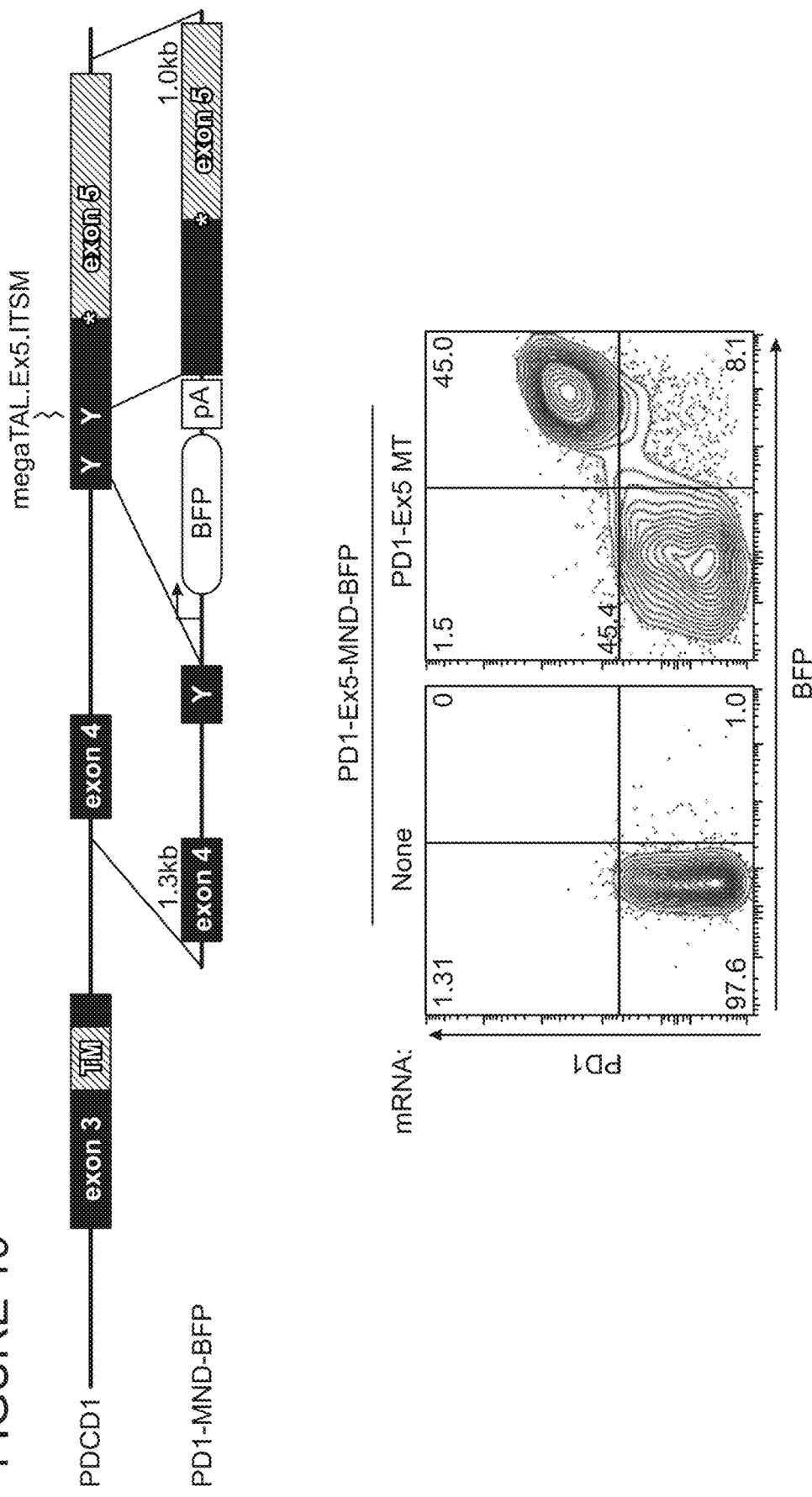
FIG. 19 shows a strategy for introducing an MND promoter-BFP expression cassette at the ITSM motif in PD-1 exon 5, and a flow cytometry analysis for PD-1 and BFP expression in T cells electroporated with vehicle or PD-1.ITSM.ex5_RD5_CV23MK megaTAL and transduced with vehicle or an rAAV targeting vector containing the pMND-BFP expression cassette.

T cells treated with both PD-1 exon 5 megaTAL mRNA and rAAV vector had a distinct PD-1 expression pattern whereby, in the absence of activation, nearly all BFP expressing cells also expressed the PD-1 protein. This indicates that the targeting strategy has altered the normal regulation of the PD-1 gene to a constitutive rather than inducible expression pattern. Moreover, due to targeting PD-1 exon 5, the constitutively expressed protein in this targeting strategy is a PD-1 variant that has impaired inhibitory signaling and that may act as a dominant negative receptor. PD-1 expression was not upregulated in T cells treated with the PD-1 exon 5 megaTAL mRNA alone or in T cells treated with megaTAL mRNA and rAAV comprising homology arms to exon 1. FIG. 19.

Example 9

Homologous Recombination of a Transgene into the PD-1 Gene is Independent of Single Nucleotide Polymorphism (SNPs)

Figure 20:
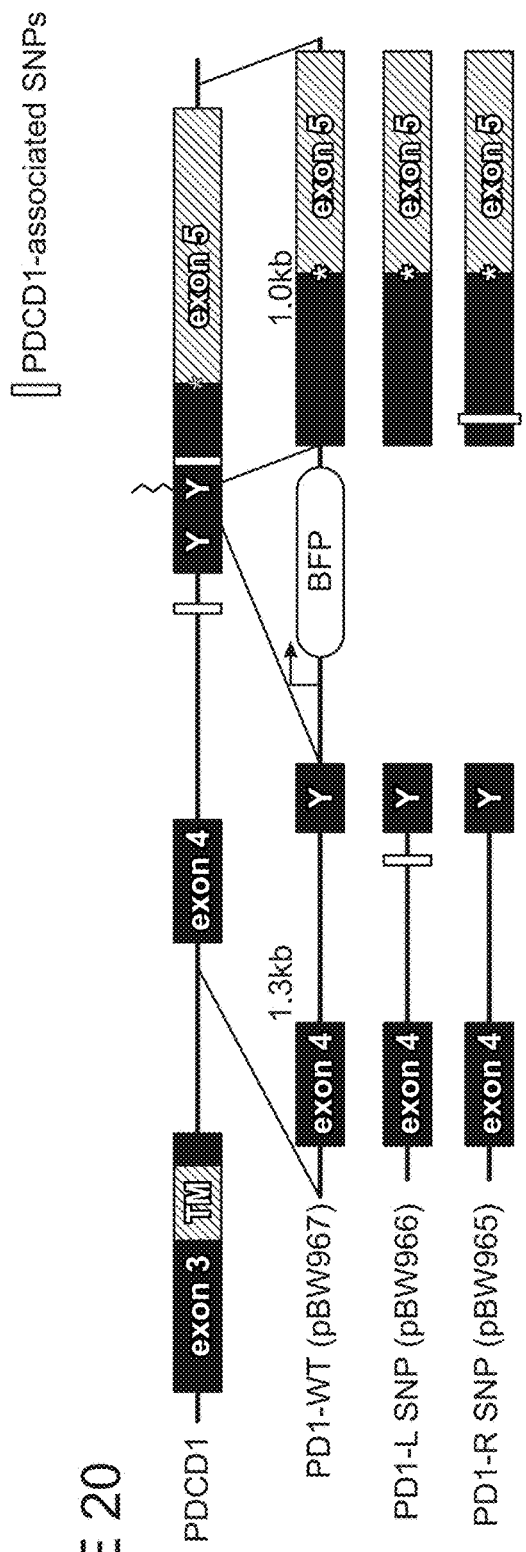
FIG. 20 shows strategies for introducing a MND promoter-BFP expression cassette at the ITSM motif in PD-1 exon 5, wherein the homology arms contain single nucleotide polymorphisms (SNPs) (upper panel). The lower panel shows a flow cytometry analysis of T cells electroporated with PD-1.ITSM.ex5_RD5_CV23MK megaTAL and transduced with rAAV targeting vector containing the pMND-BFP expression cassette with wild type homology arms, a 5' homology arm containing a SNP, or a 3' homology arm containing a SNP.
Figure 20:
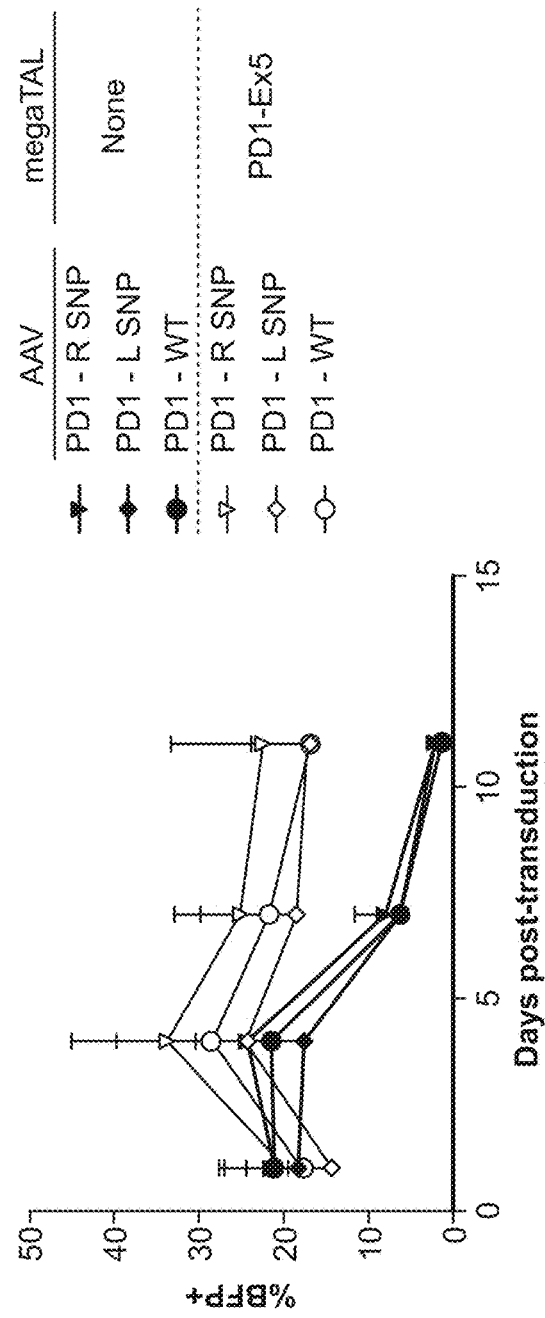

The PD-1 locus is genetically heterogenous, with a high prevalence of SNPs present in both intronic and exonic regions. The presence of diverging SNPs close to the megaTAL cleavage site could potentially impact homologous recombination efficiency at the PD-1 locus. Recombinant adeno-associated virus (rAAV) plasmids including a heterologous promoter, a fluorescent protein transgene, and a late SV40 polyadenylation signal were designed to assess the impact of SNPs, then constructed, and verified as described above (SEQ ID NOs: 47 and 48). The homology arms were either identical to the consensus PD-1 sequence or they were designed to include point mutations from common SNPs proximal to the PD-1 exon 5 megaTAL targeting site. In these designs, the 5' homology arm (L-SNP, SEQ ID NO: 49) contains an intronic G/A SNP (rs6705653) located 220 bp upstream of the megaTAL cleavage site, while the 3' homology arm (R-SNP, SEQ ID NO: 50) contains a silent C/T SNP (rs2227981) located 68 bp downstream of the PD-1 megaTAL cleavage site. FIG. 20.

Primary human T cells were activated with CD3 and CD28, electroporated with in vitro transcribed megaTAL mRNA, and transduced with rAAV encoding the consensus homology arms, or with rAAV carrying either the L-SNP or R-SNP homology arms. Controls included T cells transduced with rAAV targeting vector alone. Fluorescent protein expression was analyzed by flow cytometry at different time points post-transduction. The fluorescent protein expression declined to background levels in samples that only received rAAV, while T cells treated with megaTAL in combination with rAAV demonstrated stable levels of fluorescent protein expression. All samples exhibited similar fluorescence levels despite being treated with either non-SNP containing rAAV vectors or those containing L or R SNP variants, indicating that SNPs proximal to the megaTAL target site do not impact or do not substantially impact HR at the target site.

Example 10

Figure 21:
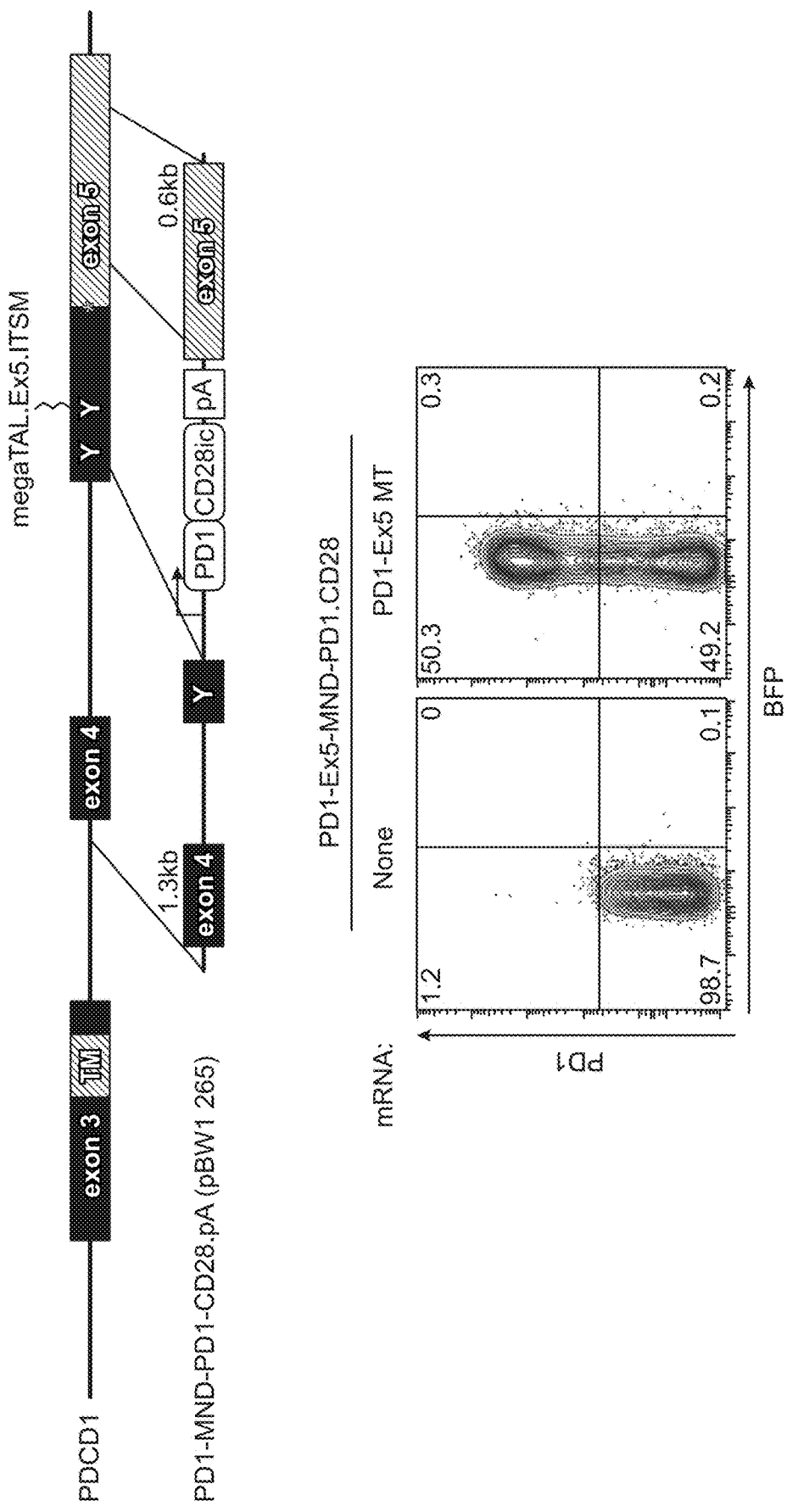
FIG. 21 shows a strategy for introducing an MND promoter-PD-1.CD28 flip receptor expression cassette at the ITSM motif in PD-1 exon 5, and a flow cytometry analysis for PD-1 and BFP expression in T cells electroporated with vehicle or PD-1.ITSM.ex5_RD5_CV23MK megaTAL and transduced with vehicle or an rAAV targeting vector containing the pMND-PD-1.CD28 flip receptor expression cassette.

Homologous Recombination of a Transgene Encoding a Switch Receptor into the PDCD1 Locus Switch Receptors are engineered chimeric molecules that are able to convert extracellular inhibitory signals into intracellular activation signals, however their effectiveness often correlates to their ability to overwhelm native expression of the natural receptors. One way to circumvent this limitation is to embed a switch receptor into the native locus and disrupt the natural receptor. A recombinant adeno-associated virus (rAAV) plasmid containing a heterologous promoter, a transgene encoding a PD-1 extracellular ligand-binding domain and an intracellular CD28 signaling domain (PD-1-Switch Receptor, SEQ ID NO: 59), and a late SV40 polyadenylation signal was designed for targeting PD-1 exon 5, constructed, and verified. The 5' homology arm included portion of PD-1 exon 5 upstream of the megaTAL cleavage site containing the ITIM and other upstream sequences. The 3' homology arm contained the terminal coding sequence of PD-1 exon 5 and a portion of the UTR region, and was shortened to ~650 bp to accommodate the switch receptor cDNA. Neither homology region contained the complete megaTAL target site. FIG. 21.

Primary human T cells were activated with CD3 and CD28, electroporated with in vitro transcribed PD-1 exon 5 megaTAL mRNA and transduced with rAAV targeting vector encoding the PD-1-Switch Receptor. Controls included samples that received megaTAL or rAAV alone. The expression of the PD-1-Switch Receptor was analyzed by staining with anti-PD-1 antibody in the absence of T cell stimulation. High expression levels in T cells treated with PD-1 exon 5 megaTAL mRNA and transduced with rAAV were observed.

Example 11

Long-Range Excision of PD-1 Intracellular Signaling Region Using HDR

Figure 22:
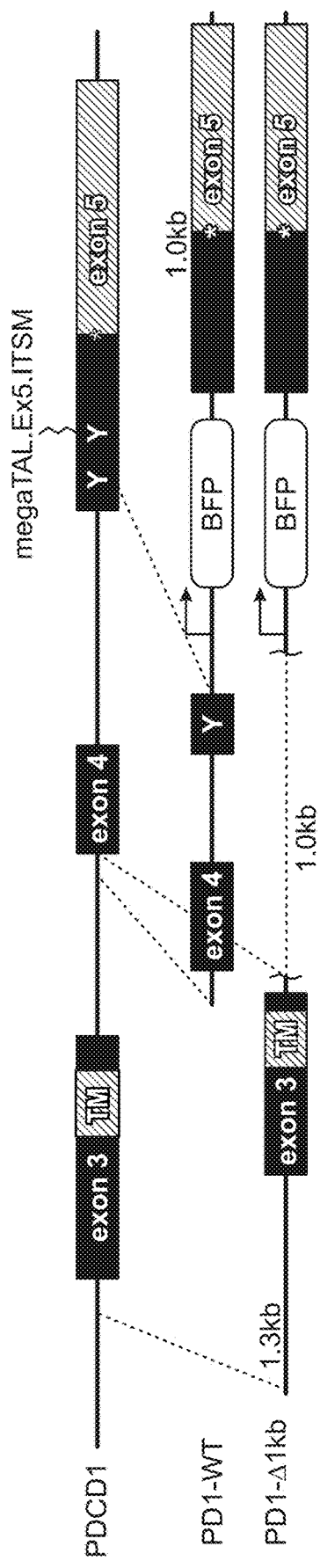
FIG. 22 shows a strategy for creating a large-scale deletion in the PD-1 gene by delivering a PD-1.ITSM.ex5_RD5_CV23MK megaTAL and a rAAV cassette containing homology arms more than a kilobase upstream of the exon 5 target site.

The homologous recombination mechanism is known to involve homology 'search' mechanisms that can span distant genomic sequences. Without wishing to be bound by any particular theory it is contemplated that more substantial spans of target genes or chromosomal regions may be prone to efficient manipulation using a combination of megaTAL and rAAV delivery. A recombinant adeno-associated virus (rAAV) plasmid including a heterologous promoter, a BFP transgene, and a late SV40 polyadenylation signal flanked by homology arms to assess distal HR events was designed, constructed, and verified (SEQ ID NO: 52). The transgene was flanked by a 1.3 kb 5' homology arm designed to begin upstream of PD-1 exon 3 and end immediately before the beginning of exon 4. The 3' homology arm contained the terminal coding sequence of PD-1 exon 5 and a portion of the UTR region. Neither homology region contained the complete megaTAL target site. Successful homologous recombination is designed to eliminate the entirety of the PD-1 intracellular signaling region, with only the extracellular and transmembrane portion of PD-1 remaining on the treated cell. FIG. 22.

Primary human T cells are activated with CD3 and CD28, electroporated with in vitro transcribed megaTAL mRNA and transduced with the BFP encoding rAAV targeting vector comprising the distal 5' homology arm. Controls include T cells treated with either megaTAL or rAAV targeting vector. Stable BFP expression is observed only in samples that received both rAAV and PDCD1 exon 5-targeting megaTAL mRNA.

Example 12

PD-1 Gene Disruption and Antibody-Mediated PD1 Blockade in Primary Human T Cells In Vitro The functional impact of the megaTALs reprogrammed to cleave various target sequences in the PD-1 gene was evaluated in primary human T cells activated with CD3 and CD28 and cultured in complete media supplemented with IL-2. Activated PBMCs were transduced with a lentiviral vector encoding an anti-BCMA CAR. Anti-BCMA CAR T cells were electroporated with in vitro transcribed mRNA encoding either the PD-1 exon 5 or PD-1 exon 1 targeting megaTALs (SEQ ID NOs: 40 and 41, resp.) and mRNA encoding Trex2 (SEQ ID NO: 43). Controls included T cells electroporated without mRNA (Mock EP) or T cells electroporated with mRNA encoding a megaTAL specific for TCRα that lacks catalytic activity.

Figure 15B:
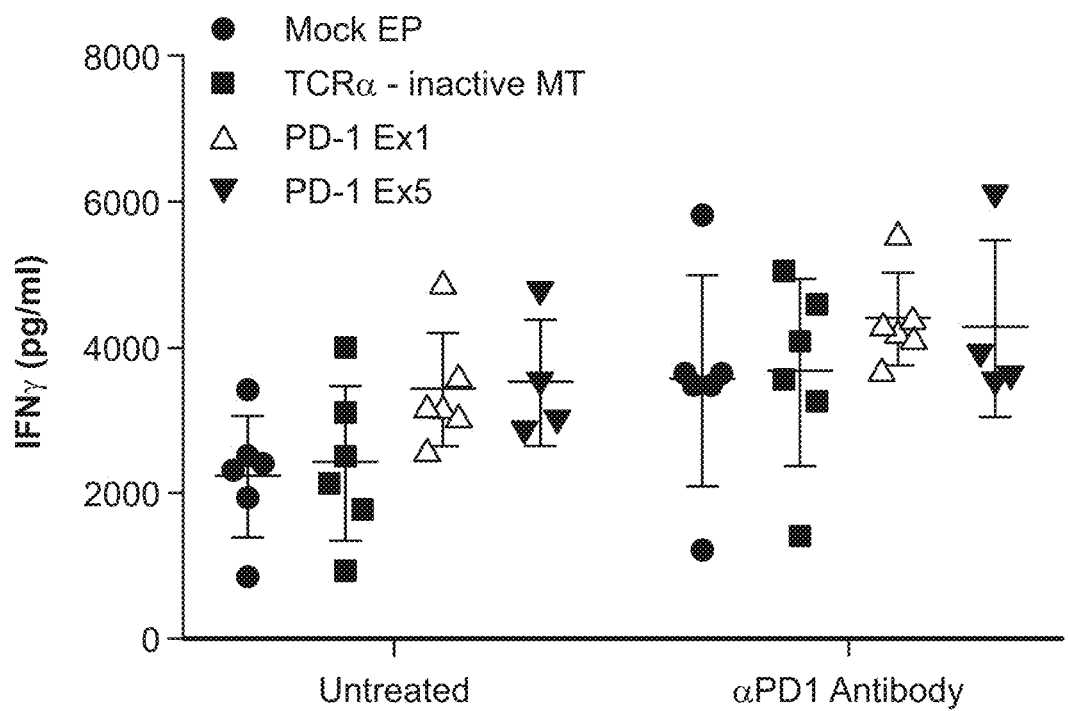
FIG. 15B shows that anti-BCMA CAR T cells electroporated with mRNA encoding PD-1.ITSM.ex5_RD5_CV23MK or PD-1.ile3.exon1_RD2_B1H8 megaTALs show reduced PD-L1 mediated cytokine suppression compared to anti-BCMA CAR T cells electroporated with vehicle, or mRNA encoding a catalytically inactive TCRα megaTAL (untreated expts.). Addition of PD-1 antibody to the cultures abrogated cytokine suppression in anti-BCMA CAR T cells electroporated with vehicle, or mRNA encoding a catalytically inactive TCRα megaTAL.
Figure 15B:
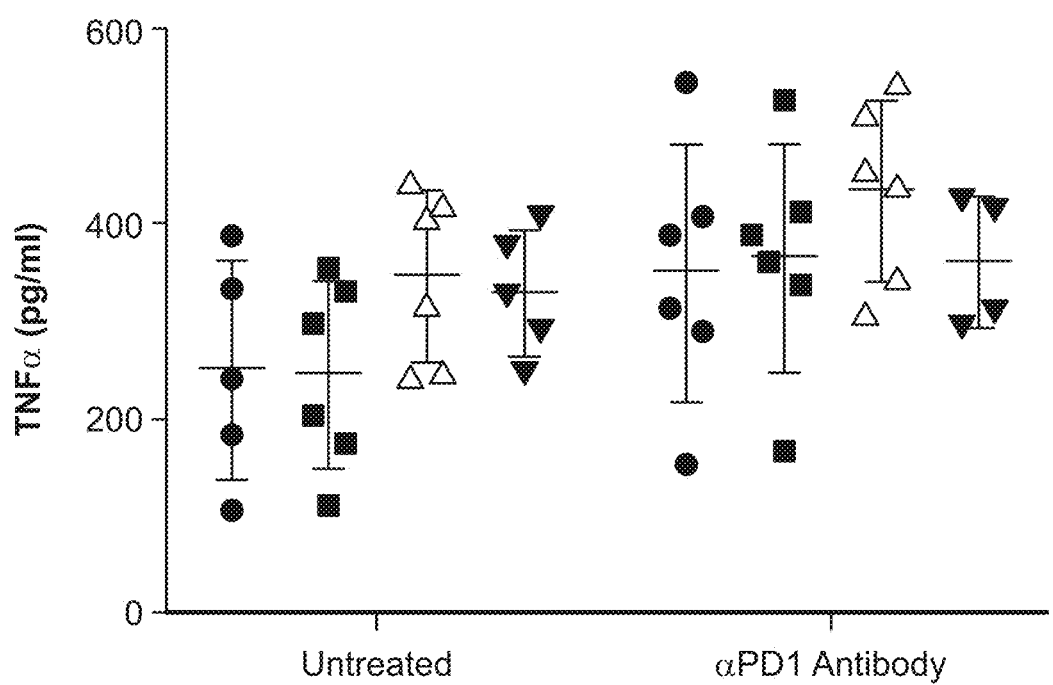

Following a 10 day expansion, T cells were co-cultured with A549 cells transduced with a lentiviral vector encoding BCMA-GFP. CAR T cells were co-cultured with A549 target cells alone or in the presence of 20 μg/ml anti-PD-1 antibody. Cells were co-cultured for 72 hrs and cytokine levels in the supernatants was analyzed using a bead-based assay (Intellicyt QBeads). In the absence of anti-PD-1 antibody, cells that were treated with either PD1-Ex1 or PD1-Ex5 megaTAL showed elevated IFNγ and TNFα production compared to mock EP and TCRα dead controls. Addition of αPD-1 antibody abrogated this difference, resulting in equivalent level of IFNγ and TNFα secretion in supernatants obtained from control and PD1 megaTAL treated cells (FIG. 15B).

Example 13

Homologous Recombination of a Promoter-Less Transgene into the PD-1 Gene

A recombinant adeno-associated virus (rAAV) plasmid containing a fluorescent reporter (mCherry) transgene and a polyadenylation signal, but lacking an exogenous promoter, was designed, constructed, and verified (SEQ ID NO: 58). FIG. 17. The mCherry start codon merges and overlaps with the endogenous PD-1 start codon, while replacing the remainder of PD-1 exon 1 with a cDNA encoding the mCherry protein. This strategy drives expression of the fluorescent protein from the endogenous PD-1 promoter while also disrupting the normal expression of the PD-1 protein.

Primary human T cells were activated, electroporated with in vitro transcribed megaTAL mRNA, and transduced with rAAV as described above. Control samples included T cells treated with either megaTAL mRNA or rAAV targeting vector. Fluorescent reporter expression was analyzed by flow cytometry at 24 hours post-stimulation, in the presence or absence of polyclonal T cell activation using phorbol 12-myristate 13-acetate (PMA)/Ionomycin (P/I). Reporter expression was not observed in the untreated T cells. Before P/I stimulation, low basal levels of fluorescent reporter expression were observed in the T cells that received both megaTAL and rAAV targeting vector for HDR. Twenty four hours of P/I stimulation upregulated the fluorescent reporter expression driven by the endogenous PD-1 from 3% to 27.3% (compare top to bottom rightmost panels in FIG. 17).

Example 14

Figure 23:
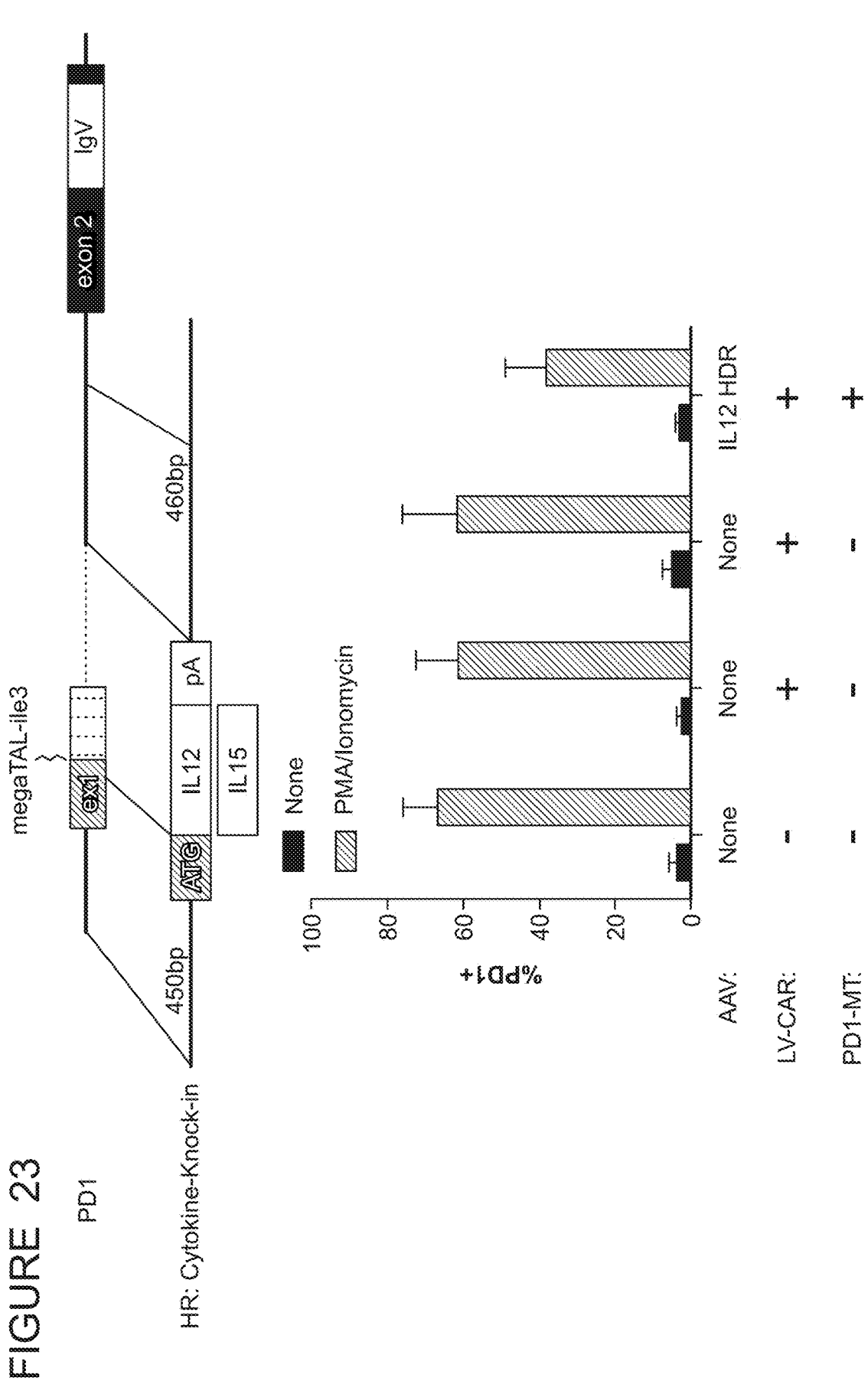
FIG. 23 shows a strategy for inserting a cytokine into the PD-1 gene, where expression is under the control of the endogenous PD-1 promoter (top panel). After 24 hours of PMA/Ionomycin treatment, anti-BCMA CAR T cells electroporated with PD-1 megaTAL mRNA and transduced with rAAV encoding IL-12 showed decreased PD-1 expression compared to control treated cells (bottom panel).

Homologous Recombination of a Promoter-Less Cytokine Transgene into the PD-1 Locus A recombinant adeno-associated virus (rAAV) plasmid containing an IL-12 or IL-15 transgenes and a polyadenylation signal, but lacking an exogenous promoter, was designed, constructed, and verified (SEQ ID NO: 58). The transgene start codon merges and overlaps with the endogenous PD-1 start codon, while replacing the remainder of PD-1 exon 1 with cDNA encoding the IL-12 or IL-15 cytokine (FIG. 23, top panel). This strategy drives expression of the transgene from the endogenous PD-1 promoter while also disrupting the normal expression of the PD-1.

Primary human T cells were activated and transduced with lentiviral vector encoding an anti-BCMA CAR 24 hrs post activation. The cells were propagated for 2 days, electroporated with in vitro transcribed megaTAL mRNA, and transduced with rAAV as described above. Control samples included untransduced T cells, T cells treated with anti-BCMA CAR alone or T cells treated with anti-BCMA CAR and cultured in the presence of recombinant IL-12. The activity of PD-1 megaTAL was accessed by flow cytometric analysis of PD-1 expression on T cells stimulated for 24 hrs with PMA/Ionomycin. Combined PD-1 megaTAL with IL-12 AAV showed about 40% decrease of PD-1 expression compared to control samples (FIG. 23, bottom panel).

Figure 24A:
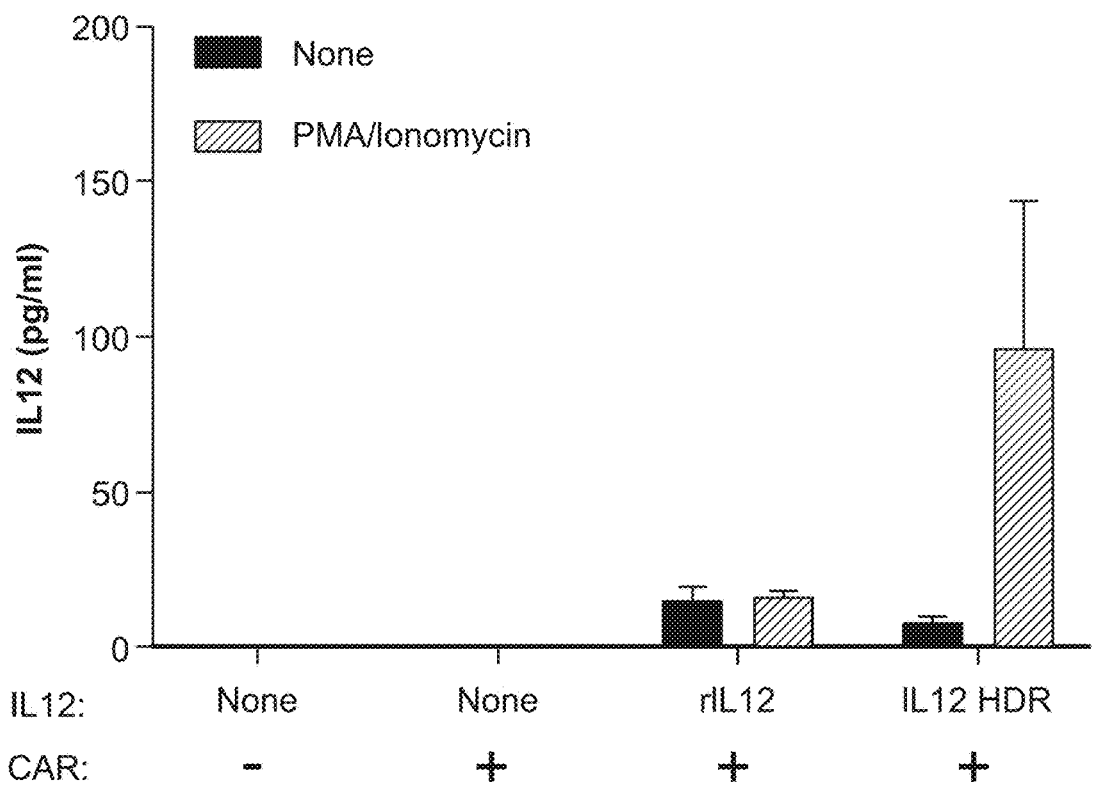
FIG. 24A shows that after 24 hrs of PMA/Ionomycin treatment, anti-BCMA CAR T cells electroporated with PD-1 megaTAL mRNA and transduced with rAAV encoding IL-12 showed increased IL-12 production compared to control treated cells (left panel). Anti-BCMA CAR T cells electroporated with PD-1 megaTAL mRNA and transduced with rAAV encoding IL-12 and cultured in the presence of K562-BCMA target cells showed increased IL-12 production compared to control treated cells (right panel).
Figure 24A:
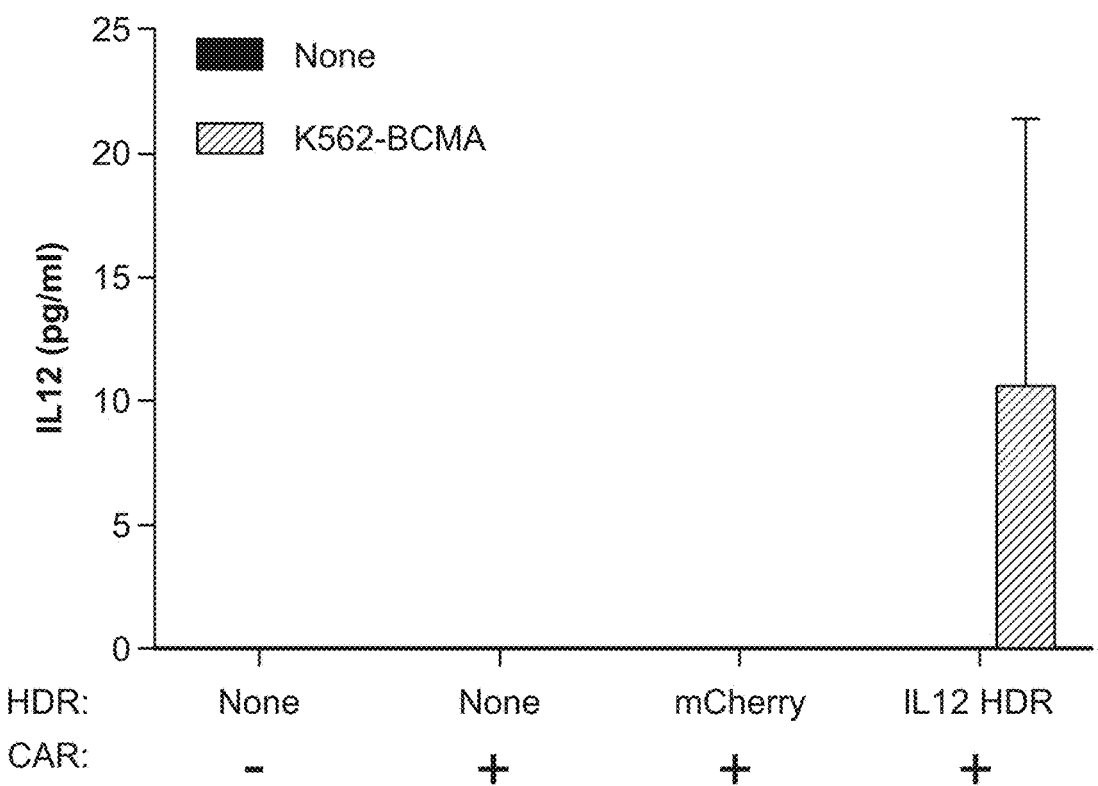
Figure 24B:
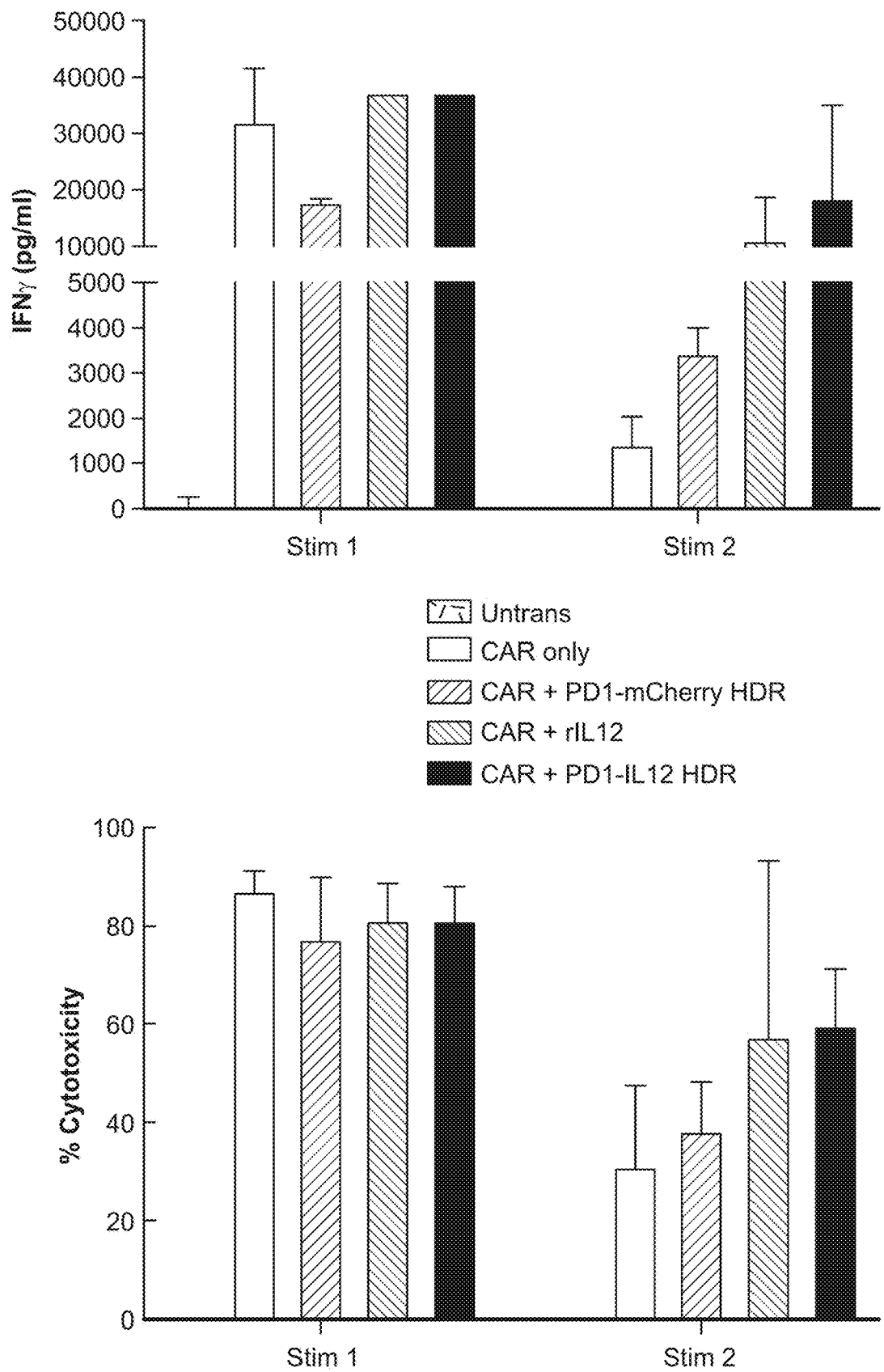
FIG. 24B shows the results from a serial stimulation assay. K52-BCMA cells and anti-BCMA-CAR T cells were mixed, cultured for 7 days and additional K562-BCMA target cells were added to mimic a repeated stimulation. After restimulation, anti-BCMA-CAR T cells treated with recombinant IL-12 or that were treated with both PD-1 megaTAL and the IL-12 HDR template showed increased IFNγ production and cytotoxicity compared to control treated cells.

IL-12 expression levels were measured by ELISA after PMA/Ionomycin activation or following co-culture of T cells with antigen expressing K562-BCMA cell line. There was minimal IL-12 production in unstimulated T cells and both PMA/Ionomycin stimulation and co-culture with antigen-positive K562 cells resulted in IL-12 secretion (FIG. 24A). Repeated stimulation assays were used to measure functional exhaustion of BCMA-CAR T cells. Tumor cells and anti-BCMA-CAR T cells were mixed, cultured for 7 days and additional K562-BCMA target cells were added to mimic a repeated stimulation. After the 1$^{st}$ stimulation, the levels of IFNγ production and cytotoxicity were similar in all T cell samples. After the 2$^{nd}$ stimulation, IFNγ production and cytotoxicity increased in anti-BCMA-CAR T cells treated with recombinant IL-12 or that were treated with both PD-1 megaTAL and the IL-12 HDR template compared to control treated cells (FIG. 24B).

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A polypeptide comprising an I-OnuI homing endonuclease (HE) variant that cleaves a target site in the human program cell death 1 (PD-1) gene, wherein the I-OnuI HE variant comprises the amino acid sequence set forth in any one of SEQ ID NOs: 11, 12, 60, 62, and 63.

2. The polypeptide of claim 1, wherein the I-OnuI HE variant comprises the amino acid sequence set forth in SEQ ID NO: 11.

3. The polypeptide of claim 1, wherein the I-OnuI HE variant comprises the amino acid sequence set forth in SEQ ID NO: 12.

4. The polypeptide of claim 1, wherein the I-OnuI HE variant comprises the amino acid sequence set forth in SEQ ID NO: 60.

5. The polypeptide of claim 1, wherein the I-OnuI HE variant comprises the amino acid sequence set forth in SEQ ID NO: 62.

6. The polypeptide of claim 1, wherein the I-OnuI HE variant comprises the amino acid sequence set forth in SEQ ID NO: 63.

7. The polypeptide of claim 1, wherein the polypeptide binds and cleaves the polynucleotide sequence set forth in SEQ ID NO: 30.

8. The polypeptide of claim 1, further comprising a TALE DNA binding domain comprising about 9.5 TALE repeat units to about 15.5 TALE repeat units.

9. The polypeptide of claim 8, wherein the TALE DNA biding domain binds a polynucleotide sequence set forth in SEQ ID NO: 31.

10. A polynucleotide encoding the polypeptide of claim 1.

11. An mRNA encoding the polypeptide of claim 1.

12. A vector comprising a polynucleotide encoding the polypeptide of claim 1.

13. A method of editing a human PD-1 gene in a cell comprising: introducing a polynucleotide encoding a polypeptide into the cell,
wherein the polypeptide comprises an I-OnuI HE variant comprising the amino acid sequence set forth in any one of SEQ ID NOs: 11, 12, 60, 62, and 63,
wherein expression of the polypeptide creates a double strand break at a target site in a human PD-1 gene; and
wherein the cell is a hematopoietic cell.

14. The method of claim 13, wherein the I-OnuI HE variant comprises the amino acid sequence set forth in SEQ ID NO: 11.

15. The method of claim 13, wherein the I-OnuI HE variant comprises the amino acid sequence set forth in SEQ ID NO: 12.

16. The method of claim 13, wherein the I-OnuI HE variant comprises the amino acid sequence set forth in SEQ ID NO: 60.

17. The method of claim 13, wherein the I-OnuI HE variant comprises the amino acid sequence set forth in SEQ ID NO: 62.

18. The method of claim 13, wherein the I-OnuI HE variant comprises the amino acid sequence set forth in SEQ ID NO: 63.

19. The method of claim 13, wherein the polypeptide binds and cleaves the polynucleotide sequence set forth in SEQ ID NO: 30.

20. The method of claim 13, wherein the polypeptide further comprises a TALE DNA binding domain comprising about 9.5 TALE repeat units to about 15.5 TALE repeat units.

21. The method of claim 20, wherein the TALE DNA biding domain binds a polynucleotide sequence set forth in SEQ ID NO: 31.

22. The method of claim 13, wherein the double strand break is repaired by non-homologous end joining (NHEJ).

23. The method of claim 13, comprising introducing a donor repair template into the cell, wherein the donor repair template is incorporated into the human PD-1 gene by homology directed repair (HDR) at the site of the double-strand break.

24. The method of claim 13, wherein the hematopoietic cell is a T cell; a $CD3^+$, $CD4^+$, and/or $CD8^+$ cell; an immune effector cell; a cytotoxic T lymphocytes (CTLs), a tumor infiltrating lymphocytes (TILs) or a helper T cells; and/or a natural killer (NK) cell or natural killer T (NKT) cell.

25. The method of claim 13, wherein the source of the cell is peripheral blood mononuclear cells, bone marrow, lymph nodes tissue, cord blood, thymus issue, tissue from a site of infection, ascites, pleural effusion, spleen tissue, or tumors.

26. The method of claim 13, wherein the polynucleotide encoding the polypeptide is an mRNA.

27. The method of claim 23, wherein the donor repair template encodes a PD-1 gene or portion thereof comprising one or more mutations compared to the wild type PD-1 gene; or wherein the donor repair template encodes one or more of an immunopotency enhancer, an immunosuppressive signal damper, or an engineered antigen receptor.

* * * * *